United States Patent
Zhao et al.

(10) Patent No.: US 11,053,239 B2
(45) Date of Patent: Jul. 6, 2021

(54) COMPOUNDS AS BLC-2-SELECTIVE APOPTOSIS-INDUCING AGENTS

(71) Applicant: Fochon Pharmaceuticals, Ltd., Chongqing (CN)

(72) Inventors: Xingdong Zhao, Chongqing (CN); Zuwen Zhou, Chongqing (CN); Chengxi He, Chongqing (CN); Zhifu Li, Chongqing (CN); Yue Rong, Chongqing (CN); Rui Tan, Chongqing (CN); Huajie Zhang, Chongqing (CN); Hongbin Liu, Chongqing (CN); Weipeng Zhang, Chongqing (CN); Haohan Tan, Chongqing (CN); Zhifang Chen, Chongqing (CN); Lihua Jiang, Chongqing (CN); Yanxin Liu, Chongqing (CN); Min Lin, Chongqing (CN); Jing Sun, Chongqing (CN); Weibo Wang, Moraga, CA (US)

(73) Assignee: Fochon Pharmaceuticals, Ltd., Chongqing (CN)

( * ) Notice: Subject to any disclaimer, the term of this patent is extended or adjusted under 35 U.S.C. 154(b) by 0 days.

(21) Appl. No.: 16/475,826

(22) PCT Filed: Jan. 5, 2018

(86) PCT No.: PCT/CN2018/071562
§ 371 (c)(1),
(2) Date: Jul. 3, 2019

(87) PCT Pub. No.: WO2018/127130
PCT Pub. Date: Jul. 12, 2018

(65) Prior Publication Data
US 2019/0345156 A1    Nov. 14, 2019

Related U.S. Application Data

(60) Provisional application No. 62/443,660, filed on Jan. 7, 2017.

(51) Int. Cl.
*C07D 471/04*    (2006.01)

(52) U.S. Cl.
CPC .................. *C07D 471/04* (2013.01)

(58) Field of Classification Search
CPC ........ A61K 45/06; A61P 35/00; C07D 471/04
USPC ........................................ 514/228
See application file for complete search history.

(56) References Cited

U.S. PATENT DOCUMENTS

| | | | |
|---|---|---|---|
| 8,426,422 B2 | 4/2013 | Hexamer et al. | |
| 2011/0124628 A1* | 5/2011 | Bruncko | C07D 471/04 514/210.21 |
| 2012/0108590 A1* | 5/2012 | Birtalan | A61K 47/26 514/234.5 |

FOREIGN PATENT DOCUMENTS

| | | | |
|---|---|---|---|
| EP | 3112361 | | 1/2017 |
| WO | 2006/127364 | | 11/2006 |
| WO | 2010/065865 | | 6/2010 |
| WO | 2010065824 | * | 6/2010 |
| WO | 2010/083441 | | 7/2010 |
| WO | 2010/083442 | | 7/2010 |
| WO | 2010138588 | A2 | 12/2010 |
| WO | 2011/150016 | | 5/2011 |
| WO | 2011149492 | A1 | 12/2011 |
| WO | 2012/058392 | | 5/2012 |
| WO | 2014158528 | * | 10/2014 |

(Continued)

OTHER PUBLICATIONS

International Search Report dated Mar. 30, 2018 in International Patent Application No. PCT/CN2018/071562.

(Continued)

*Primary Examiner* — Tracy Vivlemore
*Assistant Examiner* — Ebenezer O Sackey
(74) *Attorney, Agent, or Firm* — Meunier Carlin & Curfman LLC

(57) ABSTRACT

Bcl-2 inhibitors, pharmaceutical compositions thereof, and methods of use thereof are provided. In particular, Bcl-2 inhibitors of formula (I) are provided, wherein the variable groups are as defined in the specification. The Bcl-2 inhibitors can be used to treat cell proliferative disorders.

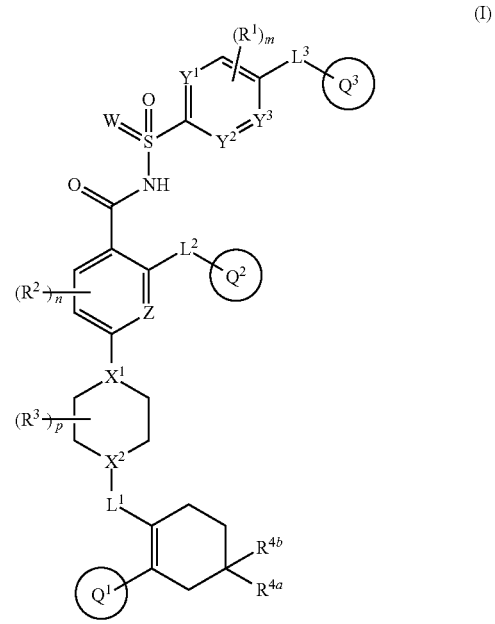

13 Claims, No Drawings

(56) References Cited

FOREIGN PATENT DOCUMENTS

| WO | 2014158528 A1 | 10/2014 |
| WO | 2017/132474 | 8/2017 |
| WO | 2018/027097 | 2/2018 |
| WO | 2018/041248 | 3/2018 |
| WO | 2018/192462 | 10/2018 |
| WO | 2019/139899 | 7/2019 |
| WO | 2019/210828 | 11/2019 |

OTHER PUBLICATIONS

International Preliminary Report on Patentability dated Jul. 9, 2019 in International Patent Application No. PCT/CN2018/071562. 6 pages.
International Preliminary Report on Patentability dated Oct. 22, 2019 in International Patent Application No. PCT/CN2018/083268. 8 pages.
International Search Report and Written Opinion dated Mar. 30, 2018 in International Patent Application No. PCT/CN2018/071562. 11 pages.
International Search Report and Written Opinion dated Jul. 23, 2018 in International Patent Application No. PCT/CN2018/083268. 14 pages.

* cited by examiner

COMPOUNDS AS BLC-2-SELECTIVE APOPTOSIS-INDUCING AGENTS

CROSS-REFERENCE TO RELATED APPLICATION

This application is a Section 371 of International Application No. PCT/CN2018/071562, filed Jan. 5, 2018, which was published in the English language on Jul. 12, 2018 under International Publication No. WO 2018/127130 A1, which claims priority under to U.S. Provisional Patent Application No. 62/443,660, filed Jan. 7, 2017, and the disclosures of which are incorporated herein by reference.

FIELD OF THE INVENTION

Provided are certain compounds or pharmaceutically acceptable salts thereof which can inhibit anti-apoptotic Bcl-2 family proteins and may be useful for the treatment of hyper-proliferative diseases like cancer and inflammation, or immune and autoimmune diseases.

BACKGROUND OF THE INVENTION

Hyper-proliferative diseases like cancer and inflammation are attracting the scientific community to provide therapeutic benefits. In this regard efforts have been made to identify and target specific mechanisms which play a role in proliferating the diseases.

Protein-protein interactions (PPIs) control many biological process, such as cell proliferation, growth, differentiation, signal transduction and apoptosis. Abnormal regulation of PPIs leads to different diseases. Thus, PPIs represent an important class of molecular targets for novel human therapeutics.

The B-cell lymphoma-2 (Bcl-2) family of proteins is central to the regulation of apoptosis, which is vital for proper tissue development and cellular homeostasis. Apoptosis occurs via activation of two different pathways. The extrinsic pathway, triggered by activation of the intrinsic pathway involving members of the Bcl-2 family of proteins. The Bcl-2 family protein includes anti-apoptotic proteins, such as Bcl-2, Bcl-XL and Mcl-1, and pro-apoptotic proteins, including Bid, Bim, Bad, Bak and Bax.

Anti-apoptotic Bcl-2 family members are often found to be up-regulated in cancers and are associated with stage of disease and prognosis. Therefore, Bcl-2 proteins are under investigation as potential therapeutic drug targets which include, for example, Bcl-2 and Bcl-XL. Expression of Bcl-2 proteins is an independent indicator of poor prognosis in tumors including chronic lymphocytic leukemia (CLL), prostate cancer, and small cell lung cancer (SCLC). In other tumors such as colorectal cancer, Bcl-$X_L$ expression is linked to grade and stage, and in hepatocellular cancer, Bcl-XL expression is an independent marker of poorer overall and disease-free survival.

Therefore, a compound having an inhibitory activity on Bcl-2 will be useful for the prevention or treatment of cancer. In this regard, a novel class of Bcl-2 inhibitors is provided herein. Although Bcl-2 inhibitors were disclosed in the arts, many suffer from having short half-life or toxicity. Therefore, there is a need for new Bcl-2 inhibitors that have at least one advantageous property selected from potency, stability, selectivity, toxicity, pharmacodynamic and pharmacokinetic properties as an alternative for the treatment of hyper-proliferative diseases. In this regard, a novel class of Bcl-2 inhibitors is provided herein.

DISCLOSURE OF THE INVENTION

Disclosed herein are certain novel compounds, pharmaceutically acceptable salts thereof, and pharmaceutical compositions thereof, and their use as pharmaceuticals.

In one aspect, disclosed herein is a compound of formula (I):

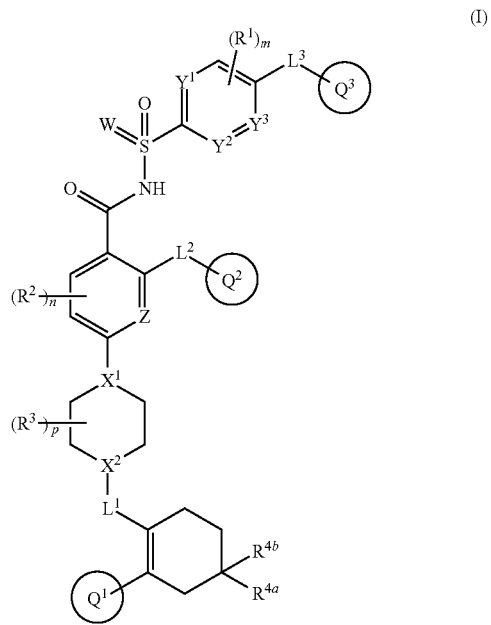

or a pharmaceutically acceptable salt thereof, wherein $L^1$ is selected from —$(CR^{C5}R^{D5})_u$—, —$(CR^{C5}R^{D5})_uO(CR^{C5}R^{D5})_t$—, —$(CR^{CR}R^{D5})_uNR^{A5}(CR^{C5}R^{D5})_t$—, —$(CR^{C5}R^{D5})_uS(CR^{C5}R^{D5})_t$—, —$(CR^{C5}R^{D5})_uC(O)(CR^{C5}R^{D5})_t$—, —$(CR^{C5}R^{D5})_uC(=NR^{E5})(CR^{C5}R^{D5})_t$—, —$(CR^{C5}R^{D5})_uC(S)(CR^{C5}R^{D5})_t$—, —$(CR^{C5}R^{D5})_uC(O)O(CR^{C5}R^{D5})_t$—, —$(CR^{C5}R^{D5})_uOC(O)(CR^{C5}R^{D5})_t$—, —$(CR^{C5}R^{D5})_uC(O)NR^{A5}(CR^{C5}R^{D5})_t$—, —$(CR^{C5}R^{D5})_uNR^{A5}C(O)(CR^{C5}R^{D5})_t$—, —$(CR^{C5}R^{D5})_uNR^{A5}C(O)NR^{B5}(CR^{C5}R^{D5})_t$—, —$(CR^{C5}R^{D5})_uC(=NR^{E5})NR^{B5}(CR^{C5}R^{D5})_t$—, —$(CR^{C5}R^{D5})_uNR^{B5}C(=NR^{E5})(CR^{C5}R^{D5})_t$—, —$(CR^{C5}R^{D5})_uNR^{A5}C(=NR^{E5})NR^{B5}(CR^{C5}R^{D5})_t$—, —$(CR^{C5}R^{D5})_uC(S)NR^{A5}(CR^{C5}R^{D5})_t$—, —$(CR^{C5}R^{D5})_uNR^{A5}C(S)(CR^{C5}R^{D5})_t$—, —$(CR^{C5}R^{D5})_uNR^{A5}C(S)NR^{B5}(CR^{C5}R^{D5})_t$—, —$(CR^{C5}R^{D5})_uS(O)_r(CR^{C5}R^{D5})_t$—, —$(CR^{C5}R^{D5})_uS(O)_rNR^{A5}(CR^{C5}R^{D5})_t$—, —$(CR^{C5}R^{D5})_uNR^{A5}S(O)_r(CR^{C5}R^{D5})_t$— and —$(CR^{C5}R^{D5})_uNR^{A5}S(O)_rNR^{B5}(CR^{C5}R^{D5})_t$—;

$L^2$ is selected from —$(CR^{C6}R^{D6})_u$—, —$(CR^{C6}R^{D6})_uO(CR^{C6}R^{D6})_t$—, —$(CR^{C6}R^{D6})_uNR^{A6}(CR^{C6}R^{D6})_t$—, —$(CR^{C6}R^{D6})_uS(CR^{C6}R^{D6})_t$—, —$(CR^{C6}R^{D6})_uC(O)(CR^{C6}R^{D6})_t$—, —$(CR^{C6}R^{D6})_uC(=NR^{E6})(CR^{C6}R^{D6})_t$—, —$(CR^{C6}R^{D6})_uC(S)(CR^{C6}R^{D6})_t$—, —$(CR^{C6}R^{D6})_uC(O)O(CR^{C6}R^{D6})_t$—, —$(CR^{C6}R^{D6})_uOC(O)(CR^{C6}R^{D6})_t$—, —$(CR^{C6}R^{D6})_uC(O)NR^{A6}(CR^{C6}R^{D6})_t$—, —$(CR^{C6}R^{D6})_uNR^{A6}C(O)(CR^{C6}R^{D6})_t$—, —$(CR^{C6}R^{D6})_uNR^{A6}C(O)NR^{B6}(CR^{C6}R^{D6})_t$—, —$(CR^{C6}R^{D6})_uC(=NR^{E6})NR^{B6}(CR^{C6}R^{D6})_t$—, —$(CR^{C6}R^{D6})_uNR^{B6}C(=NR^{E6})(CR^{C6}R^{D6})_t$—, —$(CR^{C6}R^{D6})_uNR^{A6}C(=NR^{E6})NR^{B6}(CR^{C6}R^{D6})_t$—, —$(CR^{C6}R^{D6})_uC(S)NR^{A6}(CR^{C6}R^{D6})_t$—, —$(CR^{C6}R^{D6})_u$ $NR^{A6}C(S)(CT^{C6}R^{D6})_t$—, —$(CR^{C6}R^{D6})_u NR^{A6}C(S)NR^{B6}$ $(CR^{C6}R^{D6})_t$—, —$(CR^{C6}R^{D6})_u S(O)_r (CR^{C6}R^{D6})_t$—, —$(CR^{C6}R^{D6})_u S(O)_r NR^{A6}(CR^{C6}R^{D6})_t$—, —$(CR^{C6}R^{D6})_u NR^{A6}S(O)_r (CR^{C6}R^{D6})_t$— and —$(CR^{C6}R^{D6})_u NR^{A1}S(O)_r NR^{B6}(CR^{C6}R^{D6})_t$—;

$L^3$ is selected from —$(CR^{C7}R^{D7})_u$—, —$(CR^{C7}R^{D7})_u O$ $(CR^{C7}R^{D7})_t$—, —$(CR^{C7}R^{D7})_u NR^{A7}(CR^{C7}R^{D7})_t$—, —$(CR^{C7}R^{D7})_u S(CR^{C7}R^{D7})_t$—, —$(CR^{C7}R^{D7})_u C(O)$ $(CR^{C7}R^{D7})_t$—, —$(CR^{C7}R^{D7})_u C(=NR^{E7})(CR^{C7}R^{D7})_t$—, —$(CR^{C7}R^{D7})_u C(S)(CR^{C7}R^{D7})_t$—, —$(CR^{C7}R^{D7})_u C(O)O$ $(CR^{C7}R^{D7})_t$—, —$(CR^{C7}R^{D7})_u OC(O)(CR^{C7}R^{D7})_t$—, —$(CR^{C7}R^{D7})_u C(O)NR^{A7}(CR^{C7}R^{D7})_t$—, —$(CR^{C7}R^{D7})_u$ $NR^{A7}C(O)(CR^{C7}R^{D7})_t$—, —$(CR^{C7}R^{D7})_u NR^{A7}C(O)NR^{B7}$ $(CR^{C7}R^{D7})_t$—, —$(CR^{C7}R^{D7})_u C(=NR^{E7})NR^{B7}(CR^{C7} R^{D7})_t$—, —$(CR^{C7}R^{D7})_u NR^{B7}C(=NR^{E7})(CR^{C7}R^{D7})_t$—, —$(CR^{C7}R^{D7})_u NR^{A7}C(=NR^{E7})NR^{B7}(CR^{C7}R^{D7})_t$—, —$(CR^{C7}R^{D7})_u C(S)NR^{A7}(CR^{C7}R^{D7})_t$—, —$(CR^{C7}R^{D7})_u$ $NR^{A7}C(S)(CR^{C7}R^{D7})_t$—, —$(CR^{C7}R^{D7})_u NR^{A7}C(S)NR^{B7}$ $(CR^{C7}R^{D7})_t$—, —$(CR^{C7}R^{D7})_u S(O)_r (CR^{C7}R^{D7})_t$—, —$(CR^{C7}R^{D7})_u S(O)_r NR^{A7}(CR^{C7}R^{D7})_t$—, —$(CR^{C7}R^{D7})_u$ $NR^{A7}S(O)_r (CR^{C7}R^{D7})_t$— and —$(CR^{C7}R^{D7})_u NR^{A7}S(O)_r NR^{B7}(CR^{C7}R^{D7})_t$—;

W is selected from $NR^{E9}$ and O;

$X^1$ and $X^2$ are independently selected from C and N;

$Y^1$, $Y^2$ and $Y^3$ are independently selected from C and N;

Z is selected from C and N;

$Q^1$ and $Q^2$ are independently selected from aryl and heteroaryl, wherein aryl and heteroaryl are each unsubstituted or substituted with at least one substituent, such as one, two, three or four substituents, independently selected from $R^X$;

When W is O, $Q^3$ is heterocyclyl containing the moiety —$(O=)S(=NR^{E8})$—, —$(R^{E8}N=)S(=NR^{E8'})$— or —$P(O)(R^{A8})$— as a ring member, wherein heterocyclyl is unsubstituted or substituted with at least one substituent, such as one, two, three or four substituents, independently selected from $R^X$, or $Q^3$ is heterocyclyl or cycloalkyl which is substituted with at least one substituent, such as one, two, three, or four substituents, independently selected from —$(CR^{C8}R^{D8})_t$- $N=S(=O)R^{A8}R^{B8}$, —$(CR^{C8}R^{D8})_t N=S(=NR^{E8})R^{A8}R^{B8}$, —$C(O)N=S(=O)R^{A8}R^{B8}$, —$(CR^{C8}R^{D8})_t(R^{E8}N=)S(=O)$ $R^{A8}$, —$N(R^{A8})(R^{E8}N=)S(=O)R^{B8}$, —$(CR^{C8}R^{D8})_t N(R^{A8})$ $(R^{E8}N=)S(=O)R^{B8}$, —$(R^{E8}N=)S(=O)NR^{A8}R^{B8}$, —$P(O)$ $R^{A8}R^{B8}$, —$P(O)(OR^{A8})(OR^{B8})$, —$(CR^{C8}R^{D8})_t P(O)R^{A8}R^{B8}$, —$(CR^{C8}R^{D8})_t P(O)(OR^{A8})(OR^{B8})$;

When W is $NR^{E9}$, $Q^3$ is selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —$NO_2$, —$NR^{A8}R^{B8}$, —$OR^{A8}$, —$S(O)_r R^{A8}$, —$S(O)_2 OR^{A8}$, —$OS(O)_2 R^{A8}$, —$P(O)R^{A8}R^{B8}$, —$P(O)(OR^{A8})$ $(OR^{B8})$, —$C(O)R^{A8}$, —$C(O)OR^{A8}$, —$OC(O)R^{A8}$, —$C(O)$ $NR^{A8}R^{B8}$, —$NR^{A8}C(O)R^{B8}$, —$OC(O)NR^{A8}R^{B8}$, —$NR^{A8}C$ $(O)OR^{B8}$, —$NR^{A8}C(O)NR^{A8}R^{B8}$, —$NR^{A8}C(S)NR^{A8}R^{B8}$, —$S(O)_r NR^{A8}R^{B8}$, —$NR^{A8}S(O)_r R^{B8}$, —$NR^{A8}S(O)_2$ $NR^{A8}R^{B8}$, —$S(O)(=NR^{E8})R^{B8}$, —$N=S(O)R^{A8}R^{B8}$, —$NR^{A8}S(O)(=NR^{E8})R^{B8}$, —$S(O)(=NR^{E8})NR^{A8}R^{B8}$, —$NR^{A8}S(O)(=NR^{E8})NR^{A8}R^{B8}$, —$C(=NR^{E8})R^{A8}$, —$C(=N—OR^{B8})R^{A8}$, —$C(=NR^{E8})NR^{A8}R^{B8}$, —$NR^{A8}C$ $(=NR^{E8})R^{B8}$ and —$NR^{A8}C(=NR^{E8})NR^{A8}R^{B8}$, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

each $R^1$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —$NO_2$, —$NR^{A1}R^{B1}$, —$OR^{A1}$, —$S(O)_r R^{A1}$, —$S(O)_2 OR^{A1}$, —$OS(O)_2 R^{A1}$, —$P(O)R^{A1}R^{B1}$, —$P(O)$ $(OR^{A1})(OR^{B1})$, —$C(O)R^{A1}$, —$C(O)OR^{A1}$, —$OC(O)R^{A1}$, —$C(O)NR^{A1}R^{B1}$, —$NR^{A1}C(O)R^{B1}$, —$OC(O)NR^{A1}R^{B1}$, —$NR^{A1}C(O)OR^{B1}$, —$NR^{A1}C(O)R^{A1}R^{B1}$, —$NR^{A1}C(S)$ $NR^{A1}R^{B1}$, —$S(O)_r NR^{A1}R^{B1}$, —$NR^{A1}S(O)_r R^{B1}$, —$NR^{A1}S$ $(O)_2 NR^{A1}R^{B1}$, —$S(O)(=NR^{E1})R^{B1}$, —$N=S(O)R^{A1}R^{B1}$, —$NR^{A1}S(O)(=NR^{E1})R^{B1}$, —$S(O)(=NR^{E1})NR^{A1}R^{B1}$, —$NR^{A1}S(O)(=NR^{E1})NR^{A1}R^{B1}$, —$C(=NR^{E1})R^{A1}$, —$C(=N—OR^{B1})R^{A1}$, —$C(=NR^{E1})NR^{A1}R^{B1}$, —$NR^{A1}C$ $(=NR^{E1})R^{B1}$ and —$NR^{A1}C(=NR^{E1})NR^{A1}R^{B1}$, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

each $R^2$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —$NO_2$, —$NR^{A2}R^{B2}$, —$OR^{A2}$, —$S(O)_r R^{A2}$, —$S(O)_2 OR^{A2}$, —$OS(O)_2 R^{A2}$, —$P(O)R^{A2}R^{B2}$, —$P(O)$ $(OR^{A2})(OR^{B2})$, —$C(O)R^{A2}$, —$C(O)OR^{A2}$, —$OC(O)R^{A2}$, —$C(O)NR^{A2}R^{B2}$, —$NR^{A2}C(O)R^{B2}$, —$OC(O)NR^{A2}R^{B2}$, —$NR^{A2}C(O)OR^{B2}$, —$NR^{A2}C(O)NR^{A2}R^{B2}$, —$NR^{A2}C(S)$ $NR^{A2}R^{B2}$, —$S(O)_r NR^{A2}R^{B2}$, —$NR^{A2}S(O)_r R^{B2}$, —$NR^{A2}S$ $(O)_2 NR^{A2}R^{B2}$, —$S(O)(=NR^{E2})R^{B2}$, —$N=S(O)R^{A2}R^{B2}$, —$NR^{A2}S(O)(=NR^{E2})R^{B2}$, —$S(O)(=NR^{E2})NR^{A2}R^{B2}$, —$NR^{A2}S(O)(=NR^{E2})NR^{A2}R^{B2}$, —$C(=NR^{E2})R^{A2}$, —$C(=N—OR^{B2})R^{A2}$, —$C(=NR^{E2})NR^{A2}R^{B2}$, —$NR^{A2}C$ $(=NR^{E2})R^{B2}$ and —$NR^{A2}C(=NR^{E2})NR^{A2}R^{B2}$, wherein alkyl, alkenyl, alkynyl, cycloalkyl, heterocyclyl, aryl and heteroaryl are each unsubstituted or substituted with at least one substituent, such as one, two, three or four substituents, independently selected from 10;

each $R^3$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —$NO_2$, —$NR^{A3}R^{B3}$, —$OR^{A3}$, —$S(O)_r R^{A3}$, —$S(O)_2 OR^{A3}$, —$OS(O)_2 R^{A3}$, —$P(O)R^{A3}R^{B3}$, —$P(O)$ $(OR^{A3})(OR^{B3})$, —$C(O)R^{A3}$, —$C(O)OR^{A3}$, —$OC(O)R^{A3}$, —$C(O)NR^{A3}R^{B3}$, —$NR^{A3}C(O)R^{B3}$, —$OC(O)NR^{A3}R^{B3}$, —$NR^{A3}C(O)OR^{B3}$, —$NR^{A3}C(O)NR^{A3}R^{B3}$, —$NR^{A3}C(S)$ $NR^{A3}R^{B3}$, —$S(O)_r NR^{A3}R^{B3}$, —$NR^{A3}S(O)_r R^{B3}$, —$NR^{A3}S$ $(O)_2 NR^{A3}R^{B3}$, —$S(O)(=NR^{E3})R^{B3}$, —$N=S(O)R^{A3}R^{B3}$, —$NR^{A3}S(O)(=NR^{E3})R^{B3}$, —$S(O)(=NR^{E3})NR^{A3}R^{B3}$, —$NR^{A3}S(O)(=NR^{E3})NR^{A3}R^{B3}$, —$C(=NR^{E3})R^{A3}$, —$C(=N—OR^{B3})R^{A3}$, —$C(=NR^{E3})NR^{A3}R^{B3}$, —$NR^{A3}C$ $(=NR^{E3})R^{B3}$ and —$NR^{A3}C(=NR^{E3})NR^{A3}R^{B3}$, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

each $R^{4a}$ and $R^{4b}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —$NO_2$, —$NR^{A4}R^{B4}$, —$OR^{A4}$, —$S(O)_r R^{A4}$, —$S(O)_2 OR^{A4}$, —$OS(O)_2 R^{A4}$, —$P(O)R^{A4}R^{B4}$, —$P(O)(OR^{A4})(OR^{B4})$, —$C(O)R^{A4}$, —$C(O)OR^{A4}$, —$OC(O)$ $R^{A4}$, —$C(O)NR^{A4}R^{B4}$, —$NR^{A4}C(O)R^{B4}$, —$OC(O)$ $NR^{A4}R^{B4}$, —$NR^{A4}C(O)OR^{B4}$, —$NR^{A4}C(O)NR^{A4}R^{B4}$, —$NR^{A4}C(S)NR^{A4}R^{B4}$, —$S(O)_r NR^{A4}R^{B4}$, —$NR^{A4}S(O)_r$ $R^{B4}$, —$NR^{A4}S(O)_2 NR^{A4}R^{B4}$, —$S(O)(=NR^{E4})R^{B4}$, —$N=S$ $(O)R^{A4}R^{B4}$, —$NR^{A4}S(O)(=NR^{E4})R^{B4}$, —$S(O)$ $(=NR^{E4})NR^{A4}R^{B4}$, $-NR^{A4}S(O)(=NR^{E4})NR^{A4}R^{B4}$, $-C(=NR^{E4})R^{A4}$, $-C(=N-OR^{B4})R^{A4}$, $-C(=NR^{E4})NR^{A4}R^{B4}$, $-NR^{A4}C(=NR^{E4})R^{B4}$, and $-NR^{A4}C(=NR^{E4})NR^{A4}R^{B4}$, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

or $R^{4a}$ and $R^{4b}$ together with the carbon atoms to which they are attached form a 3- to 7-membered ring containing 0, 1 or 2 heteroatoms independently selected from oxygen, sulfur, nitrogen, and phosphorus, and optionally substituted with 1, 2 or 3 $R^X$ groups;

each $R^{A1}$, $R^{A2}$, $R^{A3}$, $R^{A4}$, $R^{A5}$, $R^{A6}$, $R^{A7}$, $R^{A8}$, $R^{B1}$, $R^{B2}$, $R^{B3}$, $R^{B4}$, $R^{B5}$, $R^{B6}$, $R^{B7}$ and $R^{B8}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from $R^X$;

or each "$R^{A1}$ and $R^{B1}$", "$R^{A2}$ and $R^{B2}$", "$R^{A3}$ and $R^{B3}$", "$R^{A4}$ and $R^{B4}$", "$R^{A5}$ and $R^{B5}$", "$R^{A6}$ and $R^{B6}$", "$R^{A7}$ and $R^{B7}$" and "$R^{A8}$ and $R^{B8}$" together with the atom(s) to which they are attached form a 4- to 12-membered heterocyclic ring containing 0, 1 or 2 additional heteroatoms independently selected from oxygen, sulfur, nitrogen and phosphorus, and optionally substituted with 1, 2 or 3 $R^X$ groups;

each $R^{C5}$, $R^{C6}$, $R^{C7}$, $R^{C8}$, $R^{D5}$, $R^{D6}$, $R^{D7}$ and $R^{D8}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

or each "$R^{C5}$ and $R^{D5}$", "$R^{C6}$ and $R^{D6}$", "$R^{C7}$ and $R^{D7}$" and "$R^{C8}$ and $R^{D8}$" together with the carbon atom(s) to which they are attached form a 3- to 12-membered ring containing 0, 1 or 2 heteroatoms independently selected from oxygen, sulfur and nitrogen, and optionally substituted with 1, 2 or 3 $R^X$ groups;

each $R^{E1}$, $R^{E2}$, $R^{E3}$, $R^{E4}$, $R^{E5}$, $R^{E7}$, $R^{E8}$, $E^{E8'}$ and $R^{E9}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, $-CN$, $-NO_2$, $-OR^{a1}$, $-SR^{a1}$, $-S(O)_rR^{a1}$, $-C(O)R^{a1}$, $-C(O)OR^{a1}$, $-C(O)NR^{a1}R^{b1}$ and $-S(O)_rNR^{a1}R^{b1}$, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

each $R^X$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, $-CN$, $-NO_2$, $-(CR^{c1}R^{d1})_tNR^{a1}R^{b1}$, $-(CR^{c1}R^{d1})_tOR^{b1}$, $-(CR^{c1}R^{d1})_tS(O)_rR^{b1}$, $-(CR^{c1}R^{d1})_tS(O)_2OR^{b1}$, $-(CR^{c1}R^{d1})_tOS(O)_2R^{b1}$, $-(CR^{c1}R^{d1})_tP(O)R^{a1}R^{b1}$, $-(CR^{c1}R^{d1})_tP(O)(OR^{a1})(OR^{b1})$, $-(CR^{c1}R^{d1})_tC(O)R^{a1}$, $-(CR^{c1}R^{d1})_tC(O)OR^{b1}$, $-(CR^{c1}R^{d1})_tC(O)NR^{a1}R^{b1}$, $-(CR^{c1}R^{d1})_tNR^{a1}C(O)R^{b1}$, $-(CR^{c1}R^{d1})_tOC(O)NR^{a1}R^{b1}$, $-(CR^{c1}R^{d1})_tNR^{a1}C(O)OR^{b1}$, $-(CR^{c1}R^{d1})_tNR^{a1}C(O)NR^{a1}R^{b1}$, $-(CR^{c1}R^{d1})_tNR^{a1}C(S)NR^{a1}R^{b1}$, $-(CR^{c1}R^{d1})_tS(O)_rNR^{a1}R^{b1}$, $-(CR^{c1}R^{d1})_tNR^{a1}S(O)_rR^{b1}$, $-(CR^{c1}R^{d1})_tNR^{a1}S(O)_2NR^{a1}R^{b1}$, $-(CR^{c1}R^{d1})_tS(O)(=NR^{e1})R^{b1}$, $-(CR^{c1}R^{d1})_tN=S(O)R^{a1}R^{b1}$, $-(CR^{c1}R^{d1})_t(NR^{a1}S(O)(=NR^{e1})R^{b1}$, $-(CR^{c1}R^{d1})_tS(O)(=NR^{e1})NR^{a1}R^{b1}$, $-(CR^{c1}R^{d1})_tNR^{a1}S(O)(=NR^{e1})NR^{a1}R^{b1}$, $-(CR^{c1}R^{d1})_tC(=NR^{e1})R^{a1}$, $-(CR^{c1}R^{d1})_tC(=N-OR^{b1})R^{a1}$, $-(CR^{c1}R^{d1})_tC(=NR^{e1})NR^{a1}R^{b1}$, $-(CR^{c1}R^{d1})_tNR^{a1}C(=NR^{e1})R^{b1}$ and $-(CR^{c1}R^{d1})_tNR^{a1}C(=NR^{e1})NR^{a1}R^{b1}$, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

each $R^{a1}$ and each $R^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

or $R^{a1}$ and $R^{b1}$ together with the atom(s) to which they are attached form a 4- to 12-membered heterocyclic ring containing 0, 1 or 2 additional heteroatoms independently selected from oxygen, sulfur, nitrogen and phosphorus, and optionally substituted with 1, 2 or 3 $R^Y$ groups;

each $R^{c1}$ and each $R^{d1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

or $R^{c1}$ and $R^{d1}$ together with the carbon atom(s) to which they are attached form a 3- to 12-membered ring containing 0, 1 or 2 heteroatoms independently selected from oxygen, sulfur and nitrogen, and optionally substituted with 1, 2 or 3 $R^Y$ groups;

each $R^{e1}$ is independently selected from hydrogen, $C_{1-10}$ alkyl, $C_{3-10}$ cycloalkyl, $C_{3-10}$ cycloalkyl-$C_{1-4}$ alkyl, $-CN$, $-NO_2$, $-OR^{a2}$, $-SR^{a2}$, $-S(O)_rR^{a2}$, $-S(O)'NR^{a2}R^{b2}$, $-C(O)R^{a2}$, $-C(O)OR^{a2}$ and $-C(O)NR^{a2}R^{b2}$;

$R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, $-CN$, $-NO_2$, $-(CR^{c2}R^{d2})_tNR^{a2}R^{b2}$, $-(CR^{c2}R^{d2})_tOR^{b2}$, $-(CR^{c2}R^{d2})_tS(O)_rR^{b2}$, $-(CR^{c2}R^{d2})_tS(O)_2OR^{b2}$, $-(CR^{c2}R^{d2})_tOS(O)_2R^{b2}$, $-(CR^{c2}R^{d2})_tP(O)R^{a2}R^{b2}$, $-(CR^{c2}R^{d2})_tP(O)(OR^{a2})(OR^{b2})$, $-(CR^{c2}R^{d2})_tC(O)R^{a2}$, $-(CR^{c2}R^{d2})_tC(O)OR^{b2}$, $-(CR^{c2}R^{d2})_tOC(O)R^{b2}$, $-(CR^{c2}R^{d2})_tC(O)NR^{a2}R^{b2}$, $-(CR^{c2}R^{d2})_tNR^{a2}C(O)R^{b2}$, $-(CR^{c2}R^{d2})_tOC(O)NR^{a2}R^{b2}$, $-(CR^{c2}R^{d2})_tNR^{a2}C(O)OR^{b2}$, $-(CR^{c2}R^{d2})_tNR^{a2}C(O)NR^{a2}R^{b2}$, $-(CR^{c2}R^{d2})_tNR^{a2}C(S)NR^{a2}R^{b2}$, $-(CR^{c2}R^{d2})_tS(O)_rNR^{a2}R^{b2}$, $-(CR^{c2}R^{d2})_tNR^{a2}S(O)_rR^{b2}$, $-(CR^{c2}R^{d2})_tNR^{a2}S(O)_2NR^{a2}R^{b2}$, $-(CR^{c2}R^{d2})_tS(O)(=NR^{e2})R^{b2}$, $-(CR^{c2}R^{d2})_tN=S(O)R^{a2}R^{b2}$, $-(CR^{c2}R^{d2})_tNR^{a2}S(O)(=NR^{e2})R^{b2}$, $-(CR^{c2}R^{d2})_tS(O)(=NR^{e2})NR^{a2}R^{b2}$, $-(CR^{c2}R^{d2})_tNR^{a2}S(O)(=NR^{e2})NR^{a2}R^{b2}$, $-(CR^{c2}R^{d2})_tC(=NR^{e2})R^{a2}$, $-(CR^{c2}R^{d2})_tC(=N-OR^{b2})R^{a2}$, $-(CR^{c2}R^{d2})_tC(=NR^{e2})NR^{a2}R^{b2}$, $-(CR^{c2}R^{d2})_tNR^{a2}C(=NR^{e2})R^{b2}$ and $-(CR^{c2}R^{d2})_tNR^{a2}C(=NR^{e2})NR^{a2}R^{b2}$, wherein alkyl, alkenyl, alkynyl, cycloalkyl, heterocyclyl, aryl and heteroaryl are each unsubstituted or substituted with at least one substituent, such as one, two, three or four substituents, independently selected from —OH, —CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three or four substituents, independently selected from halogen, CN, $C_{1-10}$ alkyl, $C_{2-10}$ alkenyl, $C_{2-10}$ alkynyl, $C_{3-10}$ cycloalkyl, —OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a2}$ and $R^{b2}$ together with the atom(s) to which they are attached form a 4- to 12-membered heterocyclic ring containing 0, 1 or 2 additional heteroatoms independently selected from oxygen, sulfur, nitrogen and phosphorus, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl) amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl) amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a 3- to 12-membered ring containing 0, 1 or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, —CN, —$NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, —C(O)$C_{1-4}$ alkyl, —C(O)$C_{3-10}$ cycloalkyl, —C(O)O$C_{1-4}$ alkyl, —C(O)O$C_{3-10}$ cycloalkyl, —C(O)$NH_2$, —C(O)NH($C_{1-4}$ alkyl), —C(O)N($C_{1-4}$ alkyl)$_2$, —C(O)NH($C_{3-10}$ cycloalkyl), —C(O)N($C_{3-10}$ cycloalkyl)$_2$, —S(O)$_2C_{1-4}$ alkyl, —S(O)$_2C_{3-10}$ cycloalkyl, —S(O)$_2NH_2$, —S(O)$_2$NH($C_{1-4}$ alkyl), —S(O)$_2$N($C_{1-4}$ alkyl)$_2$, —S(O)$_2$NH($C_{3-10}$ cycloalkyl) and —S(O)$_2$N($C_{3-10}$ cycloalkyl)$_2$;

m is selected from 0, 1, 2, 3 and 4;

n is selected from 0, 1, 2 and 3;

p is selected from 0, 1, 2, 3 and 4;

each r is independently selected from 0, 1 and 2;

each t is independently selected from 0, 1, 2, 3 and 4;

each u is independently selected from 0, 1, 2, 3 and 4.

In some embodiment, $Q^1$ is aryl, wherein aryl is unsubstituted or substituted with at least one substituent, such as one, two, three, or four substituents, independently selected from $R^X$.

In some embodiment, $Q^1$ is phenyl, wherein phenyl is unsubstituted or substituted with at least one substituent independently selected from $R^X$.

In some embodiment, $Q^1$ is phenyl, wherein phenyl is unsubstituted or substituted with at least one substituent independently selected from $C_{1-4}$ alkyl, $C_{3-6}$ cycloalkyl, halogen, —CN, —$CF_3$ and —$OCF_3$, wherein alkyl and cycloalkyl are each unsubstituted or substituted with at least one substituent independently selected from $R^Y$.

In some embodiment, $Q^1$ is heteroaryl, wherein heteroaryl is unsubstituted or substituted with at least one substituent, such as one, two, three, or four substituents, independently selected from $R^X$.

In some embodiment, $Q^2$ is aryl, wherein aryl is unsubstituted or substituted with at least one substituent independently selected from $R^X$.

In some embodiment, $Q^2$ is heteroaryl, wherein heteroaryl is unsubstituted or substituted with at least one substituent independently selected from $R^X$.

In some embodiment, $Q^2$ is 1H-pyrrolo[2,3-b]pyridin-5-yl, which is unsubstituted or substituted with at least one substituent independently selected from $R^X$.

In some embodiment, W is $NR^{E9}$.

In some embodiment, W is O.

In some embodiment, $Q^3$ is heterocyclyl containing the moiety —P(O)($R^{48}$)— as a ring member, wherein heterocyclyl is unsubstituted or substituted with at least one substituent independently selected from $R^X$.

In some embodiment, $Q^3$ is selected from

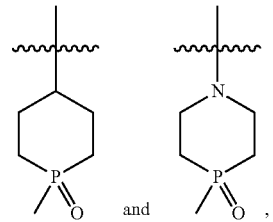

which is unsubstituted or substituted with at least one substituent independently selected from $R^X$, wherein the ⁓ symbol indicates the point of attachment to the rest of the molecule.

In some embodiment, $Q^3$ is heterocyclyl containing the moiety —(O═)S(═$NR^{E8}$)— or —($R^{E8}N$═)S(═$NR^{E8'}$)— as a ring member.

In some embodiment, $Q^3$ is

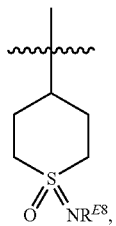

which is unsubstituted or substituted with at least one substituent independently selected from $R^X$, wherein the ⁓ symbol indicates the point of attachment to the rest of the molecule.

In some embodiment, $Q^3$ is

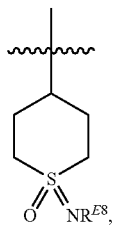

wherein $R^{E8}$ is selected from hydrogen, —CN, $C_{1-10}$ alkyl, $C_{3-10}$ cycloalkyl, —$(CR^{c1}R^{d1})_tC(O)R^{a1}$ and —$(CR^{c1}R^{d1})_tC(O)OR^{b1}$.

In some embodiment, $Q^3$ is

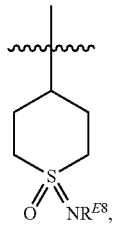

wherein $R^{E8}$ is selected from hydrogen, —CN, methyl, ethyl, cyclopropyl, —C(O)CH$_3$ and —C(O)OCH$_3$.

In some embodiment, $Q^3$ is cycloalkyl, which is substituted with —$(CR^{C8}R^{D8})_xN$=S(=O)$R^{A8}R^{B8}$.

In some embodiment, $Q^3$ is cyclohexyl, which is substituted with —$(CR^{C8}R^{D8})_xN$=S(=O)$R^{A8}R^{B8}$.

In some embodiment, $Q^3$ is cyclohexyl, which is substituted with —N=S(=O)$R^{A8}R^{B8}$, wherein $R^{A8}$ and $R^{B8}$ are independently selected from $C_{1-10}$ alkyl.

In some embodiment, $Q^3$ is cyclohexyl, which is substituted with —N=S(=O)$R^{A8}R^{B8}$, wherein $R^{A8}$ and $R^{B8}$ are independently selected from methyl and ethyl.

In some embodiment, $Q^3$ is cyclohexyl, which is substituted with —N=S(=O)$R^{A8}R^{B8}$, wherein $R^{A8}$ and $R^{B8}$ together with the atom to which they are attached form a 4- to 12-membered heterocyclic ring containing 0, 1 or 2 additional heteroatoms independently selected from oxygen, sulfur, nitrogen and phosphorus, and optionally substituted with 1, 2 or 3 $R^X$ groups;

In some embodiment, $L^1$ is selected from a bond and —$(CR^{C5}R^{D5})_u$—.

In some embodiment, $L^1$ is —CH$_2$—.

In some embodiment, $L^2$ is selected from —$(CR^{C6}R^{D6})_uO(CR^{C6}R^{D6})_t$—, —$(CR^{C6}R^{D6})_uS(CR^{C6}R^{D6})_t$—, —$(CR^{C6}R^{D6})_uS(O)_r(CR^{C6}R^{D6})_t$—.

In some embodiment, $L^2$ is selected from —O—, —S—, and —S(O)$_r$—.

In some embodiment, $L^2$ is —O—.

In some embodiment, $L^2$ is —S—.

In some embodiment, $L^3$ is selected from —$(CR^{C7}R^{D7})_uNR^{A7}(CR^{C7}R^{D7})_t$—, —$(CR^{C7}R^{D7})_uC(O)NR^{A7}(CR^{C7}R^{D7})_t$—, —$(CR^{C7}R^{D7})_uNR^{A7}C(O)(CR^{C7}R^{D7})_t$—, —$(CR^{C7}R^{D7})_uNR^{A7}C(O)NR^{B7}(CR^{C7}R^{D7})_t$—, —$(CR^{C7}R^{D7})_uS(O)_rNR^{A7}(CR^{C7}R^{D7})_t$—, —$(CR^{C7}R^{D7})_uNR^{A7}S(O)_r(CR^{C7}R^{D7})_t$— and —$(CR^{C7}R^{D7})_uNR^{A7}S(O)_tNR^{B7}(CR^{C7}R^{D7})_t$.

In some embodiment, $L^3$ is —$(CR^{C7}R^{D7})_uNR^{A7}(CR^{C7}R^{D7})_t$—.

In some embodiment, $L^3$ is selected from —NHCH$_2$— and —NH(CH$_2$)$_2$—, —NH(CH$_2$)$_3$—, —NHCH$_2$CH(CH$_3$)—, —NHCH$_2$CH(CH$_2$F)—, —NHCH$_2$CH(CF$_3$)—, —NHCH$_2$CH(CH$_2$OH)—, —NHCH$_2$CH(CH$_2$OCH$_3$)—, —NHCH(CH$_3$)CH$_2$—, —NHCH(CH$_2$OH)CH$_2$—, —NHCH(CH$_2$F)CH$_2$—, and —NHCH(CH$_2$OCH$_3$)CH$_2$—.

In some embodiment, $L^3$ is —$(CR^{C7}R^{D7})_uNR^{A7}(CR^{C7}R^{D7})_t$—, wherein $R^{C7}$ and $R^{D7}$ together with the carbon atom(s) to which they are attached form a 3- to 12-membered ring containing 0, 1 or 2 heteroatoms independently selected from oxygen, sulfur and nitrogen, and optionally substituted with 1-3 $R^X$ groups;

In some embodiment, $L^3$ is —$(CR^{C7}R^{D7})_uNR^{A7}(CR^{C7}R^{D7})_t$—, wherein u is 1, and $R^{C7}$ and $R^{D7}$ together with the carbon atom to which they are attached form cyclopropyl.

In some embodiment, $X^1$ is C.

In some embodiment, $X^1$ is N.

In some embodiment, $X^2$ is C.

In some embodiment, $X^2$ is N.

In some embodiment, $Y^1$ is C.

In some embodiment, $Y^1$ is N.

In some embodiment, $Y^2$ is C.

In some embodiment, $Y^2$ is N.

In some embodiment, $Y^3$ is C.

In some embodiment, $Y^3$ is N.

In some embodiment, Z is C.

In some embodiment, Z is N.

In some embodiment, $R^1$ is selected from —NO$_2$ and —SO$_2$CF$_3$.

In some embodiment, $R^1$ is NO$_2$.

In some embodiment, $R^1$ is —SO$_2$CF$_3$.

In some embodiment, $R^2$ is selected from hydrogen, $C_{1-4}$ alkyl, halogen and —CN.

In some embodiment, $R^3$ is selected from hydrogen, $C_{1-4}$ alkyl, halogen and —CN.

In some embodiment, $R^{4a}$ and $R^{4b}$ are independently selected from hydrogen and $C_{1-10}$ alkyl.

In some embodiment, $R^{4a}$ and $R^{4b}$ are methyl.

In some embodiment, $R^{4a}$ and $R^{4b}$ together with the carbon atoms to which they are attached form a 3- to 7-membered ring containing 0, 1 or 2 heteroatoms independently selected from oxygen, sulfur, nitrogen, and phosphorus, and optionally substituted with 1, 2 or 3 $R^X$ groups.

Also provided is a compound, selected from
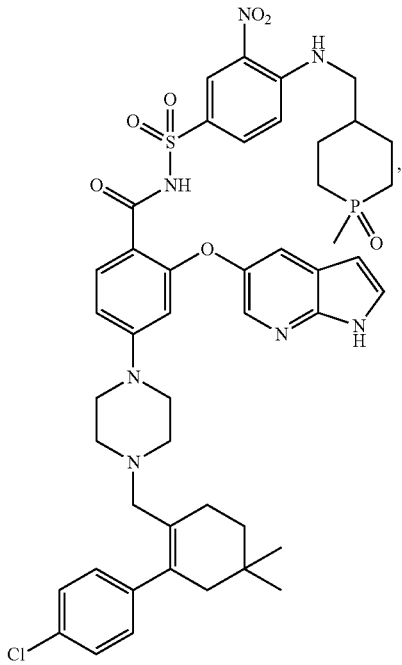
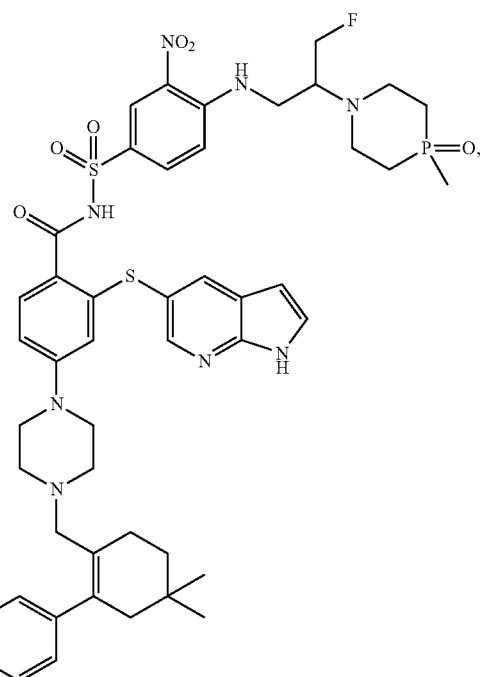
-continued
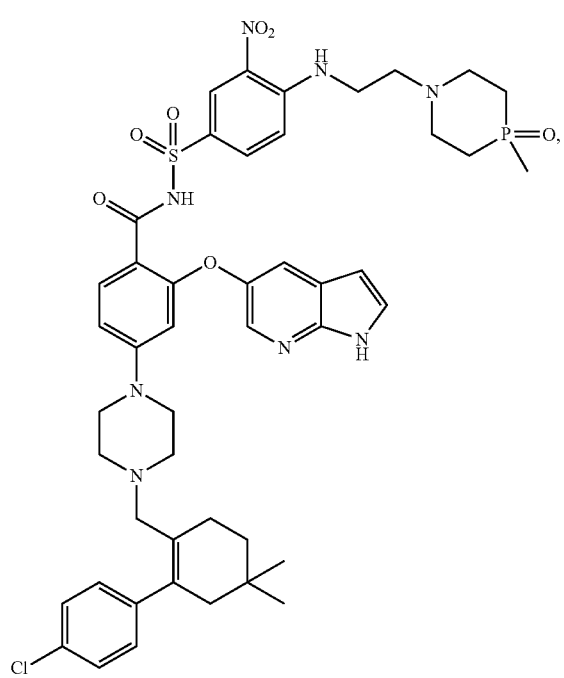
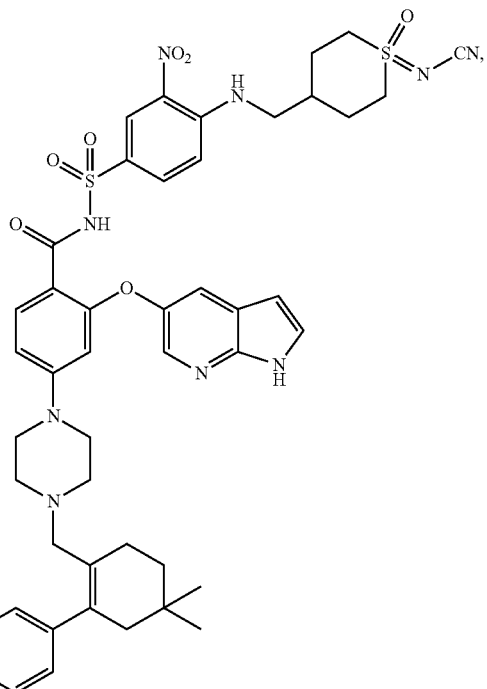

13
-continued
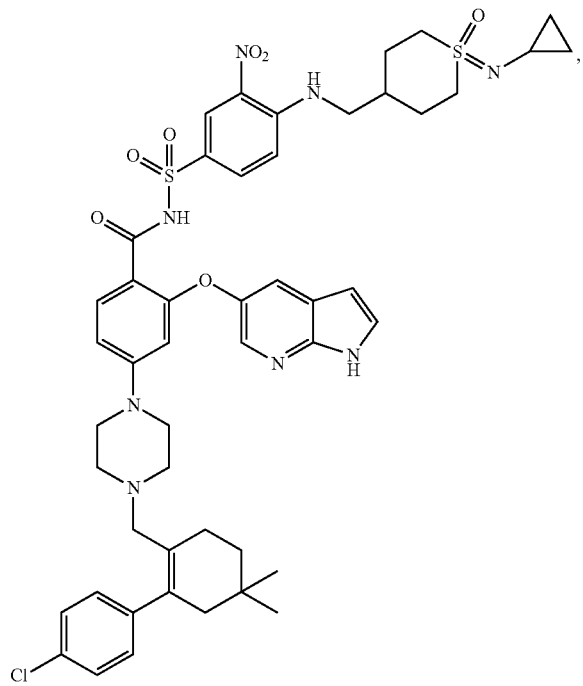
14
-continued
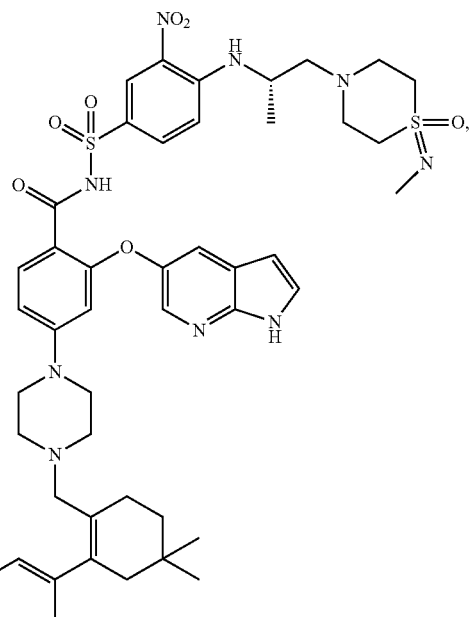
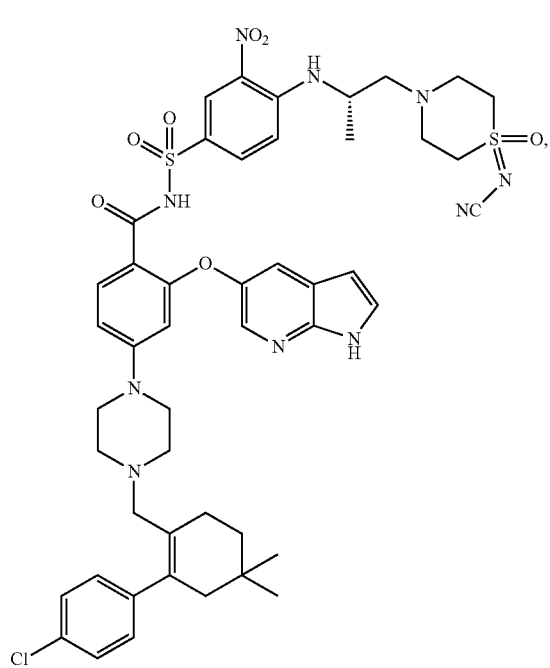

15
-continued
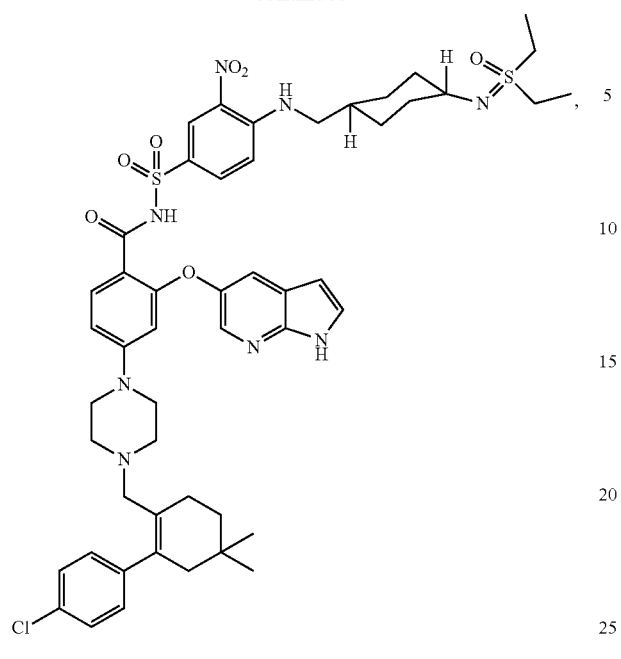
16
-continued
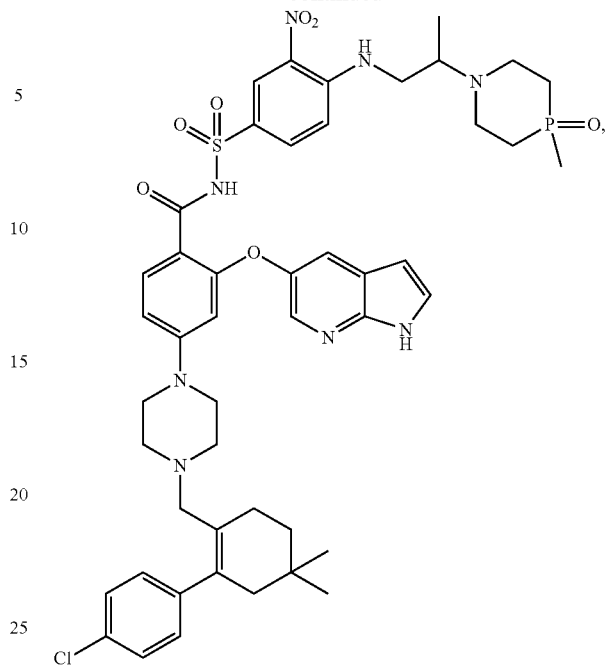
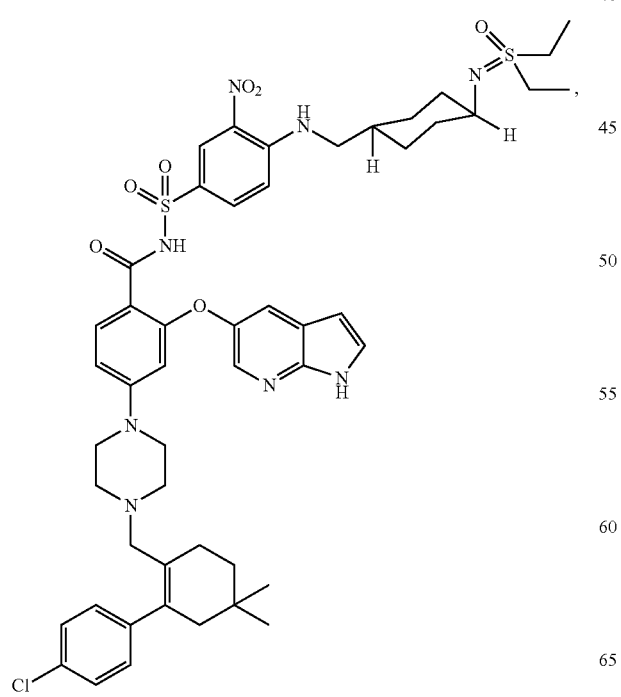
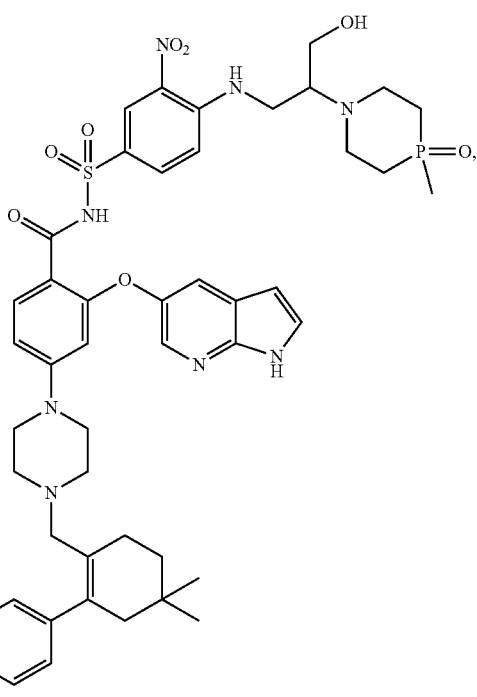

17
-continued
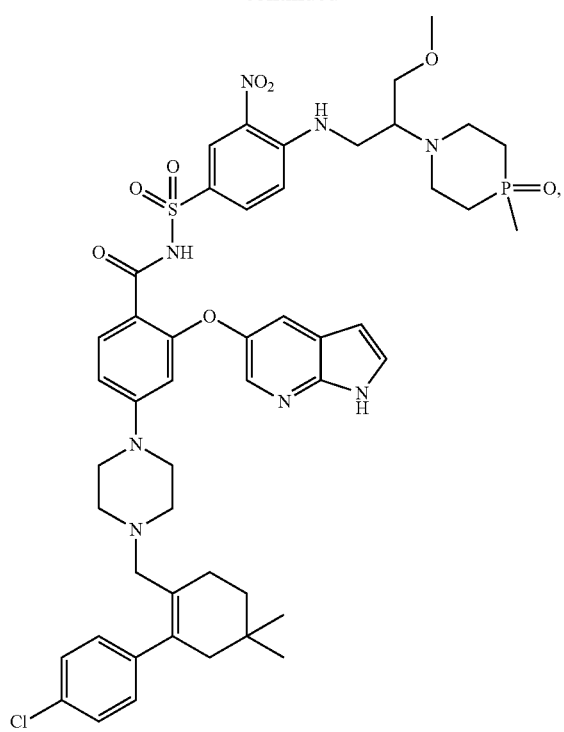
18
-continued
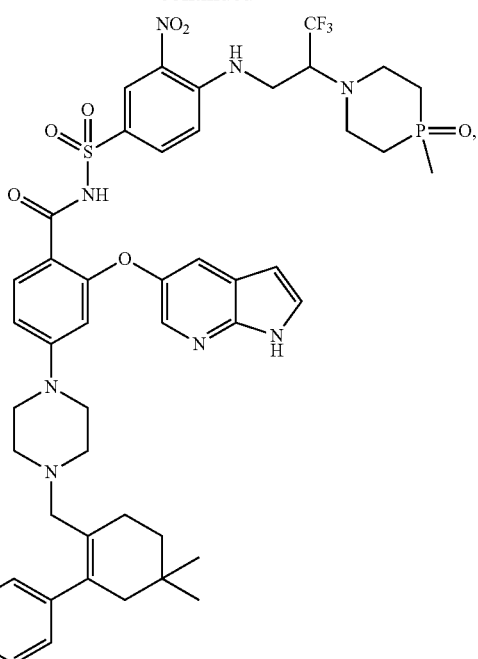
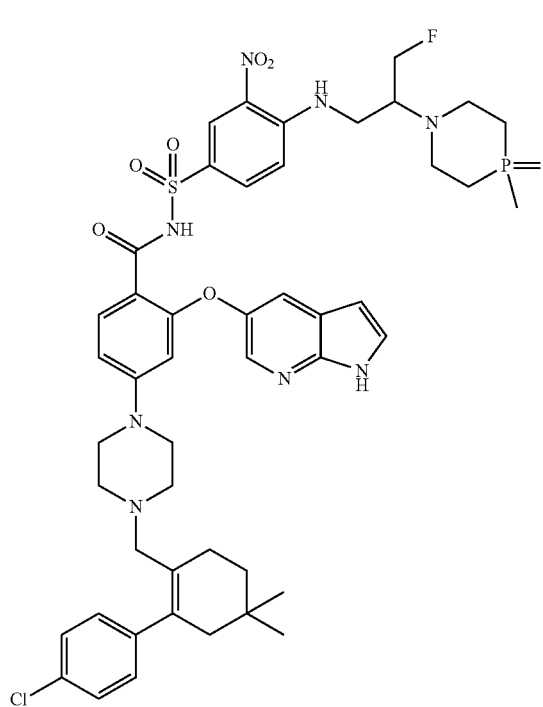

19
-continued
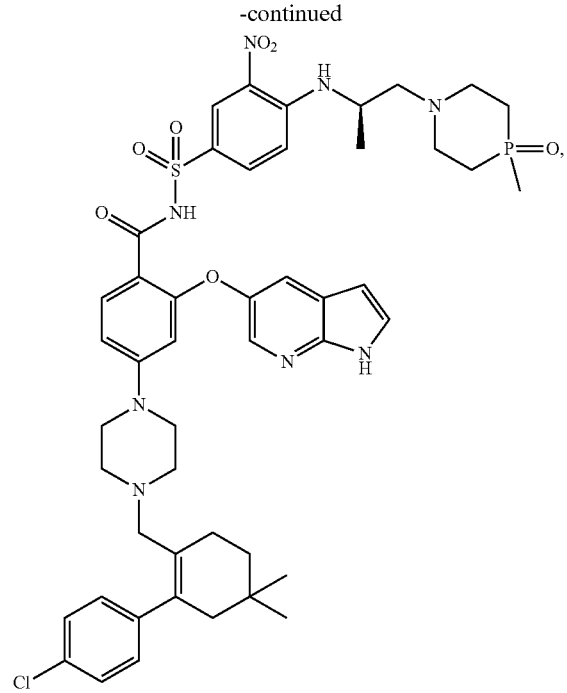
20
-continued
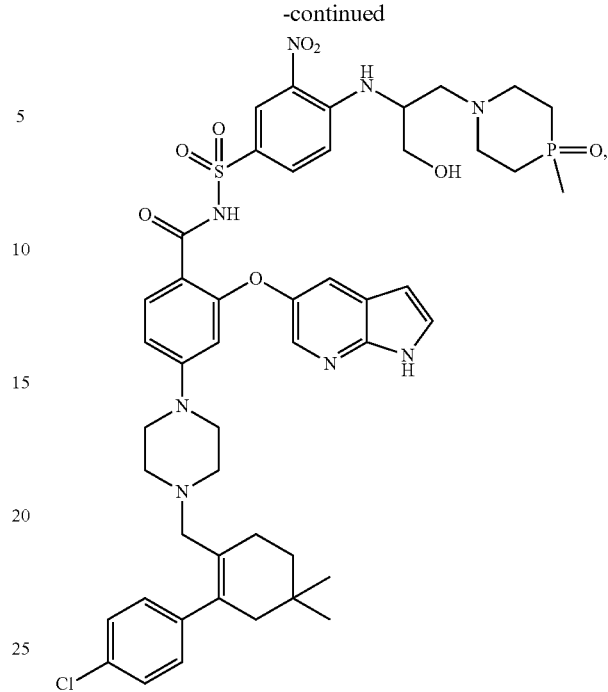
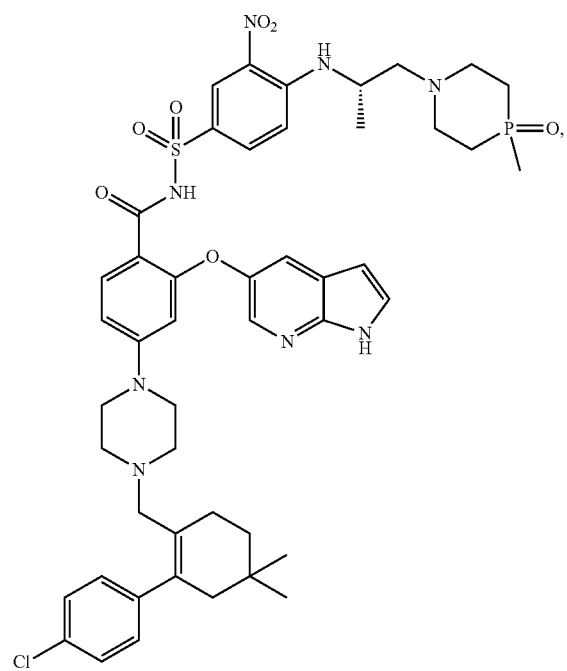
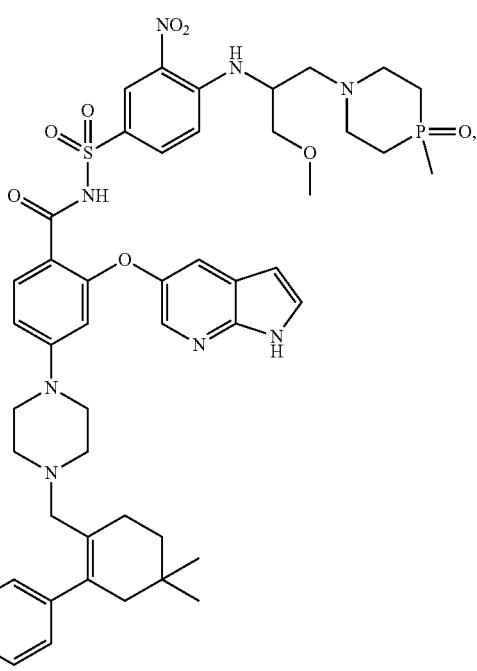

21
-continued
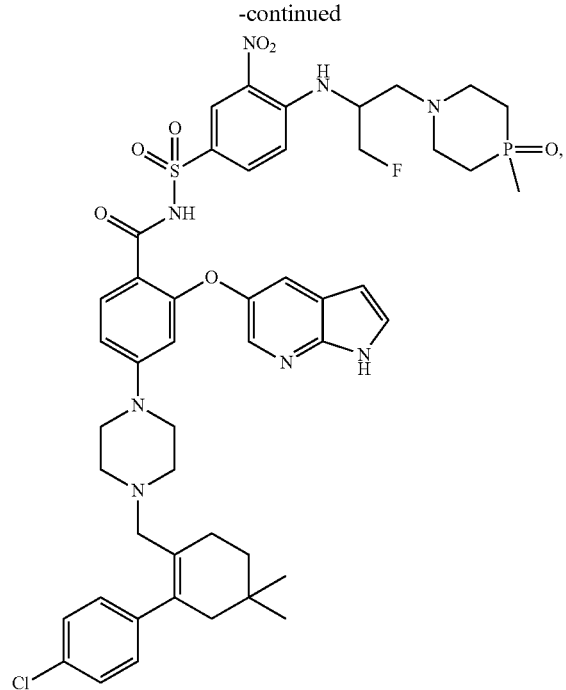
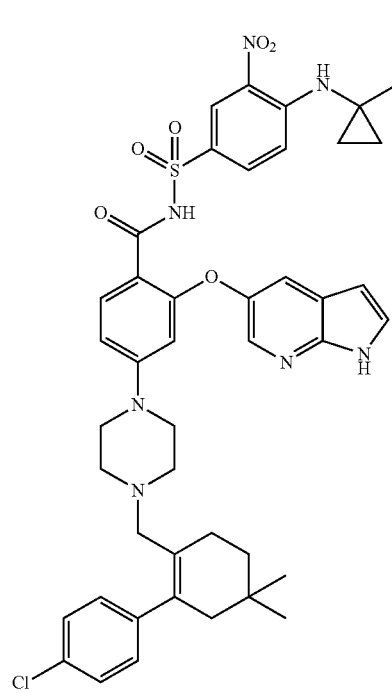
22
-continued
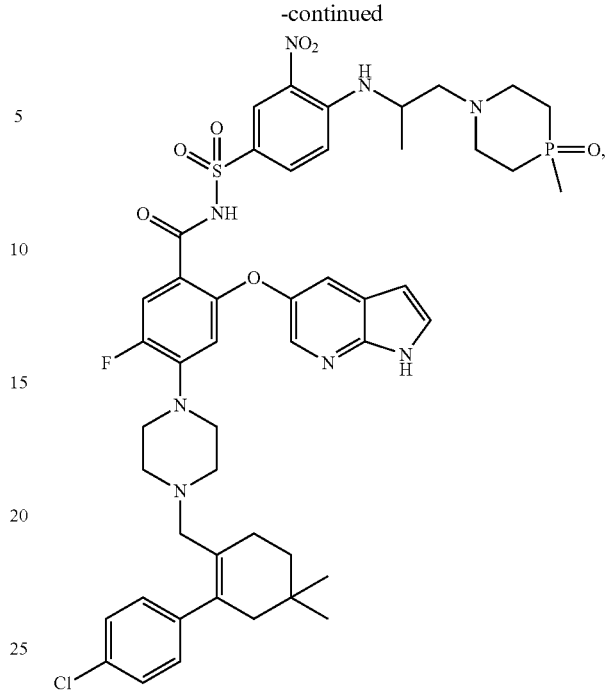
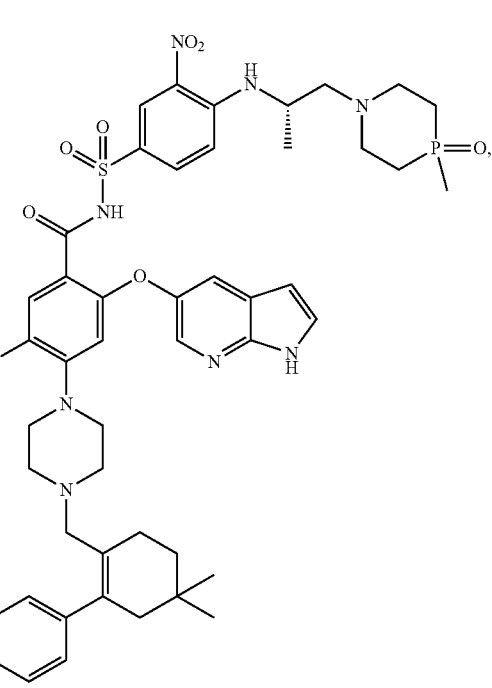

23
-continued
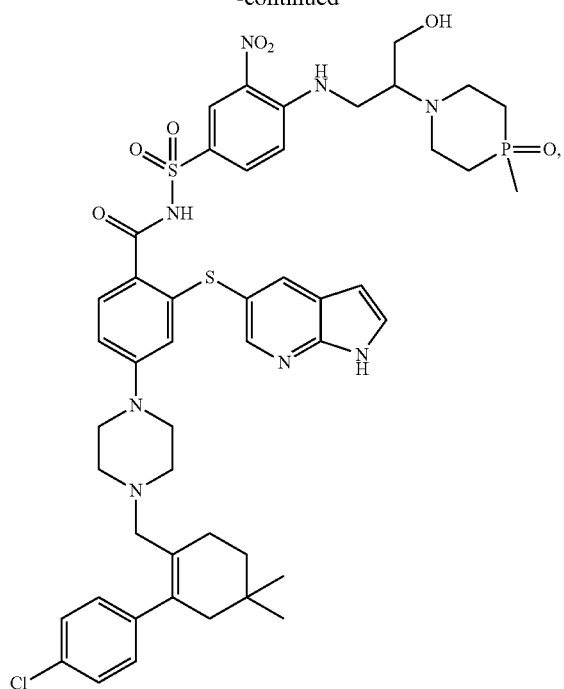
24
-continued
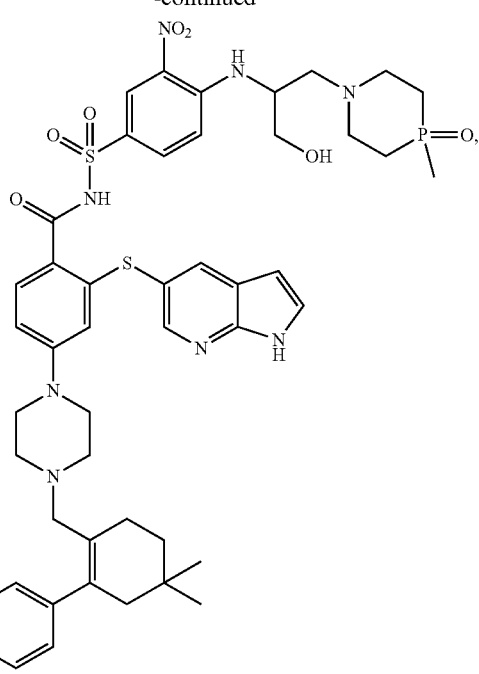
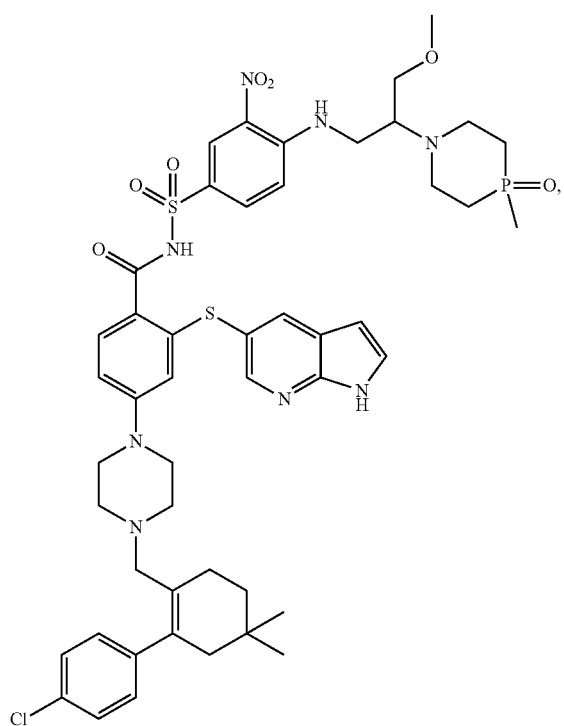
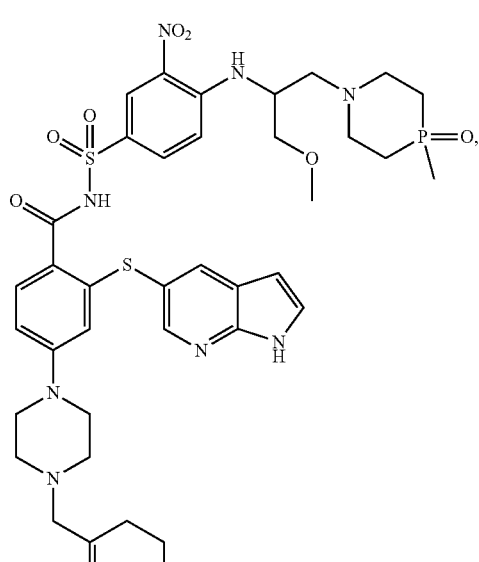

25
-continued
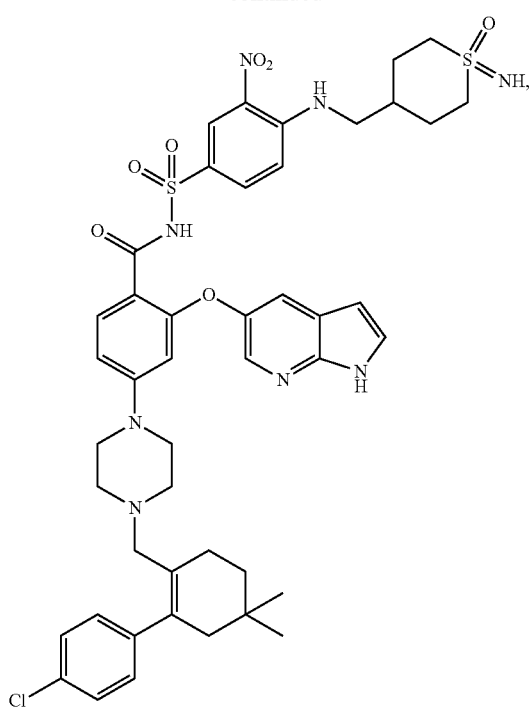
26
-continued
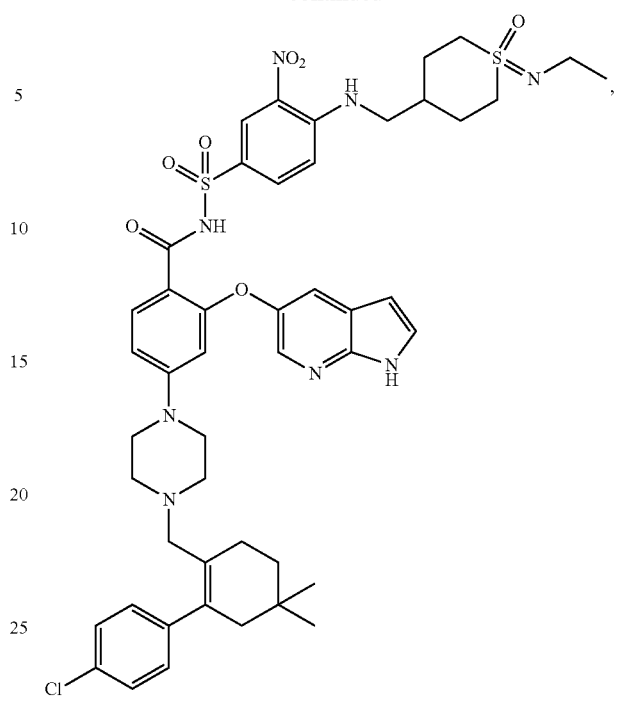

27
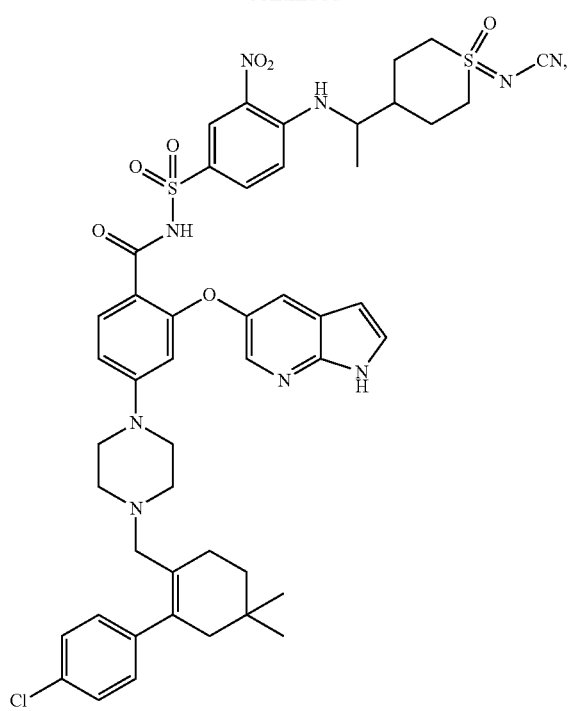
28
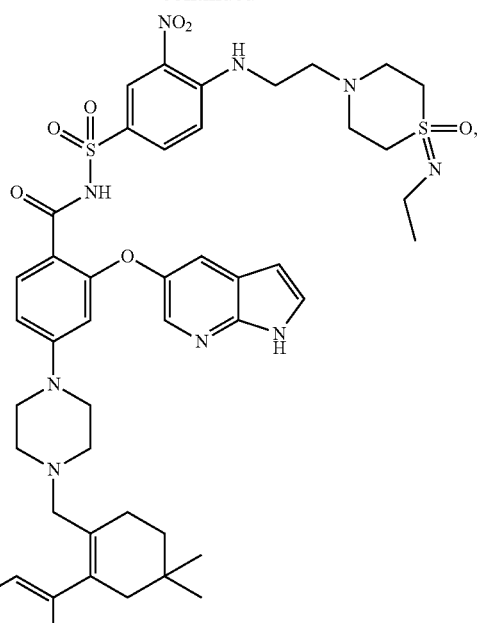
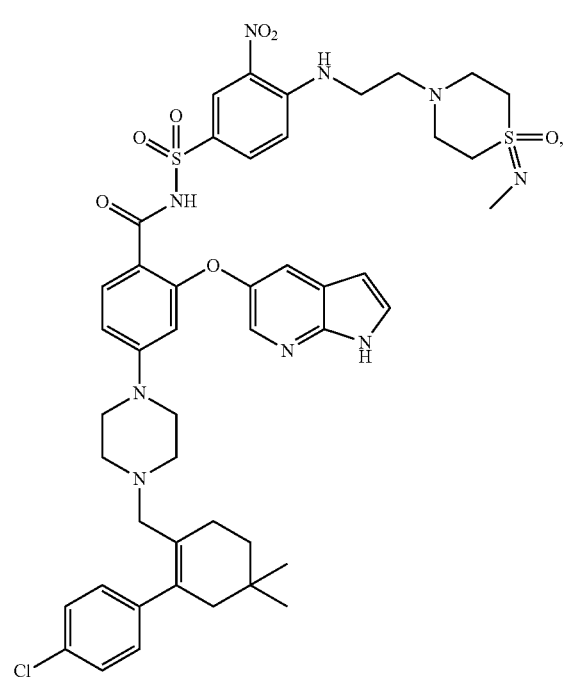
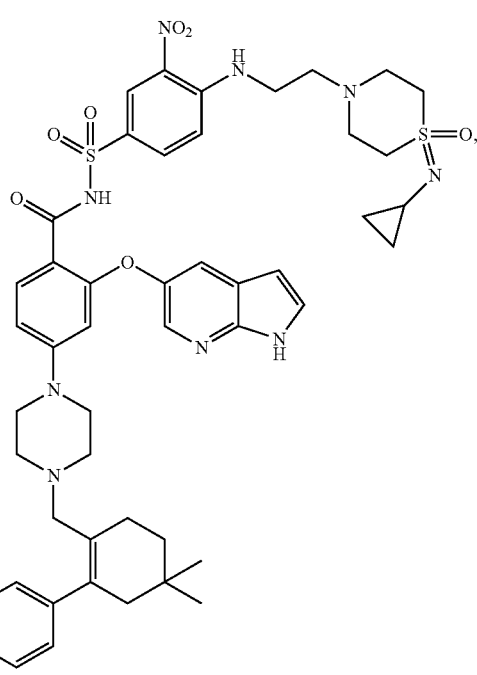

29
-continued
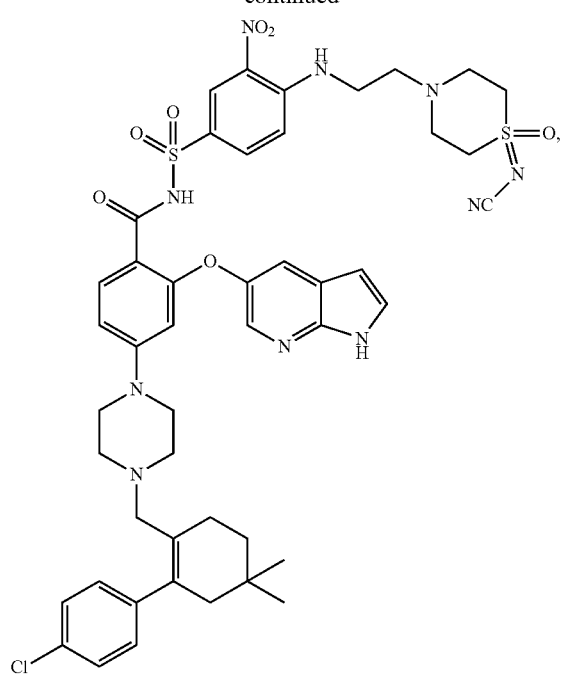
30
-continued
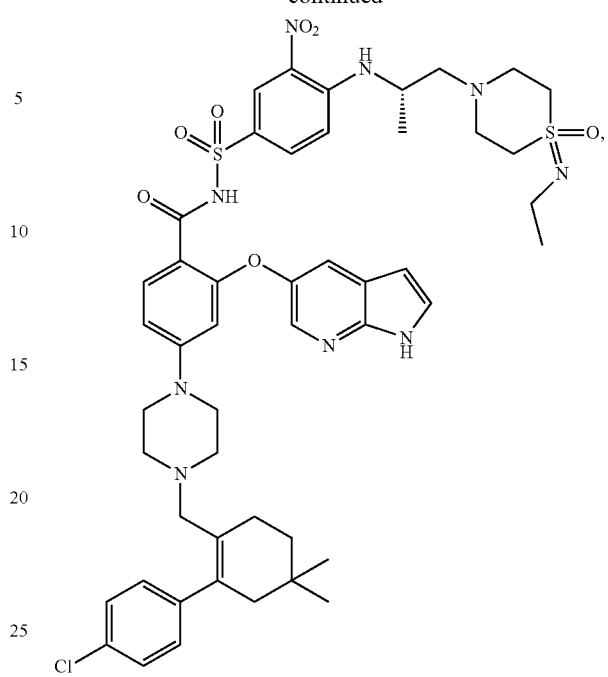
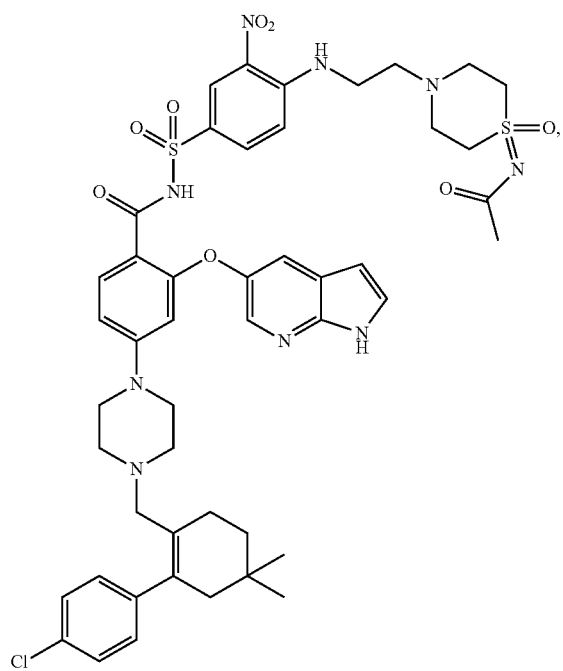 [SMILES: CC(=O)N=S1(=O)CCN(C[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1]
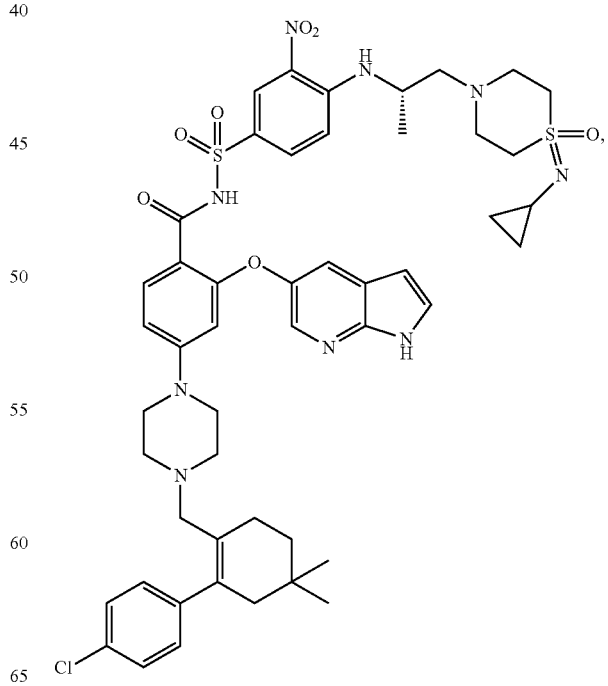

31
-continued
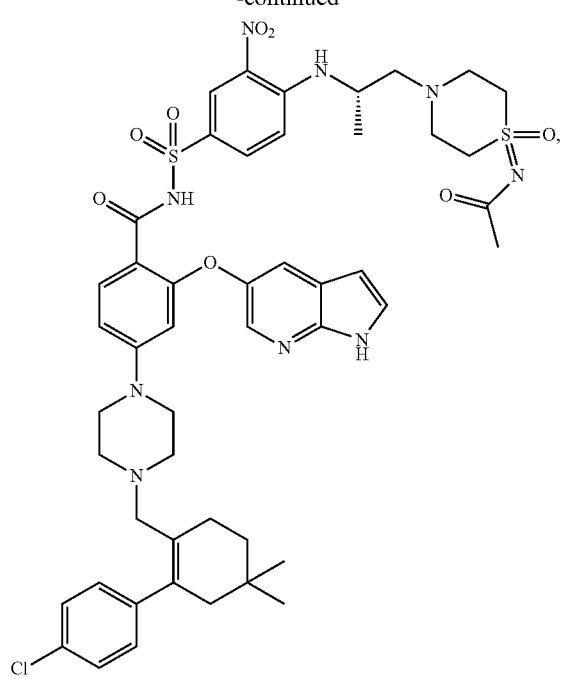
32
-continued
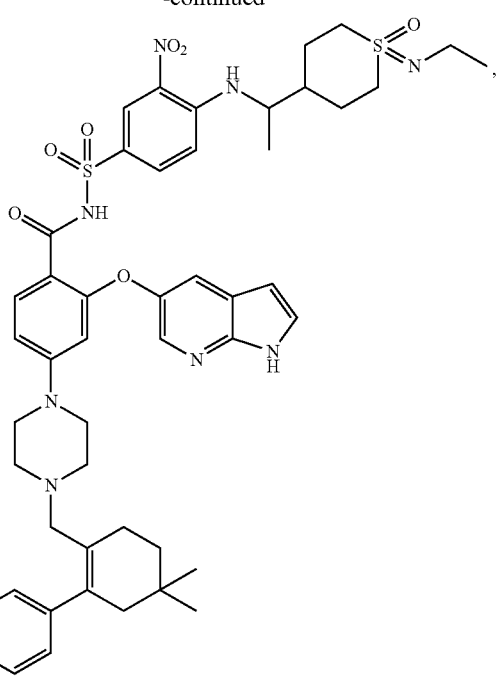
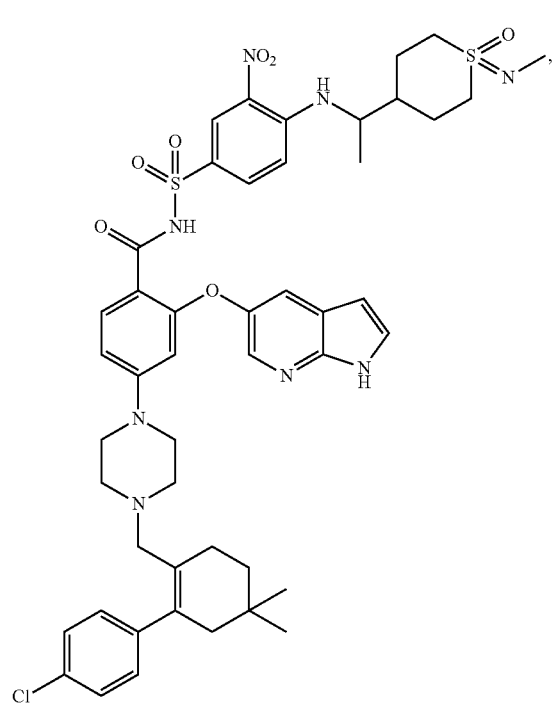
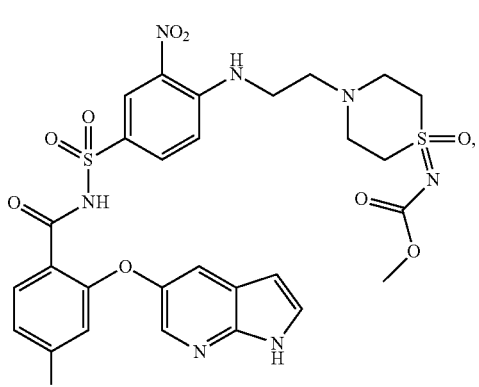
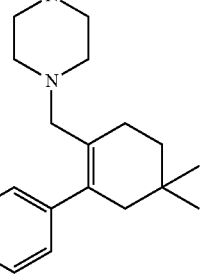

33
-continued
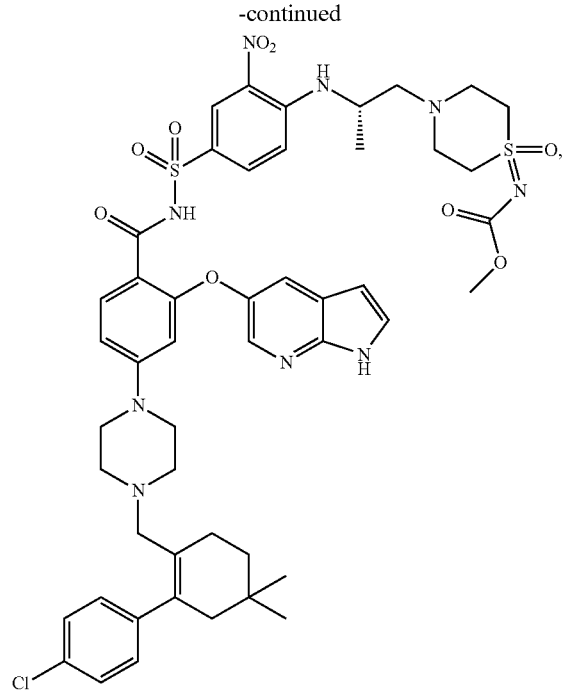
34
-continued
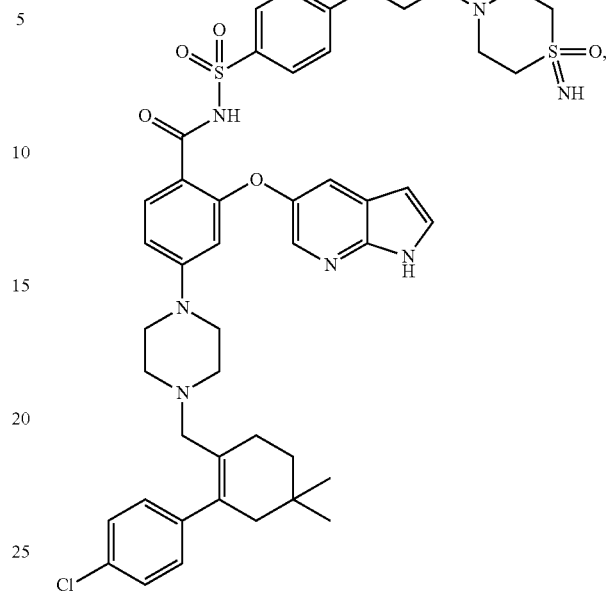
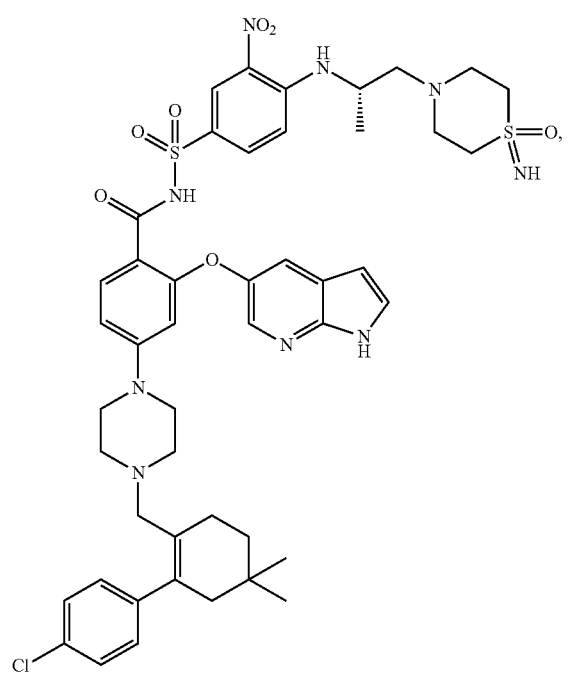
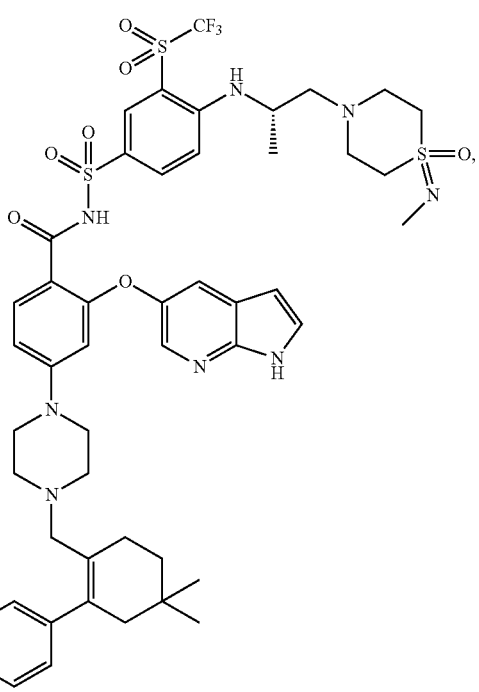

35
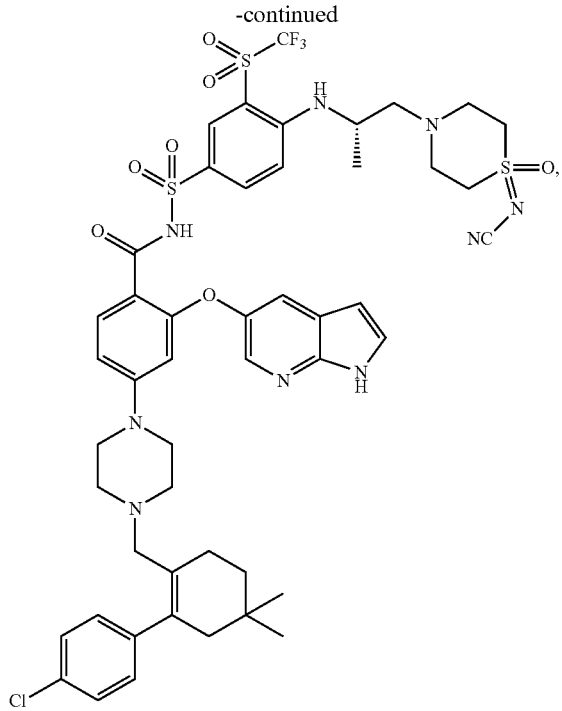
36
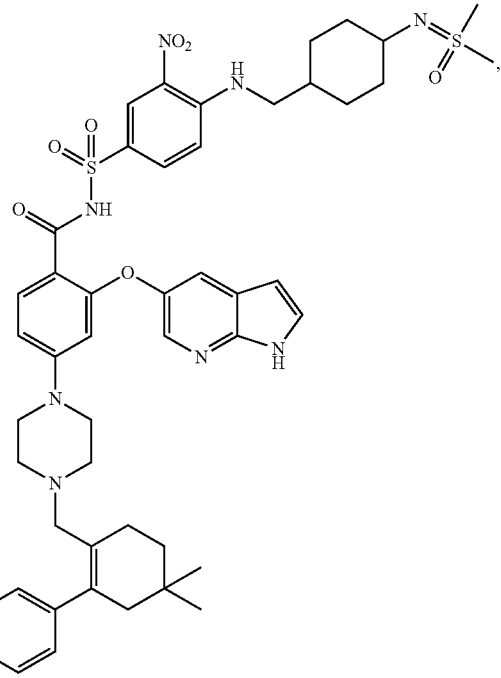
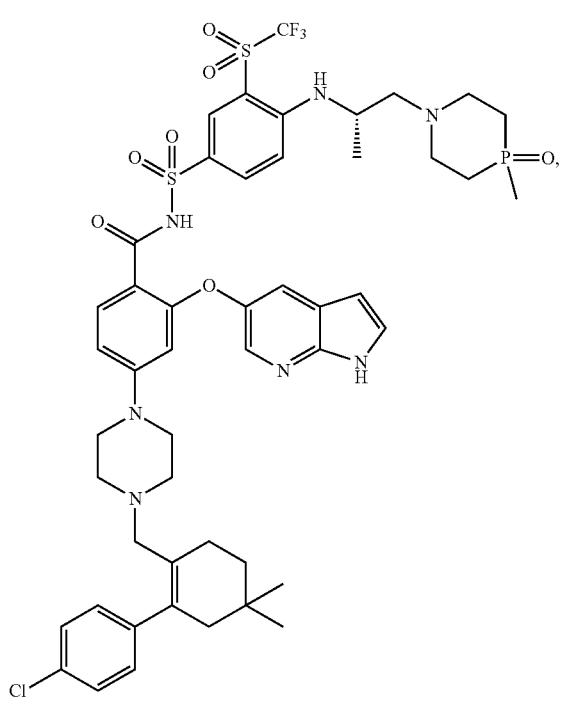

37
-continued
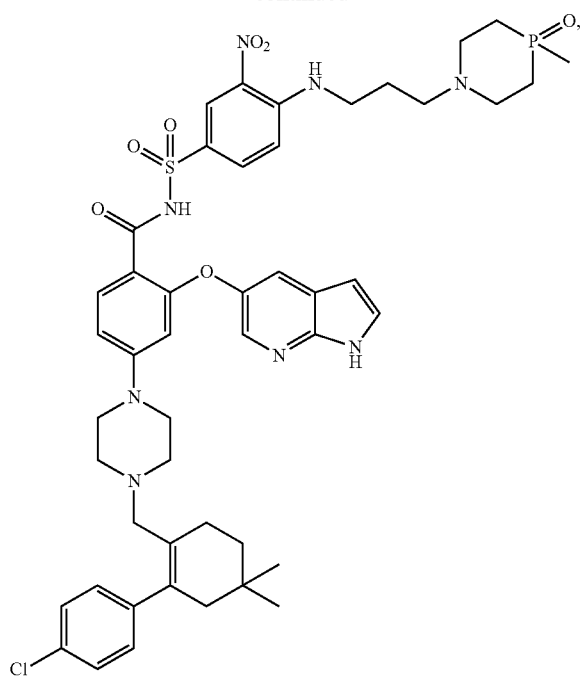
38
-continued
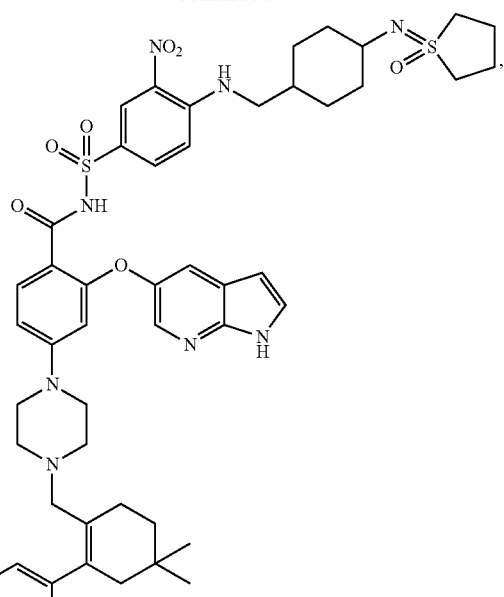
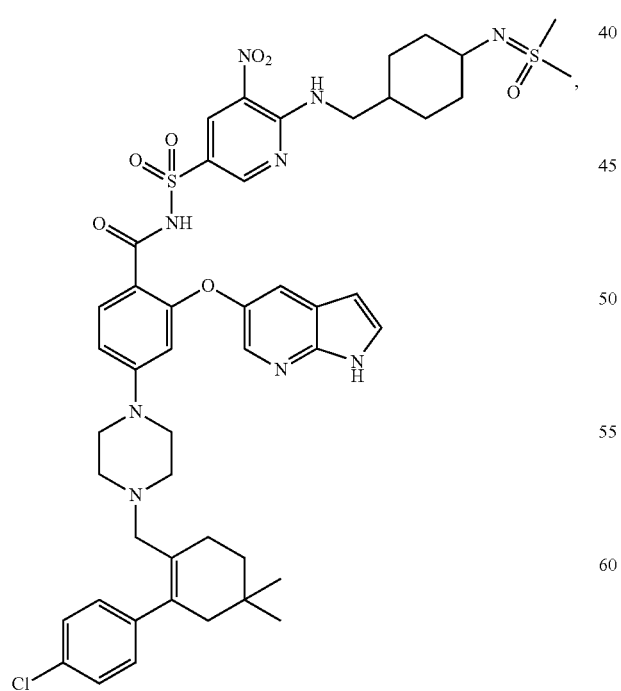

39
-continued
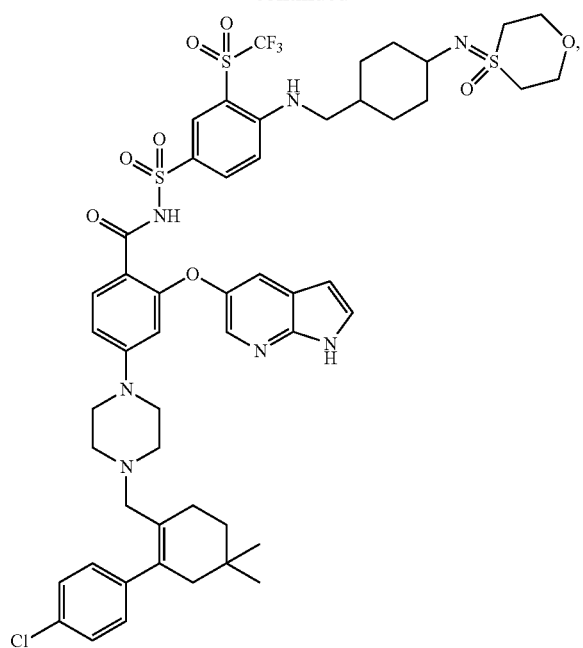
40
-continued
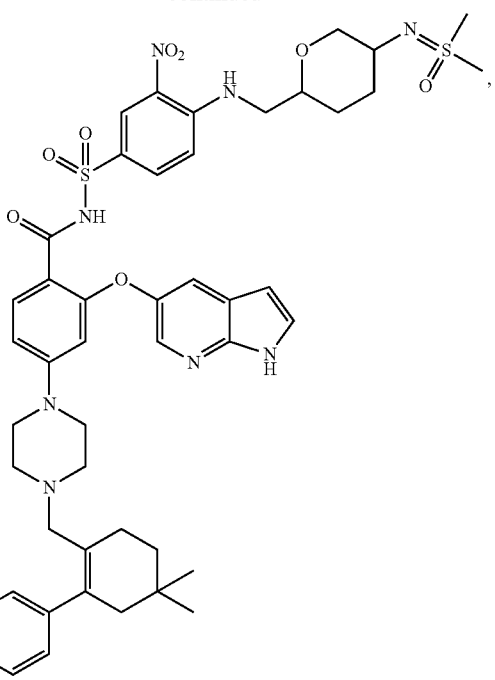

41
-continued
42
-continued
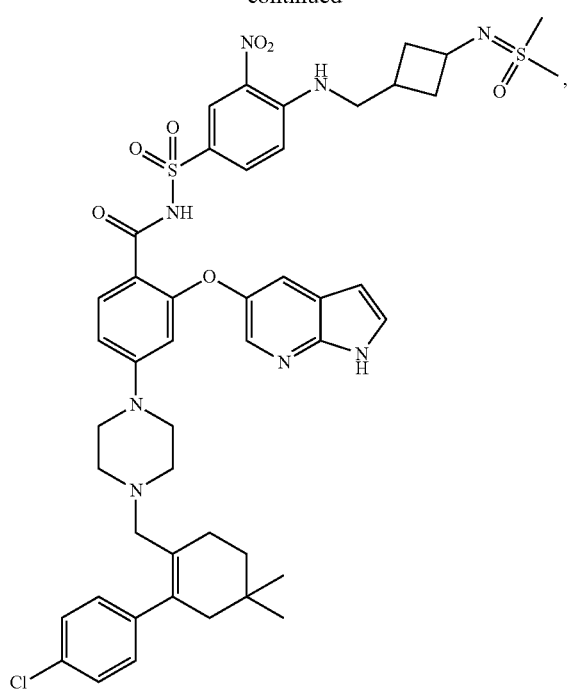
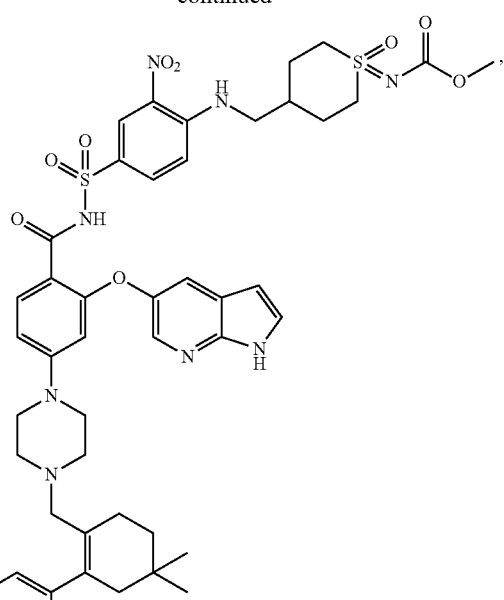

43
-continued
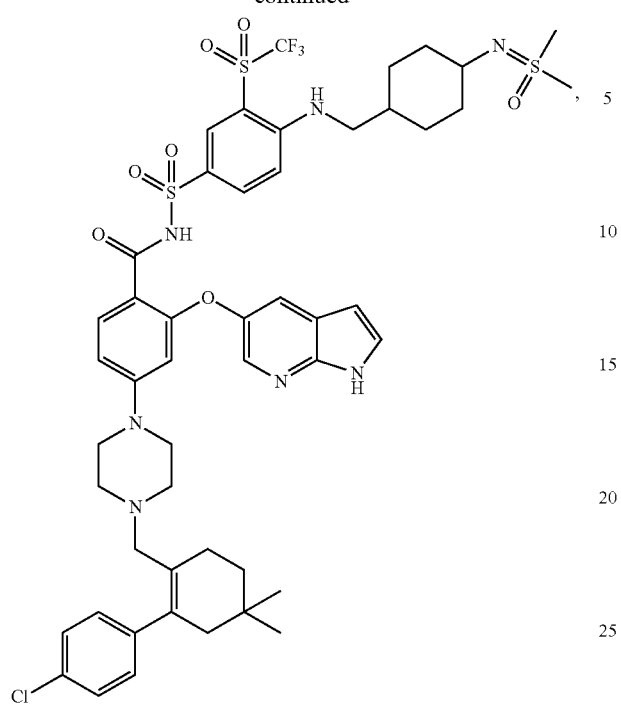
44
-continued
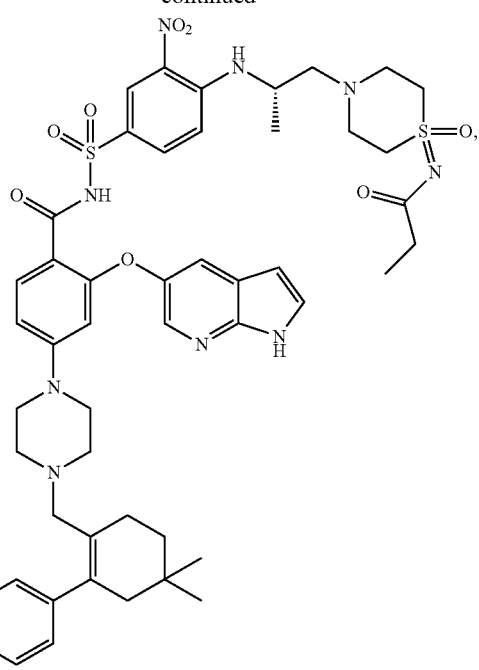

45
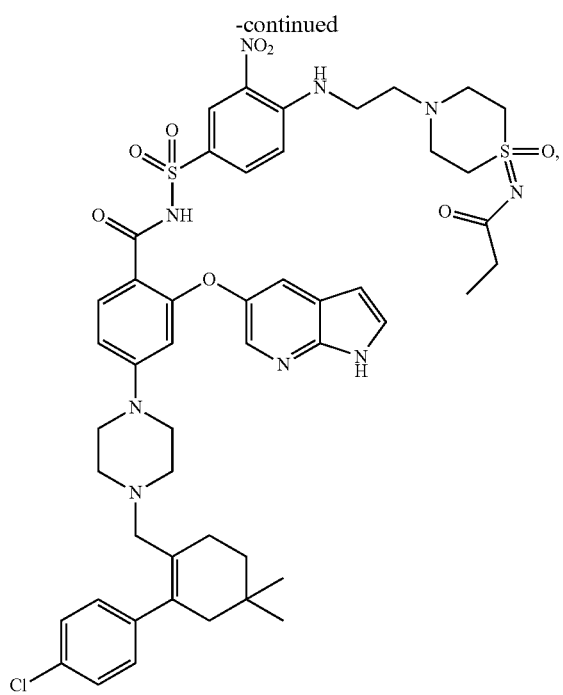
46
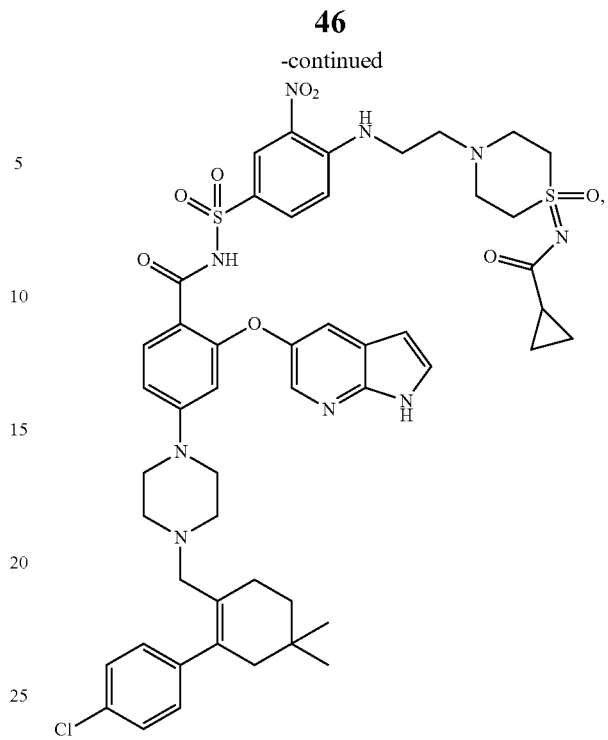
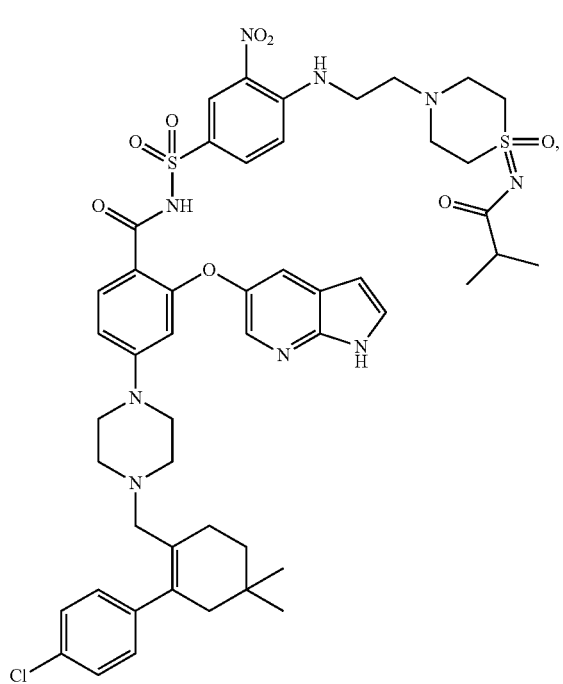
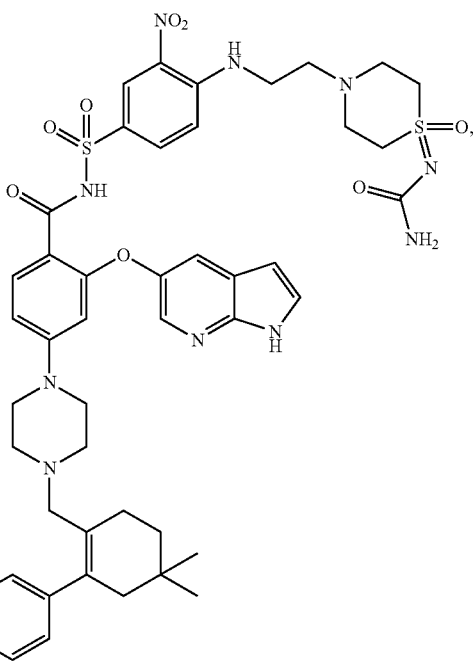

47
-continued
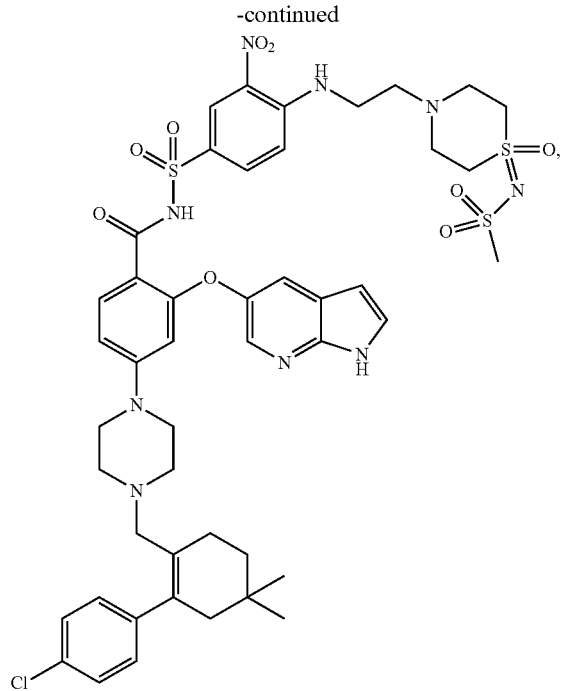
48
-continued
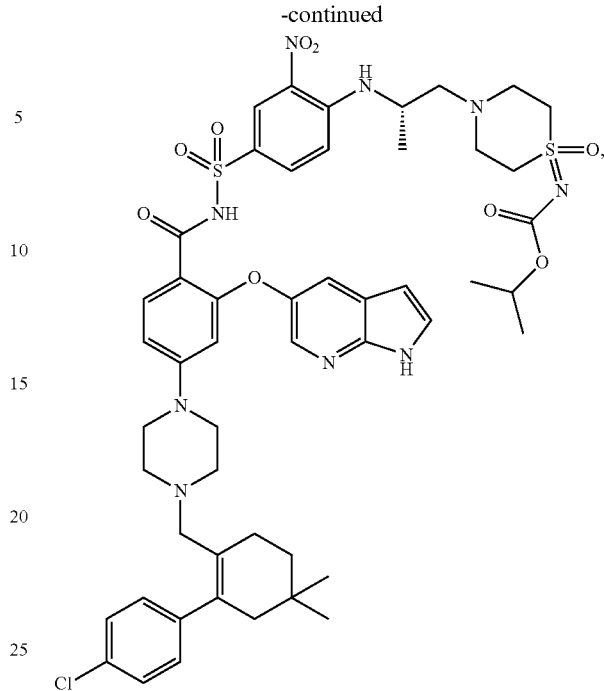
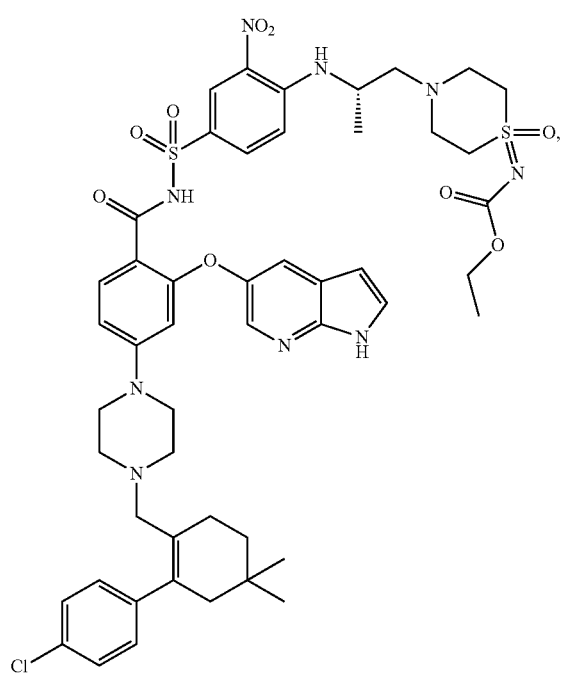
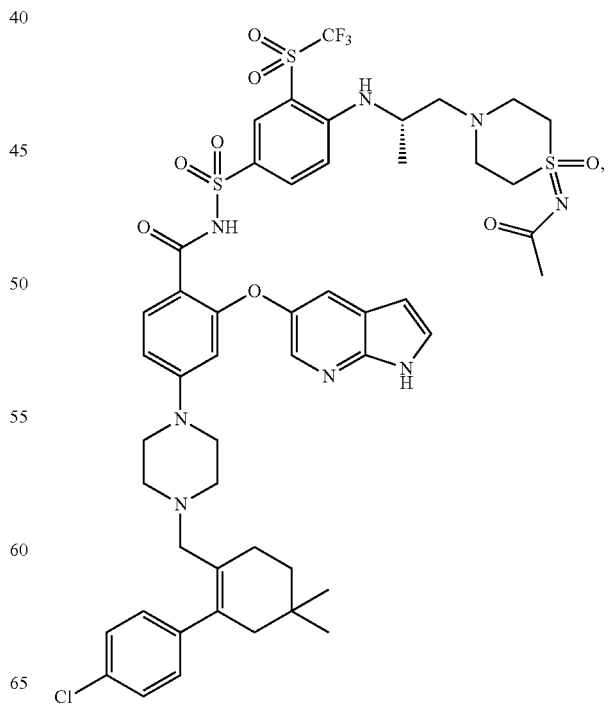

49
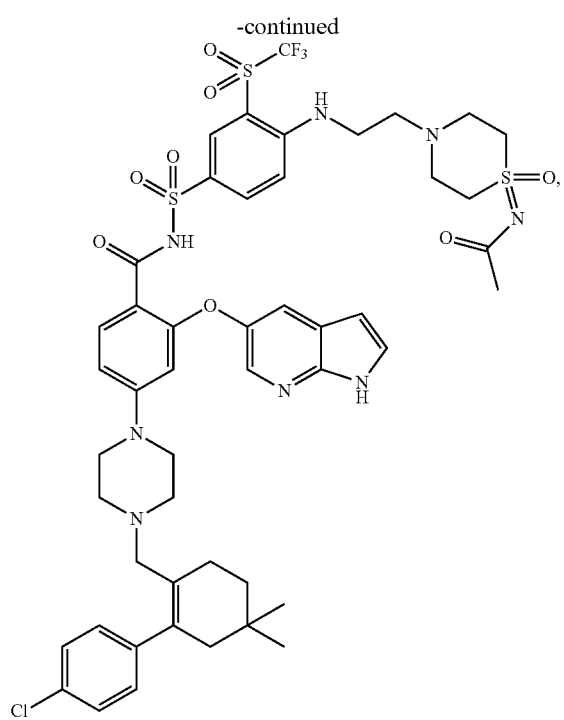
50
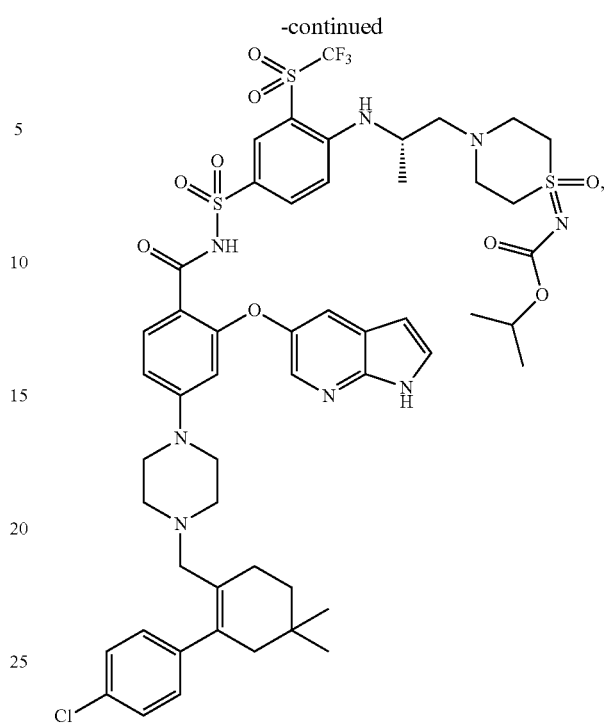
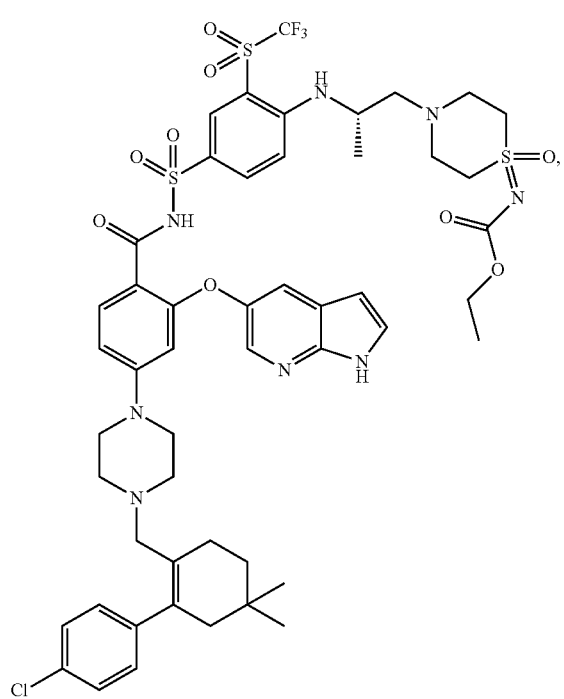
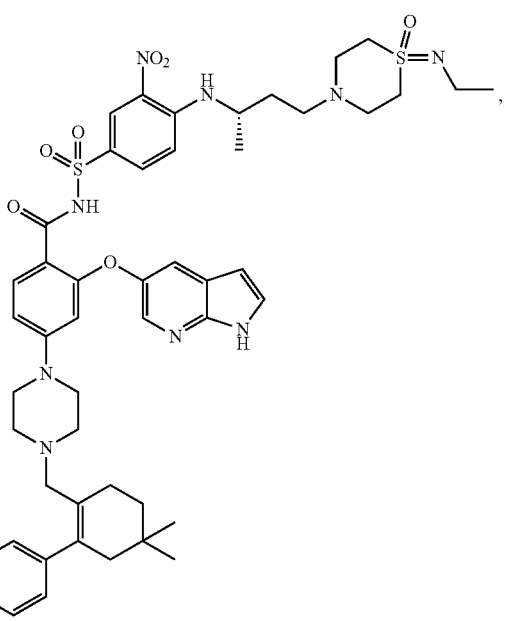

51
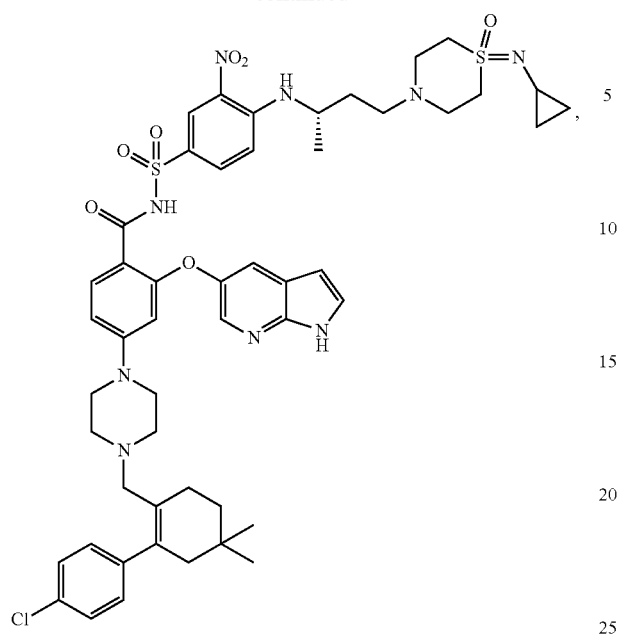
52
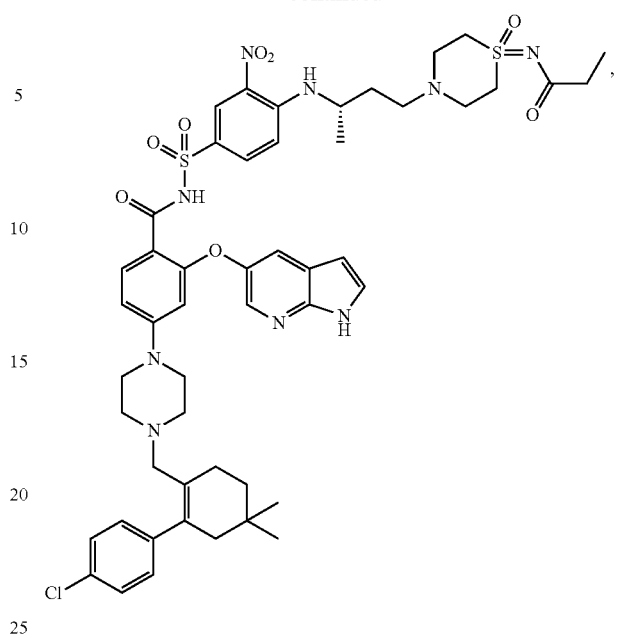
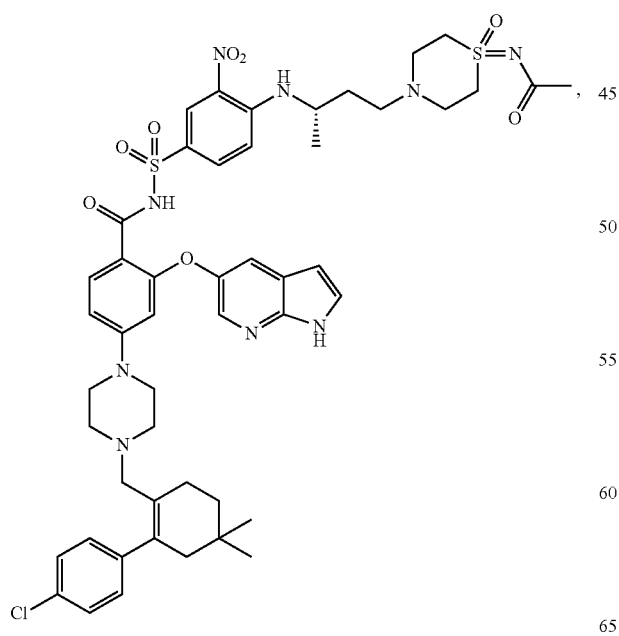
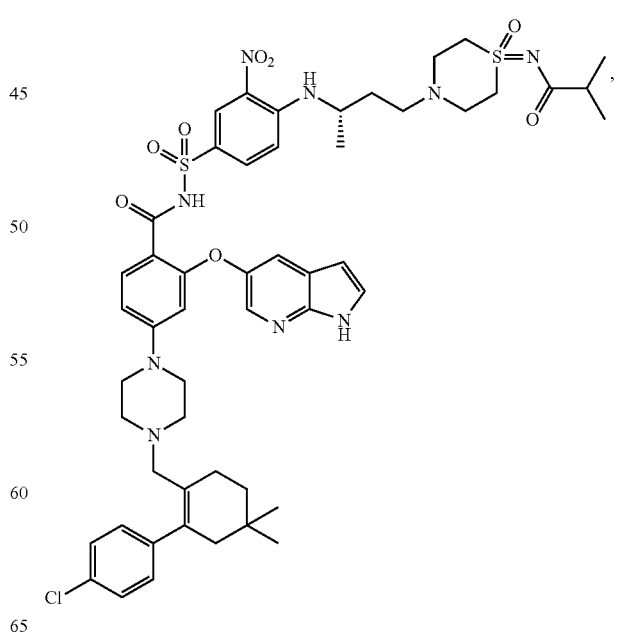

53
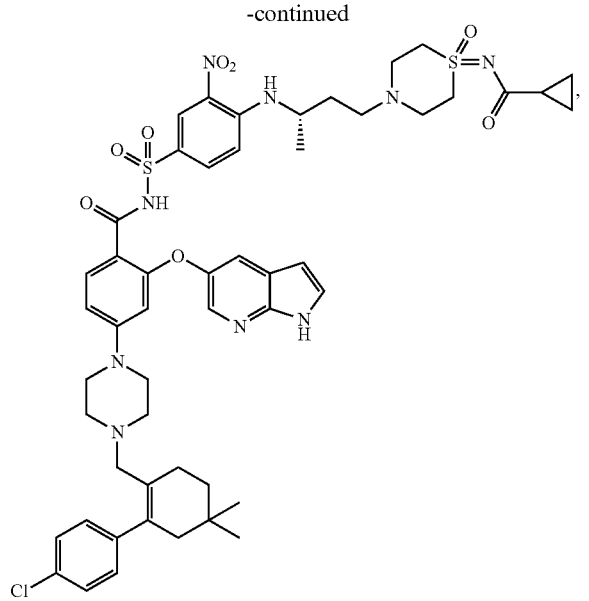
54
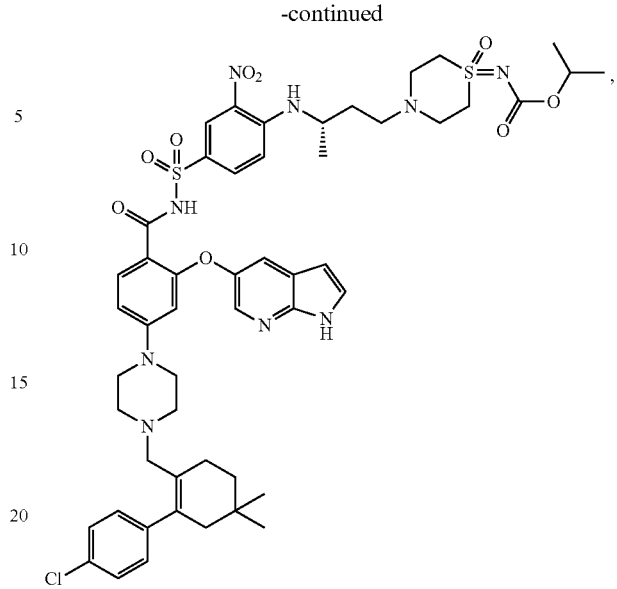
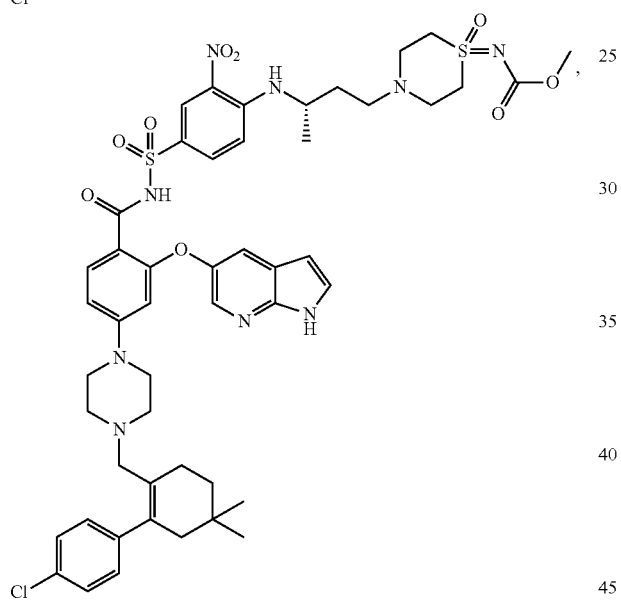
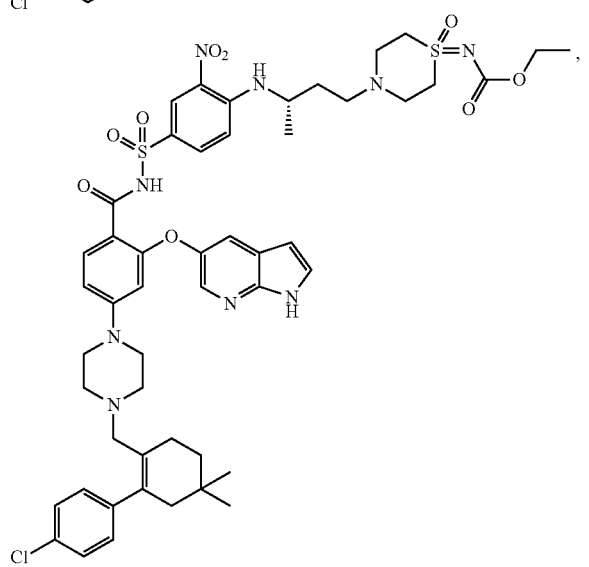
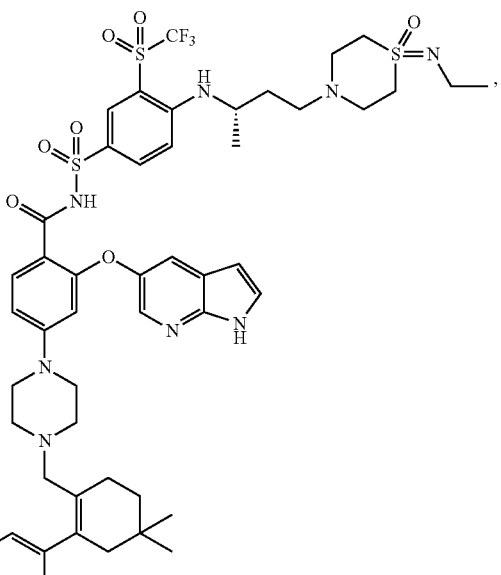

55
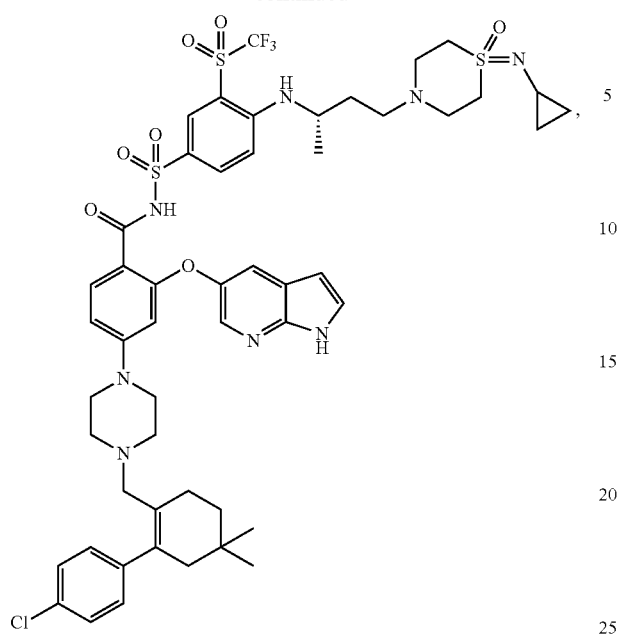
56
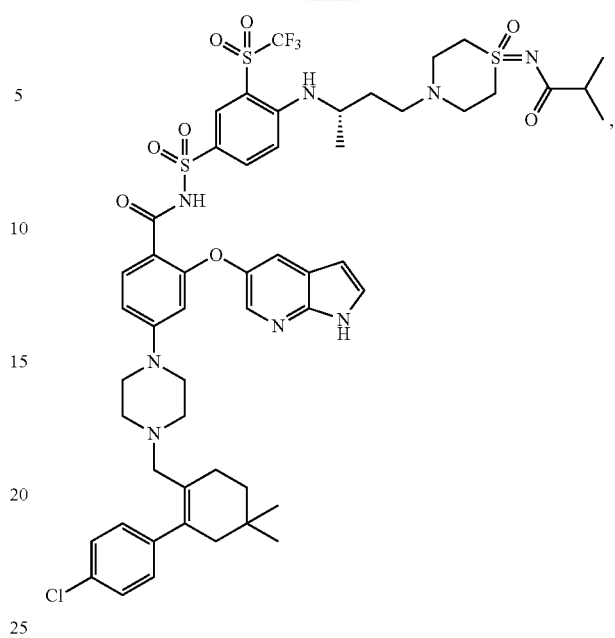
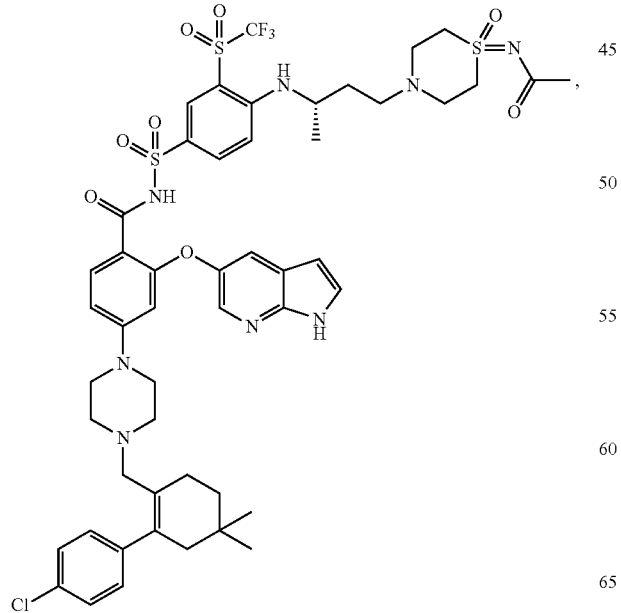
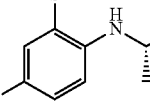

57
-continued
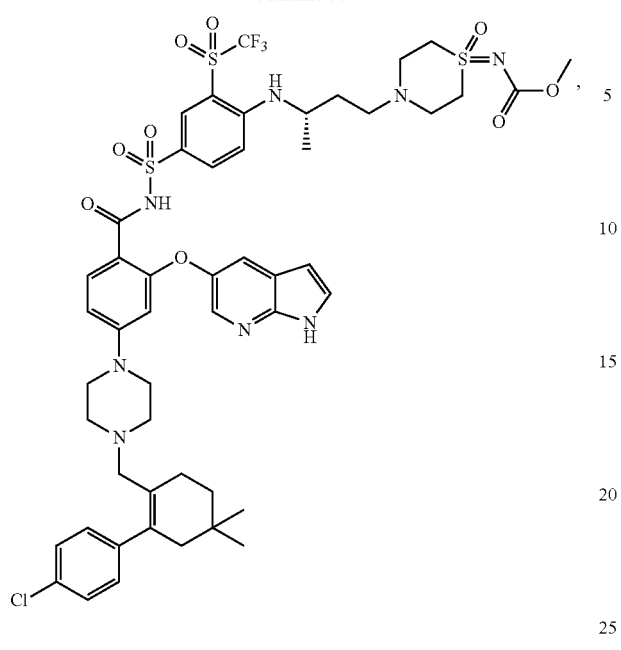
58
-continued
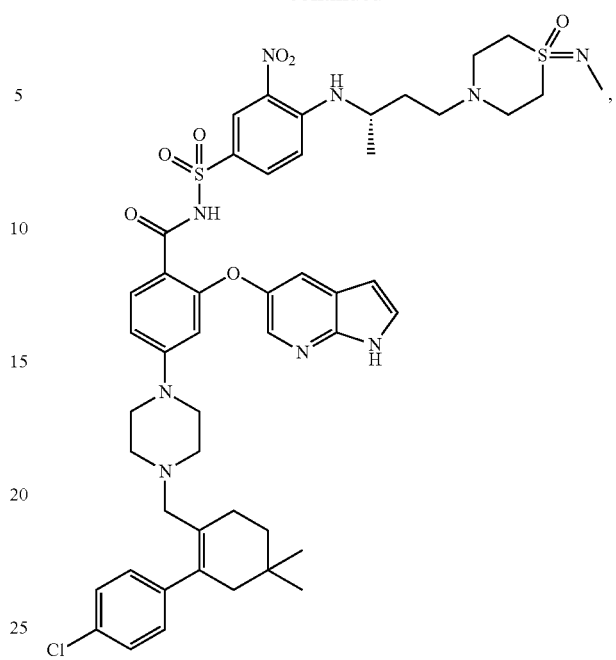
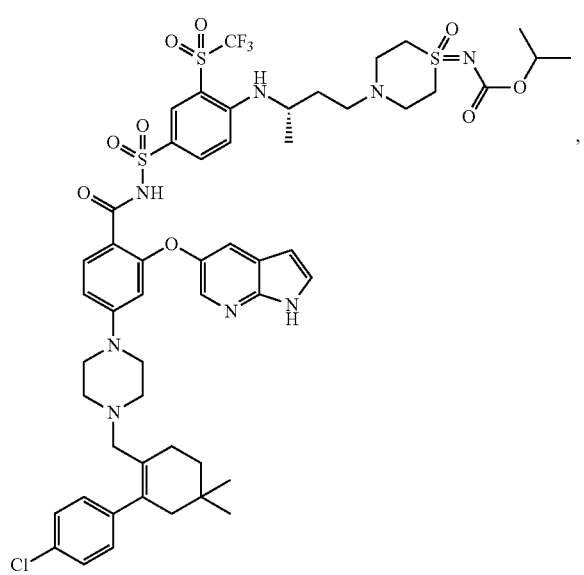

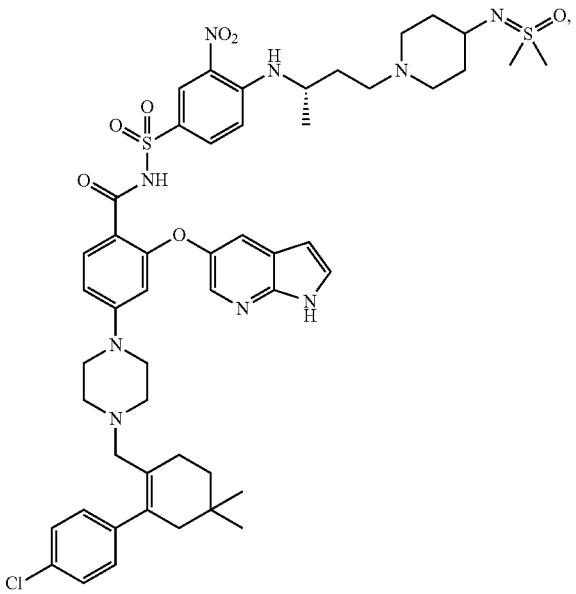

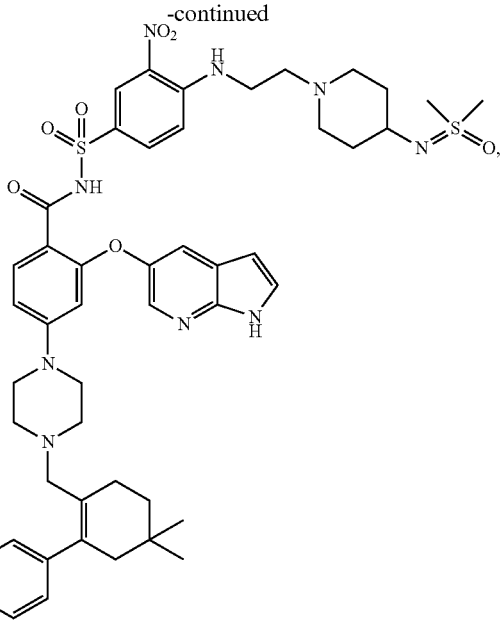

and pharmaceutically acceptable salts thereof.

In yet another aspect, the present disclosure provides pharmaceutical compositions comprising a compound of formula (I) or a pharmaceutically acceptable salt thereof and a pharmaceutically acceptable excipient.

In yet another aspect, the disclosure provides methods for modulating Bcl-2, comprising administering to a system or a subject in need thereof, a therapeutically effective amount of a compound of formula (I) or a pharmaceutically acceptable salt thereof or pharmaceutical compositions thereof, thereby modulating said Bcl-2.

In yet another aspect, disclosed is a method to treat, ameliorate or prevent a condition which responds to inhibition of Bcl-2 comprising administering to a system or subject in need of such treatment an effective amount of a compound of formula (I) or a pharmaceutically acceptable salt thereof or pharmaceutical compositions thereof, and optionally in combination with a second therapeutic agent, thereby treating said condition.

Alternatively, the present disclosure provides the use of a compound of formula (I) or a pharmaceutically acceptable salt thereof in the manufacture of a medicament for treating a condition mediated by Bcl-2. In particular embodiments, the compounds of the disclosure may be used alone or in combination with a second therapeutic agent to treat a condition mediated by Bcl-2.

Alternatively, disclosed is a compound of formula (I) or a pharmaceutically acceptable salt thereof for treating a condition mediated by Bcl-2.

Specifically, the condition herein includes but not limited to, an autoimmune disease, a transplantation disease, an infectious disease or a cell proliferative disorder.

Furthermore, the disclosure provides methods for treating a cell proliferative disorder, comprising administering to a system or subject in need of such treatment an effective amount of a compound of formula (I) or a pharmaceutically acceptable salt thereof or pharmaceutical compositions thereof, and optionally in combination with a second therapeutic agent, thereby treating said condition.

Alternatively, the present disclosure provides the use of a compound of formula (I) or a pharmaceutically acceptable salt thereof in the manufacture of a medicament for treating a cell-proliferative disorder. In particular examples, the compounds of the disclosure may be used alone or in combination with a chemotherapeutic agent to treat a cell proliferative disorder.

Specifically, the cell proliferative disorder disclosed herein includes but not limited to, lymphoma, osteosarcoma, melanoma, or a tumor of breast, renal, prostate, colorectal, thyroid, ovarian, pancreatic, neuronal, lung, uterine or gastrointestinal tumor.

In the above methods for using the compounds of the disclosure, a compound of formula (I) or a pharmaceutically acceptable salt thereof may be administered to a system comprising cells or tissues, or to a subject including a mammalian subject such as a human or animal subject.

Certain Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

The term "substituted" means that a hydrogen atom is removed and replaced by a substituent. It is to be understood that substitution at a given atom is limited by valency. Throughout the definitions, the term "$C_{i-j}$" indicates a range which includes the endpoints, wherein i and j are integers and indicate the number of carbons. Examples include $C_{1-4}$, $C_{1-10}$, $C_{3-10}$, and the like.

The term "alkyl", employed alone or in combination with other terms, refers to both branched and straight-chain saturated aliphatic hydrocarbon groups having the specified number of carbon atoms. Unless otherwise specified, "alkyl" refers to $C_{1-10}$ alkyl. For example, $C_{1-6}$, as in "$C_{1-6}$ alkyl" is defined to include groups having 1, 2, 3, 4, 5, or 6 carbons in a linear or branched arrangement. For example, "$C_{1-8}$ alkyl" includes but is not limited to methyl, ethyl, n-propyl, i-propyl, n-butyl, t-butyl, i-butyl, pentyl, hexyl, heptyl, and octyl.

The term "cycloalkyl", employed alone or in combination with other terms, refers to a monocyclic or bridged hydrocarbon ring system. The monocyclic cycloalkyl is a carbocyclic ring system containing three to ten carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Representative examples of such bridged cycloalkyl ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.03,7]nonane and tricyclo[3.3.1.13,7]decane (adamantane). The monocyclic and bridged cycloalkyl can be attached to the parent molecular moiety through any substitutable atom contained within the ring system.

The term "alkenyl", employed alone or in combination with other terms, refers to a non-aromatic hydrocarbon radical, straight, branched or cyclic, containing from 2 to 10 carbon atoms and at least one carbon to carbon double bond. In some embodiments, one carbon to carbon double bond is present, and up to four non-aromatic carbon-carbon double bonds may be present. Thus, "$C_{2-6}$ alkenyl" means an alkenyl radical having from 2 to 6 carbon atoms. Alkenyl groups include but are not limited to ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl", employed alone or in combination with other terems, refers to a hydrocarbon radical straight, branched or cyclic, containing from 2 to 10 carbon atoms and at least one carbon to carbon triple bond. In some embodiments, up to three carbon-carbon triple bonds may be present. Thus, "$C_{2-6}$ alkynyl" means an alkynyl radical having from 2 to 6 carbon atoms. Alkynyl groups include but are not limited to ethynyl, propynyl, butynyl, and 3-methylbutynyl. The straight, branched or cyclic portion of the alkynyl group may contain triple bonds and may be substituted if a substituted alkynyl group is indicated.

The term "halogen" (or "halo") refers to fluorine, chlorine, bromine and iodine.

The term "alkoxy", employed alone or in combination with other terms, refers to an alkyl radical that is single bonded to an oxygen atom. The attachment point of an alkoxy radical to a molecule is through the oxygen atom. An alkoxy radical may be depicted as —O-alkyl. The term "$C_{1-10}$ alkoxy" refers to an alkoxy radical containing from one to ten carbon atoms, having straight or branched moieties. Alkoxy groups, includes but is not limited to, methoxy, ethoxy, propoxy, isopropoxy, butoxy, pentyloxy, hexyloxy, and the like.

The term "cycloalkoxy", employed alone or in combination with other terms, refers to cycloalkyl radical that is single bonded to an oxygen atom. The attachment point of a cycloalkoxy radical to a molecule is through the oxygen atom. A cycloalkoxy radical may be depicted as —O-cycloalkyl. "$C_{3-10}$ cycloalkoxy" refers to a cycloalkoxy radical containing from three to ten carbon atoms. Cycloalkoxy groups, includes but is not limited to, cyclopropoxy, cyclobutoxy, cyclopentyloxy, cyclohexyloxy, and the like.

The term "alkylthio", employed alone or in combination with other terms, refers to an alkyl radical that is single bonded to a sulfur atom. The attachment point of an alkylthio radical to a molecule is through the sulfur atom. An alkylthio radical may be depicted as —S-alkyl. The term "$C_{1-10}$ alkylthio" refers to an alkylthio radical containing from one to ten carbon atoms, having straight or branched moieties. Alkylthio groups, includes but is not limited to, methylthio, ethylthio, propylthio, isopropylthio, butylthio, hexylthio, and the like.

The term "cycloalkylthio", employed alone or in combination with other terms, refers to cycloalkyl radical that is single bonded to a sulfur atom. The attachment point of a cycloalkylthio radical to a molecule is through the sulfur atom. A cycloalkylthio radical may be depicted as —S-cycloalkyl. "$C_{3-10}$ cycloalkylthio" refers to a cycloalkylthio radical containing from three to ten carbon atoms. Cycloalkylthio groups, includes but is not limited to, cyclopropylthio, cyclobutylthio, cyclohexylthio, and the like.

The term "alkylamino", employed alone or in combination with other terms, refers to an alkyl radical that is single bonded to a nitrogen atom. The attachment point of an alkylamino radical to a molecule is through the nitrogen atom. An alkylamino radical may be depicted as —NH(alkyl). The term "$C_{1-10}$ alkylamino" refers to an alkylamino radical containing from one to ten carbon atoms, having straight or branched moieties. Alkylamino groups, includes but is not limited to, methylamino, ethylamino, propylamino, isopropylamino, butylamino, hexylamoino, and the like.

The term "cycloalkylamino", employed alone or in combination with other terms, refers to cycloalkyl radical that is single bonded to a nitrogen atom. The attachment point of a cycloalkylamino radical to a molecule is through the nitrogen atom. A cycloalkylamino radical may be depicted as —NH(cycloalkyl). "$C_{3-10}$ cycloalkylamino" refers to a cycloalkylamino radical containing from three to ten carbon atoms. Cycloalkylamino groups, includes but is not limited to, cyclopropylamino, cyclobutylamino, cyclohexylamino, and the like.

The term "di(alkyl)amino", employed alone or in combination with other terms, refers to two alkyl radicals that are single bonded to a nitrogen atom. The attachment point of an di(alkyl)amino radical to a molecule is through the nitrogen atom. A di(alkyl)amino radical may be depicted as —N(alkyl)$_2$. The term "di($C_{1-10}$ alkyl)amino" refers to a di($C_{1-10}$ alkyl)amino radical wherein the alkyl radicals each independently contains from one to ten carbon atoms, having straight or branched moieties.

The term "aryl", employed alone or in combination with other terms, encompasses: 5- and 6-membered carbocyclic aromatic rings, for example, benzene; bicyclic ring systems wherein at least one ring is carbocyclic and aromatic, for example, naphthalene, indane, and 1, 2, 3, 4-tetrahydroquinoline; and tricyclic ring systems wherein at least one ring is carbocyclic and aromatic, for example, fluorene. In cases where the aryl substituent is bicyclic or tricyclic and at least one ring is non-aromatic, it is understood that attachment is via the aromatic ring.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "heteroaryl", employed alone or in combination with other terms, refers to
  5- to 8-membered aromatic, monocyclic rings containing one or more, for example, from 1 to 4, or, in some embodiments, from 1 to 3, heteroatoms selected from N, O and S, with the remaining ring atoms being carbon;
  8- to 12-membered bicyclic rings containing one or more, for example, from 1 to 4, or, in some embodiments, from 1 to 3, heteroatoms selected from N, O and S, with the remaining ring atoms being carbon and wherein at least one heteroatom is present in an aromatic ring; and
  11- to 14-membered tricyclic rings containing one or more, for example, from 1 to 4, or in some embodiments, from 1 to 3, heteroatoms selected from N, O and S, with the remaining ring atoms being carbon and wherein at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl and 5,6,7,8-tetrahydroi soquinoline.

Further heteroaryl groups include but are not limited to pyrrolyl, isothiazolyl, triazinyl, pyrazinyl, pyridazinyl, indolyl, benzotriazolyl, quinoxalinyl and isoquinolinyl. As with the definition of heterocycle below, "heteroaryl" is also understood to include the N-oxide derivative of any nitrogen-containing heteroaryl.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In cases where the heteroaryl substituent is bicyclic or tricyclic and at least one ring is non-aromatic or contains no heteroatoms, it is understood that attachment is via the aromatic ring or via the heteroatom containing ring, respectively.

The term "heterocycle", employed alone or in combination with other terms, (and variations thereof such as "heterocyclic", or "heterocyclyl") broadly refers to a single aliphatic ring, usually with 3 to 12 ring atoms, containing at least 2 carbon atoms in addition to one or more, preferably one to three heteroatoms independently selected from oxygen, sulfur, nitrogen and phosphorus as well as combinations comprising at least one of the foregoing heteroatoms. Alternatively, a heterocycle as defined above may be multicyclic ring system (e.g. bicyclic) in which two or more rings may be fused or bridged or spiro together, wherein at least one such ring contains one or more heteroatoms independently selected from oxygen, sulfur, nitrogen and phosphorus. "Heterocycle" also refers to 5- to 7-membered heterocyclic ring containing one or more heteroatoms selected from oxygen, sulfur, nitrogen and phosphorus fused with 5- and 6-membered carbocyclic aromatic ring, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring, provided that attachment results in the creation of a stable structure. When the heterocyclic ring has substituents, it is understood that the substituents may be attached to any atom in the ring, whether a heteroatom or a carbon atom, provided that a stable chemical structure results. Heterocycle does not overlap with heteroaryl.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, 1,4-piperazinyl and 2,3-pyridazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl. Bicyclic heterocycles include, for example:

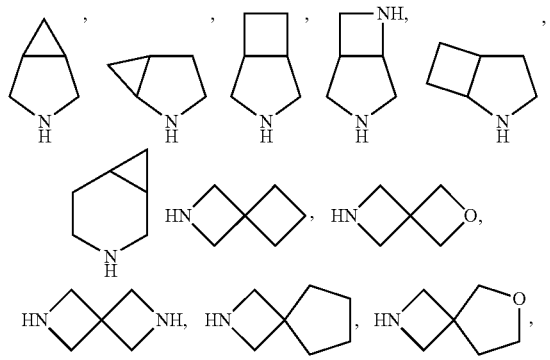

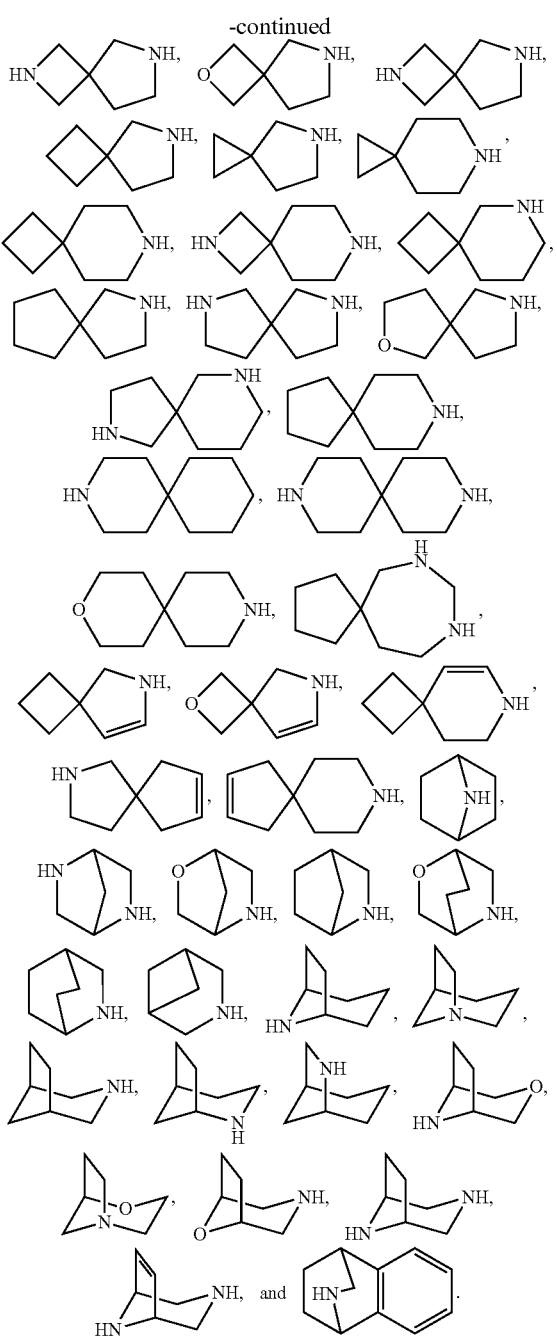

As used herein, "aryl-alkyl" refers to an alkyl moiety substituted by an aryl group. Example aryl-alkyl groups include benzyl, phenethyl and naphthylmethyl groups. In some embodiments, aryl-alkyl groups have from 7 to 20 or 7 to 11 carbon atoms. When used in the phrase "aryl-$C_{1-4}$ alkyl", the term "$C_{1-4}$" refers to the alkyl portion of the moiety and does not describe the number of atoms in the aryl portion of the moiety.

As used herein, "heterocyclyl-alkyl" refers to alkyl substituted by heterocyclyl. When used in the phrase "heterocyclyl-$C_{1-4}$ alkyl", the term "$C_{1-4}$" refers to the alkyl portion of the moiety and does not describe the number of atoms in the heterocyclyl portion of the moiety.

As used herein, "cycloalkyl-alkyl" refers to alkyl substituted by cycloalkyl. When used in the phrase "$C_{3-10}$ cycloalkyl-$C_{1-4}$ alkyl", the term "$C_{3-10}$" refers to the cycloalkyl portion of the moiety and does not describe the number of atoms in the alkyl portion of the moiety, and the term "$C_{1-4}$" refers to the alkyl portion of the moiety and does not describe the number of atoms in the cycloalkyl portion of the moiety.

As used herein, "heteroaryl-alkyl" refers to alkyl substituted by heteroaryl. When used in the phrase "heteroaryl-$C_{1-4}$ alkyl", the term "$C_{1-4}$" refers to the alkyl portion of the moiety and does not describe the number of atoms in the heteroaryl portion of the moiety.

For avoidance of doubt, reference, for example, to substitution of alkyl, cycloalkyl, heterocyclyl, aryl and/or heteroaryl refers to substitution of each of those groups individually as well as to substitutions of combinations of those groups. That is, if $R^1$ is aryl-$C_{1-4}$ alkyl, the aryl portion may be unsubstituted or substituted with at least one substituent, such as one, two, three, or four substituents, independently selected from $R^X$ and the alkyl portion may also be unsubstituted or substituted with at least one substituent, such as one, two, three, or four substituens, independently selected from $R^X$.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium and zinc salts. Further, for example, the pharmaceutically acceptable salts derived from inorganic bases may be selected from ammonium, calcium, magnesium, potassium and sodium salts. Salts in the solid form may exist in one or more crystal structures, and may also be in the form of hydrates. Salts derived from pharmaceutically acceptable organic non-toxic bases may be selected, for example, from salts of primary, secondary and tertiary amines, substituted amines including naturally occurring substituted amines, cyclic amines and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine and tripropylamine, tromethamine.

When the compound disclosed herein is basic, salts may be prepared using at least one pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric and p-toluenesulfonic acids. In some embodiments, such acid may be selected, for example, from citric, hydrobromic, hydrochloric, maleic, phosphoric, sulfuric, fumaric and tartaric acids.

The terms "administration of" and or "administering" a compound or a pharmaceutically acceptable salt should be understood to mean providing a compound or a pharmaceutically acceptable salt thereof to the individual in recognized need of treatment.

The term "effective amount" means the amount of the a compound or a pharmaceutically acceptable salt that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s) and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

The term "pharmaceutically acceptable" it is meant compatible with the other ingredients of the formulation and not unacceptably deleterious to the recipient thereof.

The term "subject" as used herein in reference to individuals suffering from a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The term "protecting group" or "Pg" refers to a substituent that can be commonly employed to block or protect a certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxycarbonyl (CBZ) and 9-fluorenylmethyleneoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl) ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The term "NH protecting group" as used herein includes, but not limited to, trichloroethoxycarbonyl, tribromoethoxycarbonyl, benzyloxycarbonyl, para-nitrobenzylcarbonyl, ortho-bromobenzyloxycarbonyl, chloroacetyl, di chl oroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxyb enzyloxy carb onyl, 4-(phenylazo)-benzyloxycarbonyl, 2-furfuryloxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthylmethylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclo-hexylidene, diphenylphosphoryl, dibenzylphosphoryl, 5-methyl-2-oxo-2H-1,3-dioxol-4-yl-methyl, trimethylsilyl, triethylsilyl and triphenylsilyl.

The term "C(O)OH protecting group" as used herein includes, but not limited to, methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl) methyl, acetylmethyl, benzoylmethyl, para-nitrobenzoylmethyl, para-bromobenzoylmethyl, para-methanesulfonylbenzoylmethyl, 2-tetrahydropyranyl, 2-tetrahydrofuranyl, 2,2,2-trichloro-ethyl, 2-(trimethylsilyl) ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl and tert-butylmethoxyphenylsilyl.

The term "OH or SH protecting group" as used herein includes, but not limited to, benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl) ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylm-ethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl and tert-butylmethoxyphenylsilyl.

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble J. Org. Chem. 1998, 63, 2758-2760.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85-90%, more preferably an excess of about 95-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, nitrogen, phosphorous, sulfur, fluorine, chlorine and iodine include, but are not limited to, $^2H$, $^3H$, $^{13}C$, $^{14}C$, $^{15}N$, $^{18}O$, $^{32}P$, $^{35}S$, $^{18}F$, $^{36}Cl$ and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuterated acid such as $D_2SO_4/D_2O$. In addition to the above, relevant procedures and intermediates are disclosed, for instance, in Lizondo, J et al, Drugs Fut, 21(11), 1116 (1996); Brickner, S J et al., J Med Chem, 39(3), 673 (1996); Mallesham, B et al, Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-2 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al, J. Labelled Comp. Radiopharmaceut., 36(10):927-932 (1995); Kushner et al., Can. J. Physiol. Pharmacol, 77, 79-88 (1999).

In addition, non-radio active isotope containing drugs, such as deuterated drugs called "heavy drugs" can be used for the treatment of diseases and conditions related to Bcl-2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

In an Embodiment (1), this invention provides a compound of formula (I):

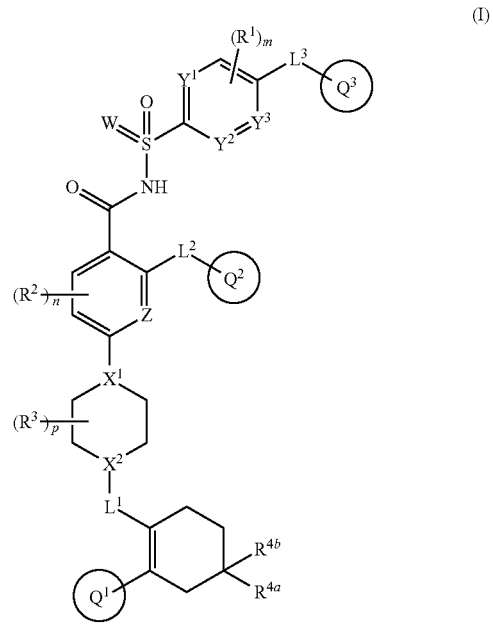

or a pharmaceutically acceptable salt thereof, wherein:
$L^1$ is selected from —$(CR^{C5}R^{D5})_u$—, —$(CR^{C5}R^{D5})_uO(CR^{C5}R^{D5})_t$—, —$(CR^{C5}R^{D5})_uNR^{A5}(CR^{C5}R^{D5})_t$—, —$(CR^{C5}R^{D5})_uS(CR^{C5}R^{D5})_t$—, —$(CR^{C5}R^{D5})_uC(O)(CR^{C5}R^{D5})_t$—, —$(CR^{C5}R^{D5})_uC(=NR^{E5})(CR^{C5}R^{D5})_t$—, —$(CR^{C5}R^{D5})_uC(S)(CR^{C5}R^{D5})_t$—, —$(CR^{C5}R^{D5})_uC(O)O(CR^{C5}R^{D5})_t$—, —$(CR^{C5}R^{D5})_uOC(O)(CR^{C5}R^{D5})_t$—, —$(CR^{C5}R^{D5})_uC(O)NR^{A5}(CR^{C5}R^{D5})_t$—, —$(CR^{C5}R^{D5})_uNR^{A5}C(O)(CR^{C5}R^{D5})_t$—, —$(CR^{C5}R^{D5})_uNR^{A5}C(O)NR^{B5}(CR^{C5}R^{D5})_t$—, —$(CR^{C5}R^{D5})_uC(=NR^{E5})NR^{B5}(CR^{C5}R^{D5})_t$—, —$(CR^{C5}R^{D5})_uNR^{B5}C(=NR^{E5})(CR^{C5}R^{D5})_t$—, —$(CR^{C5}R^{D5})_uNR^{A5}C(=NR^{E5})NR^{B5}(CR^{C5}R^{D5})_t$—, —$(CR^{C5}R^{D5})_uC(S)NR^{A5}(CR^{c5}R^{D5})_t$—, —$(CR^{C5}R^{D5})_uNR^{A5}C(S)(CR^{C5}R^{D5})_t$—, —$(CR^{C5}R^{D5})_uNR^{A5}C(S)NR^{B5}(CR^{C5}R^{D5})_t$—, —$(CR^{C5}R^{D5})_uS(O)_r(CR^{C5}R^{D5})_t$—, —$(CR^{C5}R^{D5})_uS(O)_rNR^{A5}(CR^{C5}R^{D5})_t$—, —$(CR^{C5}R^{D5})_uNR^{A5}S(O)_r(CR^{C5}R^{D5})_t$— and —$(CR^{C5}R^{D5})_uNR^{A5}S(O)_rNR^{B5}(CR^{C5}R^{D5})_t$—;

$L^2$ is selected from —$(CR^{C6}R^{D6})_u$—, —$(CR^{C6}R^{D6})_uO(CR^{C6}R^{D6})_t$—, —$(CR^{C6}R^{D6})_uNR^{A6}(CR^{C6}R^{D6})_t$—, —$(CR^{C6}R^{D6})_uS(CR^{C6}R^{D6})_t$—, —$(CR^{C6}R^{D6})_uC(O)(CR^{C6}R^{D6})_t$—, —$(CR^{C6}R^{D6})_uC(=NR^{E6})(CR^{C6}R^{D6})_t$—, —$(CR^{C6}R^{D6})_uC(S)(CR^{C6}R^{D6})_t$—, —$(CR^{C6}R^{D6})_uC(O)O(CR^{C6}R^{D6})_t$—, —$(CR^{C6}R^{D6})_uOC(O)(CR^{C6}R^{D6})_t$—, —$(CR^{C6}R^{D6})_uC(O)NR^{A6}(CR^{C6}R^{D6})_t$—, —$(CR^{C6}R^{D6})_uNR^{A6}C(O)(CR^{C6}R^{D6})_t$—, —$(CR^{C6}R^{D6})_uNR^{A6}C(O)NR^{B6}(CR^{C6}R^{D6})_t$—, —$(CR^{C6}R^{D6})_uC(=NR^{E6})NR^{B6}(CR^{C6}R^{D6})_t$—, —$(CR^{C6}R^{D6})_uNR^{B6}C(=NR^{E6})(CR^{C6}R^{D6})_t$—, —$(CR^{C6}R^{D6})_uNR^{A6}C(=NR^{E6})NR^{B6}(CR^{C6}R^{D6})_t$—, —$(CR^{C6}R^{D6})_uC(S)NR^{A6}(CR^{C6}R^{D6})_t$—, —$(CR^{C6}R^{D6})_uNR^{A6}C(S)(CR^{C6}R^{D6})_t$—, —$(CR^{C6}R^{D6})_uNR^{A6}C(S)NR^{B6}(CR^{C6}R^{D6})_t$—, —$(CR^{C6}R^{D6})_uS(O)_r(CR^{C6}R^{D6})_t$—, —$(CR^{C6}R^{D6})_uS(O)_rNR^{A6}(CR^{C6}R^{D6})_t$—, —$(CR^{C6}R^{D6})_uNR^{A6}S(O)_r(CR^{C6}R^{D6})_t$— and —$(CR^{C6}R^{D6})_uNR^{A1}S(O)_rNR^{B6}(CR^{C6}R^{D6})_t$—;

$L^3$ is selected from —$(CR^{C7}R^{D7})_u$—, —$(CR^{C7}R^{D7})_uO(CR^{C7}R^{D7})_t$—, —$(CR^{C7}R^{D7})_uNR^{A7}(CR^{C7}R^{D7})_t$—, —$(CR^{C7}R^{D7})_uS(CR^{C7}R^{D7})_t$—, —$(CR^{C7}R^{D7})_uC(O)(CR^{C7}R^{D7})_t$—, —$(CR^{C7}R^{D7})_uC(=NR^{E7})(CR^{C7}R^{D7})_t$—, —$(CR^{C7}R^{D7})_uC(S)(CR^{C7}R^{D7})_t$—, —$(CR^{C7}R^{D7})_uC(O)O(CR^{C7}R^{D7})_t$—, —$(CR^{C7}R^{D7})_uOC(O)(CR^{C7}R^{D7})_t$—, —(CR$^{C7}$R$^{D7}$)$_u$C(O)NR$^{A7}$(CR$^{C7}$R$^{D7}$)$_t$—, —(CR$^{C7}$R$^{D7}$)$_u$NR$^{A7}$C(O)(CR$^{C7}$R$^{D7}$)$_t$—, —(CR$^{C7}$R$^{D7}$)$_u$NR$^{A7}$C(O)NR$^{B7}$(CR$^{C7}$R$^{D7}$)$_t$—, —(CR$^{C7}$R$^{D7}$)$_u$C(=NR$^{E7}$)NR$^{B7}$(CR$^{C7}$R$^{D7}$)$_t$—, —(CR$^{C7}$R$^{D7}$)$_u$NR$^{B7}$C(=NR$^{E7}$)(CR$^{C7}$R$^{D7}$)$_t$—, —(CR$^{C7}$R$^{D7}$)$_u$NR$^{A7}$C(=NR$^{E7}$)NR$^{B7}$(CR$^{C7}$R$^{D7}$)$_t$—, —(CR$^{C7}$R$^{D7}$)$_u$C(S)NR$^{A7}$(CR$^{C7}$R$^{D7}$)$_t$—, —(CR$^{C7}$R$^{D7}$)$_u$NR$^{A7}$C(S)(CR$^{C7}$R$^{D7}$)$_t$—, —(CR$^{C7}$R$^{D7}$)$_u$NR$^{A7}$C(S)NR$^{B7}$(CR$^{C7}$R$^{D7}$)$_t$—, —(CR$^{C7}$R$^{D7}$)$_u$S(O)$_r$(CR$^{C7}$R$^{D7}$)$_t$—, —(CR$^{C7}$R$^{D7}$)$_u$S(O)$_r$NR$^{A7}$(CR$^{C7}$R$^{D7}$)$_t$—, —(CR$^{C7}$R$^{D7}$)$_u$NR$^{A7}$S(O)$_r$(CR$^{C7}$R$^{D7}$)$_t$— and —(CR$^{C7}$R$^{D7}$)$_u$NR$^{A7}$S(O)$_r$NR$^{B7}$(CR$^{C7}$R$^{D7}$)$_t$—;

W is selected from NR$^{E9}$ and O;

X$^1$ and X$^2$ are independently selected from C and N;

Y$^1$, Y$^2$ and Y$^3$ are independently selected from C and N;

Z is selected from C and N;

Q$^1$ and Q$^2$ are independently selected from aryl and heteroaryl, wherein aryl and heteroaryl are each unsubstituted or substituted with at least one substituent, such as one, two, three or four substituents, independently selected from R$^X$;

When W is O, Q$^3$ is heterocyclyl containing the moiety —(O=)S(=NR$^{E8}$)—, —(R$^{E8}$N=)S(=NR$^{E8'}$)— or —P(O)(R$^{A8}$)— as a ring member, wherein heterocyclyl is unsubstituted or substituted with at least one substituent, such as one, two, three or four substituents, independently selected from R$^X$, or Q$^3$ is heterocyclyl or cycloalkyl which is substituted with at least one substituent, such as one, two, three, or four substituents, independently selected from —(CR$^{C8}$R$^{D8}$)$_t$N=S(=O)R$^{A8}$R$^{B8}$, —(CR$^{C8}$R$^{D8}$)$_t$N=S(=NR$^{E8}$)R$^{A8}$R$^{B8}$, —C(O)N=S(=O)R$^{A8}$R$^{B8}$, —(CR$^{C8}$R$^{D8}$)$_t$(R$^{E8}$N=)S(=O)R$^{A8}$, —N(R$^{A8}$)(R$^{E8}$N=)S(=O)R$^{B8}$, —(CR$^{C8}$R$^{D8}$)$_t$N(R$^{A8}$)(R$^{B8}$N=)S(=O)R$^{B8}$, —(R$^{E8}$N=)S(=O)NR$^{A8}$R$^{B8}$, —P(O)R$^{A8}$R$^{B8}$, —P(O)(OR$^{A8}$)(OR$^{B8}$), —(CR$^{C8}$R$^{D8}$)$_t$P(O)R$^{A8}$R$^{B8}$, —(CR$^{C8}$R$^{D8}$)$_t$P(O)(OR$^{A8}$)(OR$^{B8}$);

When W is NR$^{E9}$, Q$^3$ is selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, —CN, —NO$_2$, —NR$^{A8}$R$^{B8}$, —OR$^{A8}$, —S(O)$_r$R$^{A8}$, —S(O)$_2$OR$^{A8}$, —OS(O)$_2$R$^{A8}$, —P(O)R$^{A8}$R$^{B8}$, —P(O)(OR$^{A8}$)(OR$^{B8}$), —C(O)R$^{A8}$, —C(O)OR$^{A8}$, —OC(O)R$^{A8}$, —C(O)NR$^{A8}$R$^{B8}$, —NR$^{A8}$C(O)R$^{B8}$, —OC(O)NR$^{A8}$R$^{B8}$, —NR$^{A8}$C(O)OR$^{B8}$, —NR$^{A8}$C(O)NR$^{A8}$R$^{B8}$, —NR$^{A8}$C(S)NR$^{A8}$R$^{B8}$, —S(O)$_r$NR$^{A8}$R$^{B8}$, —NR$^{A8}$S(O)$_r$R$^{B8}$, —NR$^{A8}$S(O)$_2$NR$^{A8}$R$^{B8}$, —S(O)(=NR$^{E8}$)R$^{B8}$, —N=S(O)R$^{A8}$R$^{B8}$, —NR$^{A8}$S(O)(=NR$^{E8}$)R$^{B8}$, —S(O)(=NR$^{E8}$)NR$^{A8}$R$^{B8}$, —NR$^{A8}$S(O)(=NR$^{E8}$)NR$^{A8}$R$^{B8}$, —C(=NR$^{E8}$)R$^{A8}$, —C(=N—OR$^{B8}$)R$^{A8}$, —C(=NR$^{E8}$)NR$^{A8}$R$^{B8}$, —NR$^{A8}$C(=NR$^{E8}$)R$^{B8}$ and —NR$^{A8}$C(=NR$^{E8}$)NR$^{A8}$R$^{B8}$, wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

each R$^1$ is independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, —CN, —NO$_2$, —NR$^{A1}$R$^{B1}$, —OR$^{A1}$, —S(O)$_r$R$^{A1}$, —S(O)$_2$OR$^{A1}$, —OS(O)$_2$R$^{A1}$, —P(O)R$^{A1}$R$^{B1}$, —P(O)(OR$^{A1}$)(OR$^{B1}$), —C(O)R$^{A1}$, —C(O)OR$^{A1}$, —OC(O)R$^{A1}$, —C(O)NR$^{A1}$R$^{B1}$, —NR$^{A1}$C(O)R$^{B1}$, —OC(O)NR$^{A1}$R$^{B1}$, —NR$^{A1}$C(O)OR$^{B1}$, —NR$^{A1}$C(O)NR$^{A1}$R$^{B1}$, —NR$^{A1}$C(S)NR$^{A1}$R$^{B1}$, —S(O)$_r$NR$^{A1}$R$^{B1}$, —NR$^{A1}$S(O)$_r$R$^{B1}$, —NR$^{A1}$S(O)$_2$NR$^{A1}$R$^{B1}$, —S(O)(=NR$^{E1}$)R$^{B1}$, —N=S(O)R$^{A1}$R$^{B1}$, —NR$^{A1}$S(O)(=NR$^{E1}$)R$^{B1}$, —S(O)(=NR$^{E1}$)NR$^{A1}$R$^{B1}$, —NR$^{A1}$S(O)(=NR$^{E1}$)NR$^{A1}$R$^{B1}$, —C(=NR$^{E1}$)R$^{A1}$, —C(=N—OR$^{B1}$)R$^{A1}$, —C(=NR$^{E1}$)NR$^{A1}$R$^{B1}$, —NR$^{A1}$C(=NR$^{E1}$)R$^{B1}$ and —NR$^{A1}$C(=NR$^{E1}$)NR$^{A1}$R$^{B1}$, wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

each R$^2$ is independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, —CN, —NO$_2$, —NR$^{A2}$R$^{B2}$, —OR$^{A2}$, —S(O)$_r$R$^{A2}$, —S(O)$_2$OR$^{A2}$, —OS(O)$_2$R$^{A2}$, —P(O)R$^{A2}$R$^{B2}$, —P(O)(OR$^{A2}$)(OR$^{B2}$), —C(O)R$^{A2}$, —C(O)OR$^{A2}$, —OC(O)R$^{A2}$, —C(O)NR$^{A2}$R$^{B2}$, —NR$^{A2}$C(O)R$^{B2}$, —OC(O)NR$^{A2}$R$^{B2}$, —NR$^{A2}$C(O)OR$^{B2}$, —NR$^{A2}$C(O)NR$^{A2}$R$^{B2}$, —NR$^{A2}$C(S)NR$^{A2}$R$^{B2}$, —S(O)$_r$NR$^{A2}$R$^{B2}$, —NR$^{A2}$S(O)$_r$R$^{B2}$, —NR$^{A2}$S(O)$_2$NR$^{A2}$R$^{B2}$, —S(O)(=NR$^{E2}$)R$^{B2}$, —N=S(O)R$^{A2}$R$^{B2}$, —NR$^{A2}$S(O)(=NR$^{E2}$)R$^{B2}$, —S(O)(=NR$^{E2}$)NR$^{A2}$R$^{B2}$, —NR$^{A2}$S(O)(=NR$^{E2}$)NR$^{A2}$R$^{B2}$, —C(=NR$^{E2}$)R$^{A2}$, —C(=N—OR$^{B2}$)R$^{A2}$, —C(=NR$^{E2}$)NR$^{A2}$R$^{B2}$, —NR$^{A2}$C(=NR$^{E2}$)R$^{B2}$ and —RR$^{A2}$C(=NR$^{E2}$)NR$^{A2}$R$^{B2}$, wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

each R$^3$ is independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, —CN, —NO$_2$, —NR$^{A3}$R$^{B3}$, —OR$^{A3}$, —S(O)$_r$R$^{A3}$, —S(O)$_2$OR$^{A3}$, —OS(O)$_2$R$^{A3}$, —P(O)R$^{A3}$R$^{B3}$, —P(O)(OR$^{A3}$)(OR$^{B3}$), —C(O)R$^{A3}$, —C(O)OR$^{A3}$, —OC(O)R$^{A3}$, —C(O)NR$^{A3}$R$^{B3}$, —NR$^{A3}$C(O)R$^{B3}$, —OC(O)NR$^{A3}$R$^{B3}$, —NR$^{A3}$C(O)OR$^{B3}$, —NR$^{A3}$C(O)NR$^{A3}$R$^{B3}$, —NR$^{A3}$C(S)NR$^{A3}$R$^{B3}$, —S(O)$_r$NR$^{A3}$R$^{B3}$, —NR$^{A3}$S(O)$_r$R$^{B3}$, —NR$^{A3}$S(O)$_2$NR$^{A3}$R$^{B3}$, —S(O)(=NR$^{E3}$)R$^{B3}$, —N=S(O)R$^{A3}$R$^{B3}$, —NR$^{A3}$S(O(=NR$^{E3}$)R$^{B3}$, —S(O)(=NR$^{E3}$)NR$^{A3}$R$^{B3}$, —NR$^{A3}$S(O)(=NR$^{E3}$)NR$^{A3}$R$^{B3}$, —C(=NR$^{E3}$)R$^{A3}$, —C(=N—OR$^{B3}$)R$^{A3}$, —C(=NR$^{E3}$)NR$^{A3}$R$^{B3}$, —NR$^{A3}$C(=NR$^{E3}$)R$^{B3}$ and —NR$^{A3}$C(=NR$^{E3}$)NR$^{A3}$R$^{B3}$ wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

each R$^{4a}$ and R$^{4b}$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, —CN, —NO$_2$, —NR$^{A4}$R$^{B4}$, —OR$^{A4}$, —S(O)$_r$R$^{A4}$, —S(O)$_2$OR$^{A4}$, —OS(O)$_2$R$^{A4}$, —P(O)R$^{A4}$R$^{B4}$, —P(O)(OR$^{A4}$)(OR$^{B4}$), —C(O)R$^{A4}$, —C(O)OR$^{A4}$, —OC(O)R$^{A4}$, —C(O)NR$^{A4}$R$^{B4}$, —NR$^{A4}$C(O)R$^{B4}$, —OC(O)NR$^{A4}$R$^{B4}$, —NR$^{A4}$C(O)OR$^{B4}$, —NR$^{A4}$C(O)NR$^{A4}$R$^{B4}$, —NR$^{A4}$C(S)NR$^{A4}$R$^{B4}$, —S(O)$_r$NR$^{A4}$R$^{B4}$, —NR$^{A4}$S(O)$_r$R$^{B4}$, —NR$^{A4}$S(O)$_2$NR$^{A4}$R$^{B4}$, —S(O)(=NR$^{E4}$)R$^{B4}$, —N=S(O)R$^{A4}$R$^{B4}$, —NR$^{A4}$S(O)(=NR$^{E4}$)R$^{B4}$, —S(O)(=NR$^{E4}$)NR$^{A4}$R$^{B4}$, —NR$^{A4}$S(O)(=NR$^{E4}$)NR$^{A4}$R$^{B4}$, —C(=NR$^{E4}$)R$^{A4}$, —C(=N—OR$^{B4}$)R$^{A4}$, —C(=NR$^{E4}$)NR$^{A4}$R$^{B4}$, —NR$^{A4}$C(=NR$^{E4}$)R$^{B4}$ and —NR$^{A4}$C(=NR$^{E4}$)NR$^{A4}$R$^{B4}$, wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

or R$^{4a}$ and R$^{4b}$ together with the carbon atoms to which they are attached form a 3- to 7-membered ring containing 0, 1 or 2 heteroatoms independently selected from oxygen, sulfur, nitrogen, and phosphorus, and optionally substituted with 1, 2 or 3 $R^X$ groups;

each $R^{A1}$, $R^{A2}$, $R^{A3}$, $R^{A4}$, $R^{A5}$, $R^{A6}$, $R^{A7}$, $R^{A8}$, $R^{B1}$, $R^{B2}$, $R^{B3}$, $R^{B4}$, $R^{B5}$, $R^{B6}$, $R^{B7}$ and $R^{B8}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from $R^X$;

or each "$R^{A1}$ and $R^{B1}$", "$R^{A2}$ and $R^{B2}$", "$R^{A3}$ and $R^{B3}$", "$R^{A4}$ and $R^{B4}$", "$R^{A5}$ and $R^{B5}$", "$R^{A6}$ and $R^{B6}$", "$R^{A7}$ and $R^{B7}$" and "$R^{A8}$ and $R^{B8}$" together with the atom(s) to which they are attached form a 4- to 12-membered heterocyclic ring containing 0, 1 or 2 additional heteroatoms independently selected from oxygen, sulfur, nitrogen and phosphorus, and optionally substituted with 1, 2 or 3 $R^X$ groups;

each $R^{C5}$, $R^{C6}$, $R^{C7}$, $R^{C8}$, $R^{D5}$, $R^{D6}$, $R^{D7}$ and $R^{D8}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

or each "$R^{C5}$ and $R^{D5}$", "$R^{C6}$ and $R^{D6}$", "$R^{C7}$ and $R^{D7}$" and "$R^{C8}$ and $R^{D8}$" together with the carbon atom(s) to which they are attached form a 3- to 12-membered ring containing 0, 1 or 2 heteroatoms independently selected from oxygen, sulfur and nitrogen, and optionally substituted with 1, 2 or 3 $R^X$ groups;

each $R^{E1}$, $R^{E2}$, $R^{E3}$, $R^{E4}$, $R^{E5}$, $R^{E7}$, $R^{E8}$, $R^{E8'}$ and $R^{E9}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —NO$_2$, —OR$^{a1}$, —SR$^{a1}$, —S(O)$_r$R$^{a1}$, —C(O)R$^{a1}$, C(O)OR$^{a1}$, —C(O)NR$^{a1}$R$^{b1}$ and —S(O)$_r$NR$^{a1}$R$^{b1}$, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

each $R^X$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, —CN, —NO$_2$, —(CR$^{c1}$R$^{d1}$)$_t$NR$^{a1}$R$^{b1}$, —(CR$^{c1}$R$^{d1}$)$_t$OR$^{b1}$, —(CR$^{c1}$R$^{d1}$)$_t$S(O)$_r$R$^{b1}$, —(CR$^{c1}$R$^{d1}$)$_t$S(O)$_2$OR$^{b1}$, —(CR$^{c1}$R$^{d1}$)$_t$OS(O)$_2$R$^{b1}$, —(CR$^{c1}$R$^{d1}$)$_t$P(O)R$^{a1}$R$^{b1}$, —(CR$^{c1}$R$^{d1}$)$_t$P(O)(OR$^{a1}$)(OR$^{b1}$), —(CR$^{c1}$R$^{d1}$)$_t$C(O)R$^{a1}$, —(CR$^{c1}$R$^{d1}$)$_t$C(O)OR$^{b1}$, —(CR$^{c1}$R$^{d1}$)$_t$OC(O)R$^{b1}$, —(CR$^{c1}$R$^{d1}$)$_t$C(O)NR$^{a1}$R$^{b1}$, —(CR$^{c1}$R$^{d1}$)$_t$NR$^{a1}$C(O)R$^{b1}$, —(CR$^{c1}$R$^{d1}$)$_t$OC(O)NR$^{a1}$R$^{b1}$, —(CR$^{c1}$R$^{d1}$)$_t$NR$^{a1}$C(O)OR$^{b1}$, —(CR$^{c1}$R$^{d1}$)$_t$NR$^{a1}$C(O)NR$^{a1}$R$^{b1}$, —(CR$^{c1}$R$^{d1}$)$_t$NR$^{a1}$C(S)NR$^{a1}$R$^{b1}$, —(CR$^{c1}$R$^{d1}$)$_t$S(O)$_r$NR$^{a1}$R$^{b1}$, —(CR$^{c1}$R$^{d1}$)$_t$NR$^{a1}$S(O)$_r$R$^{b1}$, —(CR$^{c1}$R$^{d1}$)$_t$NR$^{a1}$S(O)$_2$NR$^{a1}$R$^{b1}$, —(CR$^{c1}$R$^{d1}$)$_t$S(O)(=NR$^{e1}$)R$^{b1}$, —(CR$^{c1}$R$^{d1}$)$_t$N=S(O)R$^{a1}$R$^{b1}$, —(CR$^{c1}$R$^{d1}$)$_t$NR$^{a1}$S(O)(=NR$^{e1}$)R$^{b1}$, —(CR$^{c1}$R$^{d1}$)$_t$S(O)(=NR$^{e1}$)NR$^{a1}$R$^{b1}$, —(CR$^{c1}$R$^{d1}$)$_t$NR$^{a1}$S(O)(=NR$^{e1}$)NR$^{a1}$R$^{b1}$, —(CR$^{c1}$R$^{d1}$)$_t$C(=NR$^{e1}$)R$^{a1}$, —(CR$^{c1}$R$^{d1}$)$_t$C(=N—OR$^{b1}$)R$^{a1}$, —(CR$^{c1}$R$^{d1}$)$_t$C(=NR$^{e1}$)NR$^{a1}$R$^{b1}$, —(CR$^{c1}$R$^{d1}$)$_t$NR$^{a1}$C(=NR$^{e1}$)R$^{b1}$ and —(CR$^{c1}$R$^{d1}$)$_t$NR$^{a1}$C(=NR$^{e1}$)NR$^{a1}$R$^{b1}$, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

each $R^{a1}$ and each $R^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

or $R^{a1}$ and $R^{b1}$ together with the atom(s) to which they are attached form a 4- to 12-membered heterocyclic ring containing 0, 1 or 2 additional heteroatoms independently selected from oxygen, sulfur, nitrogen and phosphorus, and optionally substituted with 1, 2 or 3 $R^Y$ groups;

each $R^{c1}$ and each $R^{d1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

or $R^{c1}$ and $R^{d1}$ together with the carbon atom(s) to which they are attached form a 3- to 12-membered ring containing 0, 1 or 2 heteroatoms independently selected from oxygen, sulfur and nitrogen, and optionally substituted with 1, 2 or 3 $R^Y$ groups;

each $R^{e1}$ is independently selected from hydrogen, $C_{1-10}$ alkyl, $C_{3-10}$ cycloalkyl, $C_{3-10}$ cycloalkyl-$C_{1-4}$ alkyl, —CN, —NO$_2$, —OR$^{a2}$, —SR$^{a2}$, —S(O)$_r$R$^{a2}$, —S(O)$_r$NR$^{a2}$R$^{b2}$, —C(O)R$^{a2}$, —C(O)OR$^{a2}$ and —C(O)NR$^{a2}$R$^{b2}$;

$R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, —CN, —NO$_2$, —(CR$^{c2}$R$^{d2}$)$_t$NR$^{a2}$R$^{b2}$, —(CR$^{c2}$R$^{d2}$)$_t$OR$^{b2}$, —(CR$^{c2}$R$^{d2}$)$_t$S(O)$_r$R$^{b2}$, —(CR$^{c2}$R$^{d2}$)$_t$S(O)$_2$OR$^{b2}$, —(CR$^{c2}$R$^{d2}$)$_t$OS(O)$_2$R$^{b2}$, —(CR$^{c2}$R$^{d2}$)$_t$P(O)R$^{a2}$R$^{b2}$, —(CR$^{c2}$R$^{d2}$)$_t$P(O)(OR$^{a2}$)(OR$^{b2}$), —(CR$^{c2}$R$^{d2}$)$_t$C(O)R$^{a2}$, —(CR$^{c2}$R$^{d2}$)$_t$C(O)OR$^{b2}$, —(CR$^{c2}$R$^{d2}$)$_t$OC(O)R$^{b2}$, —(CR$^{c2}$R$^{d2}$)$_t$C(O)NR$^{a2}$R$^{b2}$, —(CR$^{c2}$R$^{d2}$)$_t$NR$^{a2}$C(O)R$^{b2}$, —(CR$^{c2}$R$^{d2}$)$_t$OC(O)NR$^{a2}$R$^{b2}$, —(CR$^{c2}$R$^{d2}$)$_t$NR$^{a2}$C(O)OR$^{b2}$, —(CR$^{c2}$R$^{d2}$)$_t$NR$^{a2}$C(O)NR$^{a2}$R$^{b2}$, —(CR$^{c2}$R$^{d2}$)$_t$NR$^{a2}$C(S)NR$^{a2}$R$^{b2}$, —(CR$^{c2}$R$^{d2}$)$_t$S(O)$_r$NR$^{a2}$R$^{b2}$, —(CR$^{c2}$R$^{d2}$)$_t$NR$^{a2}$S(O)$_r$R$^{b2}$, —(CR$^{c2}$R$^{d2}$)$_t$NR$^{a2}$S(O)$_2$NR$^{a2}$R$^{b2}$, —(CR$^{c2}$R$^{d2}$)$_t$S(O)(=NR$^{e2}$)R$^{b2}$, —(CR$^{c2}$R$^{d2}$)$_t$N=S(O)R$^{a2}$R$^{b2}$, —(CR$^{c2}$R$^{d2}$)$_t$NR$^{a2}$S(O)(=NR$^{e2}$)R$^{b2}$, —(CR$^{c2}$R$^{d2}$)$_t$S(O)(=NR$^{e2}$)NR$^{a2}$R$^{b2}$, —(CR$^{c2}$R$^{d2}$)$_t$NR$^{a2}$S(O)(=NR$^{e2}$)NR$^{a2}$R$^{b2}$, —(CR$^{c2}$R$^{d2}$)$_t$C(=NR$^{e2}$)R$^{a2}$, —(CR$^{c2}$R$^{d2}$)$_t$C(=N—OR$^{b2}$)R$^{a2}$, —(CR$^{c2}$R$^{d2}$)$_t$C(=NR$^{e2}$)NR$^{a2}$R$^{b2}$, —(CR$^{c2}$R$^{d2}$)$_t$NR$^{a2}$C(=NR$^{e2}$)R$^{b2}$ and —(CR$^{c2}$R$^{d2}$)$_t$NR$^{a2}$C(=NR$^{e2}$)NR$^{a2}$R$^{b2}$, wherein alkyl, alkenyl, alkynyl, cycloalkyl, heterocyclyl, aryl and heteroaryl are each unsubstituted or substituted with at least one substituent, such as one, two, three or four substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a2}$ and $R^{b2}$ together with the atom(s) to which they are attached form a 4- to 12-membered heterocyclic ring containing 0, 1 or 2 additional heteroatoms independently selected from oxygen, sulfur, nitrogen and phosphorus, and optionally substituted with 1 or 2 substituents, independently selected from halogen, —CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a 3- to 12-membered ring containing 0, 1 or 2 heteroatoms independently selected from oxygen, sulfur and nitrogen, and optionally substituted with 1 or 2 substituents, independently selected from halogen, —CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, —CN, —NO$_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, —C(O)$C_{1-4}$ alkyl, —C(O)$C_{3-10}$ cycloalkyl, —C(O)O$C_{1-4}$ alkyl, —C(O)O$C_{3-10}$ cycloalkyl, —C(O)NH$_2$, —C(O)NH($C_{1-4}$ alkyl), —C(O)N($C_{1-4}$ alkyl)$_2$, —C(O)NH($C_{3-10}$ cycloalkyl), —C(O)N($C_{3-10}$ cycloalkyl)$_2$, —S(O)$_2$$C_{1-4}$ alkyl, —S(O)$_2$$C_{3-10}$ cycloalkyl, —S(O)$_2$NH$_2$, —S(O)$_2$NH($C_{1-4}$ alkyl), —S(O)$_2$N($C_{1-4}$ alkyl)$_2$, —S(O)$_2$NH($C_{3-10}$ cycloalkyl) and —S(O)$_2$N($C_{3-10}$ cycloalkyl)$_2$;

m is selected from 0, 1, 2, 3 and 4;
n is selected from 0, 1, 2 and 3;
p is selected from 0, 1, 2, 3 and 4;
each r is independently selected from 0, 1 and 2;
each t is independently selected from 0, 1, 2, 3 and 4;
each u is independently selected from 0, 1, 2, 3 and 4.

In another Embodiment (2), the invention provides a compound of Embodiment (1) or a pharmaceutically acceptable salt thereof, wherein W is O.

In another Embodiment (3), the invention provides a compound of Embodiment (1) or a pharmaceutically acceptable salt thereof, wherein $Q^3$ is heterocyclyl containing the moiety —(O═O)S(═NR$^{E8}$)— or —P(O)(R$^{A8}$)— as a ring member, wherein heterocyclyl is unsubstituted or substituted with at least one substituent independently selected from R$^X$.

In another Embodiment (4), the invention provides a compound of Embodiment (1) or a pharmaceutically acceptable salt thereof, wherein $Q^3$ is selected from

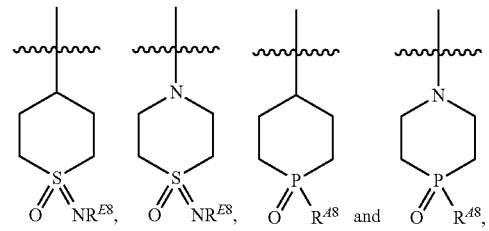

which is unsubstituted or substituted with at least one substituent independently selected from R$^X$, wherein the ⌇⌇⌇ symbol indicates the point of attachment to the rest of the molecule.

In another Embodiment (5), the invention provides a compound of any one of Embodiments (1)-(4) or a pharmaceutically acceptable salt thereof, wherein R$^{E8}$ is selected from hydrogen, $C_{3-10}$ cycloalkyl, —CN, —S(O)$_r$R$^{a1}$, —C(O)R$^{a1}$, —C(O)OR$^{a1}$, —C(O)NR$^{a1}$R$^{b1}$.

In another Embodiment (6), the invention provides a compound of any one of Embodiments (1)-(4) or a pharmaceutically acceptable salt thereof, wherein R$^{A8}$ is selected from $C_{1-10}$ alkyl.

In another Embodiment (7), the invention provides a compound of Embodiment (1) or a pharmaceutically acceptable salt thereof, wherein $Q^3$ is selected from $C_{4-6}$ cycloalkyl and heteroaryl, which is substituted with —(CR$^{C8}$R$^{D8}$)$_t$N═S(═O)R$^{A8}$R$^{B8}$ or —N(R$^{A8}$)(R$^{E8}$N═)S(═O)R$^{B8}$.

In another Embodiment (8), the invention provides a compound of Embodiment (7) or a pharmaceutically acceptable salt thereof, wherein $Q^3$ is selected from cyclobutyl, cyclohexyl, piperidinyl, tetrahydro-2H-pyranyl, which is substituted with —N═S(═O)R$^{A8}$R$^{B8}$ or —N(R$^{A8}$)(R$^{E8}$N═)S(═O)R$^{B8}$, wherein R$^{A8}$ and R$^{B8}$ are independently selected from $C_{1-10}$ alkyl, or R$^{A8}$ and R$^{B8}$ together with the sulfur atom to which they are attached form a 4- to 6-membered heterocyclic ring of containing 0, 1 or 2 additional heteroatoms independently selected from oxygen, sulfur, nitrogen and phosphorus, and optionally substituted with 1, 2 or 3 R$^X$ groups.

In another Embodiment (9), the invention provides a compound of any one of Embodiments (1)-(8) or a pharmaceutically acceptable salt thereof, wherein L$^3$ is —N(R$^{41}$)(CR$^{C1}$R$^{D1}$)$_t$—.

In another Embodiment (10), the invention provides a compound of any one of Embodiments (1)-(9) or a pharmaceutically acceptable salt thereof, wherein Y$^1$, Y$^2$ and Y$^3$ are C.

In another Embodiment (11), the invention provides a compound of any one of Embodiments (1)-(10) or a pharmaceutically acceptable salt thereof, wherein m is 1 and R$^1$ is selected from NO$_2$ and S(═O)$_2$CF$_3$.

In another Embodiment (12), the invention provides a compound of any one of Embodiments (1)-(11) or a pharmaceutically acceptable salt thereof, wherein L$^2$ is selected from O and S.

In another Embodiment (13), the invention provides a compound of any one of Embodiments (1)-(12) or a pharmaceutically acceptable salt thereof, wherein $Q^2$ is

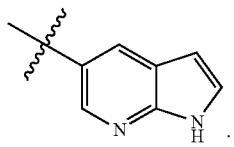 [SMILES: *c1cnc2[nH]ccc2c1]

In another Embodiment (14), the invention provides a compound of any one of Embodiments (1)-(13) or a pharmaceutically acceptable salt thereof, wherein Z is C.

In another Embodiment (15), the invention provides a compound of any one of Embodiments (1)-(14) or a pharmaceutically acceptable salt thereof, wherein $R^2$ is selected from hydrogen and halogen.

In another Embodiment (16), the invention provides a compound of any one of Embodiments (1)-(15) or a pharmaceutically acceptable salt thereof, wherein $X^1$ and $X^2$ are both N.

In another Embodiment (17), the invention provides a compound of any one of Embodiments (1)-(16) or a pharmaceutically acceptable salt thereof, wherein $R^3$ is hydrogen.

In another Embodiment (18), the invention provides a compound of any one of Embodiments (1)-(17) or a pharmaceutically acceptable salt thereof, wherein $L^1$ is —$CH_2$—.

In another Embodiment (19), the invention provides a compound of any one of Embodiments (1)-(18) or a pharmaceutically acceptable salt thereof, wherein $R^{4a}$ and $R^{4b}$ are both methyl.

In another Embodiment (20), the invention provides a compound of any one of Embodiments (1)-(19) or a pharmaceutically acceptable salt thereof, wherein $Q^1$ is

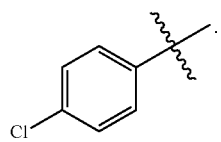 [SMILES: *c1ccc(Cl)cc1]

In another Embodiment (21), the invention provides a compound selected from

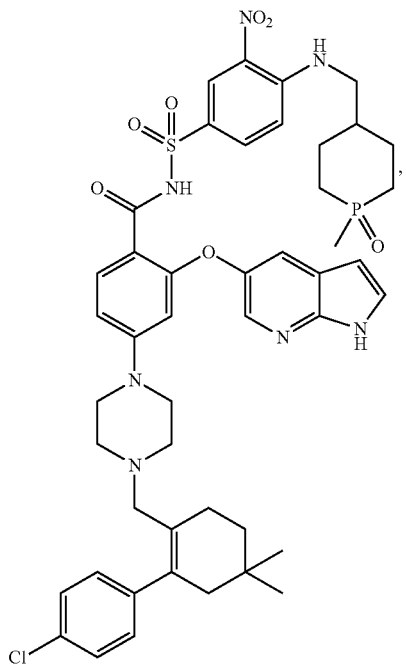

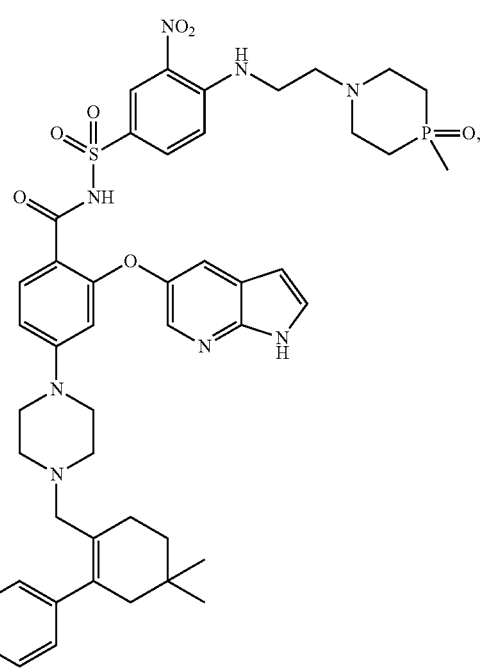

81
-continued
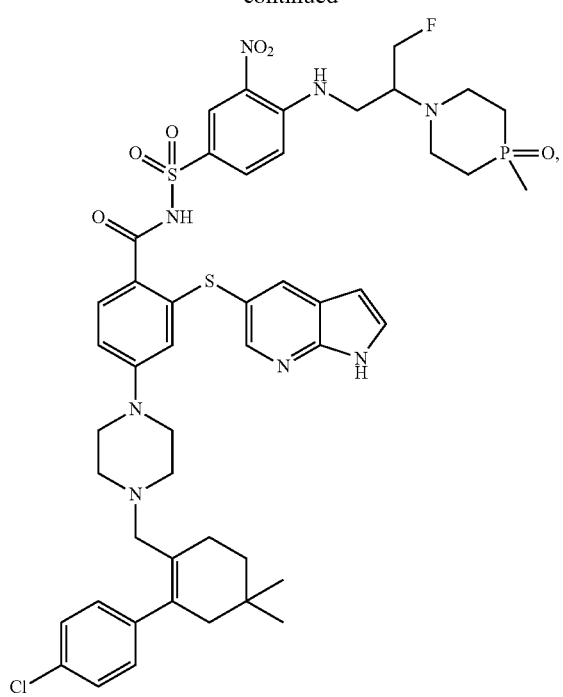
82
-continued
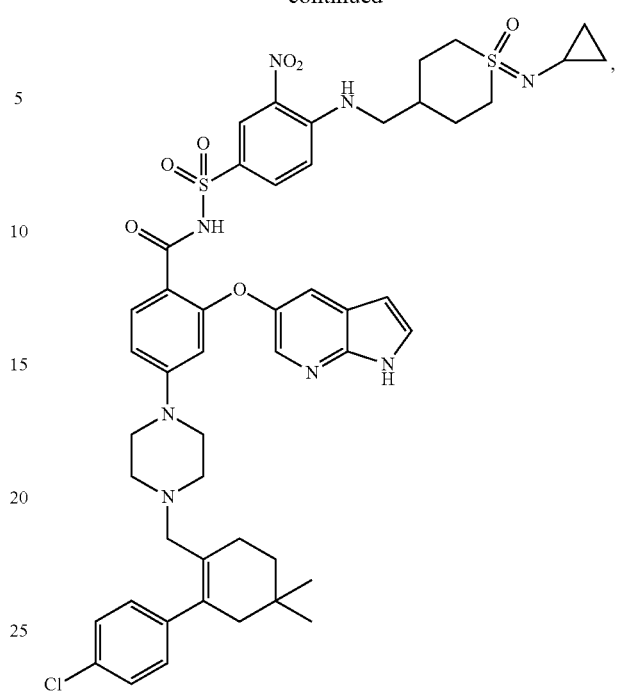
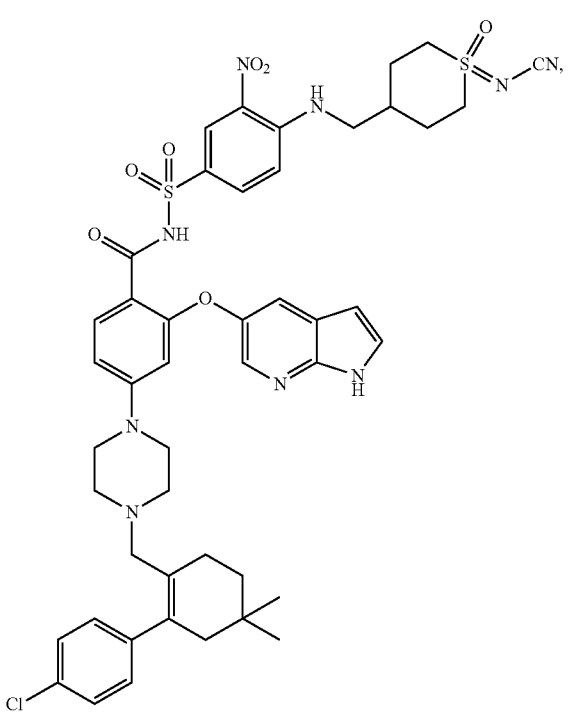
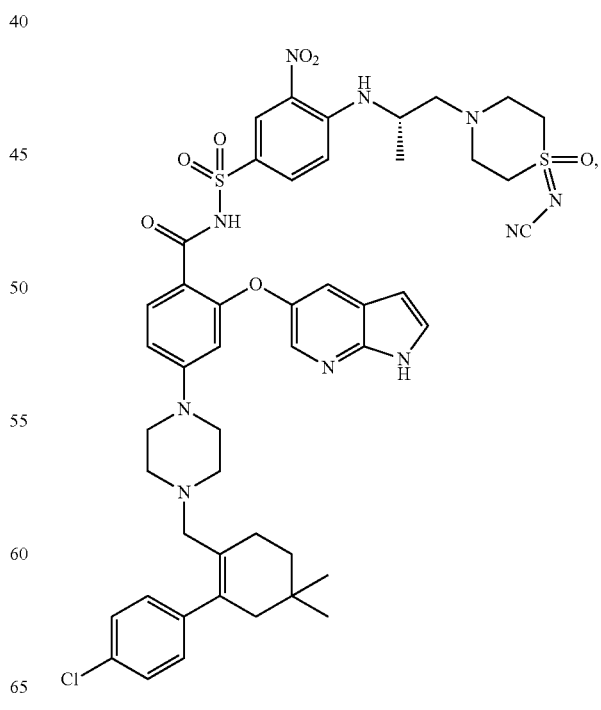

83
-continued
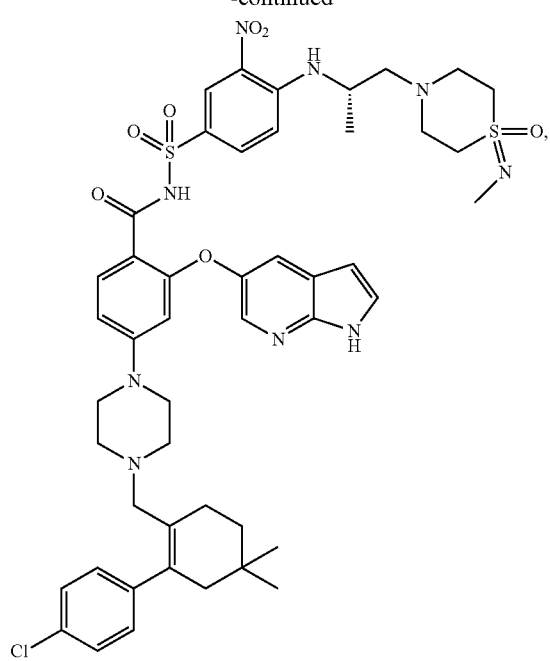
84
-continued
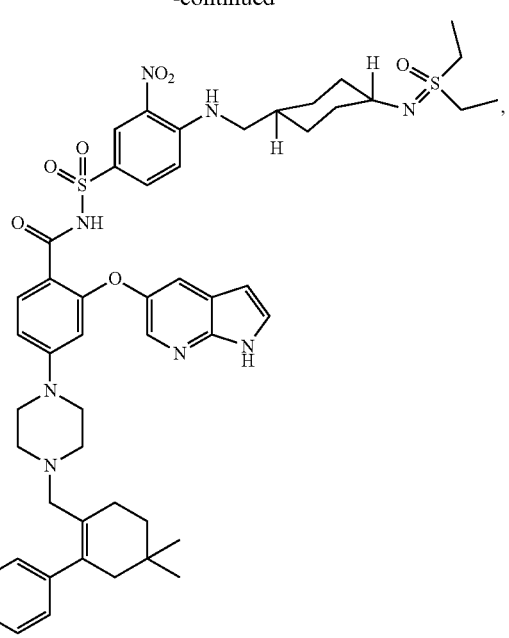
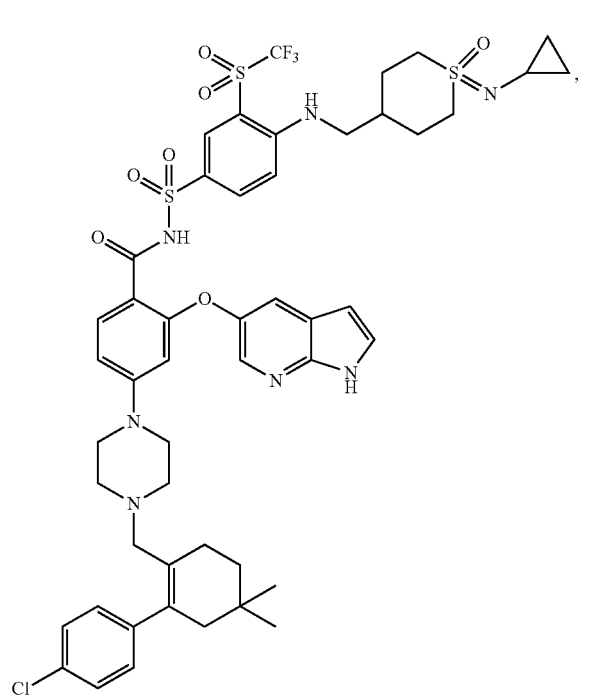
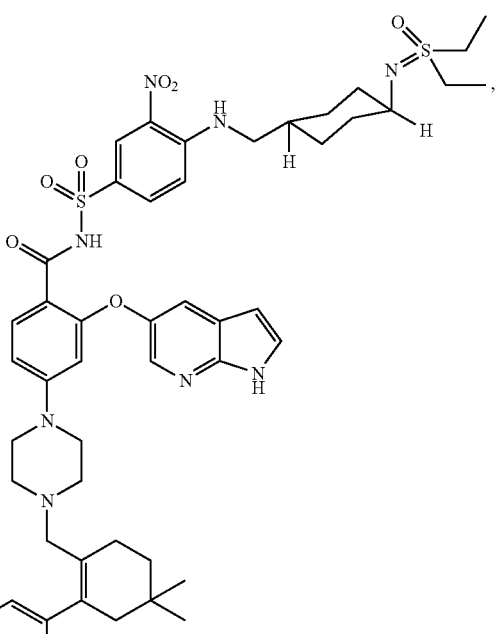

85
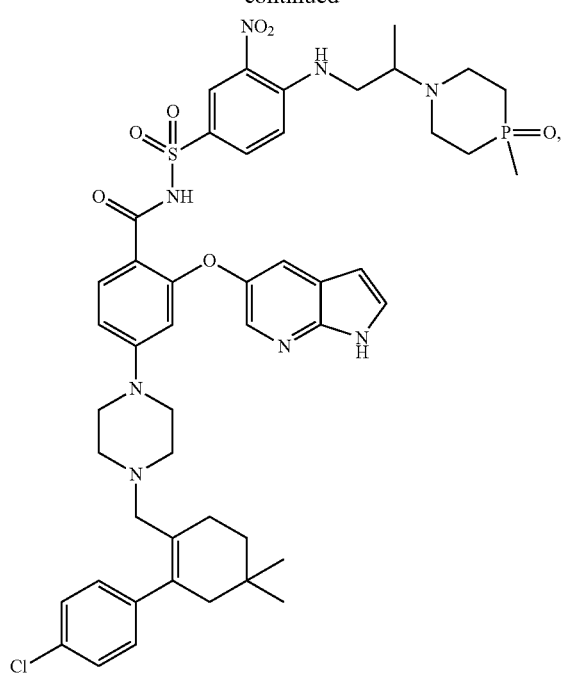
86
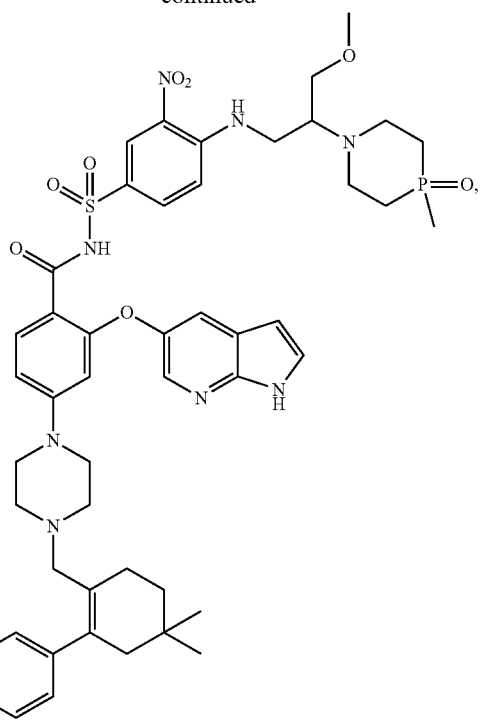
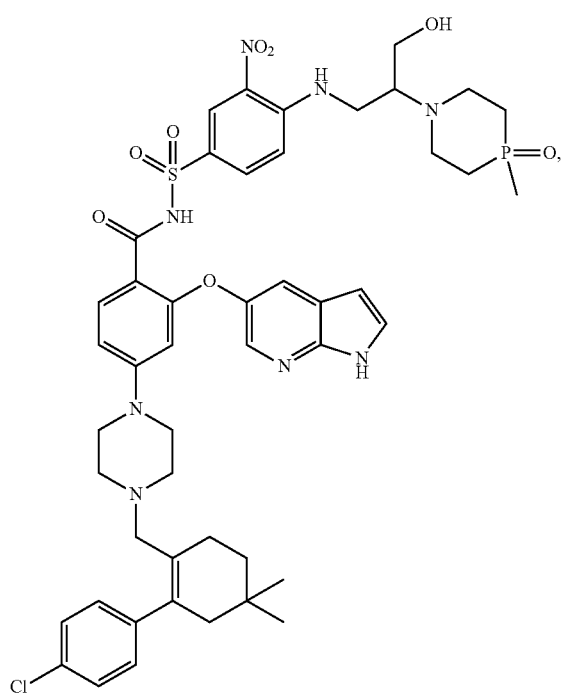
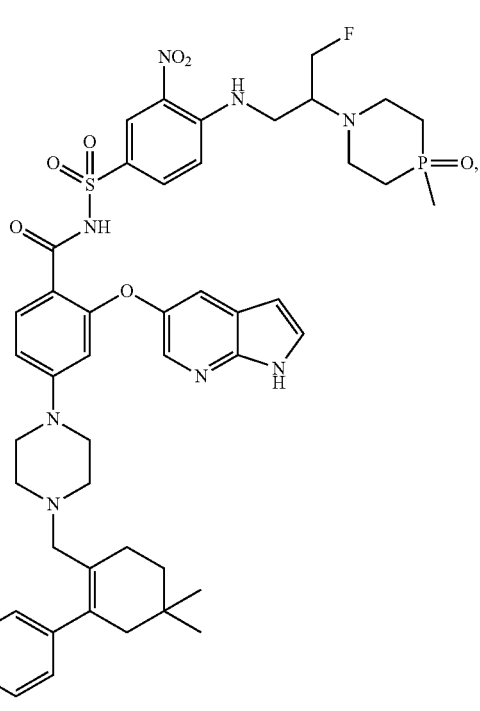

87
-continued
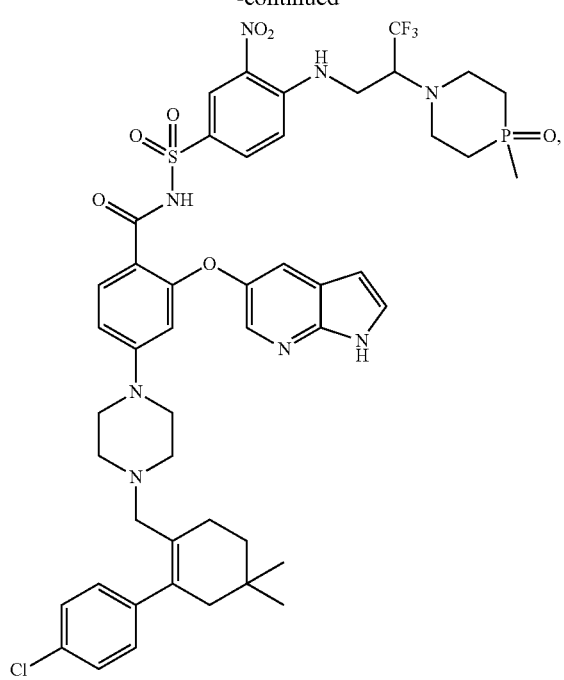
88
-continued
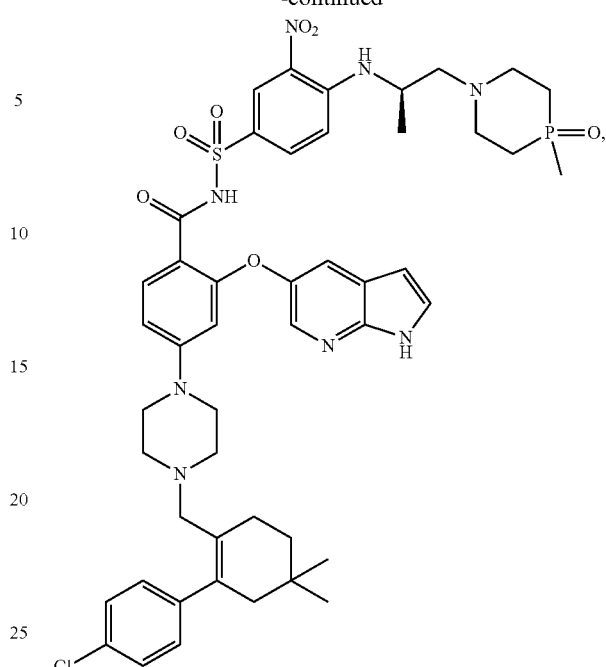
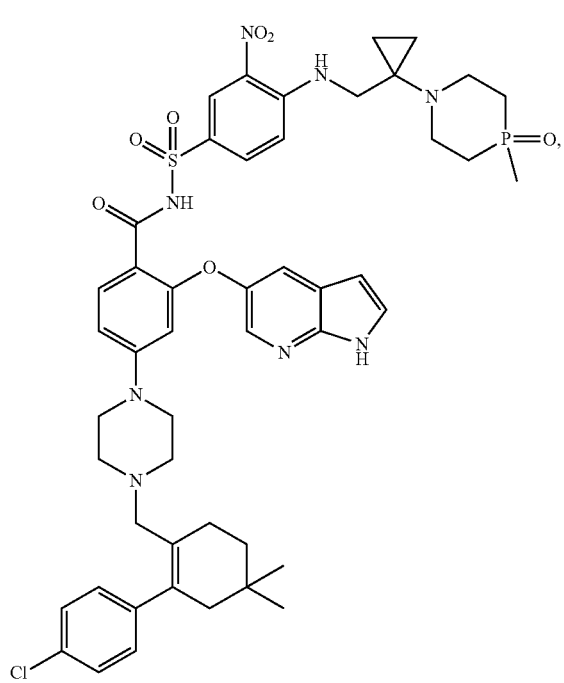
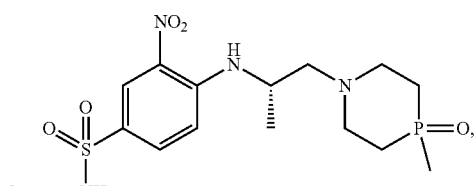

89
-continued
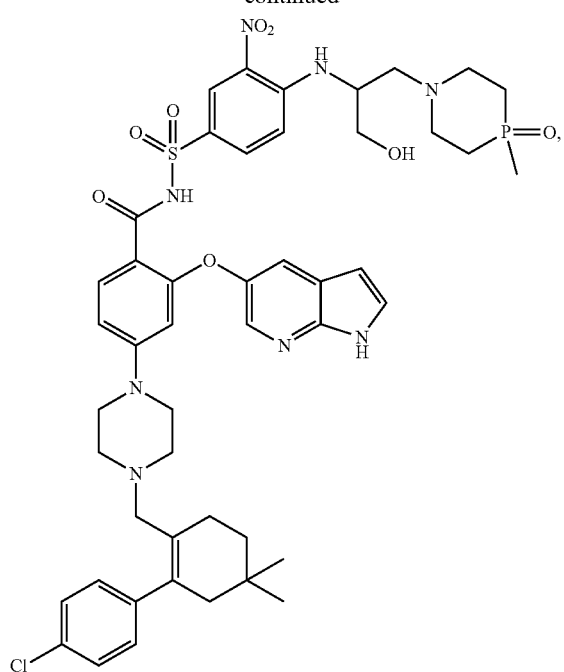
90
-continued
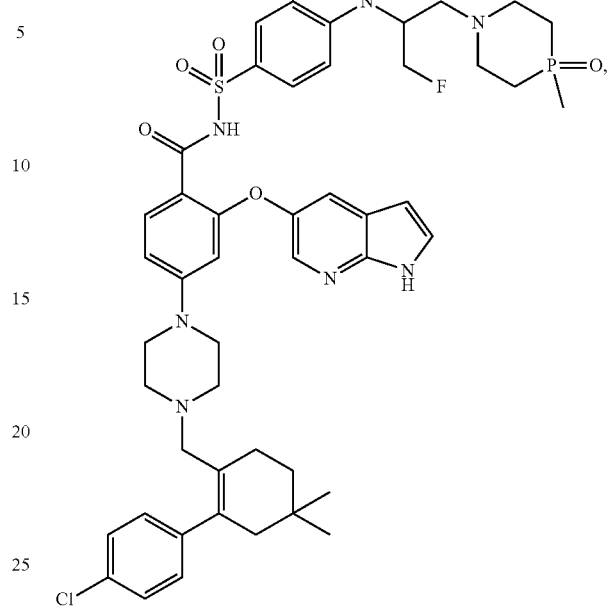
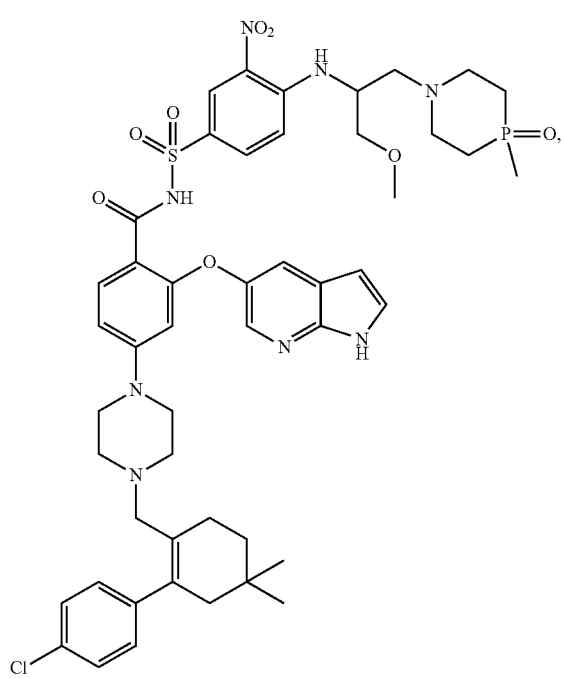

91
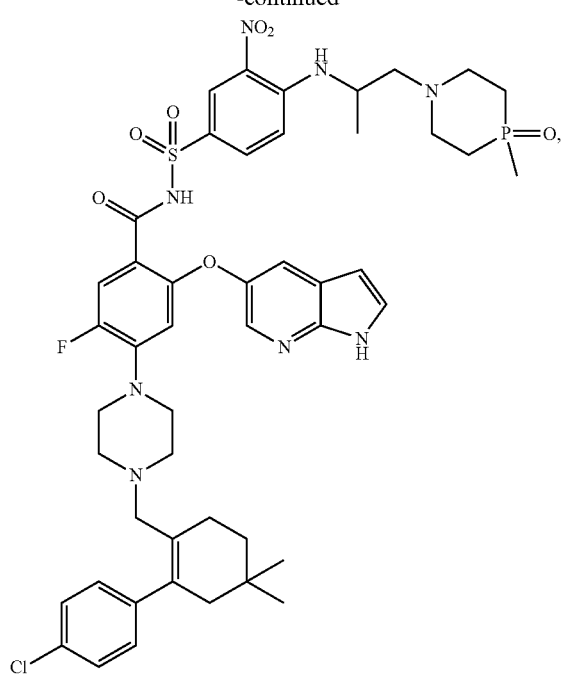
92
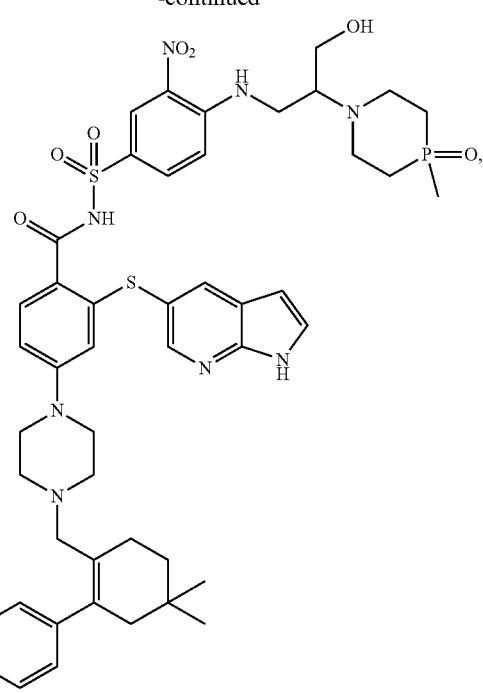
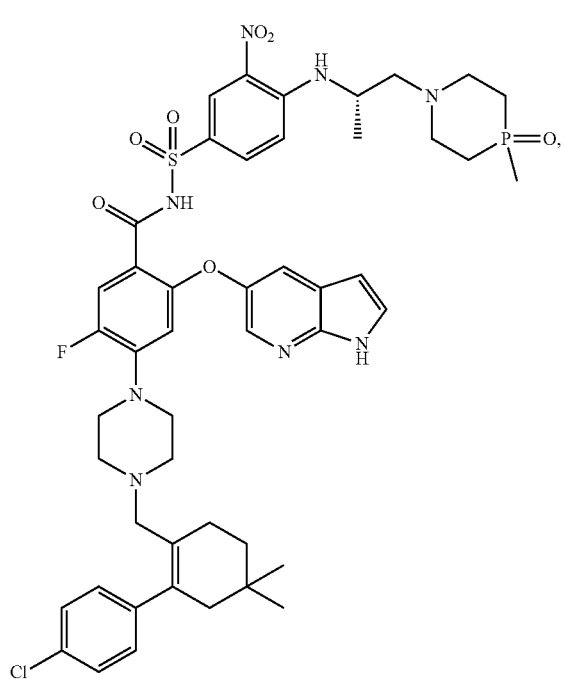
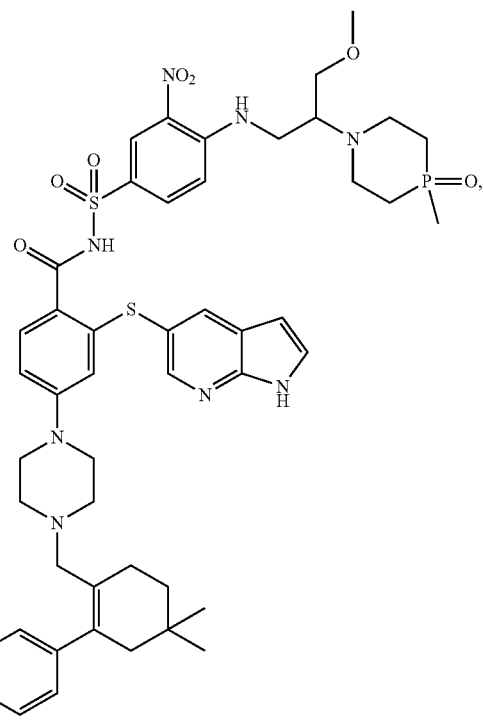

93
-continued
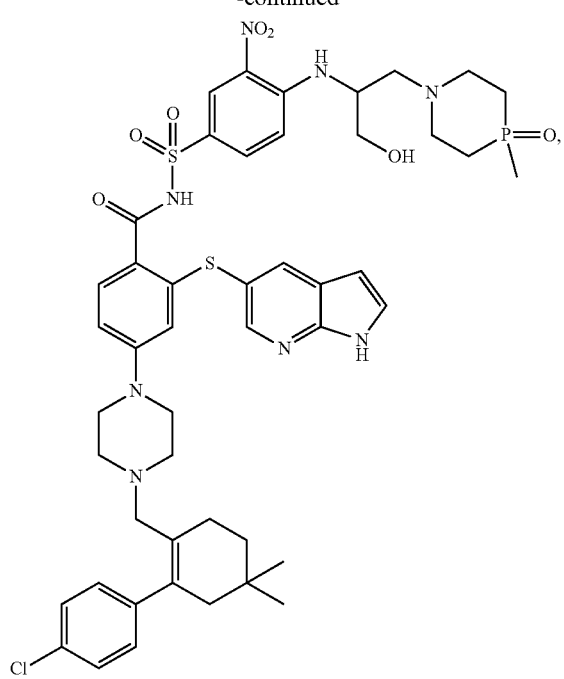
94
-continued
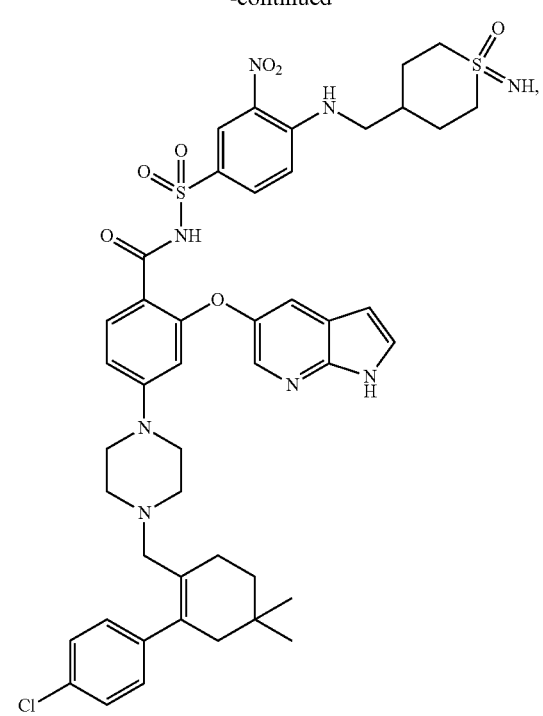
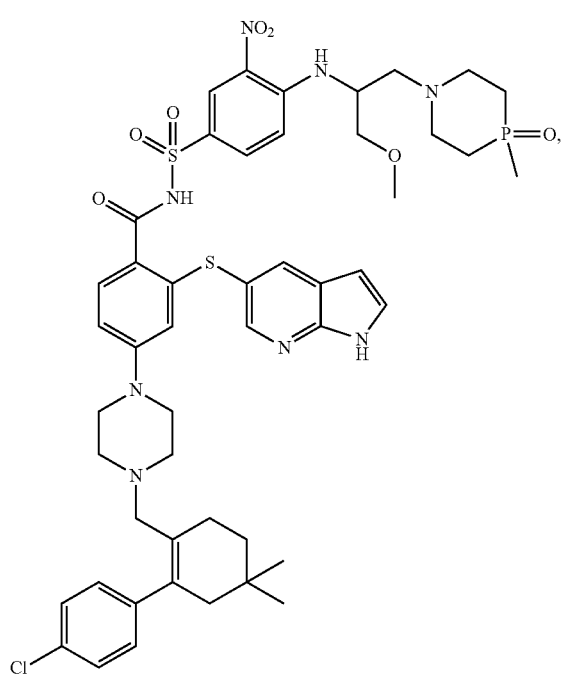
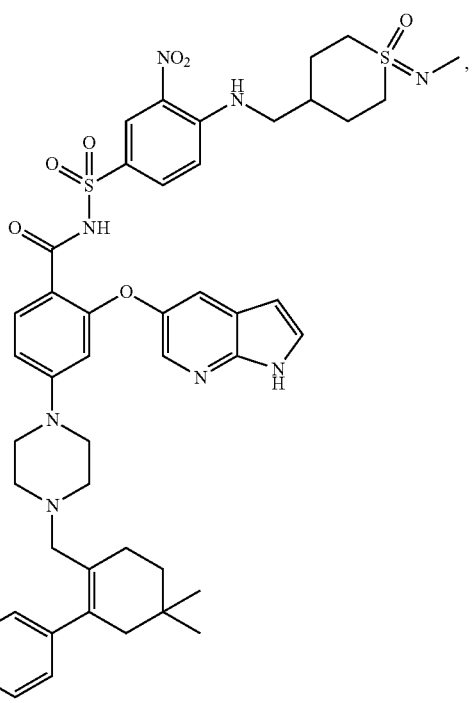

95
-continued
96
-continued
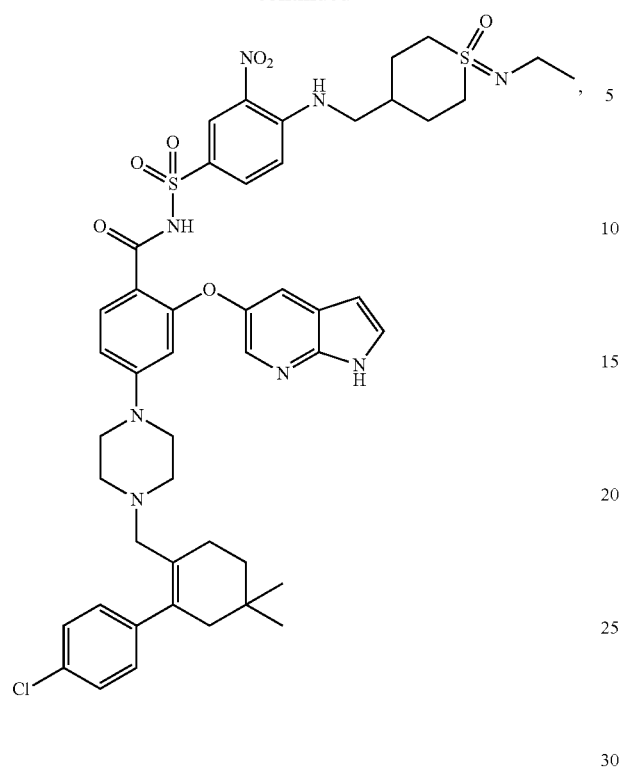
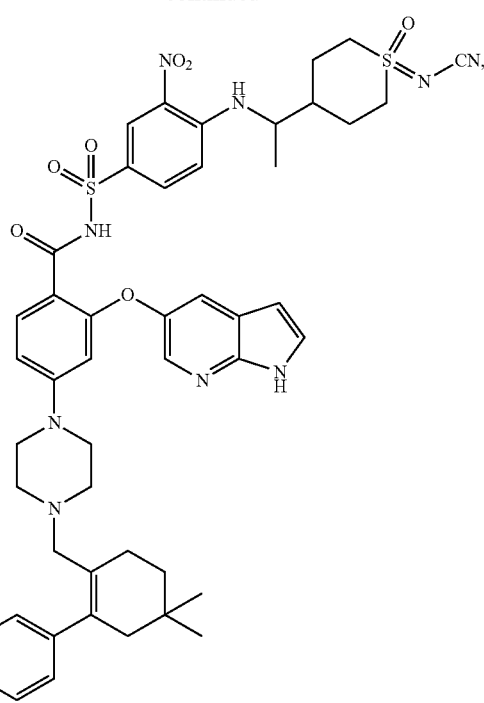
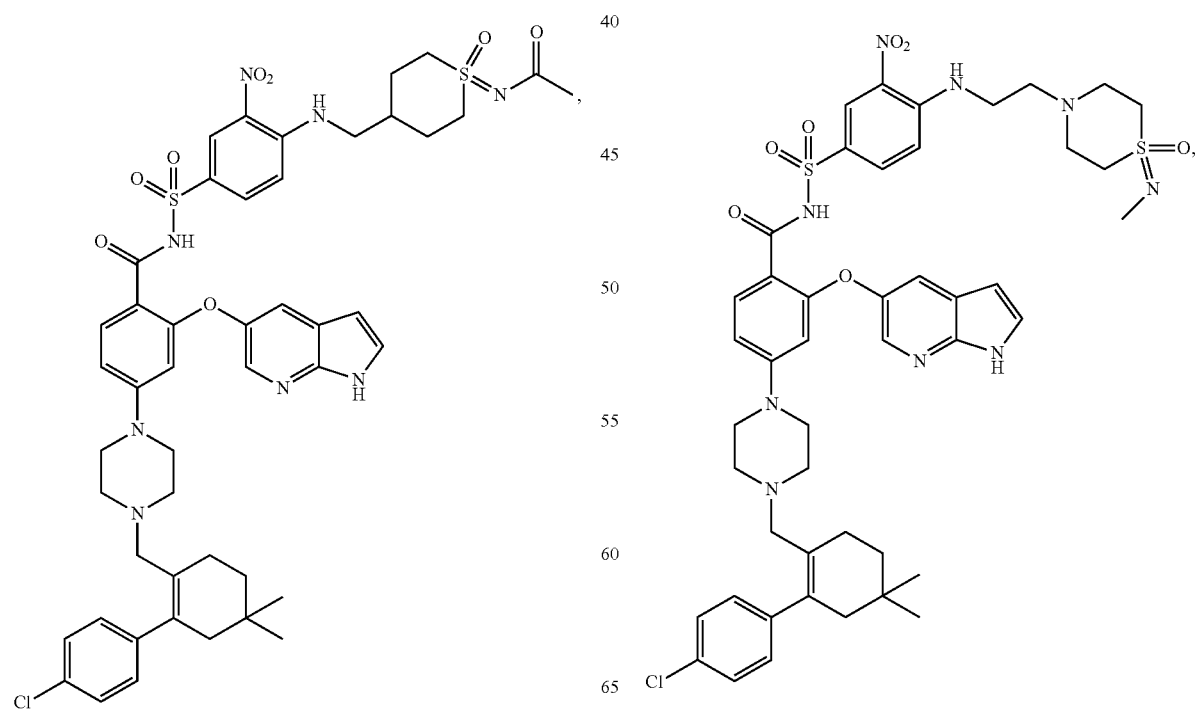

97
-continued
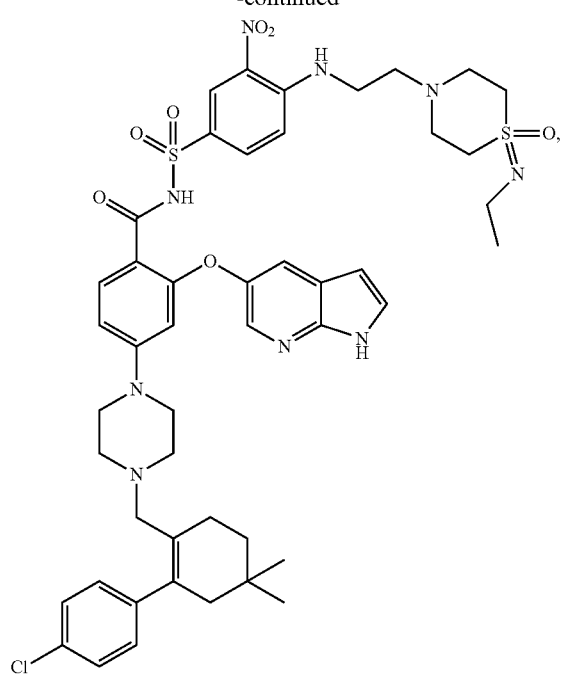
98
-continued
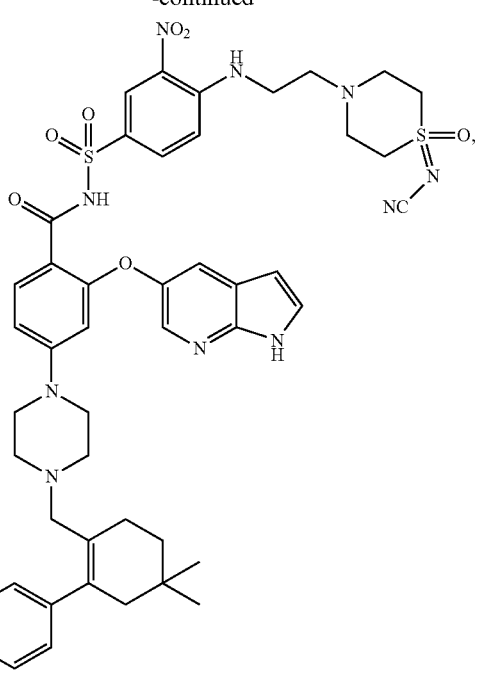
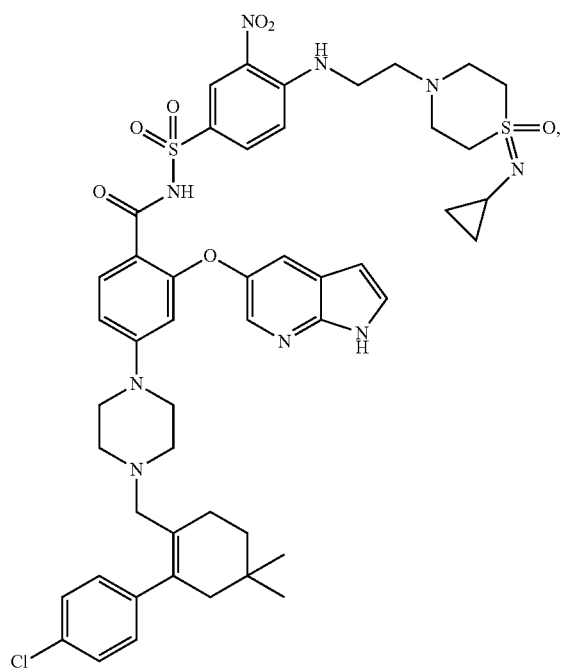
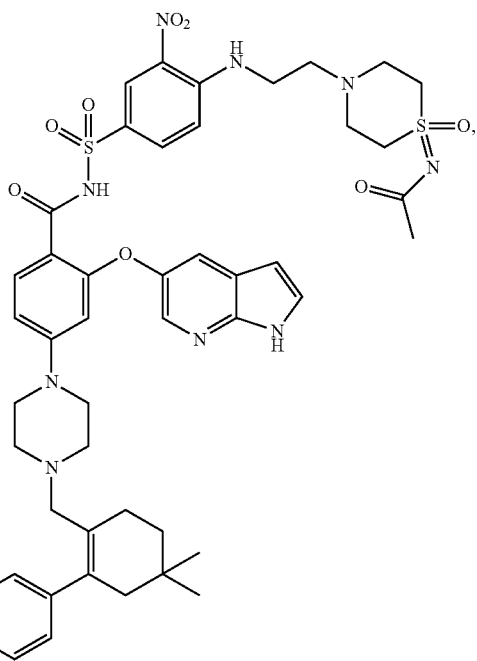

99
-continued
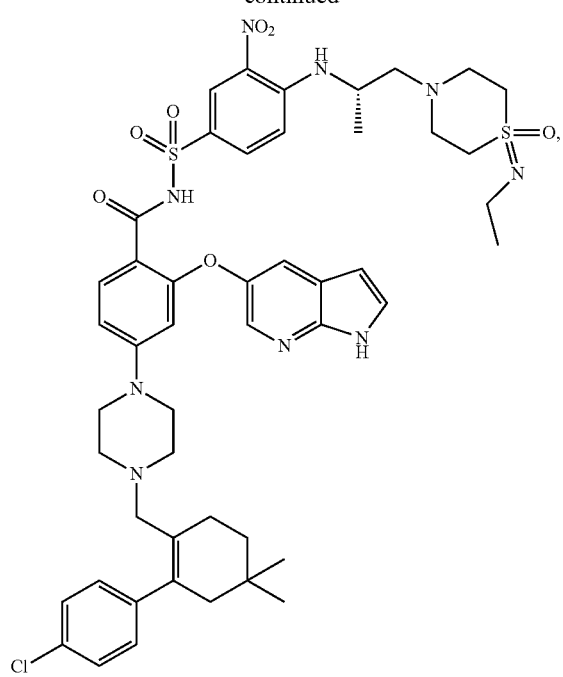
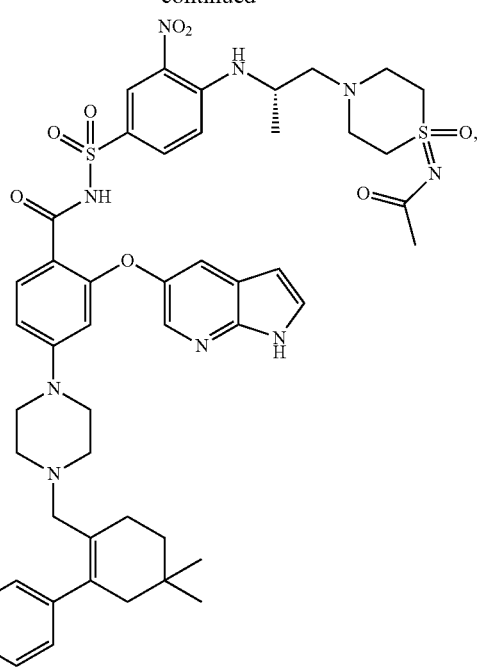
100
-continued
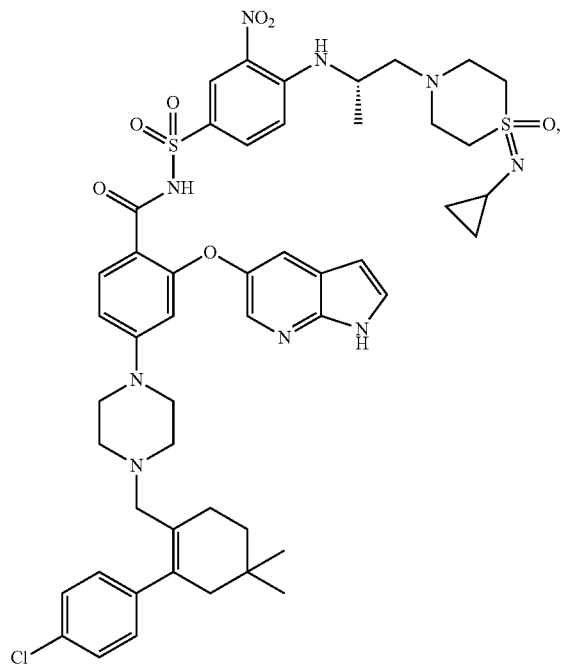
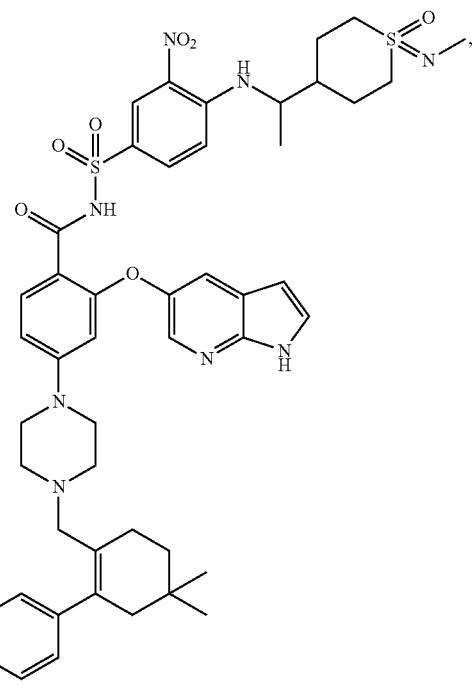

101
-continued
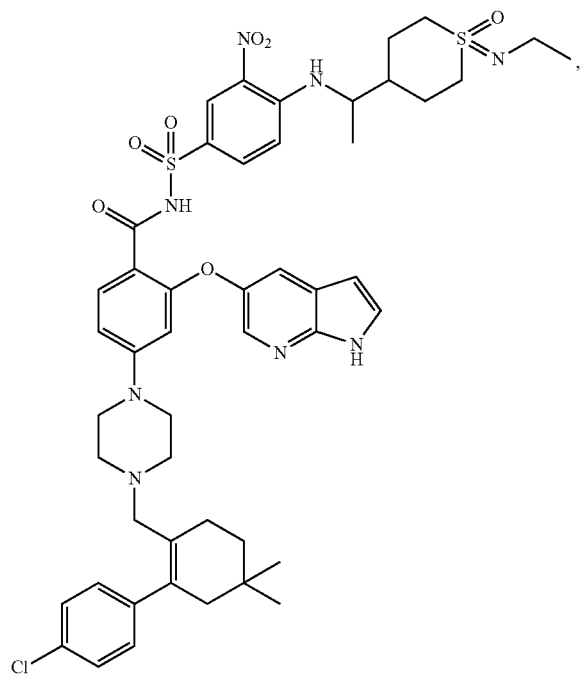
102
-continued
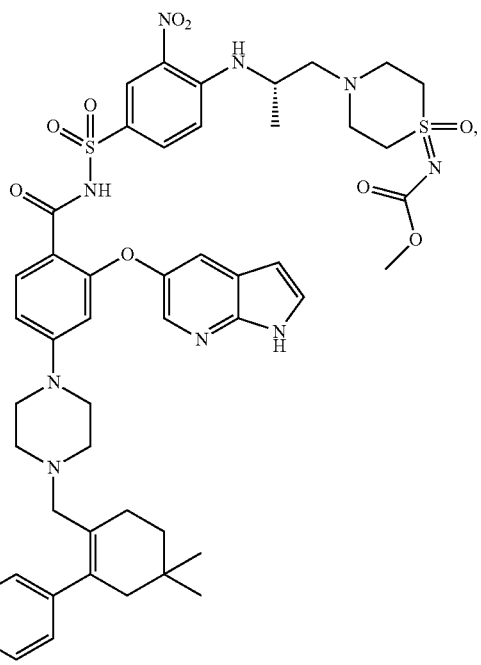
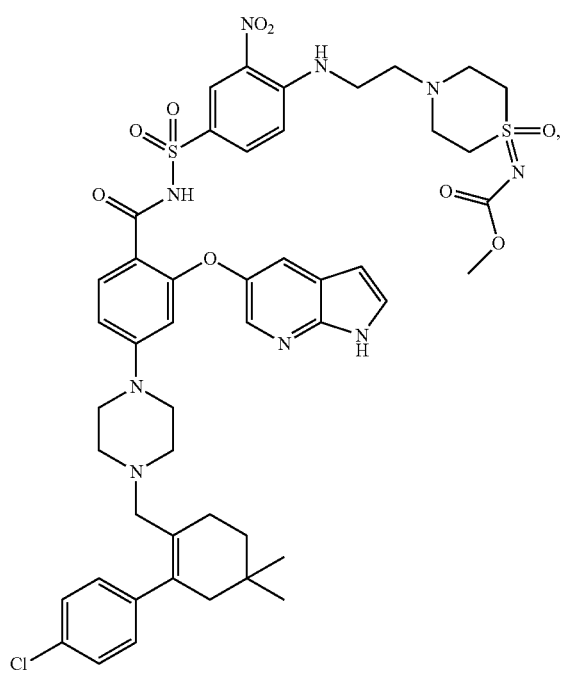
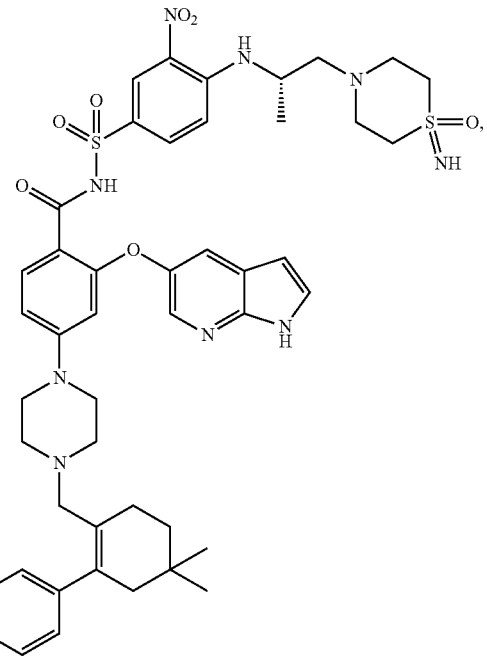

103
-continued
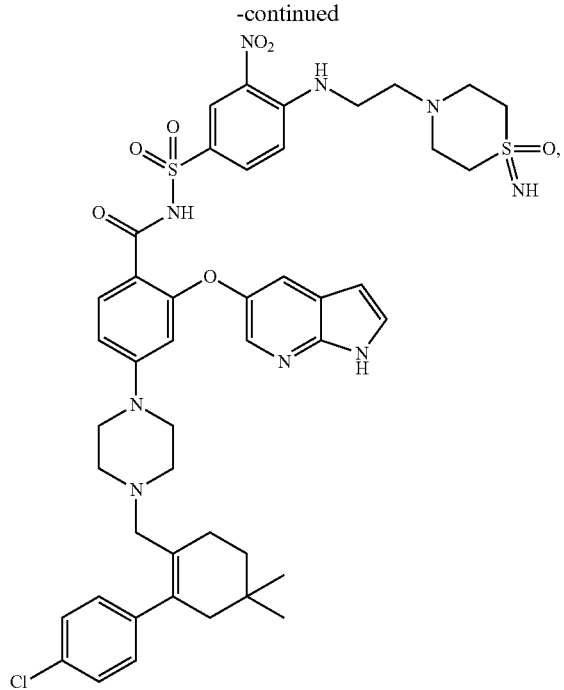
104
-continued
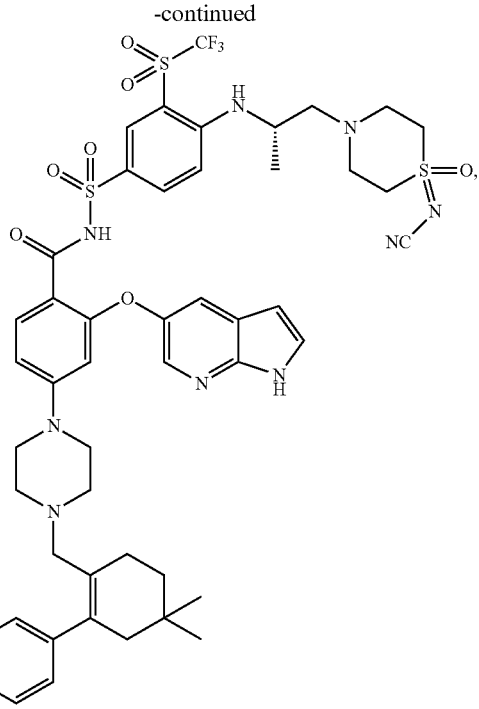
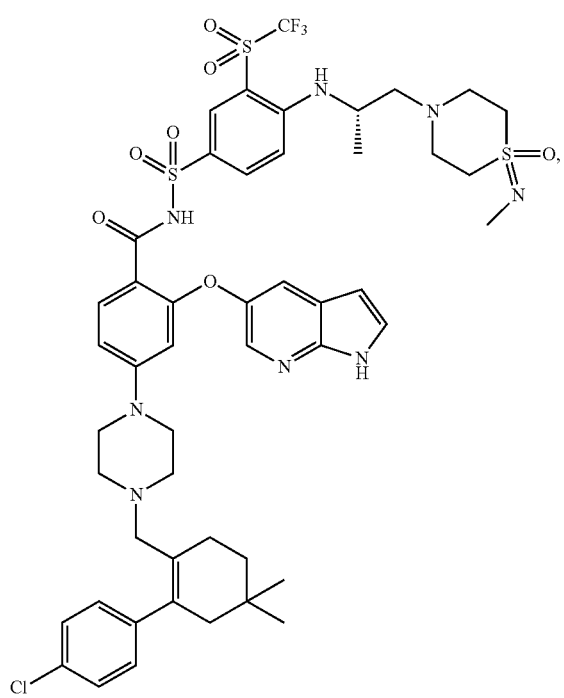
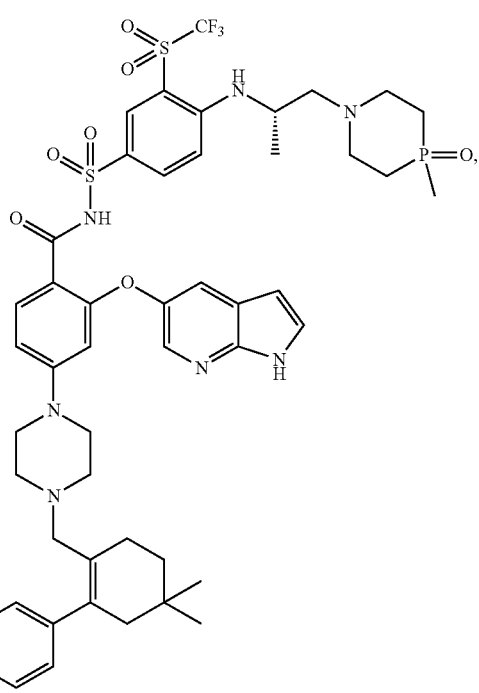

105
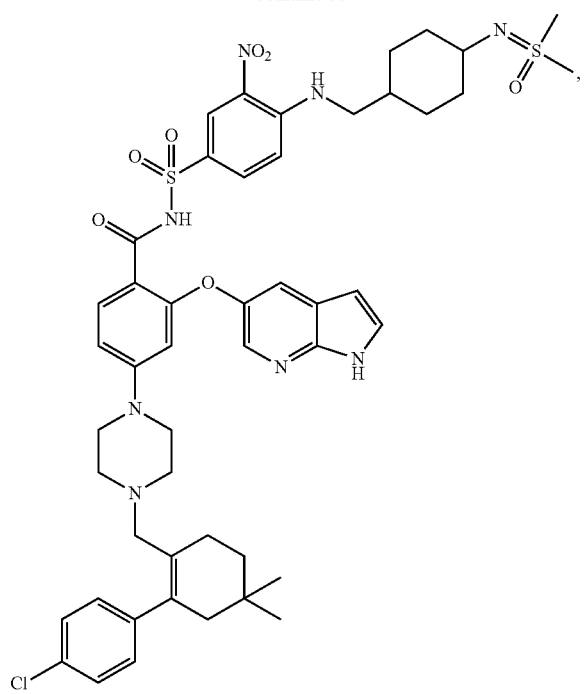
106
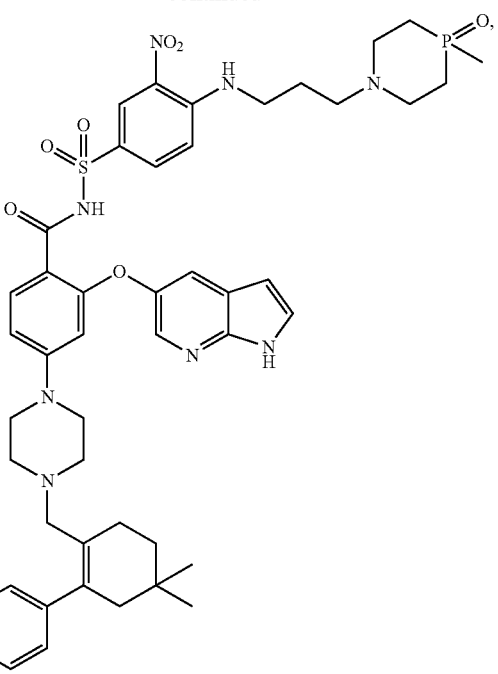

107
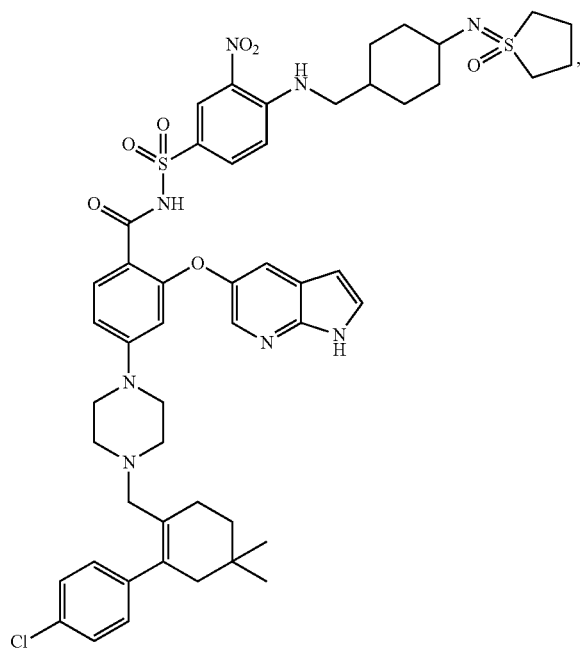
108
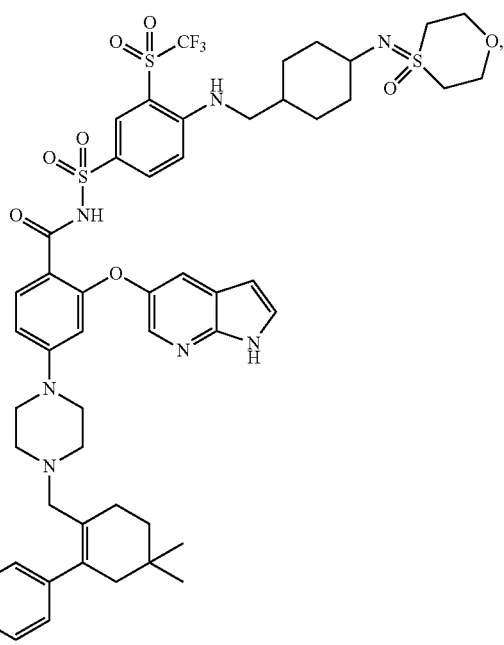
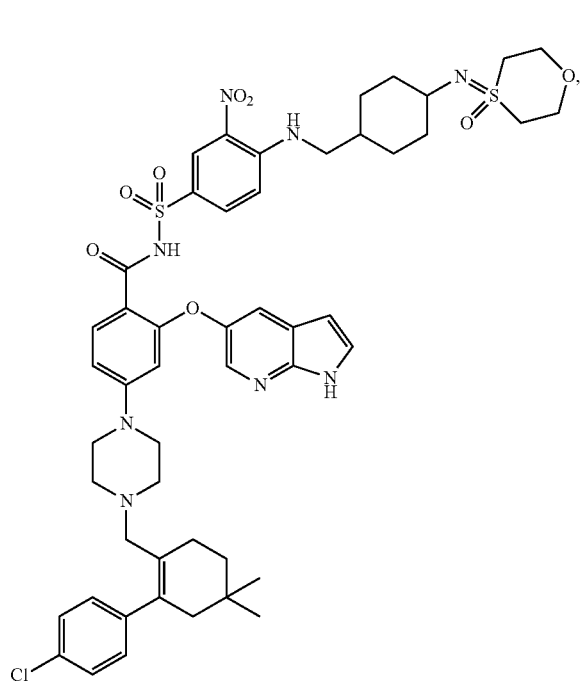

109
-continued
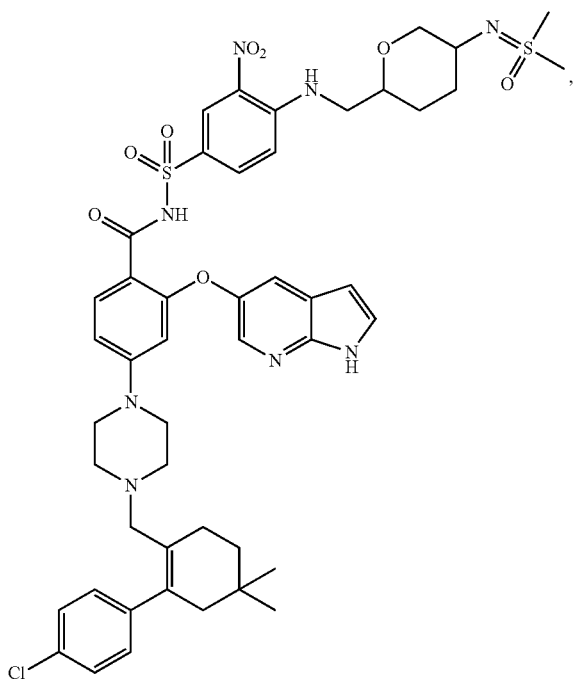
110
-continued
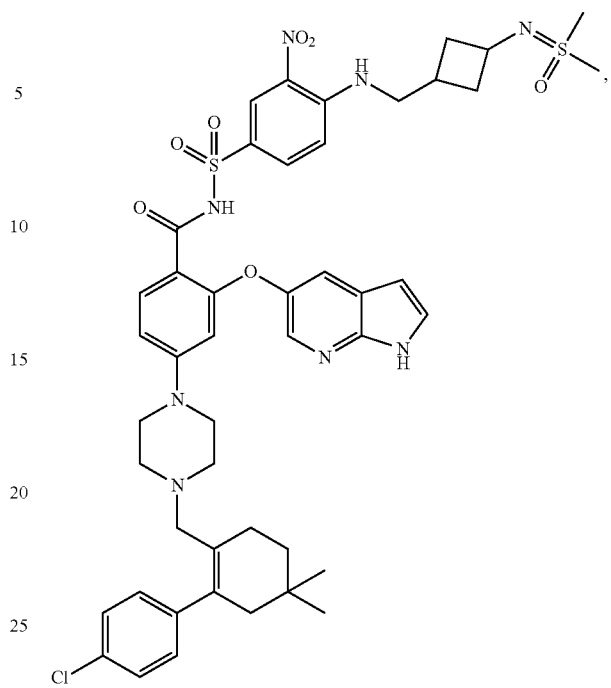
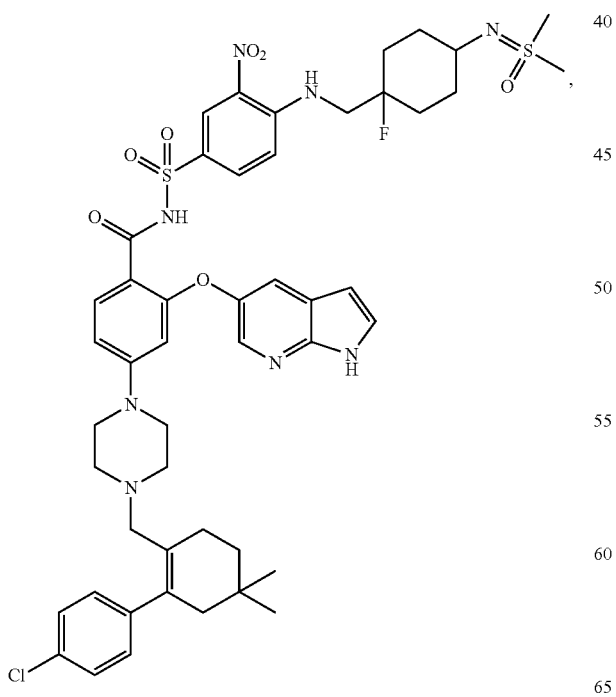
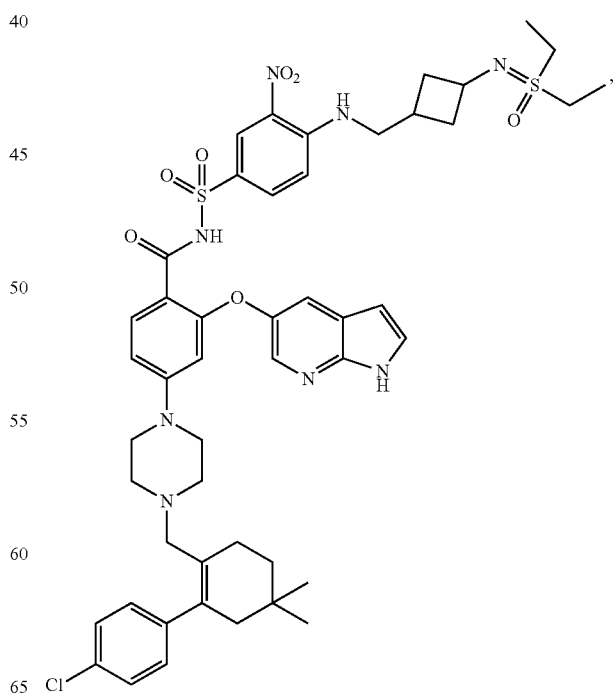

111
-continued
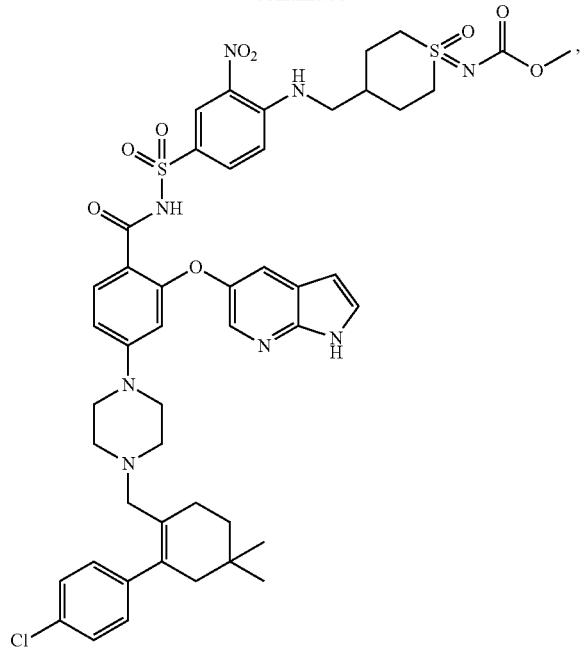
112
-continued
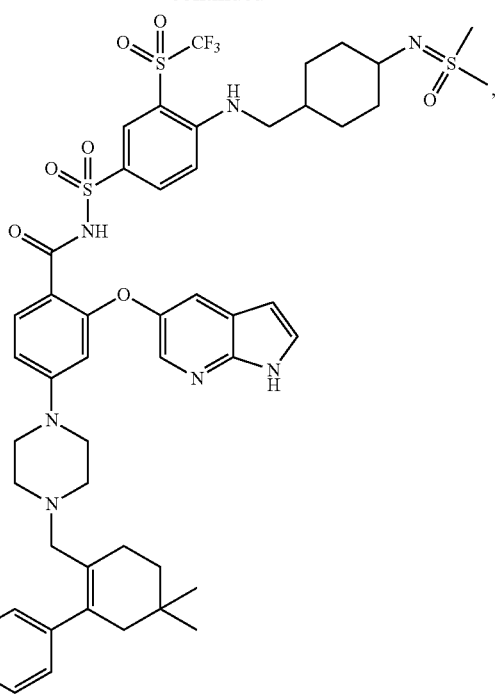
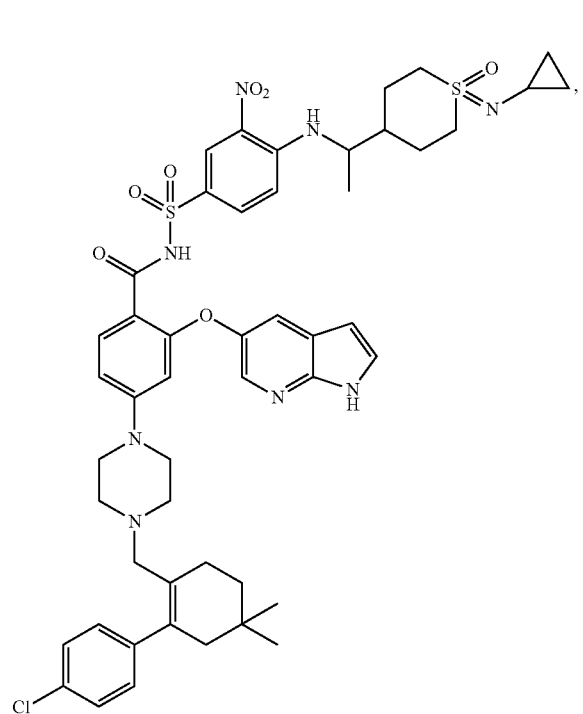

113
-continued
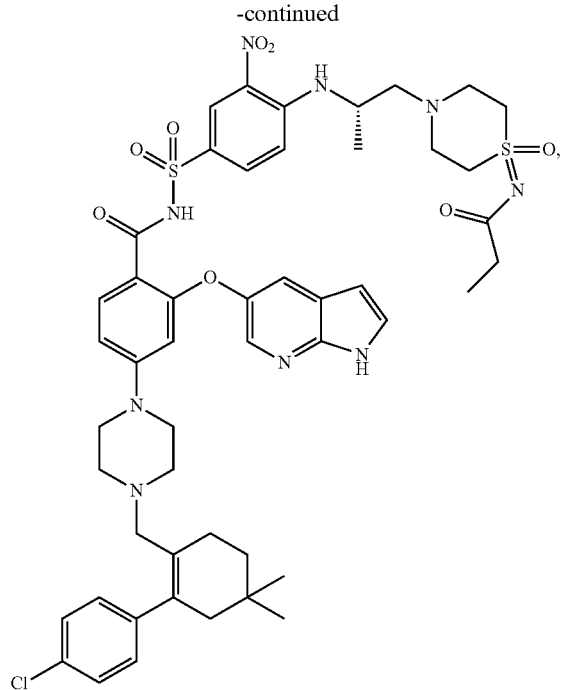
114
-continued
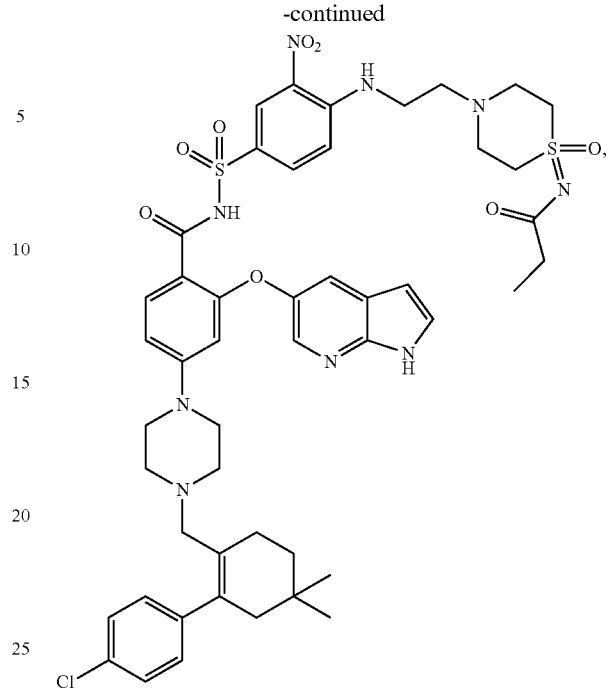
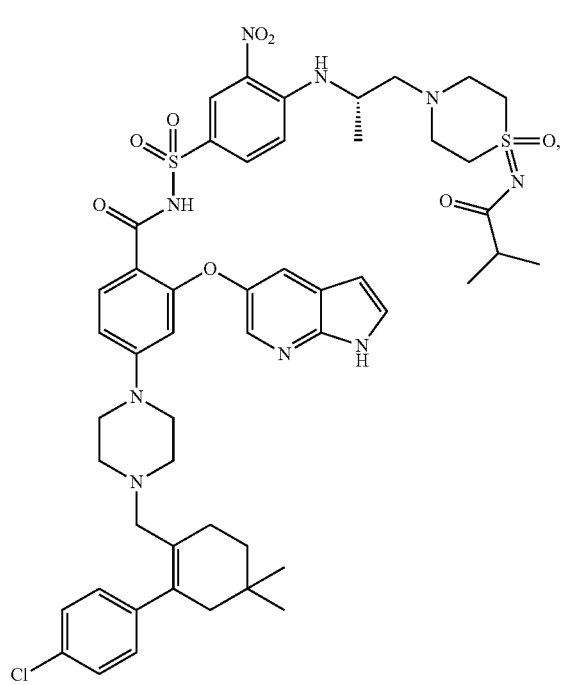
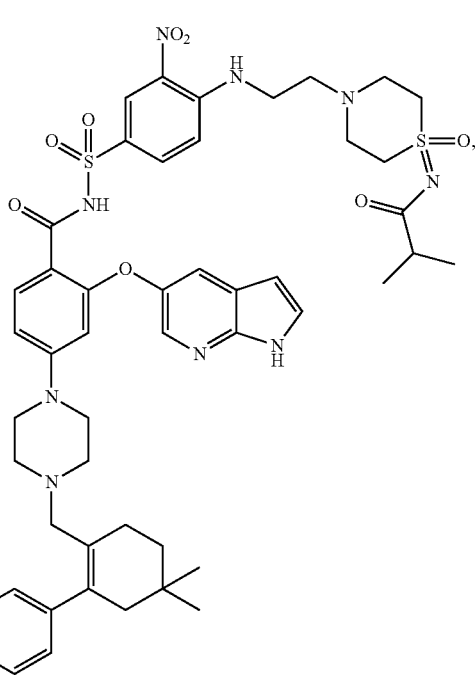

115
-continued
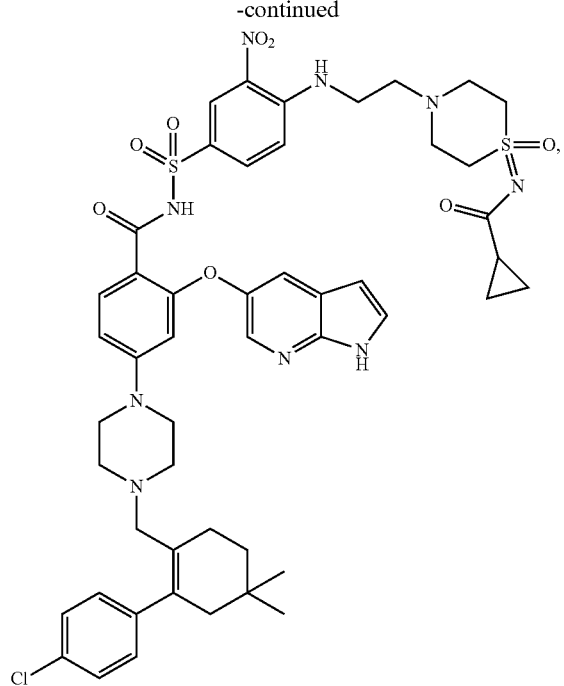
116
-continued
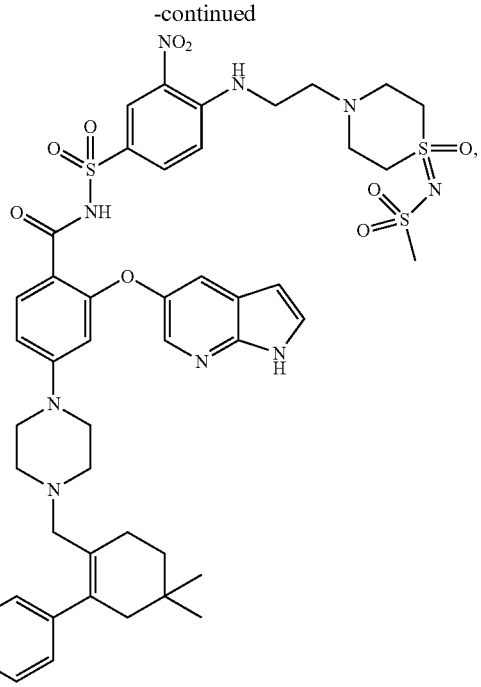
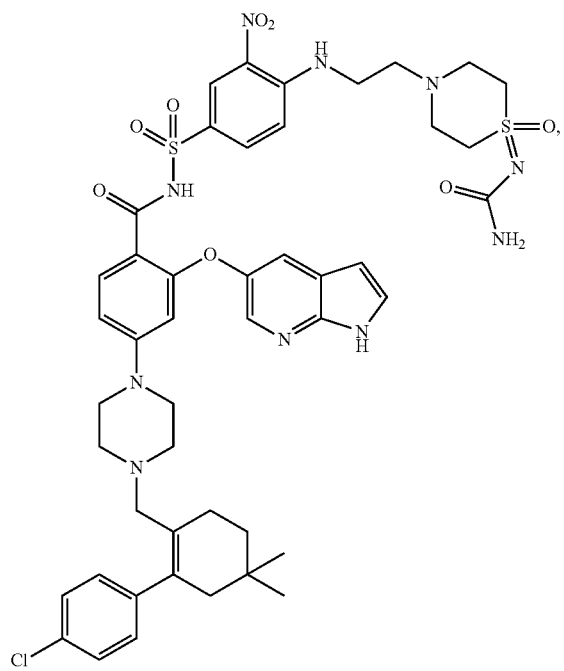 [SMILES: CC(=O)N=S1(=O)CCN(C[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1]
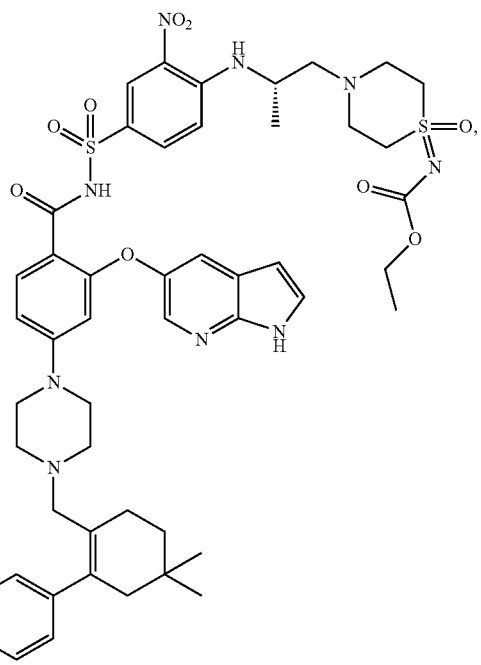

117
-continued
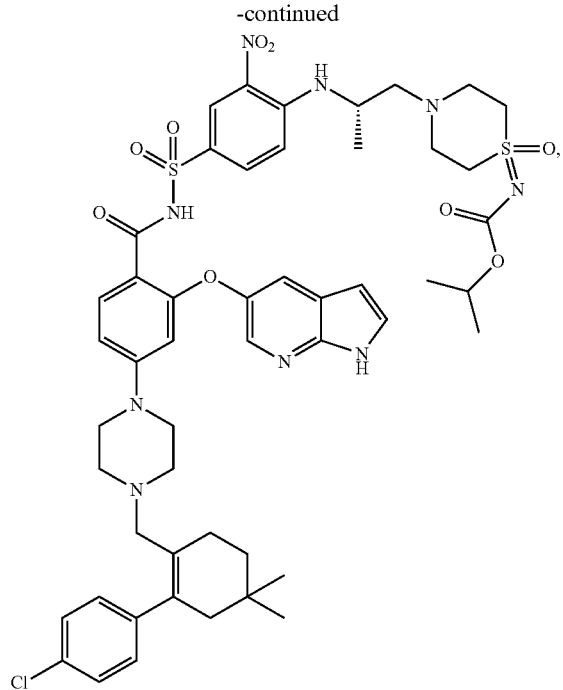
118
-continued
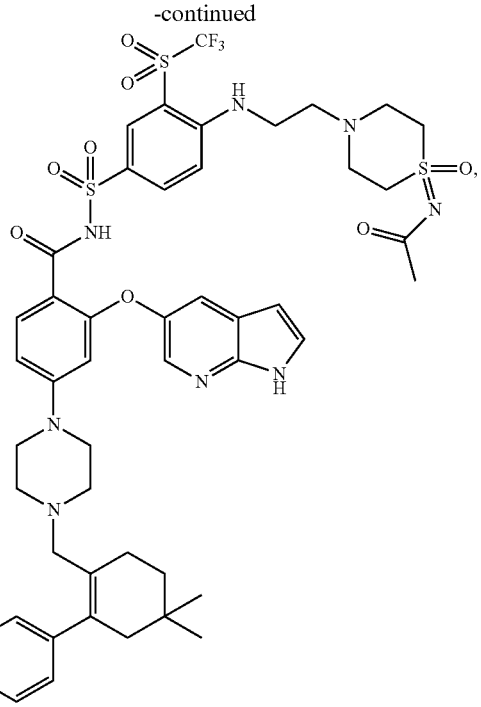
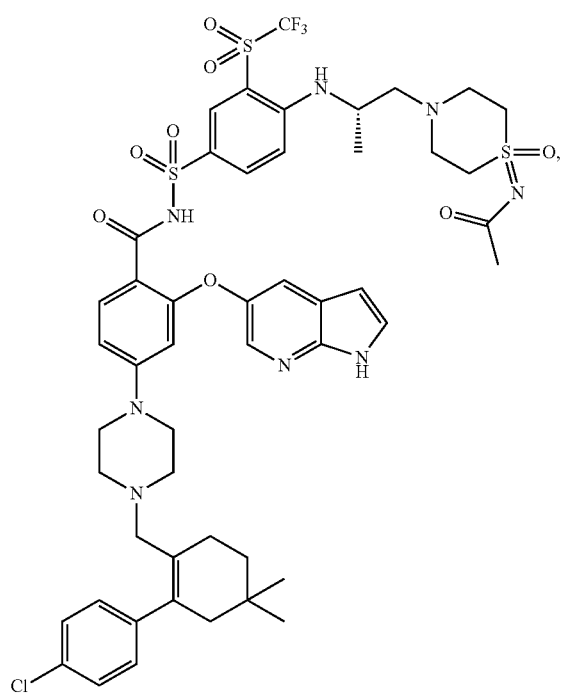

119
-continued
120
-continued
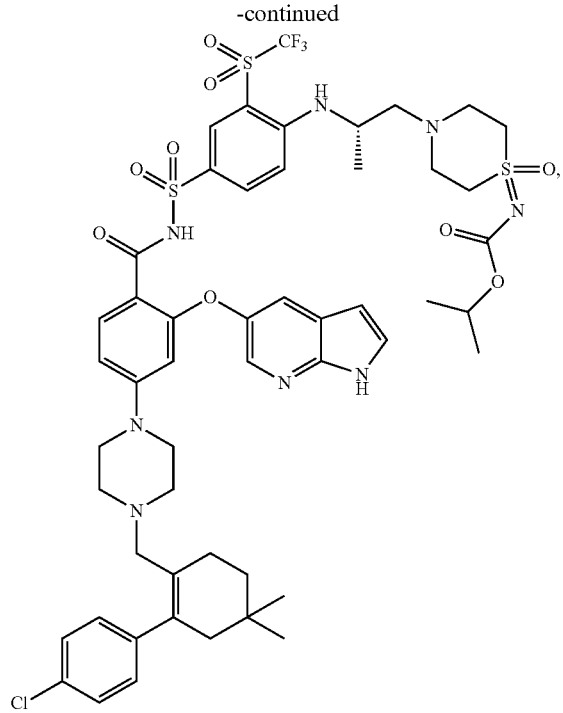
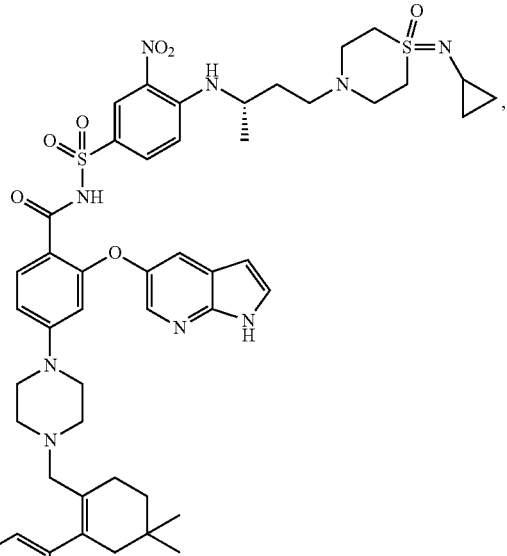

121
-continued
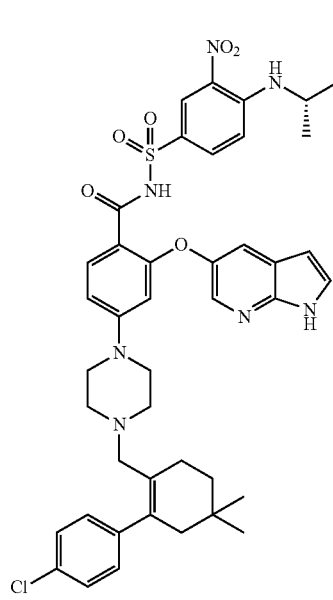
122
-continued
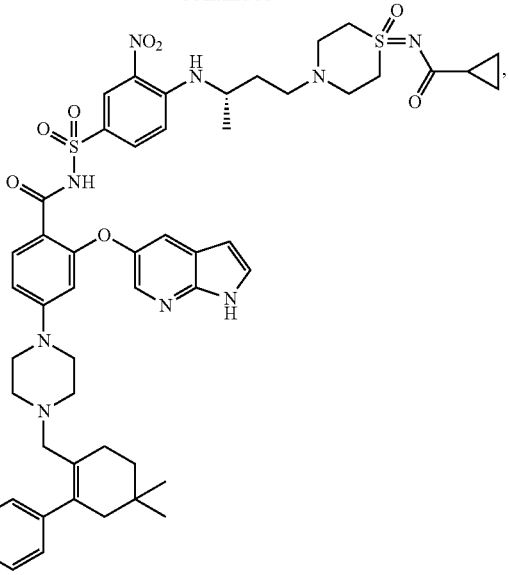
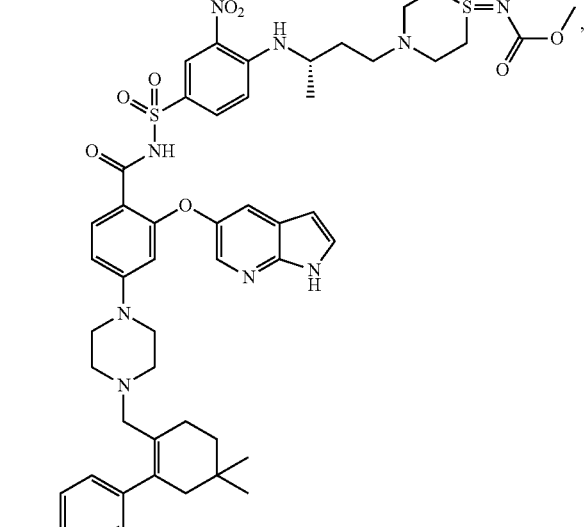
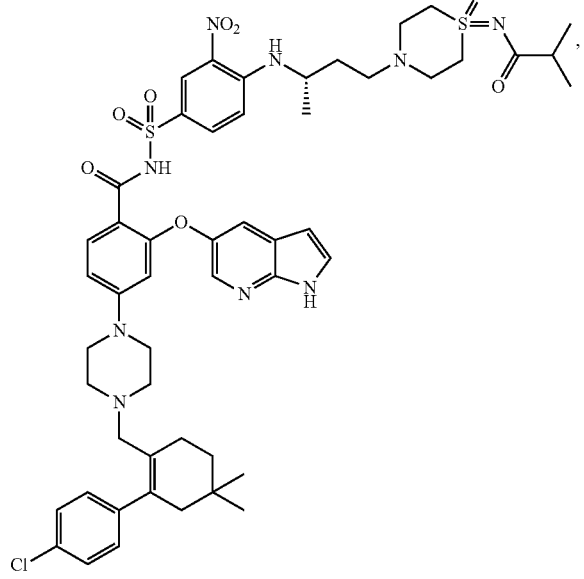

123
-continued
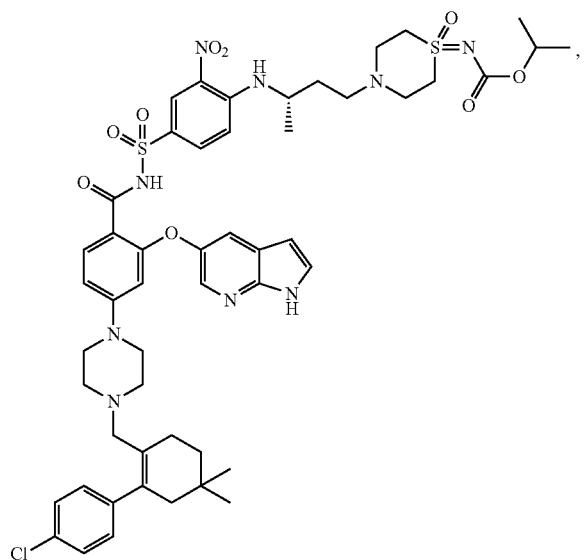
124
-continued
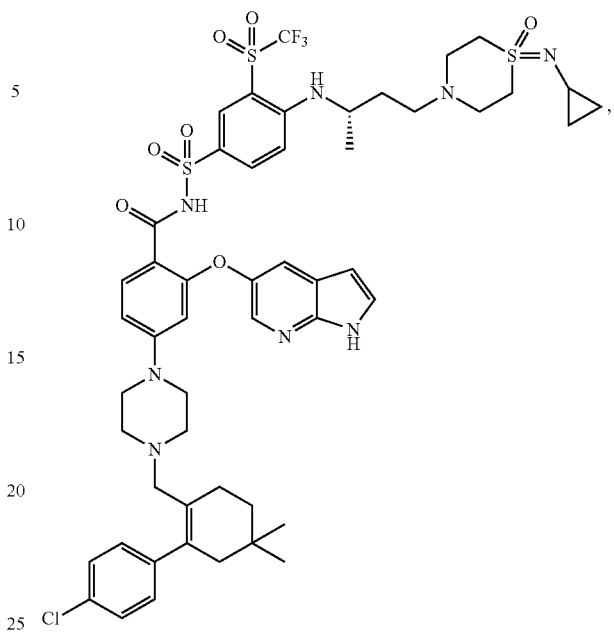

125
-continued
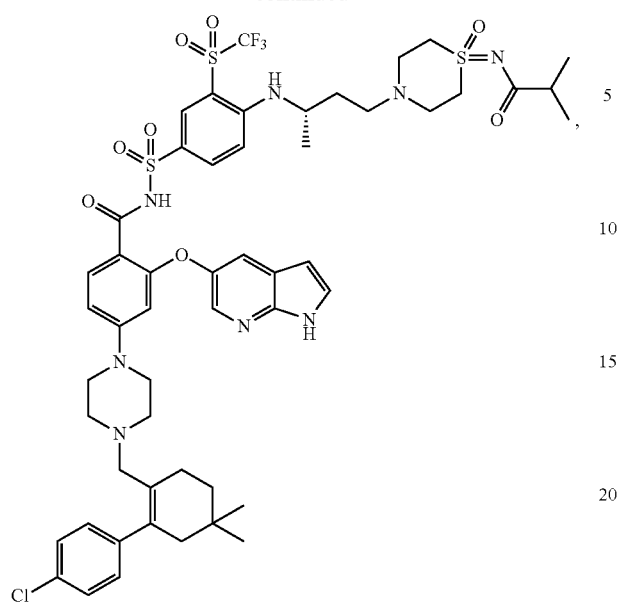
126
-continued
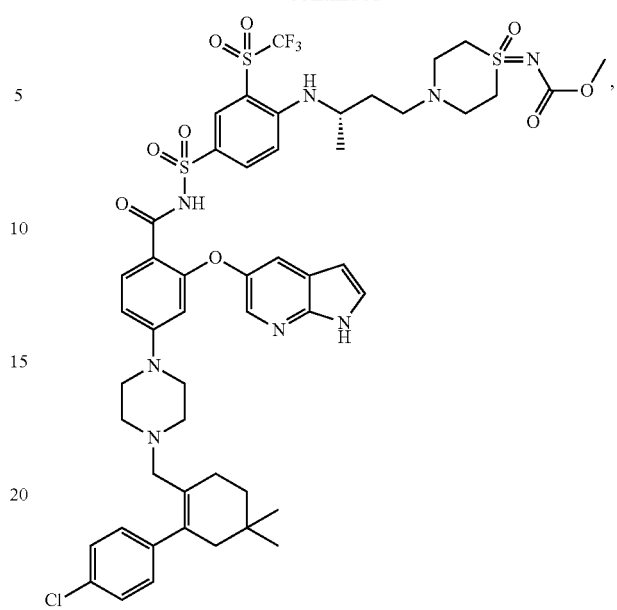
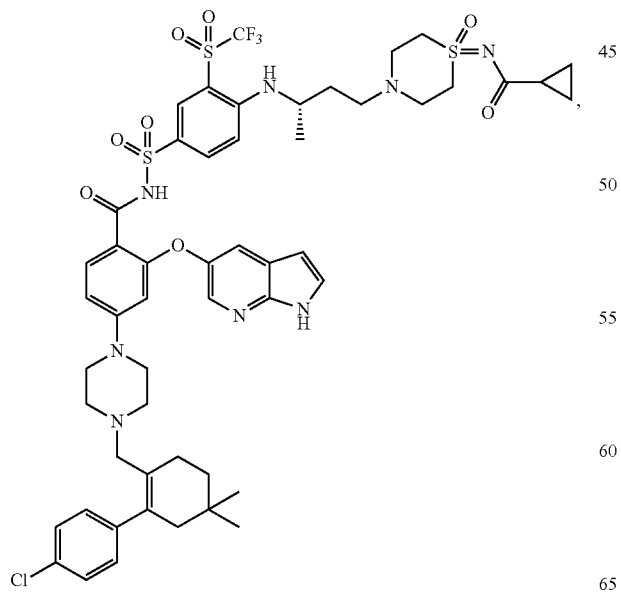
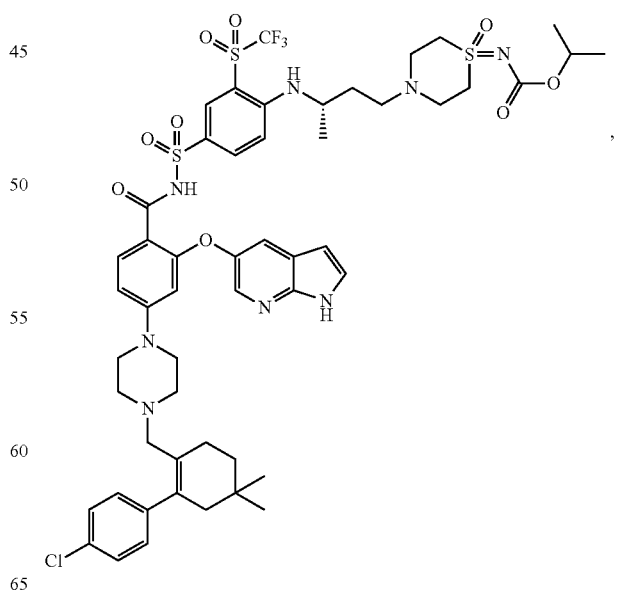

127
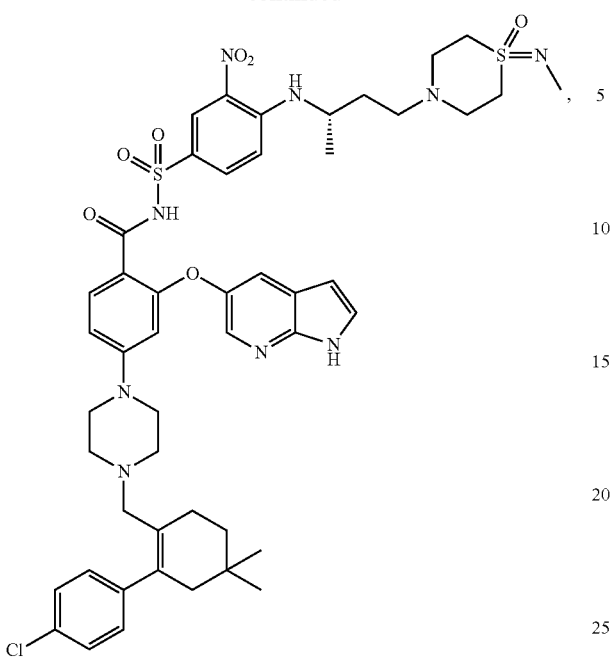
128
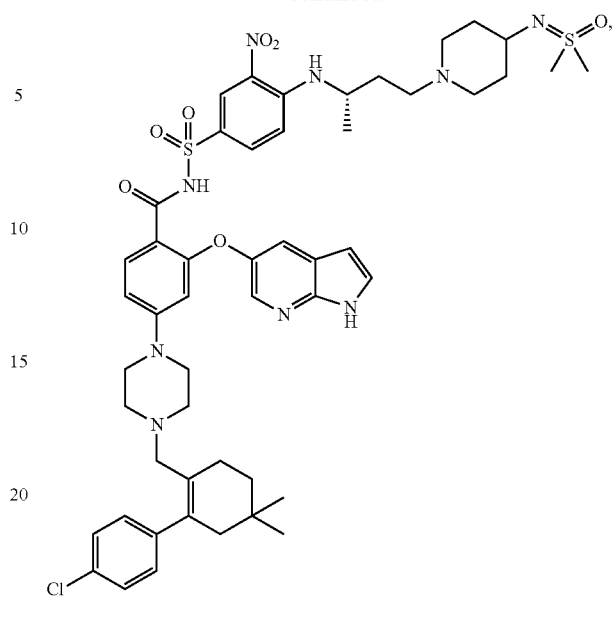
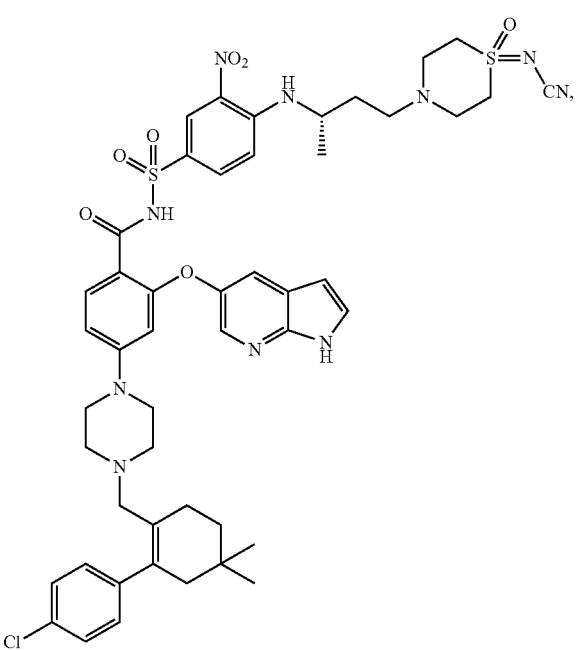

-continued

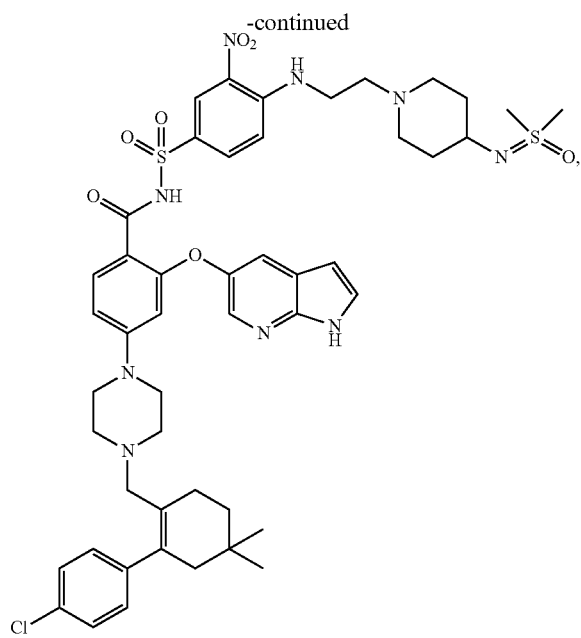

and pharmaceutically acceptable salts thereof.

In another Embodiment (22), the invention provides a pharmaceutical composition comprising a compound of any one of Embodiments (1) to (21) or a pharmaceutically acceptable salts thereof and at least one pharmaceutically acceptable carrier.

In another Embodiment (23), the invention provides a method of treating, ameliorating or preventing a condition, which responds to inhibition of Bcl-2, comprising administering to a subject in need of such treatment an effective amount of a compound of any one of Embodiments (1) to (21), or a pharmaceutically acceptable salt thereof, or a pharmaceutical composition thereof, and optionally in combination with a second therapeutic agent.

In another Embodiment (24), the invention provides a use of a compound of any one of Embodiments (1) to (21) or a pharmaceutically acceptable salt thereof in the preparation of a medicament for treating a cell-proliferative disorder.

In another of its aspects, there is provided a pharmaceutical composition comprising a compound disclosed herein, or a pharmaceutically acceptable salts thereof.

In yet another of its aspects, there is provided a kit comprising a compound disclosed herein, or a pharmaceutically acceptable salts thereof; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound disclosed herein, or a pharmaceutically acceptable salts thereof; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound disclosed herein, or a pharmaceutically acceptable salts thereof.

In another of its aspects, there is provided a method of inhibiting a Bcl-2 comprising contacting the Bcl-2 with a compound disclosed herein, or a pharmaceutically acceptable salts thereof.

In yet another of its aspects, there is provided a method of inhibiting a Bcl-2 comprising causing a compound disclosed herein, or a pharmaceutically acceptable salts thereof to be present in a subject in order to inhibit the Bcl-2 in vivo.

In a further of its aspects, there is provided a method of inhibiting Bcl-2 comprising administering a first compound to a subject that is converted in vivo to a second compound wherein the second compound inhibits the Bcl-2 in vivo, the second compound being a compound according to any one of the above embodiments and variations.

In another of its aspects, there is provided a method of treating a disease state for which a Bcl-2 possesses activity that contributes to the pathology and/or symptomology of the disease state, the method comprising causing a compound disclosed herein, or a pharmaceutically acceptable salts thereof to be present in a subject in a therapeutically effective amount for the disease state.

In a further of its aspects, there is provided a method of treating a disease state for which a Bcl-2 possesses activity that contributes to the pathology and/or symptomology of the disease state, the method comprising administering a first compound to a subject that is converted in vivo to a second compound wherein the second compound inhibits the Bcl-2 in vivo. It is noted that the compounds of the present invention may be the first or second compounds.

In one variation of each of the above methods the disease state is selected from the group consisting of cancerous hyperproliferative disorders (e.g., brain, lung, squamous cell, bladder, gastric, pancreatic, breast, head, neck, renal, kidney, ovarian, prostate, colorectal, epidermoid, esophageal, testicular, gynecological or thyroid cancer); non-cancerous hyperproliferative disorders (e.g., benign hyperplasia of the skin (e.g., psoriasis), restenosis, and benign prostatic hypertrophy (BPH)); pancreatitis; kidney disease; pain; preventing blastocyte implantation; treating diseases related to vasculogenesis or angiogenesis (e.g., tumor angiogenesis, acute and chronic inflammatory disease such as rheumatoid arthritis, atherosclerosis, inflammatory bowel disease, skin diseases such as psoriasis, exzema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer); asthma; neutrophil chemotaxis (e.g., reperfusion injury in myocardial infarction and stroke and inflammatory arthritis); septic shock; T-cell mediated diseases where immune suppression would be of value (e.g., the prevention of organ transplant rejection, graft versus host disease, lupus erythematosus, multiple sclerosis, and rheumatoid arthritis); atherosclerosis; inhibition of keratinocyte responses to growth factor cocktails; chronic obstructive pulmonary disease (COPD) and other diseases.

In another of its aspects, there is provided a method of treating a disease state for which a mutation in the Bcl-2 gene contributes to the pathology and/or symptomology of the disease state including, for example, melanomas, lung cancer, colon cancer and other tumor types.

In still another of its aspects, the present invention relates to the use of a compound of any of the above embodiments and variations as a medicament. In yet another of its aspects, the present invention relates to the use of a compound according to any one of the above embodiments and variations in the manufacture of a medicament for inhibiting a Bcl-2.

In a further of its aspects, the present invention relates to the use of a compound according to any one of the above embodiments and variations in the manufacture of a medicament for treating a disease state for which a Bcl-2 possesses activity that contributes to the pathology and/or symptomology of the disease state.

Administration and Pharmaceutical Compositions

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.001 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 1000 mg, conveniently administered, for example, in divided doses up to four times a day or in retard form. Suitable unit dosage forms for oral administration comprise from ca. 1 to 50 mg active ingredient.

Compounds of the disclosure may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present disclosure in free form or in a pharmaceutically acceptable salt form in association with at least one pharmaceutically acceptable carrier or diluent may be manufactured in a conventional manner by mixing, granulating, coating, dissolving or lyl)philizing processes. For example, pharmaceutical compositions comprising a compound of the disclosure in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid.

The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyl)xyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyl)xyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length C8 to C12 from Hills AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arable, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyl)xyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The disclosure also provides for a pharmaceutical combinations, e.g. a kit, comprising a) a first agent which is a compound of the disclosure as disclosed herein, in free form or in pharmaceutically acceptable salt form, and b) at least one co-agent. The kit can comprise instructions for its administration.

Combination Therapies

The compounds or pharmaceutical acceptable salts of the disclosure may be administered as the sole therapy, or together with other therapeutic agent or agents.

For example, the therapeutic effectiveness of one of the compounds described herein may be enhanced by administration of an adjuvant (i.e. by itself the adjuvant may only have minimal therapeutic benefit, but in combination with another therapeutic agent, the overall therapeutic benefit to the individual is enhanced). Or, by way of example only, the benefit experienced by an individual may be increased by administering one of the compounds described herein with another therapeutic agent that also has therapeutic benefit. By way of example only, in a treatment for gout involving administration of one of the compounds described herein, increased therapeutic benefit may result by also providing the individual with another therapeutic agent for gout. Or, by way of example only, if one of the side effects experienced by an individual upon receiving one of the compounds described herein is nausea, then it may be appropriate to administer an anti-nausea agent in combination with the compound. Or, the additional therapy or therapies include, but are not limited to physiotherapy, psychotherapy, radiation therapy, application of compresses to a diseased area, rest, altered diet, and the like. Regardless of the disease, disorder or condition being treated, the overall benefit experienced by the individual may be additive of the two therapies or the individual may experience a synergistic benefit.

In the instances where the compounds described herein are administered in combination with other therapeutic agents, the compounds described herein may be administered in the same pharmaceutical composition as other therapeutic agents, or because of different physical and chemical characteristics, be administered by a different route. For example, the compounds described herein may be administered orally to generate and maintain good blood levels thereof, while the other therapeutic agent may be administered intravenously. Thus the compounds described herein may be administered concurrently, sequentially or dosed separately to other therapeutic agents.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPB), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

EXAMPLES

Various methods may be developed for synthesizing a compound of formula (I) or a pharmaceutically acceptable salt thereof. Representative methods for synthesizing a compound of formula (I) or a pharmaceutically acceptable salt thereof are provided in the Examples. It is noted, however, that a compound of formula (I) or a pharmaceutically acceptable salt thereof may also be synthesized by other synthetic routes that others may devise.

It will be readily recognized that certain compounds of formula (I) have atoms with linkages to other atoms that confer a particular stereochemistry to the compound (e.g., chiral centers). It is recognized that synthesis of a compound of formula (I) or a pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

Ae compound of formula (I) can also be prepared as a pharmaceutically acceptable acid addition salt by, for example, reacting the free base form of the at least one compound with a pharmaceutically acceptable inorganic or organic acid. Alternatively, a pharmaceutically acceptable base addition salt of the at least one compound of formula (I) can be prepared by, for example, reacting the free acid form of the at least one compound with a pharmaceutically acceptable inorganic or organic base. Inorganic and organic acids and bases suitable for the preparation of the pharmaceutically acceptable salts of compounds of formula (I) are set forth in the definitions section of this Application. Alternatively, the salt forms of the compounds of formula (I) can be prepared using salts of the starting materials or intermediates.

The free acid or free base forms of the compounds of formula (I) can be prepared from the corresponding base addition salt or acid addition salt form. For example, a compound of formula (I) in an acid addition salt form can be converted to the corresponding free base thereof by treating with a suitable base (e.g., ammonium hydroxide solution, sodium hydroxide, and the like). A compound of formula (I) in a base addition salt form can be converted to the corresponding free acid thereof by, for example, treating with a suitable acid (e.g., hydrochloric acid, etc).

The N-oxides of the a compound of formula (I) or a pharmaceutically acceptable salt thereof can be prepared by methods known to those of ordinary skill in the art. For example, N-oxides can be prepared by treating an unoxidized form of the compound of formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0 to 80° C. Alternatively, the N-oxides of the compounds of formula (I) can be prepared from the N-oxide of an appropriate starting material.

Compounds of formula (I) in an unoxidized form can be prepared from N-oxides of compounds of formula (I) by, for example, treating with a reducing agent (e.g., sulfur, sulfur dioxide, triphenyl phosphine, lithium borohydride, sodium borohydride, phosphorus trichloride, tribromide, and the like) in an suitable inert organic solvent (e.g., acetonitrile, ethanol, aqueous dioxane, and the like) at 0 to 80° C.

Protected derivatives of the compounds of formula (I) can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); µL (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); Rt (retention time); RP (reverse phase); MeOH (methanol); i-PrOH (isopropanol); TEA (triethylamine); TFA (trifluoroacetic acid); TFAA (trifluoroacetic anhydride); THF (tetrahydrofuran); DMSO (dimethyl sulfoxide); EtOAc (ethyl acetate); DME (1,2-dimethoxyethane); DCM (dichloromethane); DCE (dichloroethane); DMF (N,N-dimethylformamide); DMPU (N,N'-dimethylpropyleneurea); CDI (1,1-carbonyldiimidazole); IBCF (isobutyl chloroformate); HOAc (acetic acid); HOSu (N-hydroxysuccinimide); HOBT (1-hydroxybenzotriazole); $Et_2O$ (diethyl ether); EDCI (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TMSE (2-(trimethylsilyl)ethyl); TMS (trimethylsilyl); TIPS (triisopropylsilyl); TBS (t-butyldimethylsilyl); DMAP (4-dimethylaminopyridine); Me (methyl); OMe (methoxy); Et (ethyl); tBu (tert-butyl); HPLC (high pressure liquid chomatography); BOP (bis(2-oxo-3-oxazolidinyl)phosphinic chloride); TBAF (tetra-n-butylammonium fluoride); m-CPBA (meta-chloroperbenzoic acid).

References to ether or $Et_2O$ are to diethyl ether; brine refers to a saturated aqueous solution of NaCl. Unless otherwise indicated, all temperatures are expressed in ° C. (degrees Centigrade). All reactions were conducted under an inert atmosphere at RT unless otherwise noted.

$^1$H NMR spectra were recorded on a Varian Mercury Plus 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet) and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm Superchemgroup silica gel plates (60E-254), visualized with UV light, 5% ethanolic phosphomolybdic acid, ninhydrin, or p-anisaldehyde solution. Flash column chromatography was performed on silica gel (200-300 mesh, Branch of Qingdao Haiyang Chemical Co., Ltd).

Synthetic Schemes

A compound of formula I or a pharmaceutically acceptable salt thereof may be synthesized according to a variety of reaction schemes. Some illustrative schemes are provided below and in the examples. Other reaction schemes could be readily devised by those skilled in the art in view of the present disclosure.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Synthetic methods for preparing the compounds of the present invention are illustrated in the following Schemes and Examples. Starting materials are commercially available or may be made according to procedures known in the art or as illustrated herein.

As an illustration, one of the approaches to the synthesis of compounds of formula I is shown in Scheme 1. Compounds of formula I can be easily assembled from sulfonamides or imino substituted sulfonamides of formula III with acids of formula II via cross coupling reactions such as peptide forming conditions known in the literature. Furthermore, compounds of formula II and III are readily accessible through methods known in the art.

Scheme 1

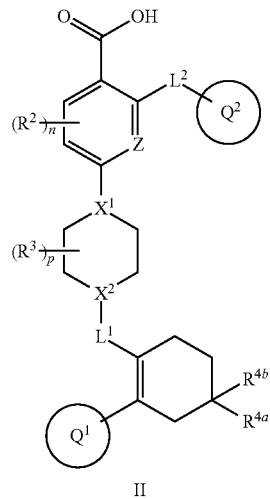

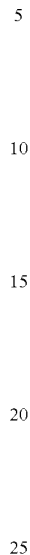

-continued

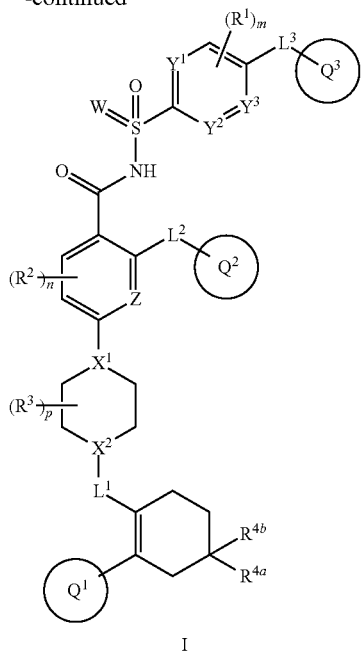

As an illustration of compounds of formula III, one of the synthetic approach to the compounds of formula IIIA is outlined in Scheme 2. As shown in the scheme, the compound of formula IIIA can be prepared from IIIA-a via a sequence of manipulations. Cyclic phosphine oxide of formula IIIA-f with atom A as nitrogen can be prepared from the double Michael addition of amine IIIA-b to divinylphosphine oxide IIIA-a followed by deprotection of protecting group on nitrogen and introduction of Rb when necessary. Similarly, cyclic phosphine oxide of formula IIIA-f with atom A as carbon can be prepared by reacting beta cyano ester IIIA-c with IIIA-a followed by decarboxylation of the ester group and conversion of the cyano group into amine and installment of Rb onto the resulting nitrogen when needed. Coupling of IIIA-f with IV in the presence of base provides IIIA via nucleophilic displacement of the halide on the aromatic ring of IV by the amine group in compounds of formula IIIA-f.

Scheme 2

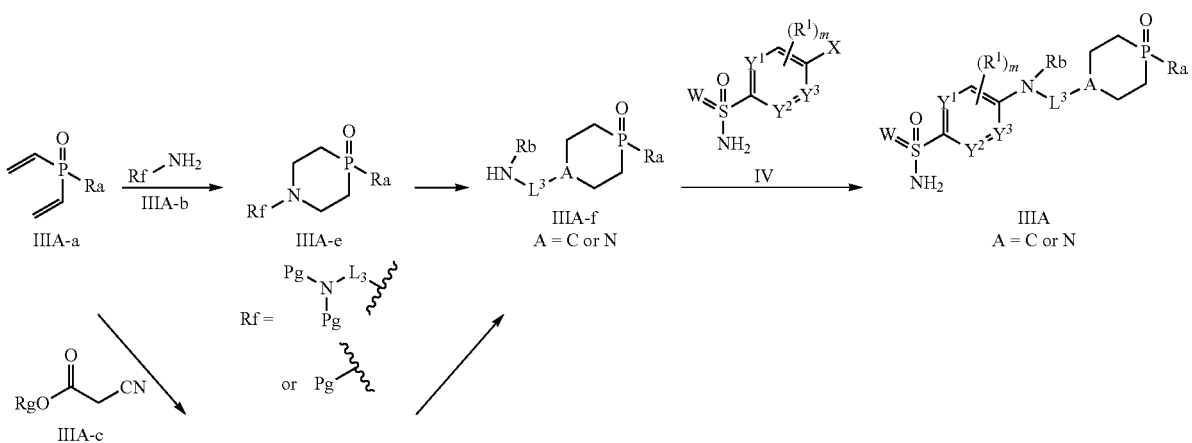

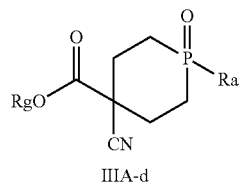

IIIA-d

Ra, Rb are selected from R¹ provided that the structure is stable
Rg is selected from alkyl
Pg is protecting group One synthetic route of compounds of formula IIIB is shown in Scheme 3. Starting from readily available compound amine IIIB-f is produced through a sequence of oxidative amination, oxidation, cleavage of the cyano group on the imino group, installment of Rc on the imino group and deprotection of the protecting group on nitrogen and coupling of the nitrogen containg fragment when needed. IIIB was prepared from IIIB-f and IV under the similar conditions to the preparation of IIIA shown in Scheme 2.

Scheme 3

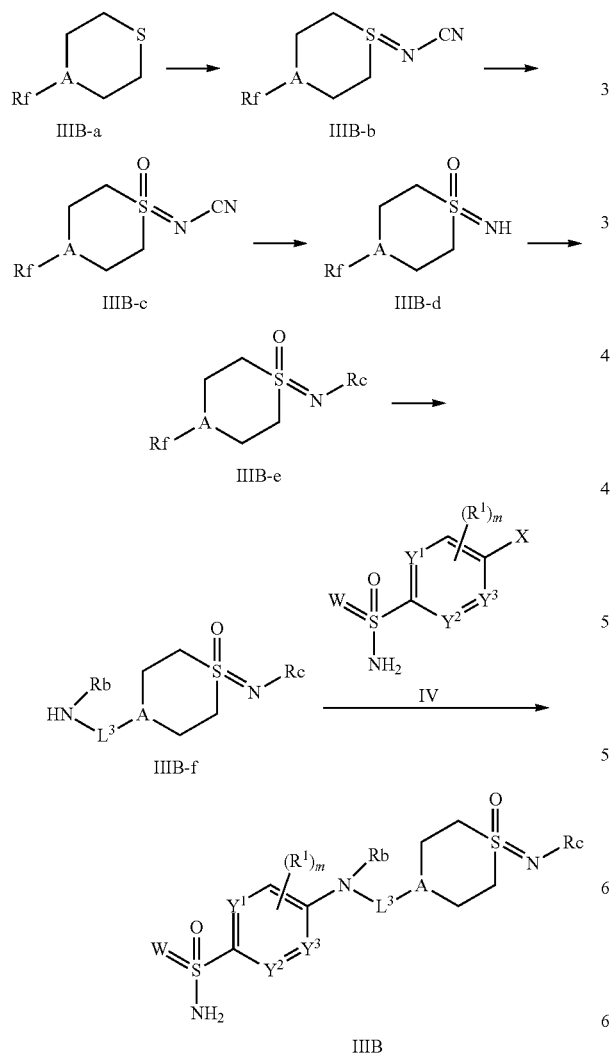

-continued

Rc, Rb are selected from R1 provided that the structure is stable
Pg is protecting group

A = N

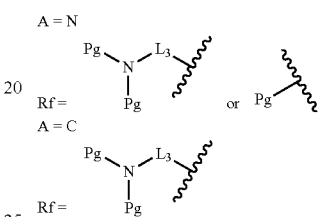

A = C

As a further illustration of compounds of formula III, the synthesis of compounds of formula IIIC is provided in Scheme 4. Reaction of sulfoximine IIIC-b with cycloketone IIIC-a provides compounds of formula IIIC-c. IIIC can be prepared from IIIC-c following the similar manipulations described in the preparation of IIIB.

Scheme 4

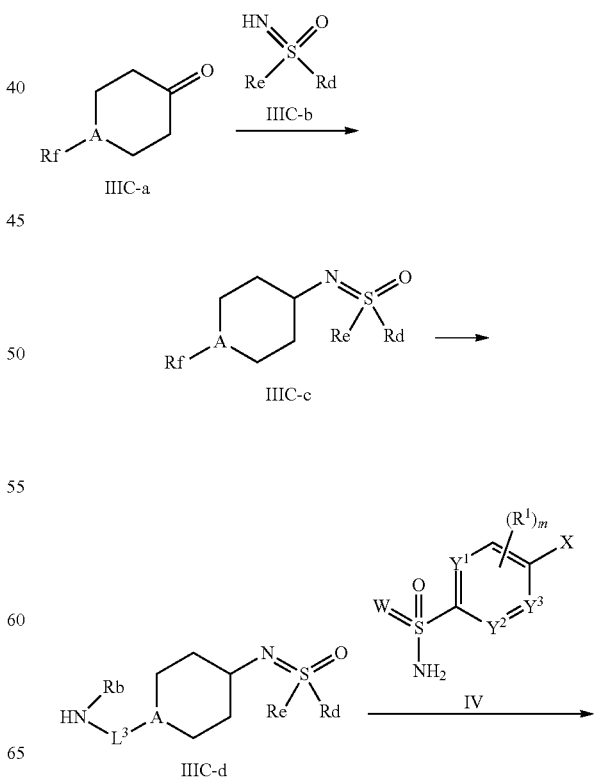

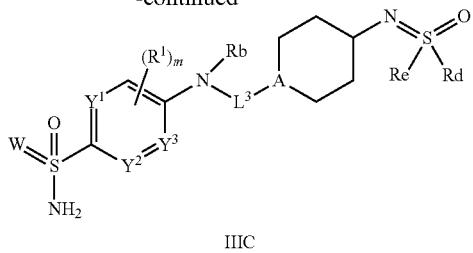

IIIC

Rb, Re and Rd are selected from R¹ provided that the structure is stable
Pg is protecting group
A = N

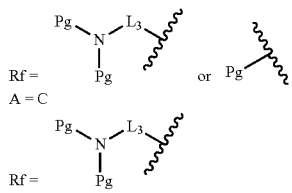

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Example 1

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-methyl-1-oxidophosphinan-4-yl)methyl)amino)-3-nitrophenyl)sulfonyl)benzamide (1)

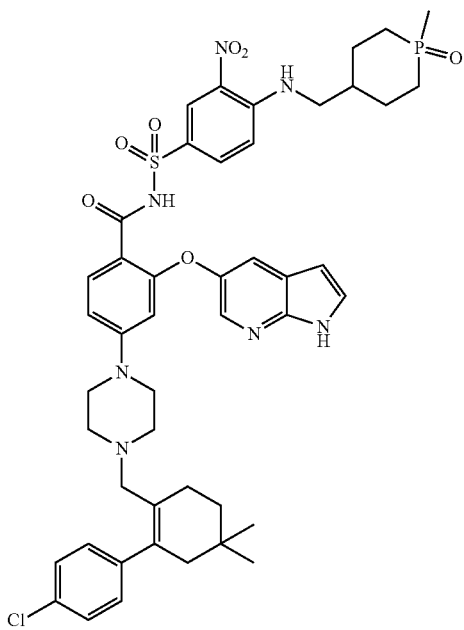

1-methylphosphinane-4-carboxylic acid 1-oxide (1a)

The title compound 1-methylphosphinane-4-carboxylic acid 1-oxide (1a) was prepared according to the method described in WO 2007/087068 (A1).

N-(2,4-dimethoxybenzyl)-1-methylphosphinane-4-carboxamide 1-oxide (1b)

A mixture of 1-methylphosphinane-4-carboxylic acid 1-oxide (1a) (0.05 g, 0.28 mmol), HATU (0.152 g, 0.40 mmol) and DIPEA (0.129 g, 1.0 mmol) in DMF (3 mL) was stirred at r.t. for 15 min, and DMBNH₂ (0.10 g, 0.56 mmol) was added. The mixture was stirred at r.t. for 1 h and the reaction was quenched with water (20 mL). The mixture was extracted by DCM/IPA (4:1, 4×30 mL), and the extracts were washed with brine (30 mL), dried over Na₂SO₄, and concentrated. The residue was purified by column chromatography on silica gel eluting with DCM/MeOH (100:1~100:5) to give title compound N-(2,4-dimethoxybenzyl)-1-methylphosphinane-4-carboxamide 1-oxide (1b). MS-ESI (m/z): 326 [M+1]⁺.

4-(((2,4-dimethoxybenzyl)amino)methyl)-1-methylphosphinane 1-oxide (1c)

A mixture of N-(2,4-dimethoxybenzyl)-1-methylphosphinane-4-carboxamide 1-oxide (1b) (0.079 g, 0.25 mmol) and BH₃.DMS (0.25 mL, 0.40 mmol) in THF (5 mL) was stirred at r.t. overnight. The reaction was quenched with MeOH (5 mL), and the mixture was concentrated. The residue was diluted with HCl aqueous (5 N, 5 mL) and washed with EtOAc (3×15 mL). The aqueous layer was concentrated and dried to give the title compound 4-(((2,4-dimethoxybenzyl)amino)methyl)-1-methylphosphinane 1-oxide (1c) used directly for next step. MS-ESI (m/z): 312 [M+1]⁺.

Tert-butyl (2,4-dimethoxybenzyl)((1-methyl-1-oxidophosphinan-4-yl)methyl)-carbamate (1d)

A mixture of 4-(((2,4-dimethoxybenzyl)amino)methyl)-1-methylphosphinane 1-oxide (1c) (0.031 g, 0.1 mmol), Boc₂O (0.043 g, 0.2 mmol) and TEA (0.050 g, 0.5 mmol) in MeOH (5 mL) was stirred at r.t. for 1 h. The reaction mixture was concentrated, diluted with water (15 mL) and extracted with ether (3×15 mL). The organic layer was discarded, and the aqueous layer was extracted by DCM/IPA (4:1, 3×20 mL). The extracts were washed with brine (30 mL), dried over Na₂SO₄, and evaporated to give title compound tert-butyl (2,4-dimethoxybenzyl)((1-methyl-1-oxidophosphinan-4-yl)methyl)carbamate (1d), which was used for next step directly. MS-ESI (m/z): 411[M+1]⁺.

Tert-butyl ((1-methyl-1-oxidophosphinan-4-yl)methyl)carbamate (1e)

A mixture of tert-butyl (2,4-dimethoxybenzyl)((1-methyl-1-oxidophosphinan-4-yl)methyl)carbamate (1d) (0.05 g, 0.125 mmol) and CAN (0.274 g, 0.5 mmol) in acetonitrile/H₂O (4/1 mL) was stirred at 0° C. for 15 min. The reaction was quenched by saturated NaHCO₃ aqueous solution (15 mL) and the mixture was extracted with DCM/IPA (4:1, 4×30 mL). The extracts were washed with brine (30 mL), dried over Na₂SO₄, and evaporated to give the crude product of tert-butyl ((1-methyl-1-oxidophosphinan-4-yl)methyl) carbamate (1e), which was used for next step directly. MS-ESI (m/z): 262 [M+1]⁺.

4-(aminomethyl)-1-methylphosphinane 1-oxide (1f)

A mixture of tert-butyl ((1-methyl-1-oxidophosphinan-4-yl)methyl)carbamate (1e) (0.03 g, ≈0.1 mmol) and TFA (0.1 mL, 1 mmol) in DCM (2 mL) was stirred at r.t. for 1 h. The reaction mixture was evaporated to give the crude product of 4-(aminomethyl)-1-methylphosphinane 1-oxide (1f), which was used for next step directly. MS-ESI (m/z): 162 [M+1]⁺.

4-chloro-3-nitrobenzenesulfonamide (1g)

The title compound 4-chloro-3-nitrobenzenesulfonamide (1g) was prepared according to the method described in US 2014/0275540, (A1).

4-(((1-methyl-1-oxidophosphinan-4-yl)methypamino)-3-nitrobenzenesulfonamide (1h)

A mixture of 4-(aminomethyl)-1-methylphosphinane 1-oxide (1f) (0.014 g, 0.1 mmol), 4-chloro-3-nitrobenzenesulfonamide (1g) (0.04 g, 0.17 mmol) and DIPEA (0.10 g, 0.77 mmol) in acetonitrile (4 mL) was stirred at 80° C. overnight. The reaction mixture was cooled to r.t. and concentrated. The residue was purified by preparative TLC to give title compound 4-(((1-methyl-1-oxidophosphinan-4-yl)methyl)amino)-3-nitrobenzenesulfonamide (1h). MS-ESI (m/z): 362 [M+1]⁺.

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoic acid (1i)

The title compound 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoic acid (1i) was prepared according to the method described in US 2014/0275540, (A1). MS-ESI (m/z): 571 [M+1]⁺.

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-methyl-1-oxidophosphinan-4-yl)methyl)amino)-3-nitrophenyl)sulfonyl)benzamide (1)

A mixture of 4-(((1-methyl-1-oxidophosphinan-4-yl)methyl)amino)-3-nitrobenzenesulfonamide (1h) (0.007 g, 0.02 mmol), EDCI (0.057 g, 0.03 mmol) and DMAP (0.0036 g, 0.03 mmol) in DCM (1.5 mL) was stirred at r.t. for 15 min, and then a mixture of 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoic acid (1i) (0.005 g, 0.01 mmol) and TEA (0.004 g, 0.04 mmol) in DCM (0.5 mL) was added. The resulted mixture was stirred at r.t. overnight and concentrated. The residue was purified by preparative TLC to give title compound 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-methyl-1-oxidophosphinan-4-yl)methyl)amino)-3-nitrophenyl)sulfonyl)benzamide (1). MS-ESI (m/z): 914 [M+1]⁺.

Example 2

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((2-(4-methyl-4-oxido-1,4-azaphosphinan-1-yl)ethyl)amino)-3-nitrophenyl)sulfonyl)benzamide (2)

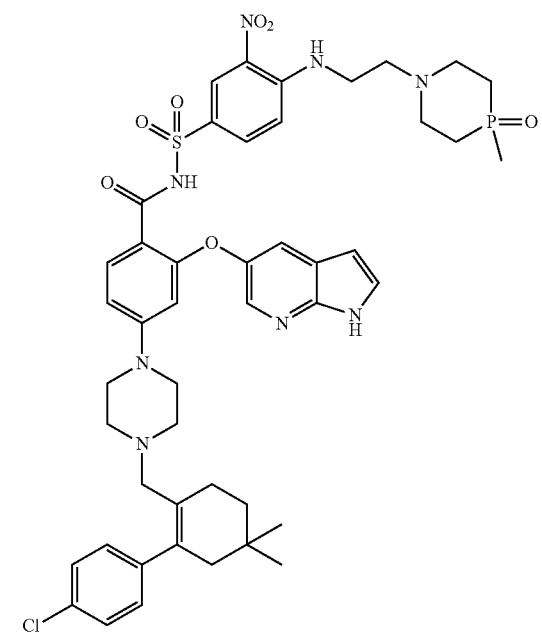

4-((2-aminoethyl)amino)-3-nitrobenzenesulfonamide (2a)

A mixture of 4-chloro-3-nitrobenzenesulfonamide (1g) (0.14 g, 0.5 mmol), ethane-1,2-diamine (0.60 g, 10 mmol) was stirred at 30° C. for 3 h. The reaction mixture was concentrated, and recrystallized with MeOH/EtOAc to give title compound 4-((2-aminoethyl)-amino)-3-nitrobenzenesulfonamide (2a). MS-ESI (m/z): 261 [M+1]⁺.

methyldivinylphosphine oxide (2b)

The title compound methyldivinylphosphine oxide (2a) was prepared according to the method described in WO 2007/087068 (A1). MS-ESI (m/z): 117 [M+1]⁺.

4-((2-(4-methyl-4-oxido-1,4-azaphosphinan-1-yl) ethyl)amino)-3-nitrobenzenesulfonamide (2c)

A mixture of 4-((2-aminoethyl)amino)-3-nitrobenzenesulfonamide (2a) (0.05 g, 0.20 mmol), methyldivinylphosphine oxide (2b) (0.10 g, 0.86 mmol) in THF/H₂O (1.5 mL/0.5 mL) was stirred at 70° C. for 24 h. The reaction mixture was concentrated, and purified by preparative TLC (DCM/MeOH=10:1) to give title compound 4-((2-(4-methyl-4-oxido-1,4-azaphosphinan-1-yl)ethyl)amino)-3-nitrobenzenesulfonamide (2c). MS-ESI (m/z): 377 [M+1]⁺.

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((2-(4-methyl-4-oxido-1,4-azaphosphinan-1-yl)ethyl)amino)-3-nitrophenyl)sulfonyl)benzamide (2)

The title compound 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((2-(4-methyl-4-oxido-1,4-azaphosphinan-1-yl)ethyl)amino)-3-nitrophenyl)sulfonyl)benzamide (2) was prepared according to the synthetic method of 1 by replacing 4-(((1-methyl-1-oxidophosphinan-4-yl)methyl)amino)-3-nitrobenzenesulfonamide (1h) with 4-((2-(4-methyl-4-oxido-1,4-azaphosphinan-1-yl)ethyl)amino)-3-nitrobenzenesulfonamide (2c). MS-ESI (m/z): 929 [M+1]$^+$.

Example 3

2-((1H-pyrrolo[2,3-b]pyridin-5-yl)thio)-4-(4-((4'-chloro-5,5-dimethyl-3,4,5,6-tetrahydro-[1,1'-biphenyl]-2-yl)methyl)piperazin-1-yl)-N-((4-((3-fluoro-2-(4-methyl-4-oxido-1,4-azaphosphinan-1-yl)propyl)amino)-3-nitrophenyl)sulfonyl)benzamide (3)

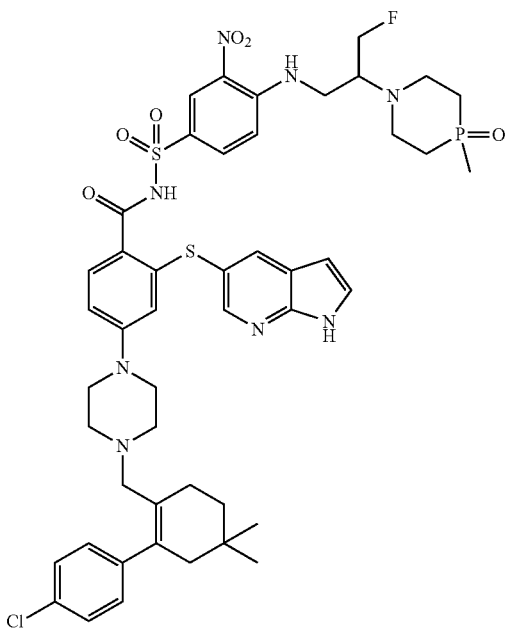

5-((4-methoxybenzypthio)-1H-pyrrolo[2,3-b]pyridine (3a)

A mixture of 5-bromo-1H-pyrrolo[2,3-b]pyridine (197 mg, 1.00 mmol), PMBSH (308 mg, 2.00 mmol), Pd$_2$(dba)$_3$ (0.05 mmol), xantphos (60.00 mg, 0.1 mmol) and DIPEA (387 mg, 3.00 mmol) in toluene (2 mL) was stirred at 120° C. in sealed-tube under N$_2$ for 15 h. The mixture was concentrated. The residue was purified by column chromatography on silica gel eluting with DCM/MeOH (100:1~100:5) to give title compound 5-((4-methoxybenzyl)thio)-1H-pyrrolo[2,3-b]pyridine (3a). MS-ESI (m/z): 271 [M+1]$^+$.

1H-pyrrolo[2,3-b]pyridine-5-thiol (3b)

A mixture of 5-((4-methoxybenzyl)thio)-1H-pyrrolo[2,3-b]pyridine (3a) (30 mg, 0.11 mmol) in TFA (1 mL) was stirred at 100° C. in sealed-tube overnight. The mixture was concentrated to give the title compound 1H-pyrrolo[2,3-b]pyridine-5-thiol (3b). MS-ESI (m/z): 151 [M+1]$^+$.

Methyl 2-((1H-pyrrolo[2,3-b]pyridin-5-yl)thio)-4-fluorobenzoate (3c)

To a solution of methyl 2,4-difluorobenzoate (34 mg, 0.20 mmol), Na$_2$CO$_3$ (21 mg, 0.226) in DMF (1 mL) was added dropwise a solution of 1H-pyrrolo[2,3-b]pyridine-5-thiol (3b) (30 mg, 0.20 mmol) in DMF (0.5 mL) at 120° C. over a period of 15 min and stirred at 120° C. for 10 min. water and EtOAc were added. The aqueous layer was extracted with EtOAc (3×30 mL). The combined organic layer was washed with brine, dried over Na$_2$SO$_4$, and concentrated. The residue was purified by column chromatography on silica gel eluting with DCM/MeOH (100:1~100:5) to give title compound methyl 2-((1H-pyrrolo[2,3-b]pyridin-5-yl)thio)-4-fluorobenzoate (3c). MS-ESI (m/z): 303[M+1]$^+$.

Methyl Dibenzylserinate (3d)

To a mixture of methyl serinate hydrochloride (3.00 g, 19.3 mmol) in DCM (20 mL) was added benzaldehyde (6.10 g, 57.85 mmol) followed by NaBH(OAc)$_3$. The mixture was stirred at r.t. for 1 h, and water and EA were added. The aqueous layer was extracted with EtOAc (3×30 mL). The combined organic layer was washed with brine, dried over Na$_2$SO$_4$, and concentrated to give title compound methyl dibenzylserinate (3d). MS-ESI (m/z): 300 [M+1]$^+$.

Methyl 2-(dibenzylamino)-3-fluoropropanoate (3e)

To a solution of methyl dibenzylserinate (3d) (200 mg, 0.33 mmol) in THF (2 mL) was added DAST (66 ∞L, 0.5 mmol) at −78° C. The mixture was warmed to r.t over 1 h, and stirred at r.t overnight. Water and EA were added. The aqueous layer was extracted with EtOAc (3×30 mL). The combined organic layer was washed with brine, dried over Na$_2$SO$_4$, and concentrated to give title compound methyl 2-(dibenzylamino)-3-fluoropropanoate (3e). MS-ESI (m/z): 302 [M+1]$^+$.

2-(dibenzylamino)-3-fluoropropanamide (3f)

A mixture of methyl 2-(dibenzylamino)-3-fluoropropanoate (3e) (100 mg, 0.33 mmol) in NH$_3$/MeOH (7 M, 3 mL) was stirred at r.t. overnight. The mixture was concentrated to give the crude product of the title compound 2-(dibenzylamino)-3-fluoropropanamide (3f). MS-ESI (m/z): 287 [M+1]$^+$.

N$^2$,N$^2$-dibenzyl-3-fluoropropane-1,2-diamine (3g)

A mixture of 2-(dibenzylamino)-3-fluoropropanamide (3f) (285 mg, 1 mmol) and BH$_3$/THF (5 mmol, 5 mL) in THF (5 mL) was stirred at 70° C. overnight. The mixture was used directly in next step.

Tert-butyl (2-(dibenzylamino)-3-fluoropropyl)carbamate (3h)

MeOH was added to the mixture, and then (Boc)$_2$O (436 mg, 2 mmol) was added. The mixture was stirred at r.t. for 1 h. water and EtOAc was added. The aqueous layer was extracted with EtOAc (3×30 mL). The combined organic layer was washed with brine, dried over Na$_2$SO$_4$, and concentrated. The residue was purified by column chromatography on silica gel eluting with EtOAc:PE (20:13:1) to give title compound tert-butyl (2-(dibenzylamino)-3-fluoropropyl)-carbamate (3h). MS-ESI (m/z): 373 [M+1]$^+$.

Tert-butyl (2-amino-3-fluoropropyl)carbamate (3i)

A mixture of tert-butyl (2-(dibenzylamino)-3-fluoropropyl)carbamate (3h) (50 mg, 0.13 mmol), Pd(OH)$_2$/C (20 mg) and AcOH (2 drops) in EtOH (3 mL) was stirred at r.t. overnight under H$_2$ balloon. The mixture was filtered, and filtrate was concentrated to give title compound tert-butyl (2-amino-3-fluoropropyl)carbamate (3i). MS-ESI (m/z): 193 [M+1]$^+$.

1-(1-amino-3-fluoropropan-2-yl)-4-methyl-1,4-azaphosphinane 4-oxide (3j)

1-(1-amino-3-fluoropropan-2-yl)-4-methyl-1,4-azaphosphinane 4-oxide (3j) was prepared according to the synthetic method of 2c by replacing 4-((2-aminoethyl)amino)-3-nitrobenzenesulfonamide (2a) with tert-butyl (2-amino-3-fluoropropyl) carbamate (3i). MS-ESI (m/z): 209 [M+1]$^+$.

4-((3-fluoro-2-(4-methyl-4-oxido-1,4-azaphosphinan-1-yl)propyl)amino)-3-nitro benzenesulfonamide (3k)

4-((3-fluoro-2-(4-methyl-4-oxido-1,4-azaphosphinan-1-yl)propyl)amino)-3-nitro benzenesulfonamide (3k) was prepared according to the synthetic method of 1h by replacing 4-(aminomethyl)-1-methylphosphinane 1-oxide (1f) with 1-(1-amino-3-fluoropropan-2-yl)-4-methyl-1,4-azaphosphinane 4-oxide (3j). MS-ESI (m/z): 409 [M+1]$^+$.

Methyl2-((1H-pyrrolo[2,3-b]pyridin-5-yl)thio)-4-(4-((4'-chloro-5,5-dimethyl-3,4,5,6-tetrahydro-[1,1'-biphenyl]-2-yl)methyl)piperazin-1-yl)benzoate (3l)

The title compound methyl2-((1H-pyrrolo[2,3-b]pyridin-5-yl)thio)-4-(4-((4'-chloro-5,5-dimethyl-3,4,5,6-tetrahydro-[1,1'-biphenyl]-2-yl)methyl)piperazin-1-yl)benzoate (3l) was prepared according to the method described in WO 2011150016.

2-((1H-pyrrolo[2,3-b]pyridin-5-yl)thio)-4-(4-((4'-chloro-5,5-dimethyl-3,4,5,6-tetrahydro-[1,1'-biphenyl]-2-yl)methyl)piperazin-1-yl)benzoic acid (3m)

The title compound 2-((1H-pyrrolo[2,3-b]pyridin-5-yl)thio)-4-(4-((4'-chloro-5,5-dimethyl-3,4,5,6-tetrahydro-[1,1'-biphenyl]-2-yl)methyl)piperazin-1-yl)benzoic acid (3m) was prepared according to the method described in US 20140275540 (A1). MS-ESI (m/z): 587 [M+1]$^+$.

2-((1H-pyrrolo[2,3-b]pyridin-5-yl)thio)-4-(4-((4'-chloro-5,5-dimethyl-3,4,5,6-tetrahydro-[1,1'-biphenyl]-2-yl)methyl)piperazin-1-yl)-N-((4-((3-fluoro-2-(4-methyl-4-oxido-1,4-azaphosphinan-1-yl)propyl)amino)-3-nitrophenyl)sulfonyl)benzamide (3)

The title compound 2-((1H-pyrrolo[2,3-b]pyridin-5-yl)thio)-4-(4-((4'-chloro-5,5-dimethyl-3,4,5,6-tetrahydro-[1,1'-biphenyl]-2-yl)methyl)piperazin-1-yl)-N-((4-((3-fluoro-2-(4-methyl-4-oxido-1,4-azaphosphinan-1-yl)propyl)amino)-3-nitrophenyl)sulfonyl)benzamide (3) was prepared according to the synthetic method of 1 by replacing 4-(((1-methyl-1-oxidophosphinan-4-yl)methyl)amino)-3-nitrobenzenesulfonamide (1h) with 4-((3-fluoro-2-(4-methyl-4-oxido-1,4-azaphosphinan-1-yl)propyl)amino)-3-nitrobenzenesulfonamide (3k) and 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoic acid (1i) with 2-((1H-pyrrolo[2,3-b]pyridin-5-yl)thio)-4-(4-((4'-chloro-5,5-dimethyl-3,4,5,6-tetrahydro-[1,1'-biphenyl]-2-yl)methyl)piperazin-1-yl)benzoic acid (3m). MS-ESI (m/z): 977 [M+1]$^+$.

Example 4

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(cyanoimino)-1-oxidohexahydro-1λ$^6$-thiopyran-4-yl)methyl)amino)-3-nitrophenyl)sulfonyl)benzamide (4)

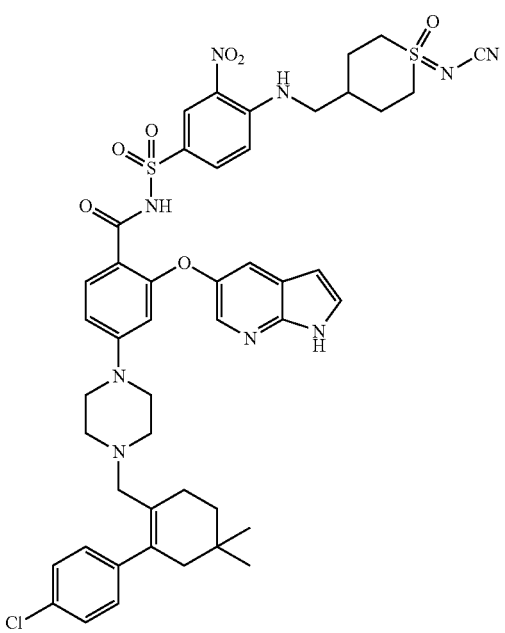

Tetrahydro-2H-thiopyran-4-carbonitrile (4a)

To a mixture of tetrahydro-4H-thiopyran-4-one (10.0 g, 0.08 mmol), TOSMIC (18.5 g, 0.09 mmol) and EtOH (7.10 g, 0.15 mmol) in DME was added t-BuOK (20.0 g, 0.18 mmol) in portions, and the mixture was stirred at 0° C. for 12 h. The reaction mixture was diluted with water (500 ml) and extracted with MTBE (2×500 mL). The extracts were washed sequentially with NaHCO$_3$ (500 ml) and brine (500 mL), dried over Na$_2$SO$_4$, and concentrated to give title compound tetrahydro-2H-thiopyran-4-carbonitrile (4a). MS-ESI (m/z): 128 [M+1]$^+$.

(tetrahydro-2H-thiopyran-4-yl)methanamine (4b)

To a mixture of LiAlH$_4$ (1.80 g, 47.0 mmol) in THF (90 mL) at 25° C. was added a solution of tetrahydro-2H-thiopyran-4-carbonitrile (4a) (3.00 g, 23.6 mmol) in THF (30 mL), The mixture was cooled to 0° C. and stirred at the same temperature for 1.5 h. To the reaction mixture was added Na$_2$SO$_4$.10H$_2$O at 0° C. The mixture was filtered through Celite. The cake was washed with EtOAc (50 mL).

The extracts were washed sequentially with water and brine, dried and concentrated to give the title compound (tetrahydro-2H-thiopyran-4-yl)methanamine (4b). MS-ESI (m/z): 132 [M+1]$^+$.

Benzyl ((tetrahydro-2H-thiopyran-4-yl)methyl)carbamate (4c)

To a mixture of (tetrahydro-2H-thiopyran-4-yl)methanamine (4b) (1.20 g, 7.10 mmol) in DCM (20 mL) was added TEA (3.10 g, 21.0 mmol). Then CBz-Cl (1.30 g, 7.80 mmol) was added dropwise. The mixture was stirred at ambient temperature for 1.5 h. The reaction mixture was diluted with water (500 ml) and then extracted with DCM (3×50 mL). The combined organic layer was washed sequentially with water and brine, dried and concentrated. The residue was purified by column chromatography on silica gel eluting with EtOAc/PE (1:20¬1:4) to give title compound benzyl ((tetrahydro-2H-thiopyran-4-yl)methyl) carbamate (4c). MS-ESI (m/z): 266 [M+1]$^+$.

Benzyl ((1-(cyanoimino)hexahydro-1$\lambda^4$-thiopyran-4-yl)methyl)carbamate (4d)

To a solution of ((tetrahydro-2H-thiopyran-4-yl)methyl) carbamate (4c) (0.20 g, 0.86 mmol), NH$_2$CN (47.0 mg, 1.10 mmol) and t-BuOK (0.12 g, 1.03 mmol) in EtOH (9 ml) was added NBS, and the mixture was stirred at ambient temperature for 12 h. The reaction mixture was diluted with water (30 ml) and then extracted with EtOAc (3×30 mL). The extracts were washed sequentially with water (2×30 mL) and brine (30 mL), dried and concentrated to give the title compound benzyl ((1-(cyanoimino)hexahydro-1$\lambda^4$-thiopyran-4-yl)methyl)carbamate (4d). MS-ESI (m/z): 306 [M+1]$^+$.

Benzyl ((1-(cyanoimino)-1-oxidohexahydro-1$\lambda^6$-thiopyran-4-yl)methyl)carbamate (4e)

A mixture of benzyl ((1-(cyanoimino)hexahydro-1$\lambda^4$-thiopyran-4-yl)methyl)carbamate (4d) (0.30 g, 0.98 mmol), m-CPBA (0.34 g, 1.97 mmol) and K$_2$CO$_3$ (0.34 g, 2.50 mmol) in EtOH (8 ml) was stirred at ambient temperature for 12 h. The reaction mixture was diluted with water (30 ml) and extracted with EtOAc (3×30 mL). The extracts were washed with water (2×30 mL), dried and concentrated. The residue was purified by column chromatography on silica gel eluting with EtOAc/PE (1:5~1:1) to give title compound benzyl((1-(cyanoimino)-1-oxidohexahydro-1$\lambda^6$-thiopyran-4-yl)methyl)carbamate (4e). MS-ESI (m/z): 322 [M+1]$^+$.

N-(4-(aminomethyl)-1-oxidotetrahydro-2H-1$\lambda^6$-thiopyran-1-ylidene)cyanamide (4f)

To a mixture of benzyl ((1-(cyanoimino)-1-oxidohexahydro-1$\lambda^6$-thiopyran-4-yl)methyl)carbamate (4e) (107 mg, 0.30 mmol), and Pd/C in MeOH (6 ml) was introduced H$_2$. The mixture was stirred at ambient temperature for 12 h. The organic layer was diluted with water (30 ml) and extracted with EtOAc (3×30 mL). The extracts were washed with water (2×30 mL), dried and concentrated to give title compound N-(4-(aminomethyl)-1-oxidotetrahydro-2H-1$\lambda^6$-thiopyran-1-ylidene)cyanamide (4f). MS-ESI (m/z): 188 [M+1]$^+$.

4-(((1-(cyanoimino)-1-oxidohexahydro-1$\lambda^6$-thiopyran-4-yl)methyl)amino)-3-nitrobenzenesulfonamide (4g)

A mixture of N-(4-(aminomethyl)-1-oxidotetrahydro-2H-1$\lambda^6$-thiopyran-1-ylidene)cyanamide (4f) (50.0 mg, 0.30 mmol), DIPEA (220 μl, 1.33 mmol), and 4-chloro-3-nitrobenzenesulfonamide (76.0 mg, 0.30 mmol) in acetonitrile (4 ml) was stirred at 80° C. for 12 h. The reaction mixture was diluted with water (30 ml) and extracted with EtOAc (3×30 mL). The extracts were washed with water (2×30 mL), dried and concentrated to give title compound 4-(((1-(cyanoimino)-1-oxidohexahydro-1$\lambda^6$-thiopyran-4-yl)methyl)amino)-3-nitrobenzenesulfonamide (4g). MS-ESI (m/z): 388 [M+1]$^+$.

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(cyanoimino)-1-oxidohexahydro-1$\lambda^6$-thiopyran-4-yl) methyl)amino)-3-nitrophenyl)sulfonyl)benzamide (4)

To a mixture of 4-(((1-(cyanoimino)-1-oxidohexahydro-1$\lambda^6$-thiopyran-4-yl)-methyl)amino)-3-nitrobenzenesulfonamide (4g) (20.0 mg, 0.05 mmol), EDCI (23.0 mg, 0.12 mmol), and DMAP (15.0 mg, 0.12 mmol) in DCM (5 ml) was added a solution of 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoic acid (1i) (23.0 mg, 0.04 mmol) and TEA (18.0 μl, 0.12 mmol) in DCM (5 ml). The mixture was stirred at ambient temperature for 12 h. The reaction mixture was diluted with water (30 ml) and extracted with DCM (4×30 mL). The extracts were washed sequentially with water (2×20 mL) and brine (20 mL), dried and concentrated to give title compound 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl) piperazin-1-yl)-N-((4-(((1-(cyanoimino)-1-oxidohexahydro-1$\lambda^6$-thiopyran-4-yl)methyl)amino)-3-nitrophenyl) sulfonyl)benzamide (4). MS-ESI (m/z): 940 [M+1]$^+$.

Example 5

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(cyclopropylimino)-1-oxidohexahydro-1$\lambda^6$-thiopyran-4-yl) methypamino)-3-nitrophenyl)sulfonyl)benzamide (5)

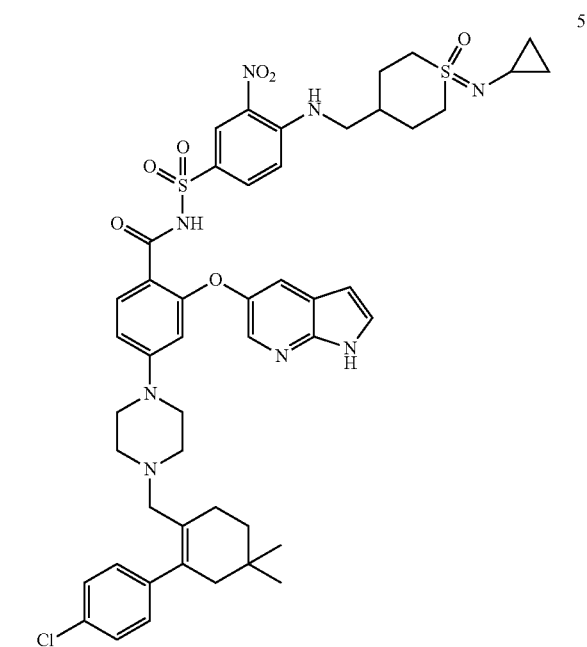 [SMILES: CC1(C)CCC(CN2CCN(c3ccc(C(=O)NS(=O)(=O)c4ccc(NCC5CCS(=O)(=NC6CC6)CC5)c([N+](=O)[O-])c4)c(Oc4cnc5[nH]ccc5c4)c3)CC2)=C(c2ccc(Cl)cc2)C1]

N-(4-cyanotetrahydro-2H-1λ⁴-thiopyran-1-ylidene)-4-methylbenzenesulfonamide (5a)

To a mixture of tetrahydro-2H-thiopyran-4-carbonitrile (4a) (500 mg, 3.93 mmol), chloromine-T (986 mg, 4.33 mmol) in DCM (15 ml) was added TETRA-N-BUTYLAMMONIUM BROMIDE (127 mg, 0.39 mmol). The mixture was stirred at ambient temperature for 18 h. The reaction mixture was diluted with water (30 ml) and extracted with EtOAc (3×30 mL). The extracts were washed with water (2×30 mL), dried and concentrated to give title compound N-(4-cyanotetrahydro-2H-1λ⁴-thiopyran-1-ylidene)-4-methylbenzenesulfonamide (5a). MS-ESI (m/z): 297 [M+1]⁺.

N-(4-cyano-1-oxidotetrahydro-2H-1λ⁶-thiopyran-1-ylidene)-4-methylbenzenesulfonamide (5b)

A mixture of N-(4-cyanotetrahydro-2H-1λ⁴-thiopyran-1-ylidene)-4-methylbenzenesulfonamide (5a) (70.0 mg, 0.24 mmol), m-CPBA (96.0 mg, 0.47 mmol) and $K_2CO_3$ (81.0 mg, 0.59 mmol) in EtOH (3 ml) was stirred at ambient temperature for 12 h. The reaction mixture was diluted with water (30 ml) and extracted with EtOAc (3×30 mL). The extracts were washed with water (2×30 mL), dried and concentrated to give title compound N-(4-cyano-1-oxidotetrahydro-2H-1λ⁶-thiopyran-1-ylidene)-4-methylbenzenesulfonamide (5b). MS-ESI (m/z): 313 [M+1]⁺.

1-iminohexahydro-1λ⁶-thiopyran-4-carbonitrile 1-oxide (5c)

To a mixture of N-(4-cyano-1-oxidotetrahydro-2H-1λ⁶-thiopyran-1-ylidene)-4-methylbenzenesulfonamide (5b) (450 mg, 1.44 mmol) and naphthalen-1-ylsodium (2.16 g, 14.4 mmol) in DME (30 ml) was stirred at −20° C. for 12 h. The reaction mixture was concentrated. The residue was purified by column chromatography on silica gel eluting with DCM/MeOH (40:1) to give title compound 1-iminohexahydro-1λ⁶-thiopyran-4-carbonitrile 1-oxide (5c). MS-ESI (m/z): 159 [M+1]⁺.

1-(cyclopropylimino)hexahydro-λ⁶-thiopyran-4-carbonitrile 1-oxide (5d)

To a mixture of 1-iminohexahydro-λ6-thiopyran-4-carbonitrile 1-oxide (5c) (0.01 g, 0.06 mmol), $Cu(OAc)_2 \cdot H_2O$ (12.6 mg, 0.06 mmol), 2,2'-bipyridine (8.00 mg, 0.05 mmol) and $Na_2CO_3$ (17.0 mg, 0.16 mmol) in DCE (1 ml) was added cyclopropylboronic acid (12.0 mg, 0.14 mmol). The mixture was stirred at 90° C. under $N_2$ for 2.5 h. The reaction mixture was diluted with water (30 mL) and extracted with DCM (3×20 mL). The extracts were washed sequentially with water and brine, dried and concentrated to give title compound 1-(cyclopropylimino)hexahydro-λ⁶-thiopyran-4-carbonitrile 1-oxide (5d). MS-ESI (m/z): 199 [M+1]⁺.

4-(aminomethyl)-1-(cyclopropylimino)hexahydro-1λ⁶-thiopyran 1-oxide (5e)

To a mixture of LAH (6.00 mg, 0.15 mmol) in THF (1 mL) was added a solution of 1-(cyclopropylimino)hexahydro-1λ⁶-thiopyran-4-carbonitrile 1-oxide (5d) (10.0 mg, 0.05 mmol) in THF (1 mL) dropwise at ambient temperature. Then the mixture was warmed to 40° C. for 1 h. The reaction mixture was added $Na_2SO_4 \cdot 10H_2O$ at 0° C. The mixture was filtered through Celite and concentrated to give the title compound 4-(aminomethyl)-1-(cyclopropylimino)-hexahydro-1λ⁶-thiopyran 1-oxide (5e). MS-ESI (m/z): 203 [M+1]⁺.

4-(((1-(cyclopropylimino)-1-oxidohexahydro-1λ⁶-thiopyran-4-yl)methyl)amino)-3-nitrobenzenesulfonamide (5f)

A mixture of 4-(aminomethyl)-1-(cyclopropylimino) hexahydro-1λ⁶-thiopyran 1-oxide (5e) (25.0 mg, 0.12 mmol), DIPEA (64.0 mg, 0.49 mmol) and 4-chloro-3-nitrobenzenesulfonamide (30.0 mg, 0.12 mmol) in acetonitrile (1 ml) was stirred at 80° C. for 12 h. The reaction mixture was concentrated. The residue was purified by column chromatography on silica gel eluting with DCM/MeOH (15:1) to give title compound 4-(((1-(cyclopropylimino)-1-oxidohexahydro-1λ⁶-thiopyran-4-yl)methyl) amino)-3-nitrobenzenesulfonamide (5f). MS-ESI (m/z): 403 [M+1]⁺.

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(cyclopropylimino)-1-oxidohexahydro-1λ⁶-thiopyran-4-yl) methyl)amino)-3-nitrophenyl)sulfonyl)benzamide (5)

The title compound 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(cyclopropylimino)-1-oxidohexahydro-1λ⁶-thiopyran-4-yl) methyl)amino)-3-nitrophenyl)sulfonyl) benzamide (5) was prepared according to the method described in Example 1 by replacing 4-(((1-methyl-1-oxidophosphinan-4-yl)methyl) amino)-3-nitrobenzenesulfonamide (1h) with 4-(((1-(cyclopropylimino)-1-oxidohexahydro-1λ⁶-thiopyran-4-yl) methyl)amino)-3-nitrobenzenesulfonamide (5f). MS-ESI (m/z): 955 [M+1]⁺.

Example 6

(S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(1-(cyanoimino)-1-oxido-1λ⁶-thiomorphohno)propan-2-yl) amino)-3-nitrophenyl)sulfonyl)benzamide (6)

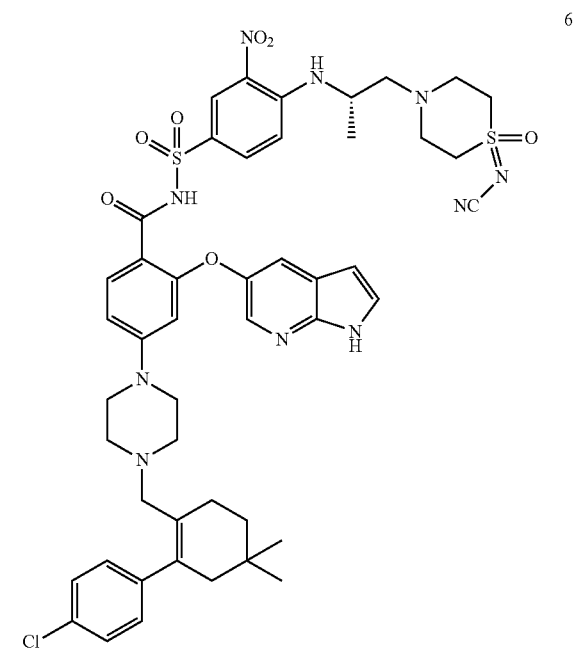 [SMILES: CN=S1(=O)CCN(C[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1]

6

Benzyl 1-(cyanoimino)-1λ⁴-thiomorpholine-4-carboxylate (6a)

To a mixture of benzyl thiomorpholine-4-carboxylate (0.90 g, 3.80 mmol), Cyanamide (0.21 g, 4.94 mmol) and t-BuOK (0.51 g, 4.55 mmol) in MeOH (20 mL) was added NBS (1.01 g, 5.70 mmol) at r.t. The reaction mixture was stirred at r.t. overnight and concentrated. To the residue was added sat. aqueous $Na_2S_2O_3$, and the mixture was extracted with DCM (3×30 ml). The combined organic layers was washed with brine (40 mL), dried over $Na_2SO_4$ and concentrated to give title compound benzyl 1-(cyanoimino)-1λ⁴-thiomorpholine-4-carboxylate (6a). MS-ESI (m/z): 278 [M+1]⁺.

Benzyl 1-(cyanoimino)-1λ⁶-thiomorphohne-4-carboxylate 1-oxide (6b)

A mixture of benzyl 1-(cyanoimino)-1λ⁴-thiomorpholine-4-carboxylate (6a) (0.85 g, 3.07 mmol) and $K_2CO_3$ (1.27 g, 9.20 mmol) in EtOH (25 mL) was stirred at 0° C. and to the mixture was added m-CPBA (0.79 g, 4.60 mmol). The reaction mixture was stirred at r.t. overnight and diluted with water (100 mL), extracted sequentially with DCM (2×30 mL) and EtOAc (2×30 mL). The combined organic layers was dried over $Na_2SO_4$ and concentrated. The residue was purified by column chromatography on silica gel eluting with EtOAc to give the title compound benzyl 1-(cyanoimino)-1λ⁶-thiomorpholine-4-carboxylate 1-oxide (6b). MS-ESI (m/z): 294 [M+1]⁺.

N-(1-oxido-1λ⁶-thiomorpholin-1-ylidene)cyanamide (6c)

A mixture of benzyl 1-(cyanoimino)-1λ⁶-thiomorpholine-4-carboxylate 1-oxide (6b) (1.30 g, 4.44 mmol) and Pd/C (0.50 g) in MeOH (60 mL) was stirred at r.t. under $H_2$ atmosphere for 2 hours. The reaction mixture was filtered through celite and concentrated to give the crude product of title compound N-(1-oxido-1λ⁶-thiomorpholin-1-ylidene)cyanamide (6c) which was used directly for next step. MS-ESI (m/z): 160 [M+1]⁺.

(9H-fluoren-9-yl)methyl (S)-(1-hydroxypropan-2-yl)carbamate (6d)

A mixture of tert-butyl (S)-(1-hydroxypropan-2-yl)carbamate (4.70 g, 26.8 mmol) and TFA (8 mL) in DCM (10 mL) was stirred at r.t. for 1 h. The reaction mixture was concentrated. The residue was dissolved in dioxane (25 mL) and added 9-fluorenylmethyl chloroformate (10.2 g, 39.4 mmol), $Na_2CO_3$ (5.60 g, 52.8 mmol) and water (25 mL). The reaction mixture was stirred at r.t. for 2 hours and extracted with DCM (3×25 mL). The combined organic layers was washed with brine (40 mL), dried over $Na_2SO_4$ and evaporated. The residue was purified by column chromatography on silica gel eluting with EtOAc to give title compound (9H-fluoren-9-yl)methyl (S)-(1-hydroxypropan-2-yl)carbamate (6d). MS-ESI (m/z): 298 [M+1]⁺.

(9H-fluoren-9-yl)methyl (S)-(1-oxopropan-2-yl)carbamate (6e)

A mixture of (9H-fluoren-9-yl)methyl (S)-(1-hydroxypropan-2-yl)carbamate (6d) (4.00 g, 13.5 mmol) and Dess-Martin periodinane (6.85 g, 16.1 mmol) in DCM (80 mL) was stirred at 0° C. for 15 min. The mixture was warmed to room temperature and stirred for 3 hours. The reaction was quenched by saturated $NaHCO_3$ aqueous solution (150 mL) and saturated $Na_2S_2O_3$ aqueous solution (150 mL). The mixture was extracted with DCM (2×150 mL). The extracts were washed with brine (80 mL), dried over $Na_2SO_4$, and evaporated to give the crude product of (9H-fluoren-9-yl)methyl (S)-(1-oxopropan-2-yl)carbamate (6e), which was used for next step directly. MS-ESI (m/z): 296 [M+1]⁺.

(9H-fluoren-9-yl)methyl (S)-(1-(1-(cyanoimino)-1-oxido-1λ⁶-thiomorphohno)propan-2-yl)carbamate (6f)

A mixture of N-(1-oxido-1λ⁶-thiomorpholin-1-ylidene)cyanamide (6c) (120 mg, 0.75 mmol), (9H-fluoren-9-yl)methyl (S)-(1-oxopropan-2-yl)carbamate (6e) (333 mg, 1.13 mmol) and AcOH (90 mg, 1.51 mmol) in DCE (2 mL) was stirred at 50° C. for 1 h. The reaction mixture was cooled to 10° C., and added $NaBH(OAc)_3$ (640 mg, 3.02 mmol). The mixture was stirred at room temperature for 1 hour. The reaction was quenched by saturated $NaHCO_3$ aqueous solution (30 mL). The mixture was extracted with DCM (3×15 mL). The extracts were washed with brine (20 mL), dried over $Na_2SO_4$, and evaporated to give the crude product, purified by column chromatography on silica gel eluting with PE/EtOAc (2/1~1/1) to give the product of (9H-fluoren-9-yl)methyl (S)-(1-(1-(cyanoimino)-1-oxido-1λ⁶-thiomorpholino)propan-2-yl)-carbamate (6f). MS-ESI (m/z): 439 [M+1]⁺.

(S)-N-(4-(2-aminopropyl)-1-oxido-1λ⁶-thiomorphohn-1-yhdene)cyanamide (6g)

A mixture of (9H-fluoren-9-yl)methyl (S)-(1-(1-(cyanoimino)-1-oxido-1λ⁶-thiomorpholino)propan-2-yl)carbamate (6f) (50 mg, 0.11 mmol) and piperidine (1 mL) in THF (1 mL) was stirred at room temperature for 3 hours. The reaction mixture was concentrated and purified by column chromatography on silica gel eluting with DCM/7M $NH_3$ in MeOH (10/1) to give the product of (S)-N-(4-(2-aminopropyl)-1-oxido-1λ⁶-thiomorpholin-1-ylidene)cyanamide (6g). MS-ESI (m/z): 217 [M+1]⁺.

(S)-4-((1-(1-(cyanoimino)-1-oxido-1λ⁶-thiomorphohno)propan-2-yl)amino)-3-nitrobenzenesulfonamide (6h)

A mixture of (S)-N-(4-(2-aminopropyl)-1-oxido-1λ⁶-thiomorpholin-1-ylidene)cyanamide (6g) (40.0 mg, 0.18 mmol), 4-chloro-3-nitrobenzenesulfonamide (52 mg, 0.22 mmol) and DIPEA (119 mg, 0.93 mmol) in acetonitrile (2 mL) was stirred at 80° C. overnight. The reaction mixture was cooled to r.t. and concentrated. The residue was purified by preparative TLC to give title compound (S)-4-((1-(1-(cyanoimino)-1-oxido-1λ⁶-thiomorpholino)propan-2-yl)amino)-3-nitrobenzenesulfonamide (6h). MS-ESI (m/z): 417 [M+1]⁺.

(S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(1-(cyanoimino)-1-oxido-1λ⁶-thiomorpholino)propan-2-yl)amino)-3-nitrophenyl)sulfonyl)benzamide (6)

A mixture of (S)-4-((1-(1-(cyanoimino)-1-oxido-1λ⁶-thiomorpholino)propan-2-yl)amino)-3-nitrobenzenesulfonamide (6h) (7.3 mg, 0.02 mmol), EDCI (8.0 g, 0.04 mmol)

and DMAP (5.0 mg, 0.04 mmol) in DCM (1.5 mL) was stirred at r.t. for 15 min, and then a mixture of 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoic acid (1i) (8 mg, 0.01 mmol) and TEA (4 mg, 0.04 mmol) in DCM (0.5 mL) was added. The resulted mixture was stirred at r.t. overnight and concentrated. The residue was purified by preparative TLC to give title compound (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(1-(cyanoimino)-1-oxido-1$\lambda^6$-thiomorpholino)-propan-2-yl)amino)-3-nitrophenyl)sulfonyl)benzamide (6). MS-ESI (m/z): 969 [M+1]$^+$.

Example 7

(S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(1-(methylimino)-1-oxidothiomorpholino)propan-2-yl)amino)-3-nitrophenyl)sulfonyl)benzamide (7)

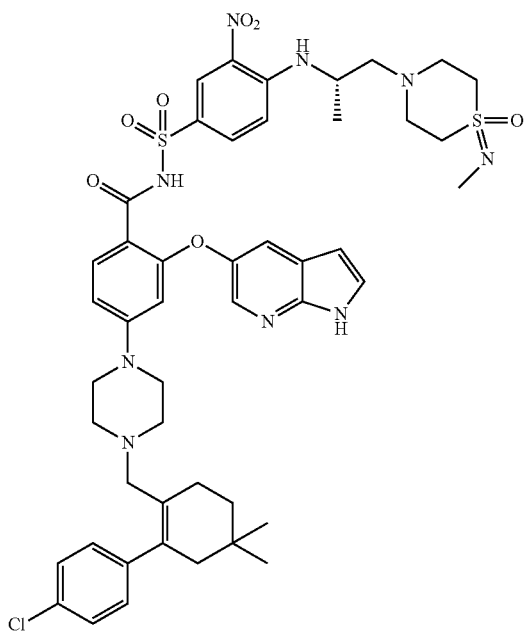

7

Tert-butyl 1-imino-1-oxo-1,4-thiazinane-4-carboxylate (7a)

The compound tert-butyl 1-imino-1-oxo-1,4-thiazinane-4-carboxylate (7a) was prepared according to the method described in Tetrahedron 70 (2014) 6613-6622.

Tert-butyl 1-(methylimino)thiomorpholine-4-carboxylate 1-oxide (7b)

To a solution of tert-butyl 1-imino-1-oxo-1,4-thiazinane-4-carboxylate (80 mg, 0.34 mmol) in DMF (1 mL) was added sodium hydride (16 mg, 0.68 mmol) at room temperature. The reaction mixture was stirred at room temperature for 10 mins. Then iodomethane (72 mg, 0.51 mmol) was added to the mixture and stirred for 0.5 h. The reaction was quenched with H$_2$O (0.1 mL) and the mixture was concentrated. The residue was washed with DCM and filtered. The filtrate was concentrated to give title compound tert-butyl 1-(methylimino)thiomorpholine-4-carboxylate 1-oxide (7b). MS-ESI (m/z): 249 [M+1]$^+$.

1-(methylimino)thiomorpholine 1-oxide hydrochloride (7c)

The mixture of tert-butyl 1-(methylimino)thiomorpholine-4-carboxylate 1-oxide in HCl/EtOAc (1.7 N) was stirred at r.t. for 2 hours. Then the mixture was concentrated to give the crude product of the title compound 1-(methylimino)thiomorpholine 1-oxide hydrochloride (7c). MS-ESI (m/z): 149 [M+1]$^+$.

(9H-fluoren-9-yl)methyl(S)-(1-(1-(methylimino)-1-oxido-1$\lambda^6$-thiomorpholino)-propan-2-yl)carbamate (7d)

A mixture of 1-(methylimino)thiomorpholine 1-oxide hydrochloride (7c) (50 mg, 0.34 mmol), (9H-fluoren-9-yl)methyl (S)-(1-oxopropan-2-yl)carbamate (6e) (118 mg, 0.4 mmol) and AcOH (41 mg, 0.68 mmol) in DCE (5 mL) was stirred at 50° C. for 1 h. The reaction mixture was cooled to 10° C., and NaBH(OAc)$_3$ (288 mg, 1.36 mmol) was added. The mixture was stirred at r.t. for 1 hour. The reaction was quenched by saturated NaHCO$_3$ aqueous solution (30 mL), extracted with DCM (3×15 mL). The extracts were washed with brine (20 mL), dried over Na$_2$SO$_4$, and evaporated to give the crude product. The residue was purified by column chromatography on silica gel eluting with PE/EtOAc (2:1 to 1:1) to give the product of (9H-fluoren-9-yl)methyl (S)-(1-(1-(methylimino)-1-oxido-1$\lambda^6$-thiomorpholino)propan-2-yl)carbamate (7d). MS-ESI (m/z): 428 [M+1]$^+$.

(S)-4-(2-aminopropyl)-1-(methylimino)-1$\lambda^6$-thiomorpholine 1-oxide (7e)

A mixture of (9H-fluoren-9-yl)methyl(S)-(1-(1-(methylimino)-1-oxithiomorpholino)propan-2-yl)carbamate (7d) (55 mg, 0.13 mmol) and piperidine (1 mL) in THF (1 mL) was stirred at room temperature for 3 hours. The reaction mixture was concentrated and purified by column chromatography on silica gel eluting with DCM/7 M NH$_3$ in MeOH (10/1) to give the product of (S)-4-(2-aminopropyl)-1-(methylimino)-1$\lambda^6$-thiomorpholine 1-oxide (7e). MS-ESI (m/z): 206 [M+1]$^+$.

(S)-4-((1-(1-(methylimino)-1-oxido-1$\lambda^6$-thiomorpholino)propan-2-yl)amino)-3-nitrobenzenesulfonamide (7f)

A mixture of (S)-4-(2-aminopropyl)-1-(methylimino)-1$\lambda^6$-thiomorpholine 1-oxide (7e) (50.0 mg, 0.24 mmol), 4-chloro-3-nitrobenzenesulfonamide (68 mg, 0.29 mmol) and DIPEA (154 mg, 1.2 mmol) in acetonitrile (2 mL) was stirred at 80° C. overnight. The reaction mixture was cooled to r.t. and concentrated. The residue was purified by preparative TLC to give title compound (S)-4-((1-(1-(methylimino)-1-oxido-1$\lambda^6$-thiomorpholino)propan-2-yl)amino)-3-nitrobenzenesulfonamide (7f). MS-ESI (m/z): 406 [M+1]$^+$.

(S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(1-(methylimino)-1-oxido-1λ⁶-thiomorpholino)propan-2-yl)amino)-3-nitrophenyl)sulfonyl)benzamide (7)

A mixture of (S)-4-((1-(1-(methylimino)-1-oxido-1λ⁶-thiomorpholino)propan-2-yl)amino)-3-nitrobenzenesulfonamide (7f) (6 mg, 0.0148 mmol), EDCI (8 mg, 0.044 mmol) and DMAP (5 mg, 0.044 mmol) in DCM (1.5 mL) was stirred at r.t. for 15 min, and then a mixture of 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoic acid (1i) (8 mg, 0.0148 mmol) and TEA (4 mg, 0.044 mmol) in DCM (0.5 mL) was added. The resulted mixture was stirred at r.t. overnight and concentrated. The residue was purified by preparative TLC to give title compound (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(1-(methylimino)-1-oxido-1λ⁶-thiomorpholino)propan-2-yl)amino)-3-nitrophenyl)sulfonyl)benzamide (7). MS-ESI (m/z): 958 [M+1]⁺.

Example 8

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(cyclopropylimino)-1-oxidohexahydro-1λ⁶-thiopyran-4-yl)methyl)amino)-3-((trifluoromethyl)sulfonyl)phenyl)sulfonyl) benzamide (8)

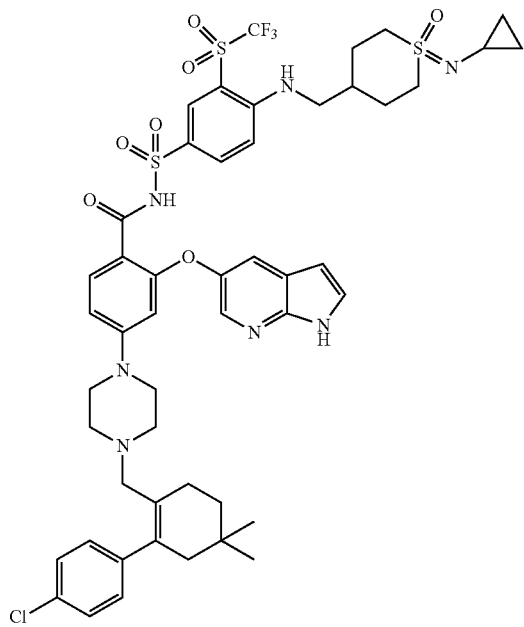

4-fluoro-3-((trifluoromethyl)sulfonyl)benzenesulfonamide (8a)

The title compound 4-fluoro-3-((trifluoromethyl)sulfonyl)benzenesulfonamide (8a) was prepared according to the method described in *Chem. Commun.*, 2010, 46, 8020-8022.

4-(((1-(cyclopropylimino)-1-oxidohexahydro-1λ⁶-thiopyran-4-yl)methyl)amino)-3-((trifluoromethyl)sulfonyl)benzenesulfonamide (8b)

The title compound 4-(((1-(cyclopropylimino)-1-oxidohexahydro-1λ⁶-thiopyran-4-yl)methyl)amino)-3-((trifluoromethyl)sulfonyl)benzenesulfonamide (8b) was prepared according to the synthetic method of 5 by replacing 4-(aminomethyl)-1-(cyclopropylimino)hexahydro-1λ⁶-thiopyran 1-oxide (5e) with 4-fluoro-3-((trifluoromethyl)-sulfonyl) benzenesulfonamide (8a). MS-ESI (m/z): 490 [M+1]⁺.

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(cyclopropylimino)-1-oxidohexahydro-1λ⁶-thiopyran-4-yl)methyl)amino)-3-((trifluoromethyl)sulfonyl)phenyl)sulfonyl)benzamide (8)

The title compound 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(cyclopropylimino)-1-oxidohexahydro-1λ⁶-thiopyran-4-yl)methyl)amino)-3-((trifluoromethyl)-sulfonyl)phenyl)sulfonyl)benzamide (8) was prepared according to the synthetic method of 1 by replacing 4-(((1-methyl-1-oxidophosphinan-4-yl)methyl)amino)-3-nitrobenzenesulfonamide (1h) with 4-(((1-(cyanoimino)-1-oxidohexahydro-1λ⁶-thiopyran-4-yl)methyl)amino)-3-nitrobenzenesulfonamide (8b). MS-ESI (m/z): 1042 [M+1]⁺.

Example 9

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((((1r,4r)-4-((diethyl(oxo)-λ⁶-sulfanylidene)amino)cyclohexyl)methyl)amino)-3-nitrophenyl)sulfonyl)benzamide (9A and 9B)

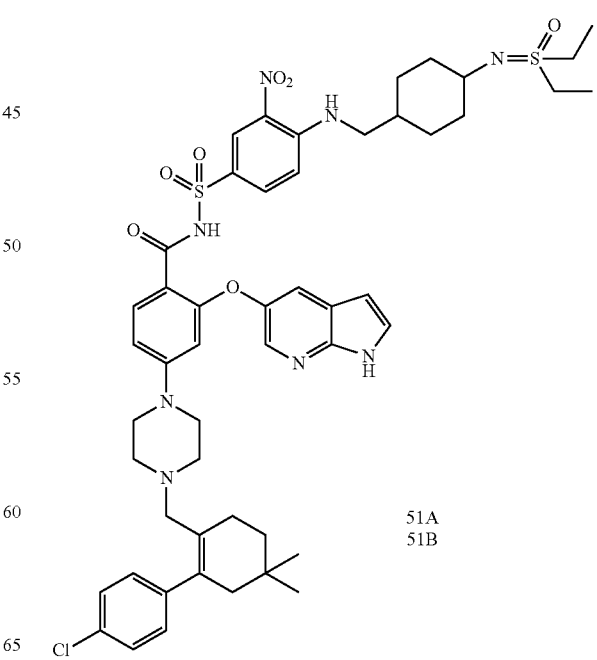

51A
51B diethyl(imino)-λ⁶-sulfanone (9a)

The title compound diethyl(imino)-λ⁶-sulfanone (9a) was prepared according to the method described in WO 2008/141843 (A1).

Ethyl 4-((diethyl(oxo)-λ⁶-sulfanylidene)amino)cyclohexane-1-carboxylate (9b)

A mixture of diethyl(imino)-λ⁶-sulfanone (9a) (310 mg, 2.56 mmol) and ethyl 4-oxocyclohexane-1-carboxylate (1.30 g, 7.68 mmol) in DCE (10 mL) was stirred at r.t. for 15 min, and NaBH(OAc)₃ (1.82 g, 8.60 mmol) was added. The resulted mixture was stirred at 0° C. overnight. The reaction was quenched by saturated NaHCO₃ aqueous solution (15 mL) and the mixture was extracted with DCM (3×30 mL). The extracts were washed with brine (30 mL), dried over Na₂SO₄ and concentrated. The residue was purified by column chromatography on silica gel eluting with DCM/MeOH (15:1) to give title compound ethyl 4-((diethyl(oxo)-λ⁶-sulfanylidene)amino)cyclohexane-1-carboxylate (9b). MS-ESI (m/z): 276 [M+1]⁺.

diethyl((4-(hydroxymethyl)cyclohexyl)imino)-λ⁶-sulfanone (9c)

A mixture of ethyl 4-((diethyl(oxo)-λ⁶-sulfanylidene)amino)cyclohexane-1-carboxylate (9b) (205 mg, 0.745 mmol) and LiAlH₄ (142 mg, 3.73 mmol) in THF (5 mL) was stirred at 50° C. for 1 h. The reaction was quenched by 10% NaOH (165 μl) and water (165 μl). The mixture was filtered, and filtrate was concentrated. The residue was purified by column chromatography on silica gel eluting with DCM/MeOH (50:1~12:1) to give title compound diethyl((4-(hydroxymethyl)cyclohexyl)imino)-λ⁶-sulfanone (9c). MS-ESI (m/z): 234 [M+1]⁺.

(4-((diethyl(oxo)-λ⁶-sulfanylidene)amino)cyclohexyl)methyl Methanesulfonate (9d)

A mixture of diethyl((4-(hydroxymethyl)cyclohexyl)imino)-λ⁶-sulfanone (9c) (46 mg, 0.197 mmol), MsCl (18 μl, 0.237 mmol) and TEA (33 μl, 0.237 mmol) in DCM (3 mL) was stirred at r.t. for 15 min, The reaction was quenched by saturated NaHCO₃ aqueous solution (15 mL) and the mixture was extracted with DCM (3×30 mL). The extracts were dried over Na₂SO₄ and concentrated to give title compound (4-((diethyl(oxo)-λ⁶-sulfanylidene)amino)-cyclohexyl)methyl methanesulfonate (9d). MS-ESI (m/z): 312 [M+1]⁺.

((4-(azidomethyl)cyclohexyl)imino)diethyl-λ⁶-sulfanone (9e)

A mixture of (4-((diethyl(oxo)-λ⁶-sulfanylidene)amino)cyclohexyl)methyl methanesulfonate (9d) (106 mg, 0.341 mmol) and NaN₃ (44 mg, 0.682 mmol) in DIVIF (2 mL) was stirred at 70° C. for 12 h. The reaction was quenched by water and the mixture was extracted with EtOAc (3×30 mL). The extracts were washed with brine (2×30 mL), dried over Na₂SO₄ and concentrated. The residue was purified by column chromatography on silica gel eluting with DCM/MeOH (10:1) to give title compound ((4-(azidomethyl)cyclohexyl)imino)diethyl-λ⁶-sulfanone (9e). MS-ESI (m/z): 259 [M+1]⁺.

((4-(aminomethyl)cyclohexyl)imino)diethyl-λ⁶-sulfanone (9f)

A mixture of ((4-(azidomethyl)cyclohexyl)imino)diethyl-λ⁶-sulfanone (9e) (33 mg, 0.128 mmol) and PPh₃ (44 mg, 0.166 mmol) in THF/H₂O (2/0.4 mL) was stirred at 30° C. overnight. The reaction mixture was acidified with HCL (PH=2) and then extracted with DCM (2×30 mL). The extracts were washed with saturated NaHCO₃ aqueous solution (30 mL) and concentrated. The residue was dissolved in DCM/MeOH (5:1), dried over Na₂SO₄, and concentrated. The residue was purified by column chromatography on silica gel eluting with DCM/MeOH (10:1~5:1) to give title compound ((4-(aminomethyl)cyclohexyl)imino)diethyl-λ⁶-sulfanone (9f). MS-ESI (m/z): 233 [M+1]⁺.

4-(((4-((diethyl(oxo)-λ⁶-sulfanylidene)amino)cyclohexyl)methyl)amino)-3-nitrobenzenesulfonamide (9g-A)

A mixture of ((4-(aminomethyl)cyclohexyl)imino)diethyl-λ⁶-sulfanone (9f) (10.0 mg, 0.043 mmol), 4-chloro-3-nitrobenzenesulfonamide (1g) (12.0 mg, 0.052 mmol) and DIPEA (28.0 mg, 0.215 mmol) in acetonitrile (1 mL) was stirred at 80° C. overnight. The reaction mixture was cooled to r.t. and concentrated. The residue was purified by preparative TLC up spot to give title compound 4-(((4-((diethyl(oxo)-λ⁶-sulfanylidene)amino)cyclohexyl)methyl)amino)-3-nitrobenzenesulfonamide (9g-A). MS-ESI (m/z): 433 [M+1]⁺.

4-(((4-((diethyl(oxo)-λ⁶-sulfanylidene)amino)cyclohexyl)methyl)amino)-3-nitrobenzenesulfonamide (9g-B)

A mixture of ((4-(aminomethyl)cyclohexyl)imino)diethyl-λ⁶-sulfanone (9f) (10.0 mg, 0.043 mmol), 4-chloro-3-nitrobenzenesulfonamide (1g) (12.0 mg, 0.052 mmol) and DIPEA (28.0 mg, 0.215 mmol) in acetonitrile (1 mL) was stirred at 80° C. overnight. The reaction mixture was cooled to r.t. and concentrated. The residue was purified by preparative TLC down spot to give title compound 4-(((4-((diethyl(oxo)-λ⁶-sulfanylidene)amino)cyclohexyl)methyl)amino)-3-nitrobenzenesulfonamide (9g-B). MS-ESI (m/z): 433 [M+1]⁺.

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((((1r,4r)-4-((diethyl(oxo)-λ⁶-sulfanylidene)amino)cyclohexyl)methyl)amino)-3-nitrophenyl)sulfonyl)benzamide (9A)

A mixture of 4-(((4-((diethyl(oxo)-λ⁶-sulfanylidene)amino)cyclohexyl)methyl)amino)-3-nitrobenzenesulfonamide (9g-A) (15.0 mg, 0.035 mmol), EDCI (16.0 mg, 0.084 mmol) and DMAP (10.0 mg, 0.084 mmol) in DCM (1.5 mL) was stirred at r.t. for 15 min, and then a mixture of 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoic acid (1i) (12.0 mg, 0.021 mmol) and TEA (12.0 μl, 0.084 mmol) in DCM (0.5 mL) was added. The resulted mixture was stirred at r.t. overnight and concentrated. The residue was purified by preparative TLC to give title compound 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((((1r,4r)-4-((diethyl(oxo)-λ⁶-sulfanylidene)amino)cyclohexyl)methyl)amino)-3-nitrophenyl)sulfonyl)benzamide (9A). MS-ESI (m/z): 985 [M+1]⁺.

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((((1r,4r)-4-((diethyl(oxo)-$\lambda^6$-sulfanylidene)amino)cyclohexyl)methyl)amino)-3-nitrophenyl)sulfonyl)benzamide (9B)

The title compound 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((((1r,4r)-4-((diethyl(oxo)-$\lambda^6$-sulfanylidene)amino)cyclohexyl)methyl)amino)-3-nitrophenyl)sulfonyl)benzamide (9B) was prepared according to the synthetic method of 9A by replacing 9g-A with 9g-B. MS-ESI (m/z): 985 [M+1]$^+$.

Following essentially the same procedures described for Examples 1-9 or using similar synthetic strategies or methods. Examples 10-98 listed in Table 1 were prepared using appropriate intermediates, which can be readily synthesized by methods known in the art, and sequential modifications as necessary. The structures and names of Examples 10-98 are given in table 1.

TABLE 1

| EXAMPLE | STRUCTURE | NAME | DATA |
| --- | --- | --- | --- |
| 10 | 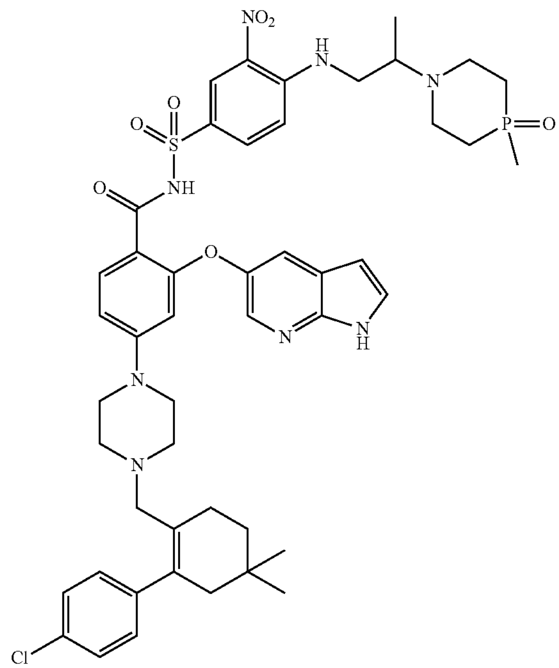 [SMILES: CC(CNc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1[N+](=O)[O-])N1CCP(C)(=O)CC1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((2-(4-methyl-4-oxido-1,4-azaphosphinan-1-yl)propyl)amino)-3-nitrophenyl)sulfonyl)benzamide | MS-ESI (m/z): 943 [M + 1]$^+$ |
| 11 | 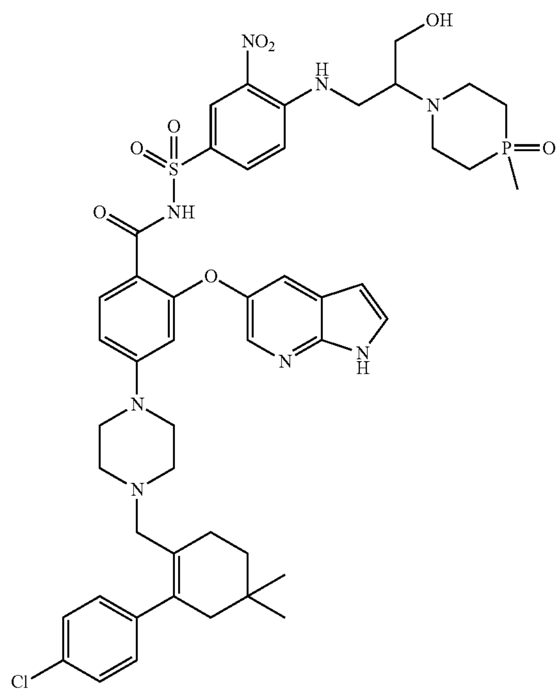 [SMILES: CC1(C)CCC(CN2CCN(c3ccc(C(=O)NS(=O)(=O)c4ccc(NCC(CO)N5CCP(C)(=O)CC5)c([N+](=O)[O-])c4)c(Oc4cnc5[nH]ccc5c4)c3)CC2)=C(c2ccc(Cl)cc2)C1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((3-hydroxy-2-(4-methyl-4-oxido-1,4-azaphosphinan-1-yl)propyl)amino)-3-nitrophenyl)sulfonyl)benzamide | MS-ESI (m/z): 959 [M + 1]$^+$ |

TABLE 1-continued

| EXAMPLE | STRUCTURE | NAME | DATA |
| --- | --- | --- | --- |
| 12 | 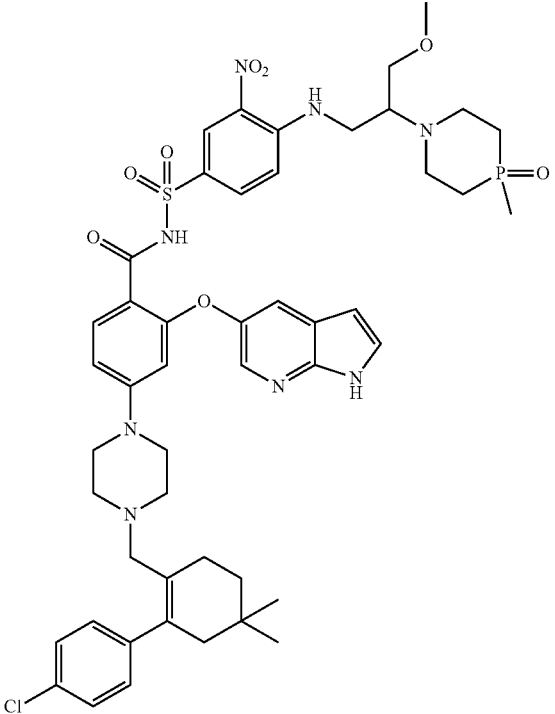 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((3-methoxy-2-(4-methyl-4-oxido-1,4-azaphosphinan-1-yl)propyl)amino)-3-nitrophenyl)sulfonyl)benzamide | MS-ESI (m/z): 973 [M + 1]+ |
| 13 | 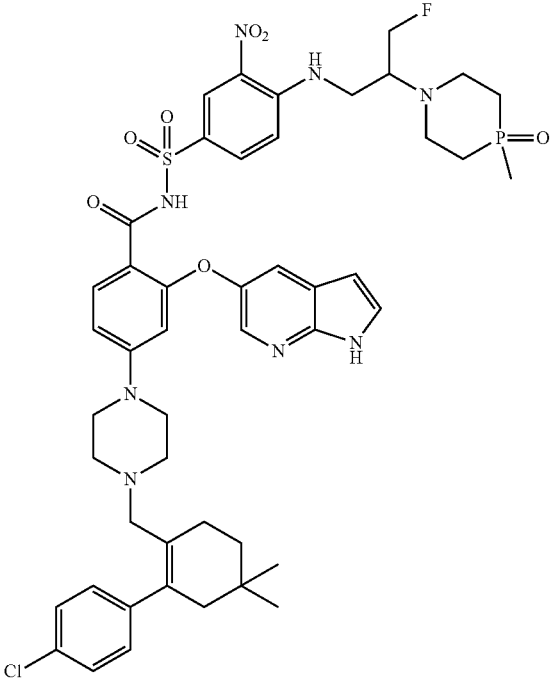 [SMILES: CC1(C)CCC(CN2CCN(c3ccc(C(=O)NS(=O)(=O)c4ccc(NCC(CF)N5CCP(C)(=O)CC5)c([N+](=O)[O-])c4)c(Oc4cnc5[nH]ccc5c4)c3)CC2)=C(c2ccc(Cl)cc2)C1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((3-fluoro-2-(4-methyl-4-oxido-1,4-azaphosphinan-1-yl)propyl)amino)-3-nitrophenyl)sulfonyl)benzamide | MS-ESI (m/z): 961 [M + 1]+ |

TABLE 1-continued

| EXAMPLE | STRUCTURE | NAME | DATA |
|---|---|---|---|
| 14 | 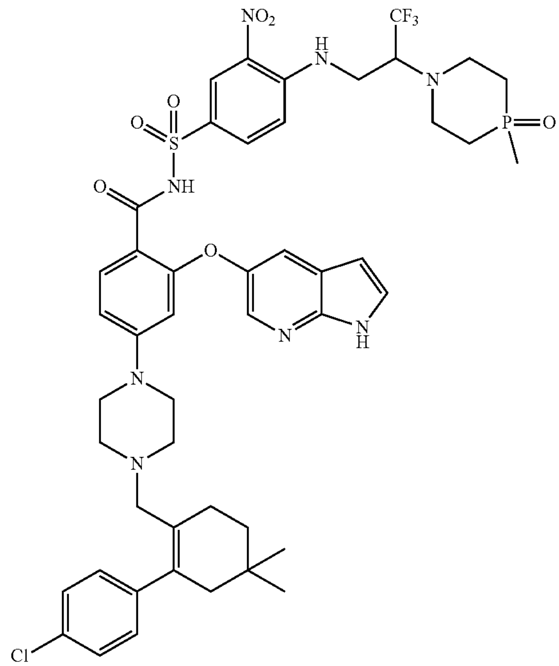 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-nitro-4-((3,3,3-trifluoro-2-(4-methyl-4-oxido-1,4-azaphosphinan-1-yl)propyl)amino)phenyl)sulfonyl)benzamide | MS-ESI (m/z): 997 [M + 1]⁺ |
| 15 | 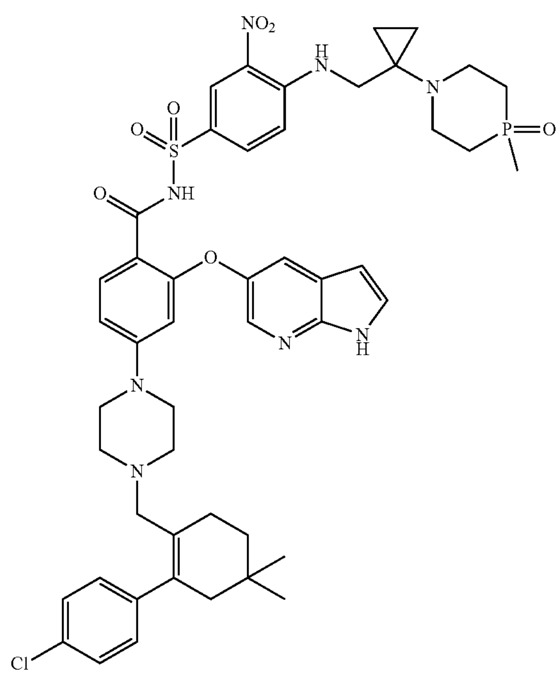 [SMILES: CC1(C)CCC(CN2CCN(c3ccc(C(=O)NS(=O)(=O)c4ccc(NCC5(N6CCP(C)(=O)CC6)CC5)c([N+](=O)[O-])c4)c(Oc4cnc5[nH]ccc5c4)c3)CC2)=C(c2ccc(Cl)cc2)C1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(4-methyl-4-oxido-1,4-azaphosphinan-1-yl)cyclopropyl)methyl)amino)-3-nitrophenyl)sulfonyl)benzamide | MS-ESI (m/z): 955 [M + 1]⁺ |

| EXAMPLE | STRUCTURE | NAME | DATA |
|---|---|---|---|
| 16 | 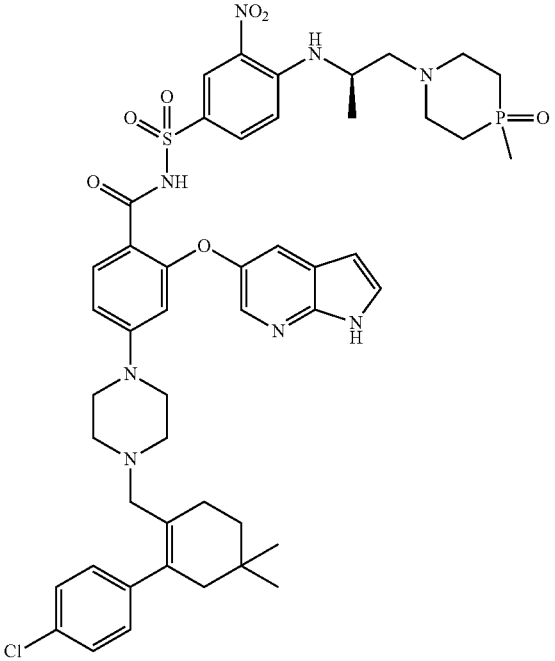 [SMILES: C[C@H](CN1CCP(C)(=O)CC1)Nc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1[N+](=O)[O-]] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(4-methyl-4-oxido-1,4-azaphosphinan-1-yl)propan-2-yl)amino)-3-nitrophenyl)sulfonyl)benzamide | MS-ESI (m/z): 943 [M + 1]+ |
| 17 | 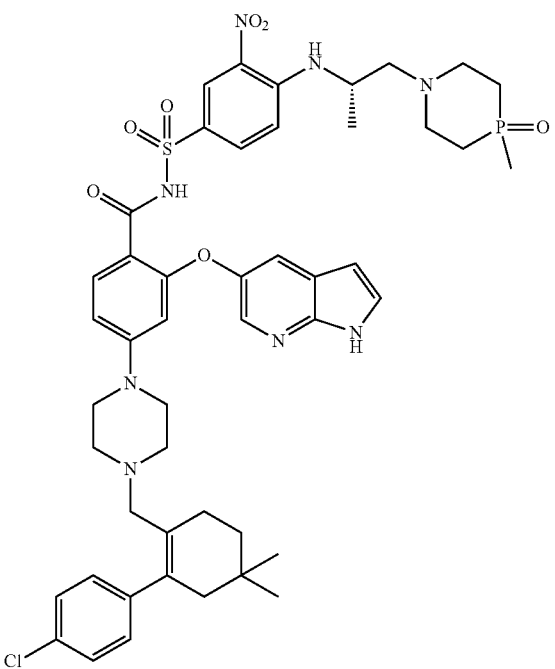 [SMILES: C[C@@H](CN1CCP(C)(=O)CC1)Nc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1[N+](=O)[O-]] | (S)-2-((1H-pyrrolo[2,3-b]pyridin-5-yl)oxy)-4-((4'-chloro-5,5-dimethyl-3,4,5,6-tetrahydro-[1,1'-biphenyl]-2-yl)methyl)piperazin-1-yl)-N-((4-((1-(4-methyl-4-oxido-1,4-azaphosphinan-1-yl)propan-2-yl)amino)-3-nitrophenyl)sulfonyl)benzamide | MS-ESI (m/z): 943 [M + 1]+ |

TABLE 1-continued

| EXAMPLE | STRUCTURE | NAME | DATA |
|---|---|---|---|
| 18 | 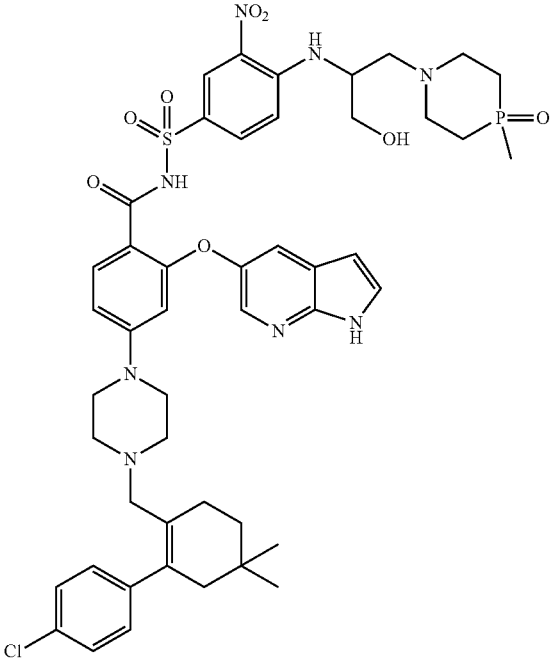 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-hydroxy-3-(4-methyl-4-oxido-1,4-azaphosphinan-1-yl)propan-2-yl)amino)-3-nitrophenyl)sulfonyl)benzamide | MS-ESI (m/z): 959 [M + 1]+ |
| 19 | 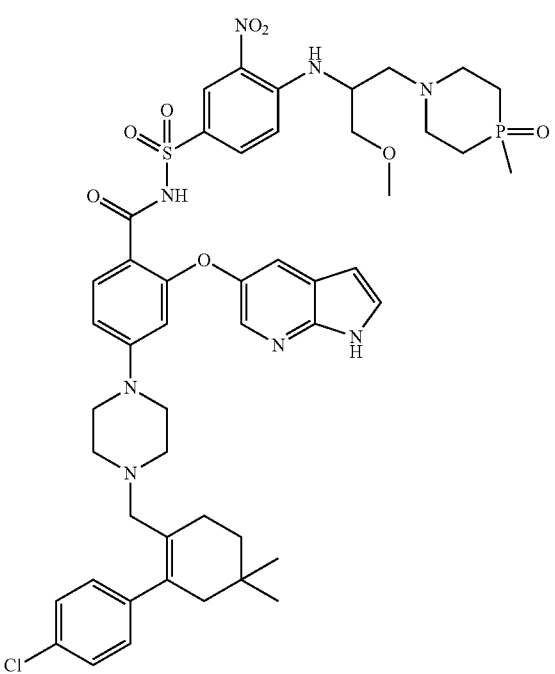 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-methoxy-3-(4-methyl-4-oxido-1,4-azaphosphinan-1-yl)propan-2-yl)amino)-3-nitrophenyl)sulfonyl)benzamide | MS-ESI (m/z): 973 [M + 1]+ |

… TABLE 1-continued

| EXAMPLE | STRUCTURE | NAME | DATA |
|---|---|---|---|
| 20 | 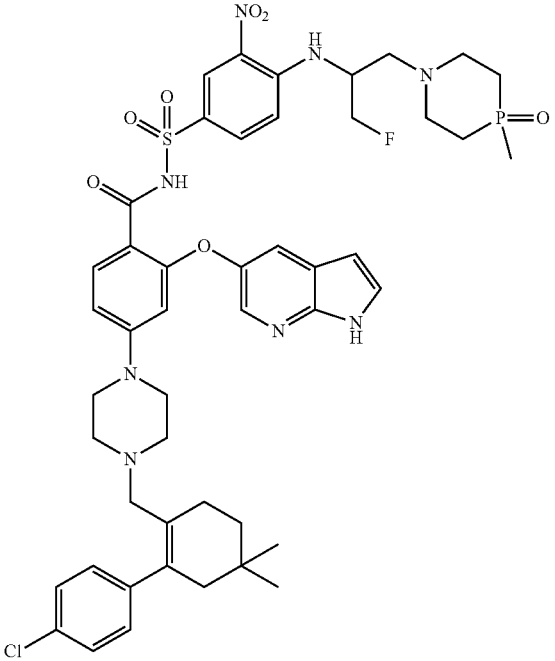 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-fluoro-3-(4-methyl-4-oxido-1,4-azaphosphinan-1-yl)propan-2-yl)amino)-3-nitrophenyl)sulfonyl)benzamide | MS-ESI (m/z): 961 [M + 1]$^+$ |
| 21 | 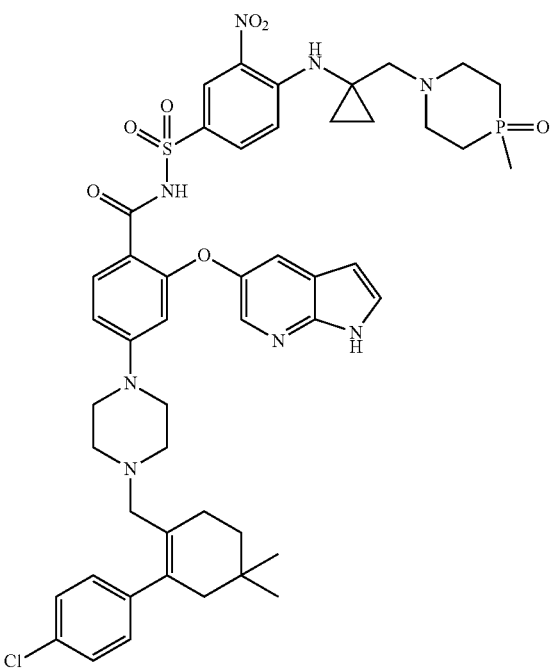 [SMILES: CC1(C)CCC(CN2CCN(c3ccc(C(=O)NS(=O)(=O)c4ccc(NC5(CN6CCP(C)(=O)CC6)CC5)c([N+](=O)[O-])c4)c(Oc4cnc5[nH]ccc5c4)c3)CC2)=C(c2ccc(Cl)cc2)C1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-((4-methyl-4-oxido-1,4-azaphosphinan-1-yl)methyl)cyclopropyl)amino)-3-nitrophenyl)sulfonyl)benzamide | MS-ESI (m/z): 955 [M + 1]$^+$ |

TABLE 1-continued

| EXAMPLE | STRUCTURE | NAME | DATA |
|---|---|---|---|
| 22 | 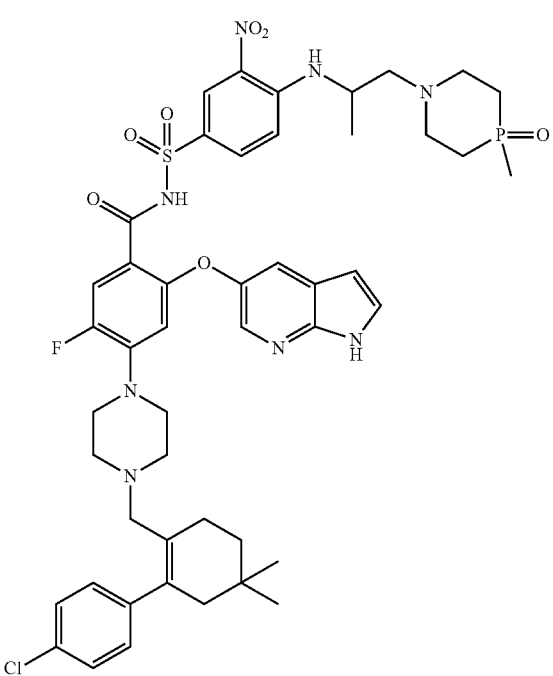 [SMILES: CC(CN1CCP(C)(=O)CC1)Nc1ccc(S(=O)(=O)NC(=O)c2cc(F)c(N3CCN(CC4=C(c5ccc(Cl)cc5)CC(C)(C)CC4)CC3)cc2Oc2cnc3[nH]ccc3c2)cc1[N+](=O)[O-]] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-5-fluoro-N-((4-((1-(4-methyl-4-oxido-1,4-azaphosphinan-1-yl)propan-2-yl)amino)-3-nitrophenyl)sulfonyl)benzamide | MS-ESI (m/z): 961 [M + 1]$^+$ |
| 23 | 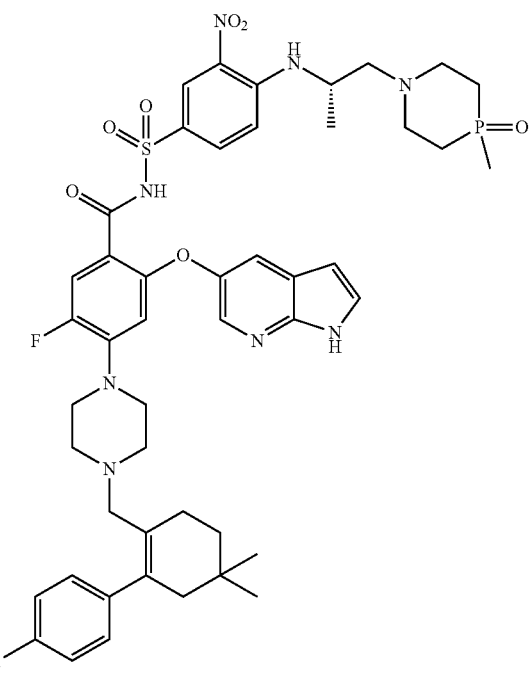 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-5-fluoro-N-((4-((1-(4-methyl-4-oxido-1,4-azaphosphinan-1-yl)propan-2-yl)amino)-3-nitrophenyl)sulfonyl)benzamide | MS-ESI (m/z): 961 [M + 1]$^+$ |

TABLE 1-continued

| EXAMPLE | STRUCTURE | NAME | DATA |
|---------|-----------|------|------|
| 24 | 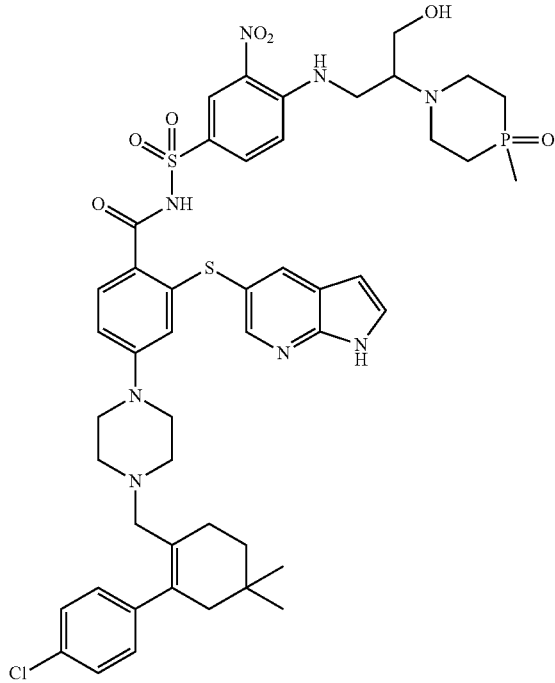 [SMILES: CC1(C)CCC(CN2CCN(c3ccc(C(=O)NS(=O)(=O)c4ccc(NCC(CO)N5CCP(C)(=O)CC5)c([N+](=O)[O-])c4)c(Sc4cnc5[nH]ccc5c4)c3)CC2)=C(c2ccc(Cl)cc2)C1] | 2-((1H-pyrrolo[2,3-b]pyridin-5-yl)thio)-4-(4-((4'-chloro-5,5-dimethyl-3,4,5,6-tetrahydro-[1,1'-biphenyl]-2-yl)methyl)piperazin-1-yl)-N-((4-((3-hydroxy-2-(4-methyl-4-oxido-1,4-azaphosphinan-1-yl)propyl)amino)-3-nitrophenyl)sulfonyl)benzamide | MS-ESI (m/z): 975 [M + 1]+ |
| 25 | 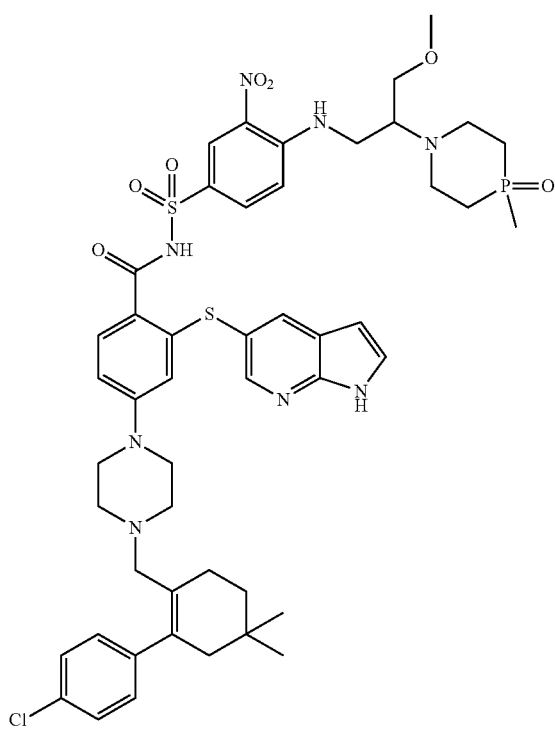 [SMILES: COCC(CNc1ccc(S(=O)(=O)NC(=O)c2ccc(N3CCN(CC4=C(c5ccc(Cl)cc5)CC(C)(C)CC4)CC3)cc2Sc2cnc3[nH]ccc3c2)cc1[N+](=O)[O-])N1CCP(C)(=O)CC1] | 2-((1H-pyrrolo[2,3-b]pyridin-5-yl)thio)-4-(4-((4'-chloro-5,5-dimethyl-3,4,5,6-tetrahydro-[1,1'-biphenyl]-2-yl)methyl)piperazin-1-yl)-N-((4-((3-methoxy-2-(4-methyl-4-oxido-1,4-azaphosphinan-1-yl)propyl)amino)-3-nitrophenyl)sulfonyl)benzamide | MS-ESI (m/z): 989 [M + 1]+ |

//

TABLE 1-continued

| EXAMPLE | STRUCTURE | NAME | DATA |
|---|---|---|---|
| 26 | 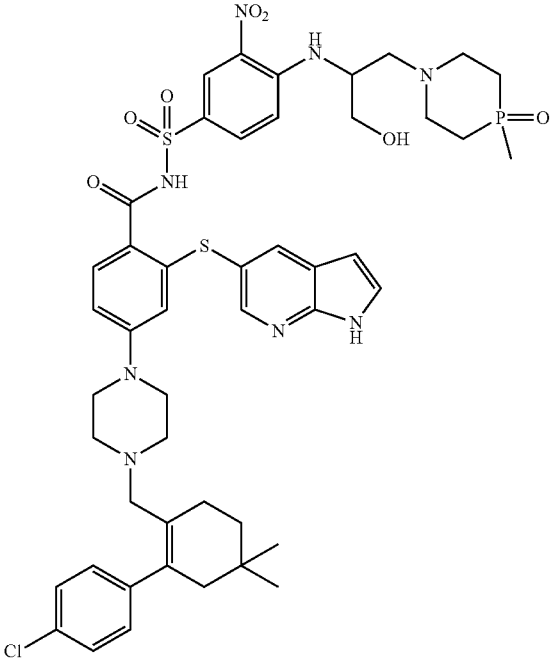 [SMILES: CC1(C)CCC(CN2CCN(c3ccc(C(=O)NS(=O)(=O)c4ccc(NC(CO)CN5CCP(C)(=O)CC5)c([N+](=O)[O-])c4)c(Sc4cnc5[nH]ccc5c4)c3)CC2)=C(c2ccc(Cl)cc2)C1] | 2-((1H-pyrrolo[2,3-b]pyridin-5-yl)thio)-4-(4-((4'-chloro-5,5-dimethyl-3,4,5,6-tetrahydro-[1,1'-biphenyl]-2-yl)methyl)piperazin-1-yl)-N-((4-((1-hydroxy-3-(4-methyl-4-oxido-1,4-azaphosphinan-1-yl)propan-2-yl)amino)-3-nitrophenyl)sulfonyl)benzamide | MS-ESI (m/z): 975 [M + 1]$^+$ |
| 27 | 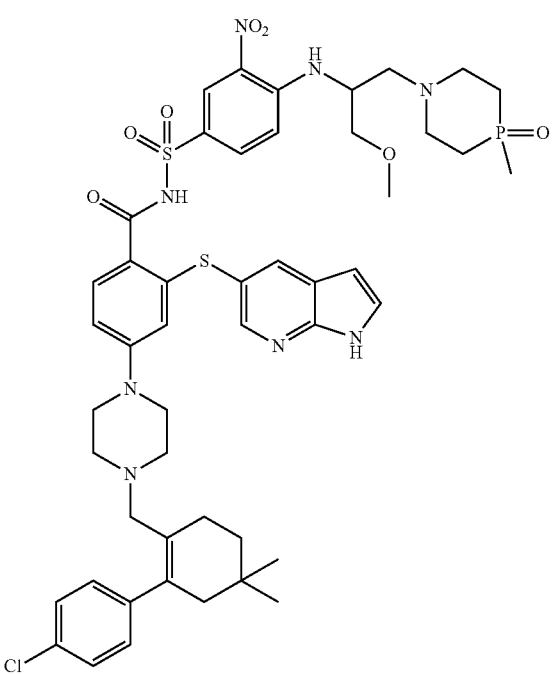 [SMILES: COCC(CN1CCP(C)(=O)CC1)Nc1ccc(S(=O)(=O)NC(=O)c2ccc(N3CCN(CC4=C(c5ccc(Cl)cc5)CC(C)(C)CC4)CC3)cc2Sc2cnc3[nH]ccc3c2)cc1[N+](=O)[O-]] | 2-((1H-pyrrolo[2,3-b]pyridin-5-yl)thio)-4-(4-((4'-chloro-5,5-dimethyl-3,4,5,6-tetrahydro-[1,1'-biphenyl]-2-yl)methyl)piperazin-1-yl)-N-((4-((1-methoxy-3-(4-methyl-4-oxido-1,4-azaphosphinan-1-yl)propan-2-yl)amino)-3-nitrophenyl)sulfonyl)benzamide | MS-ESI (m/z): 989 [M + 1]$^+$ |

TABLE 1-continued

| EXAMPLE | STRUCTURE | NAME | DATA |
| --- | --- | --- | --- |
| 28 | 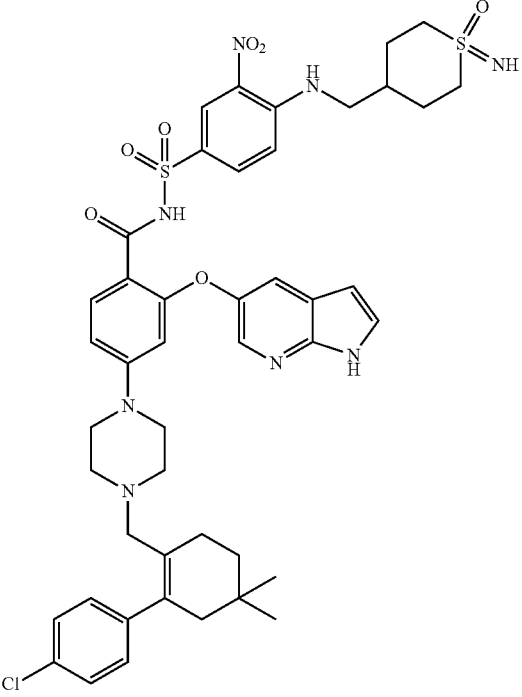 [SMILES: CC1(C)CCC(CN2CCN(c3ccc(C(=O)NS(=O)(=O)c4ccc(NCC5CCS(=N)(=O)CC5)c([N+](=O)[O-])c4)c(Oc4cnc5[nH]ccc5c4)c3)CC2)=C(c2ccc(Cl)cc2)C1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-imino-1-oxidohexahydro-1$\lambda^6$-thiopyran-4-yl)methyl)amino)-3-nitrophenyl)sulfonyl)benzamide | MS-ESI (m/z): 915 [M + 1]$^+$ |
| 29 | 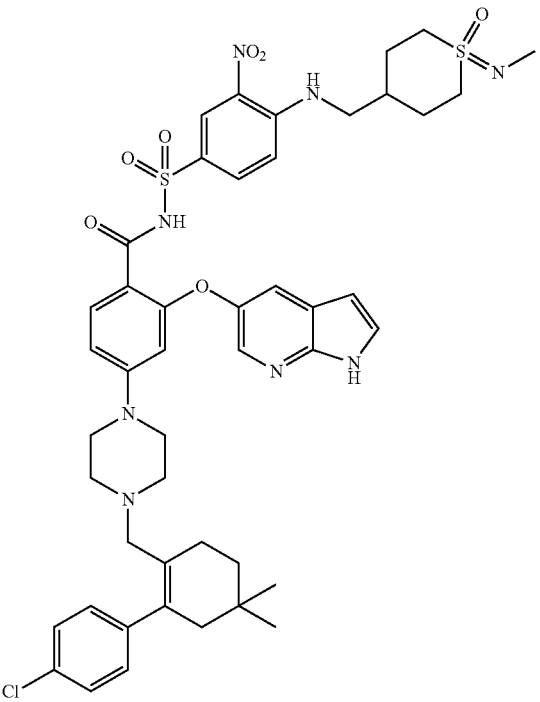 [SMILES: CN=S1(=O)CCC(CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(methylimino)-1-oxidohexahydro-1$\lambda^6$-thiopyran-4-yl)methyl)amino)-3-nitrophenyl)sulfonyl)benzamide | MS-ESI (m/z): 929 [M + 1]$^+$ |

TABLE 1-continued

| EXAMPLE | STRUCTURE | NAME | DATA |
| --- | --- | --- | --- |
| 30 | 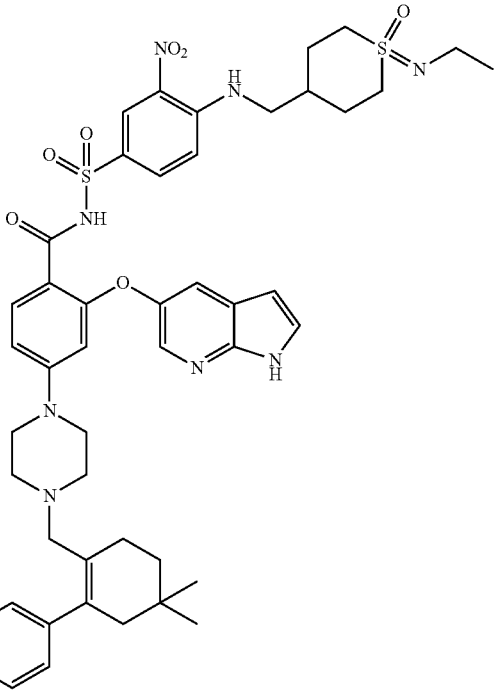 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(ethylimino)-1-oxidohexahydro-1$\lambda^6$-thiopyran-4-yl)methyl)amino)-3-nitrophenyl)sulfonyl)benzamide | MS-ESI (m/z): 943 [M + 1]$^+$ |
| 31 | 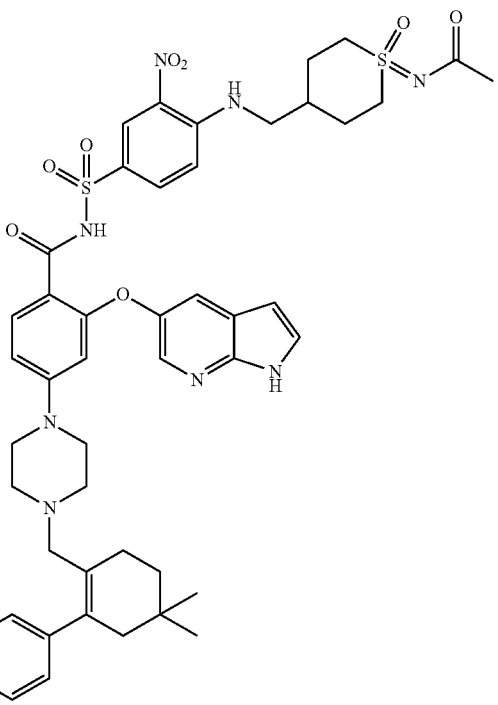 | 2-((1H-pyrrolo[2,3-b]pyridin-5-yl)oxy)-N-((4-(((1-(acetylimino)-1-oxidohexahydro-1$\lambda^6$-thiopyran-4-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 957 [M + 1]$^+$ |

TABLE 1-continued

| EXAMPLE | STRUCTURE | NAME | DATA |
|---|---|---|---|
| 32 | 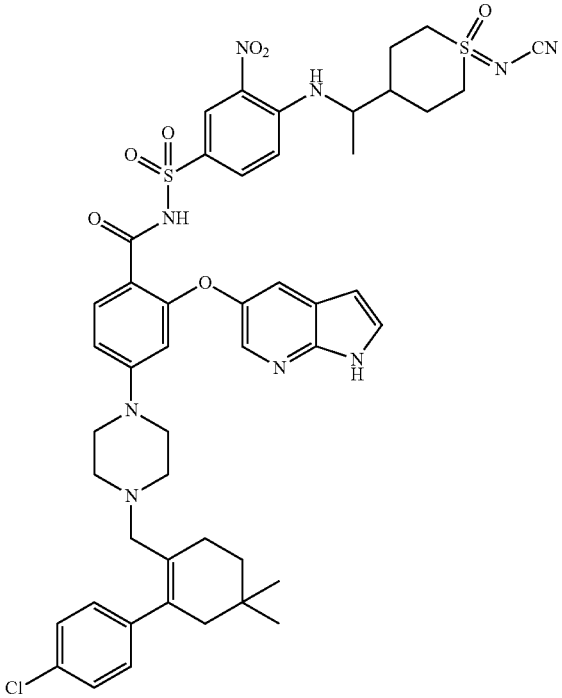 [SMILES: CC(Nc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1[N+](=O)[O-])C1CCS(=O)(=NC#N)CC1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(1-(cyanoimino)-1-oxidohexahydro-1$\lambda^6$-thiopyran-4-yl)ethyl)amino)-3-nitrophenyl)sulfonyl)benzamide | MS-ESI (m/z): 954 [M + 1]$^+$ |
| 33 | 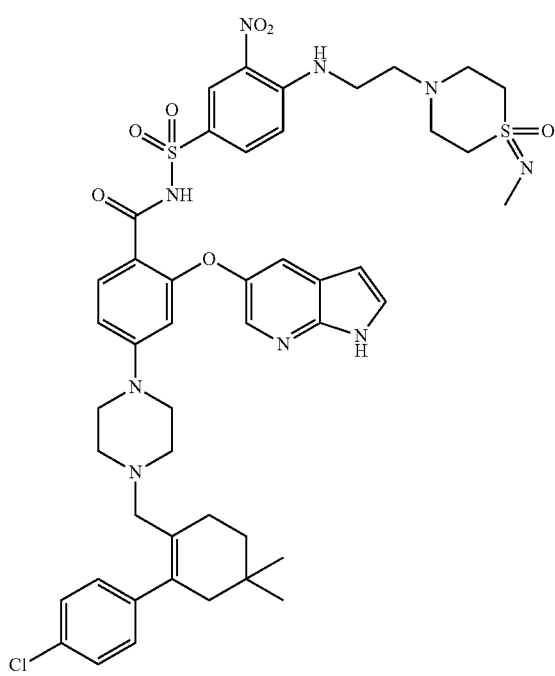 [SMILES: CN=S1(=O)CCN(CCNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((2-(1-(methylimino)-1-oxido-1$\lambda^6$-thiomorpholino)ethyl)amino)-3-nitrophenyl)sulfonyl)benzamide | MS-ESI (m/z): 944 [M + 1]$^+$ |

TABLE 1-continued

| EXAMPLE | STRUCTURE | NAME | DATA |
|---|---|---|---|
| 34 | 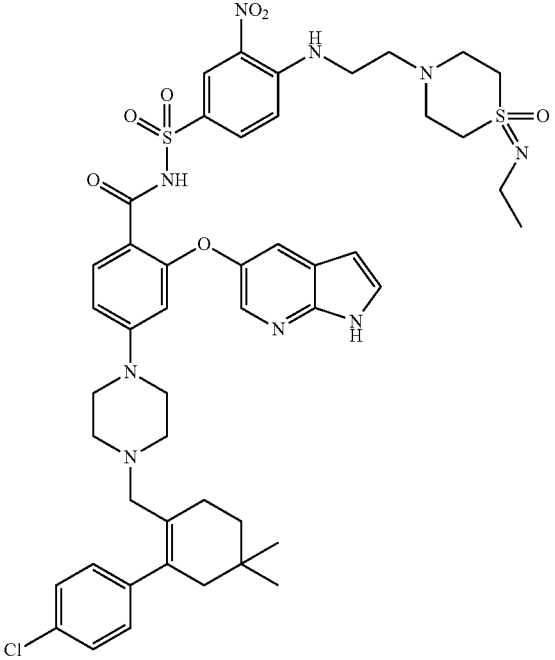 [SMILES: CCN=S1(=O)CCN(CCNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-A,-((4-((2-(1-(ethylimino)-1-oxido-1$\lambda^6$-thiomorpholino)ethyl)amino)-3-nitrophenyl)sulfonyl)benzamide | MS-ESI (m/z): 958 [M + 1]$^+$ |
| 35 | 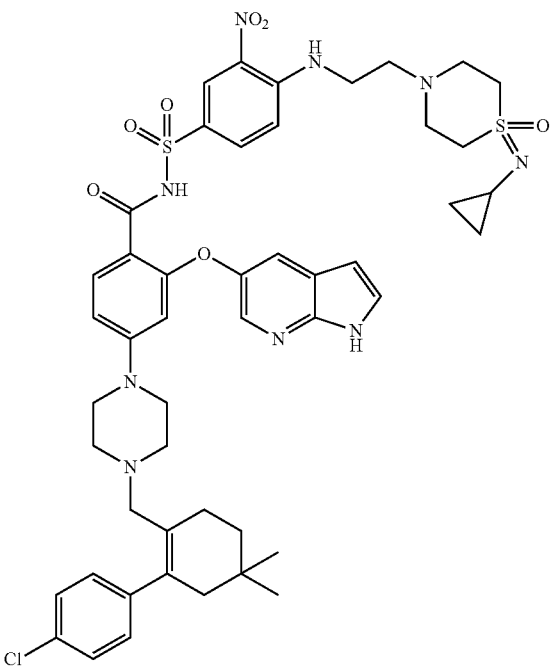 [SMILES: CC1(C)CCC(CN2CCN(c3ccc(C(=O)NS(=O)(=O)c4ccc(NCCN5CCS(=O)(=NC6CC6)CC5)c([N+](=O)[O-])c4)c(Oc4cnc5[nH]ccc5c4)c3)CC2)=C(c2ccc(Cl)cc2)C1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((2-(1-(cyclopropylimino)-1-oxido-1$\lambda^6$-thiomorpholino)ethyl)amino)-3-nitrophenyl)sulfonyl)benzamide | MS-ESI (m/z): 970 [M + 1]$^+$ |

વ

TABLE 1-continued

| EXAMPLE | STRUCTURE | NAME | DATA |
|---|---|---|---|
| 36 | 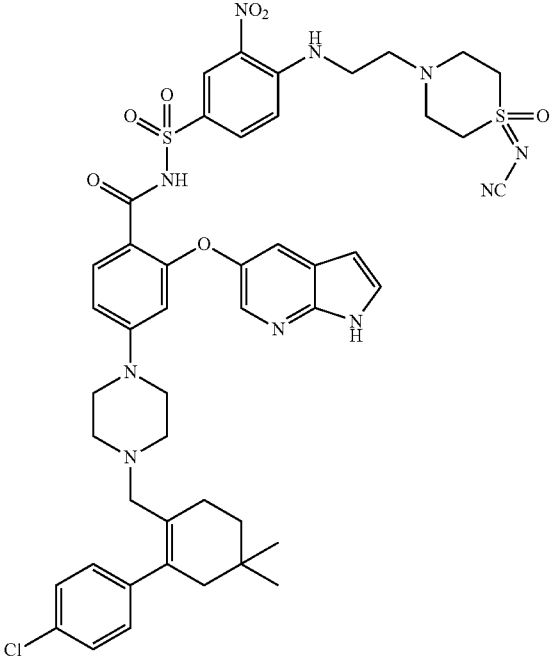 [SMILES: CC1(C)CCC(CN2CCN(c3ccc(C(=O)NS(=O)(=O)c4ccc(NCCN5CCS(=O)(=NC#N)CC5)c([N+](=O)[O-])c4)c(Oc4cnc5[nH]ccc5c4)c3)CC2)=C(c2ccc(Cl)cc2)C1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((2-(1-(cyanoimino)-1-oxido-1$\lambda^6$-thiomorpholino)ethyl)amino)-3-nitrophenyl)sulfonyl)benzamide | MS-ESI (m/z): 955 [M + 1]$^+$ |
| 37 | 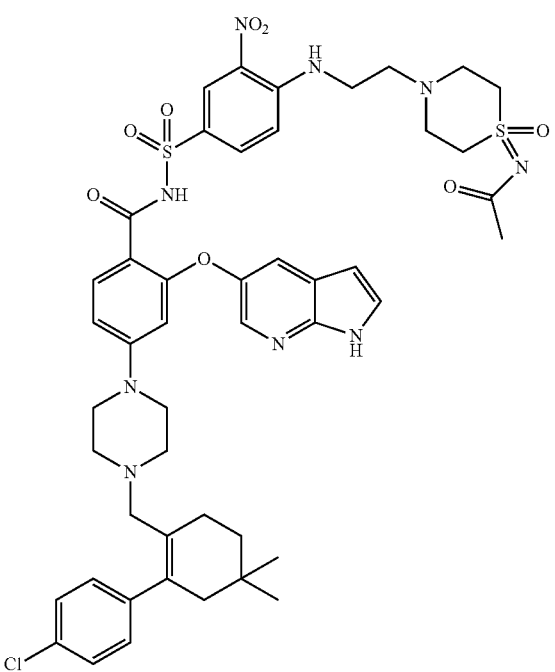 [SMILES: CC(=O)N=S1(=O)CCN(CCNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | 2-((1H-pyrrolo[2,3-b]pyridin-5-yl)oxy)-N-((4-((2-(1-(acetylimino)-1-oxido-1$\lambda^6$-thiomorpholino)ethyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 972 [M + 1]$^+$ |

TABLE 1-continued

| EXAMPLE | STRUCTURE | NAME | DATA |
|---|---|---|---|
| 38 | 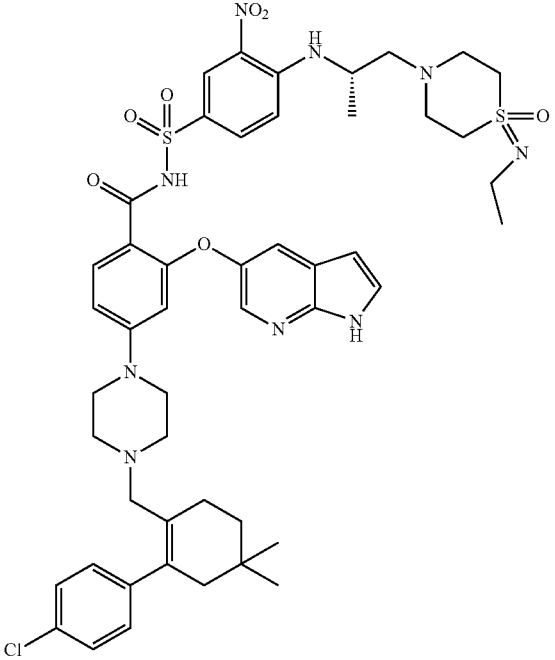 [SMILES: CCN=S1(=O)CCN(C[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | (S)-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(1-(ethylimino)-1-oxido-1$\lambda^6$-thiomorpholino)propan-2-yl)amino)-3-nitrophenyl)sulfonyl)benzamide | MS-ESI (m/z): 972 [M + 1]$^+$ |
| 39 | 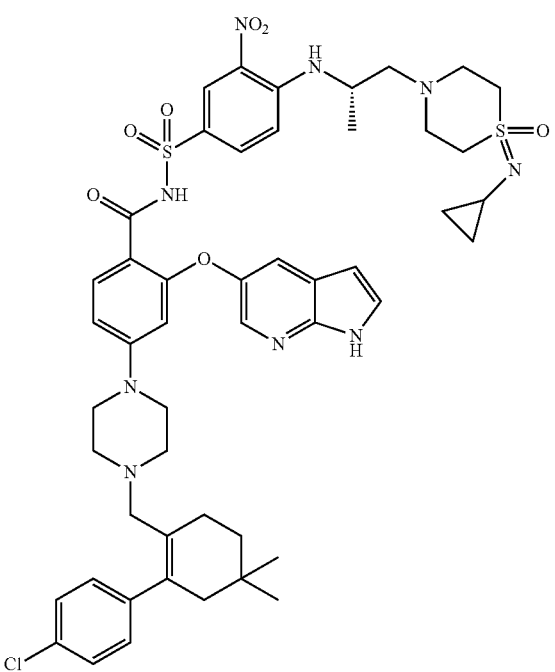 [SMILES: C[C@@H](CN1CCS(=O)(=NC2CC2)CC1)Nc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1[N+](=O)[O-]] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(1-(cyclopropylimino)-1-oxido-1$\lambda^6$-thiomorpholino)propan-2-yl)amino)-3-nitrophenyl)sulfonyl)benzamide | MS-ESI (m/z): 984 [M + 1]$^+$ |

| EXAMPLE | STRUCTURE | NAME | DATA |
|---|---|---|---|
| 40 | 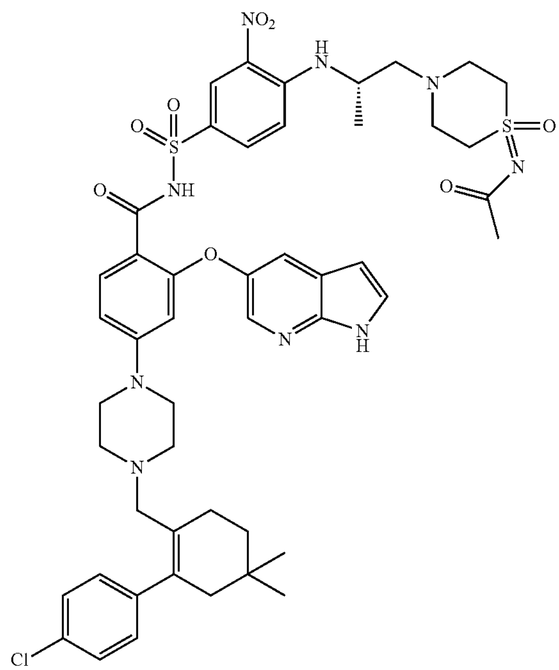 [SMILES: CC(=O)N=S1(=O)CCN(C[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | (S)-2-((1H-pyrrolo[2,3-b]pyridin-5-yl)oxy)-N-((4-((1-(1-(acetylimino)-1-oxido-1λ⁶-thiomorpholino)propan-2-yl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 986 [M + 1]⁺ |
| 41 | 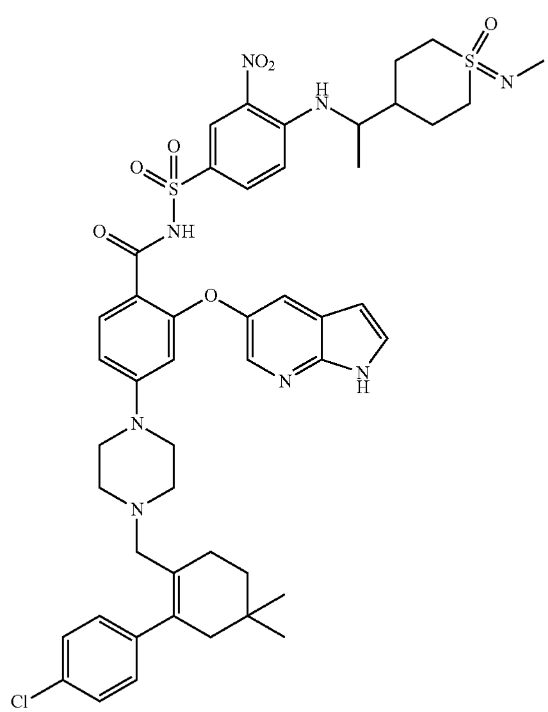 [SMILES: CN=S1(=O)CCC(C(C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(1-(methylimino)-1-oxidohexahydro-1λ⁶-thiopyran-4-yl)ethyl)amino)-3-nitrophenyl)sulfonyl)benzamide | MS-ESI (m/z): 943 [M + 1]⁺ |

TABLE 1-continued

| EXAMPLE | STRUCTURE | NAME | DATA |
|---|---|---|---|
| 42 | 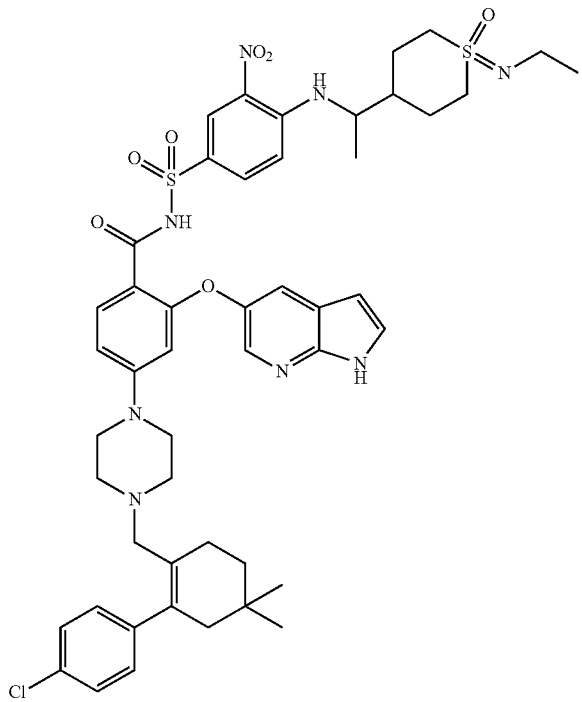 [SMILES: CCN=S1(=O)CCC(C(C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(1-(ethylimino)-1-oxidohexahydro-1λ6-thiopyran-4-yl)ethyl)amino)-3-nitrophenyl)sulfonyl)benzamide | MS-ESI (m/z): 957 [M + 1]+ |
| 43 | 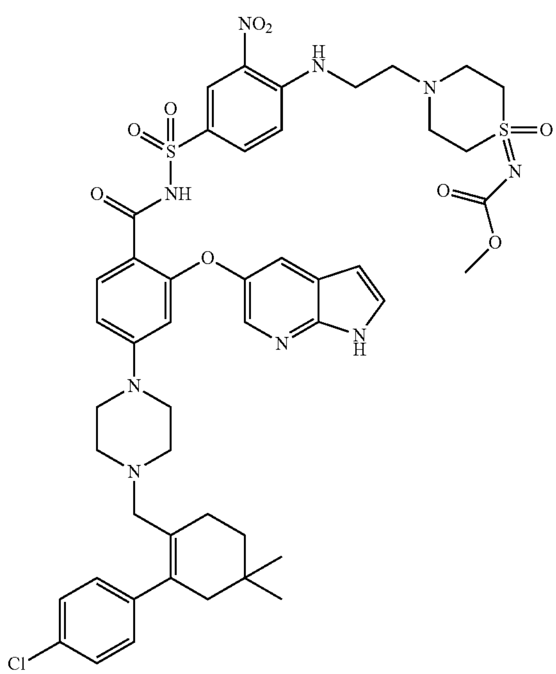 | methyl (4-(2-((4-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-2-nitrophenyl)amino)ethyl)-1-oxido-1λ6-thiomorpholin-1-ylidene)carbamate | MS-ESI (m/z): 988 [M + 1]+ |

TABLE 1-continued

| EXAMPLE | STRUCTURE | NAME | DATA |
|---|---|---|---|
| 44 | 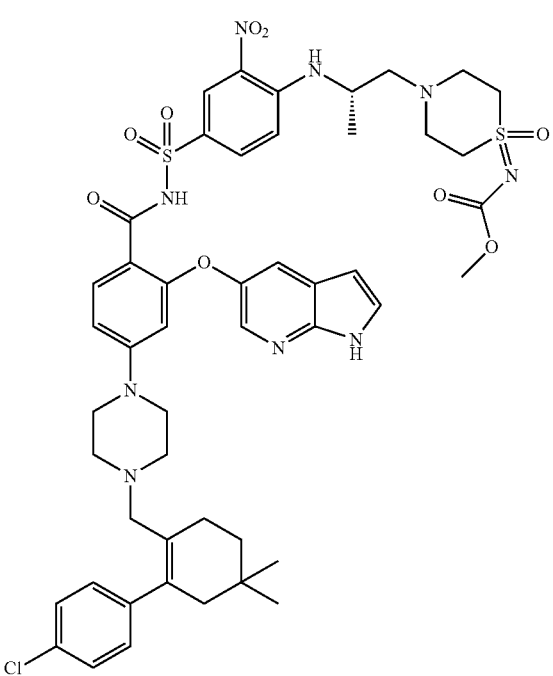 | methyl (S)-(4-(2-((4-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-2-nitrophenyl)amino)propyl)-1-oxido-1λ⁶-thiomorpholin-1-ylidene)carbamate | MS-ESI (m/z): 1002 [M + 1]⁺ |
| 45 | 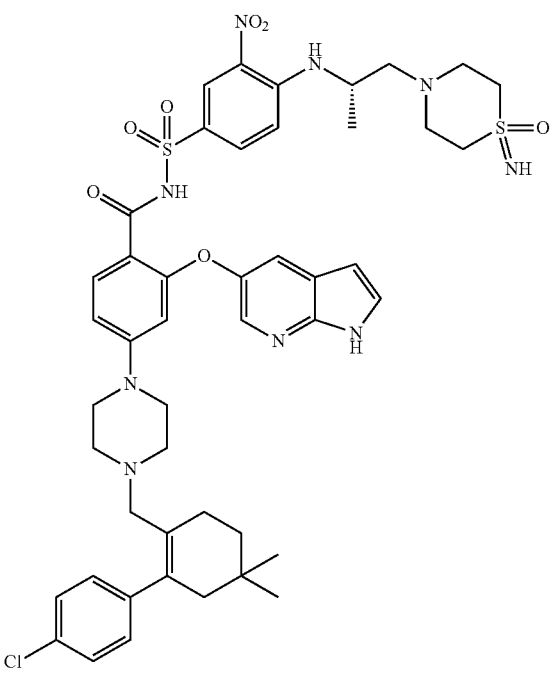 [SMILES: C[C@@H](CN1CCS(=N)(=O)CC1)Nc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1[N+](=O)[O-]] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(1-imino-1-oxido-1λ⁶-thiomorpholino)propan-2-yl)amino)-3-nitrophenyl)sulfonyl)benzamide | MS-ESI (m/z): 944 [M + 1]⁺ |

TABLE 1-continued

| EXAMPLE | STRUCTURE | NAME | DATA |
|---|---|---|---|
| 46 | 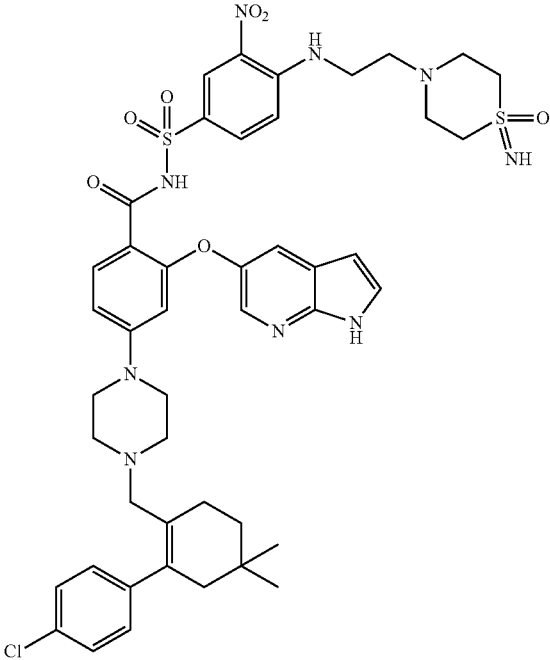 [SMILES: CC1(C)CCC(CN2CCN(c3ccc(C(=O)NS(=O)(=O)c4ccc(NCCN5CCS(=N)(=O)CC5)c([N+](=O)[O-])c4)c(Oc4cnc5[nH]ccc5c4)c3)CC2)=C(c2ccc(Cl)cc2)C1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((2-(1-imino-1-oxido-1λ$^6$-thiomorpholino)ethyl)amino)-3-nitrophenyl)sulfonyl)benzamide | MS-ESI (m/z): 930 [M + 1]$^+$ |
| 47 | 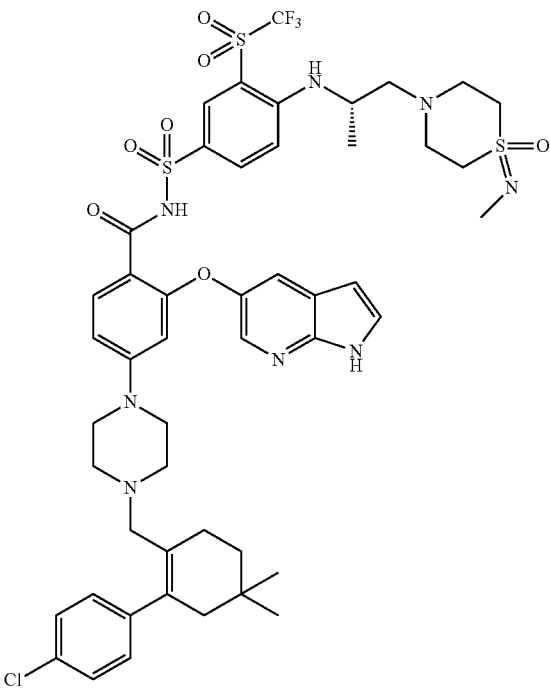 [SMILES: CN=S1(=O)CCN(C[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2S(=O)(=O)C(F)(F)F)CC1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(1-(methylimino)-1-oxido-1λ$^6$-thiomorpholino)propan-2-yl)amino)-3-((trifluoromethyl)sulfonyl)phenyl)sulfonyl)benzamide | MS-ESI (m/z): 1045 [M + 1]$^+$ |

TABLE 1-continued

| EXAMPLE | STRUCTURE | NAME | DATA |
|---|---|---|---|
| 48 | 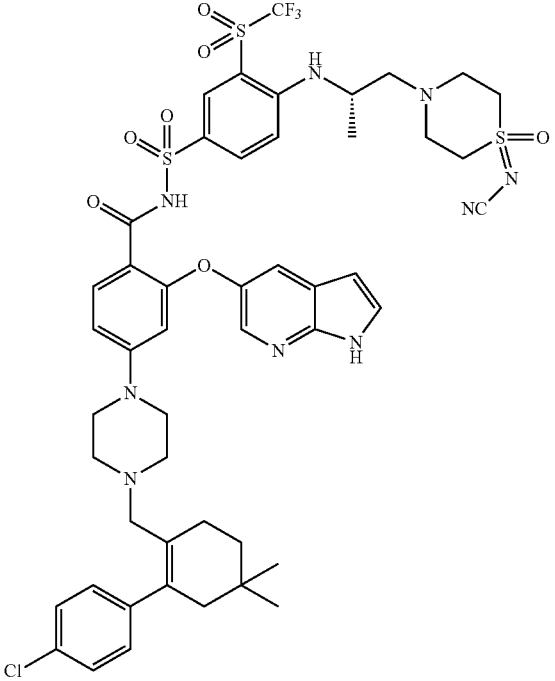 [SMILES: C[C@@H](CN1CCS(=O)(=NC#N)CC1)Nc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1S(=O)(=O)C(F)(F)F] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(1-(cyanoimino)-1-oxido-1$\lambda^6$-thiomorpholino)propan-2-yl)amino)-3-((trifluoromethyl)sulfonyl)phenyl)sulfonyl)benzamide | MS-ESI (m/z): 1056 [M + 1]$^+$ |
| 49 | 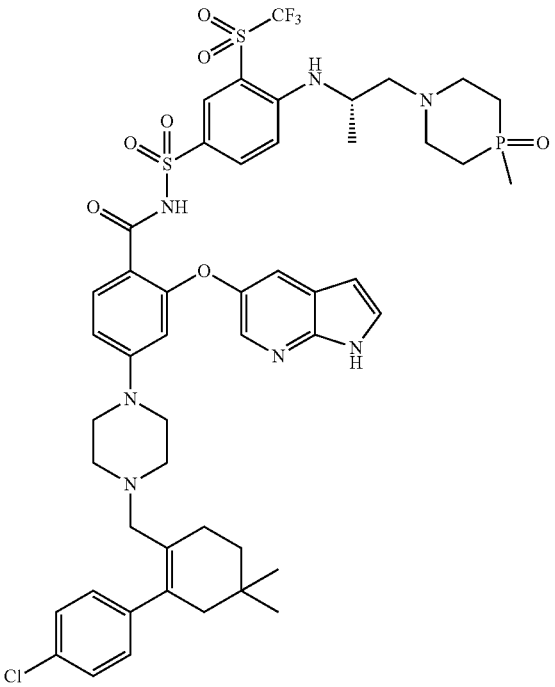 [SMILES: C[C@@H](CN1CCP(C)(=O)CC1)Nc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1S(=O)(=O)C(F)(F)F] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(4-methyl-4-oxido-1,4-azaphosphinan-1-yl)propan-2-yl)amino)-3-((trifluoromethyl)sulfonyl)phenyl)sulfonyl)benzamide | MS-ESI (m/z): 1030 [M + 1]$^+$ |

TABLE 1-continued

| EXAMPLE | STRUCTURE | NAME | DATA |
|---|---|---|---|
| 50A | 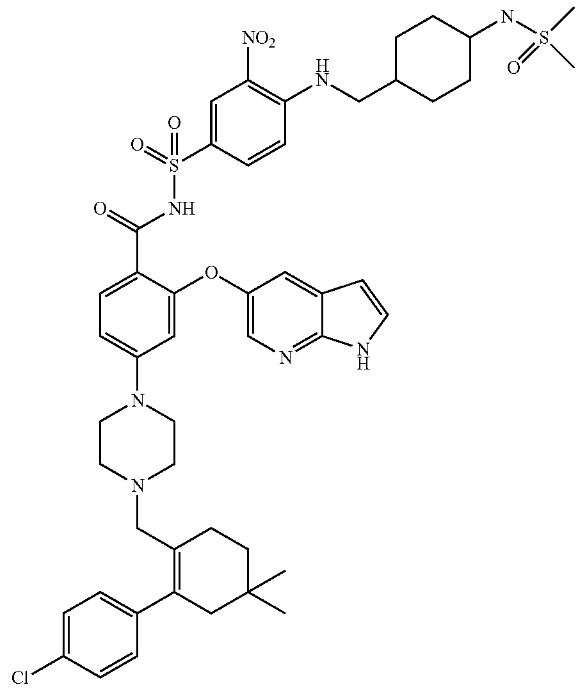 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((4-((dimethyl(oxo)-$\lambda^6$-sulfanylidene)amino)cyclohexyl)methyl)amino)-3-nitrophenyl)sulfonyl)benzamide | MS-ESI (m/z): 957 [M + 1]$^+$ |
| 50B | 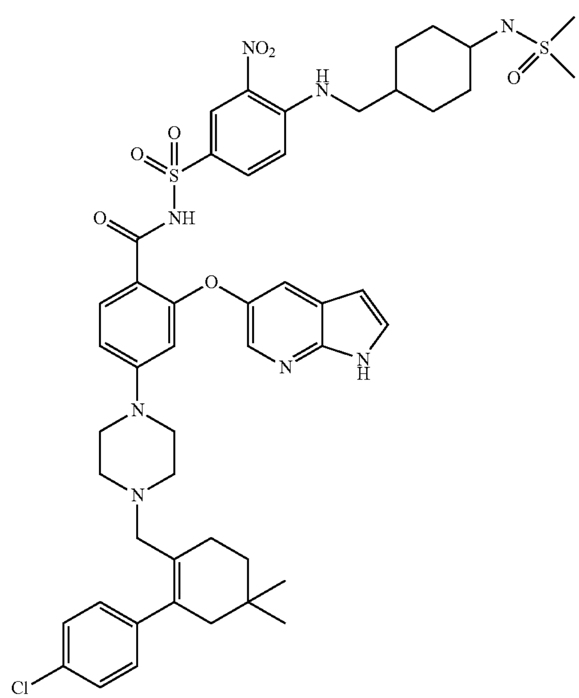 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((4-((dimethyl(oxo)-$\lambda^6$-sulfanylidene)amino)cyclohexyl)methyl)amino)-3-nitrophenyl)sulfonyl)benzamide | MS-ESI (m/z): 957 [M + 1]$^+$ |

TABLE 1-continued

| EXAMPLE | STRUCTURE | NAME | DATA |
|---|---|---|---|
| 51 | 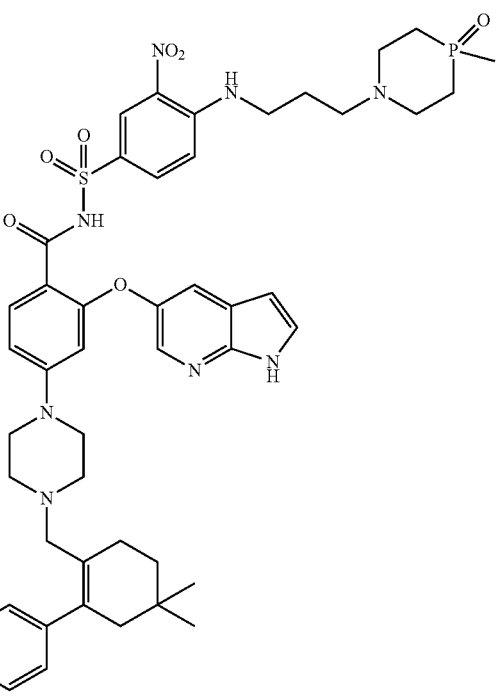 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((3-(4-methyl-4-oxido-1,4-azaphosphinan-1-yl)propyl)amino)-3-nitrophenyl)sulfonyl)benzamide | MS-ESI (m/z): 943 [M + 1]$^+$ |
| 52 | 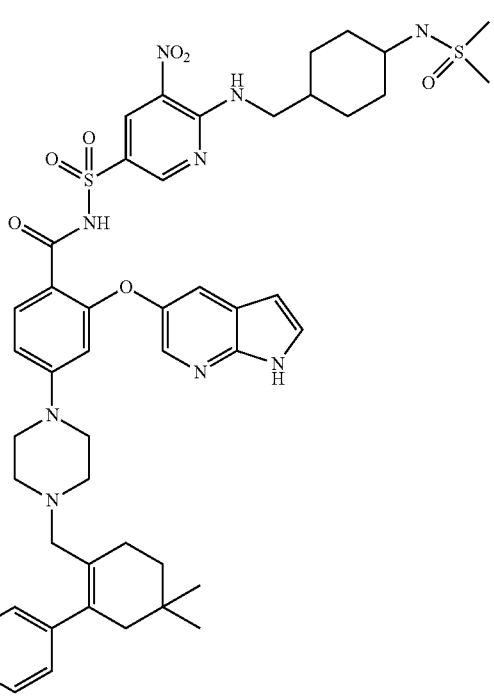 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((6-(((4-((dimethyl(oxo)-$\lambda^6$-sulfanylidene)amino)cyclohexyl)methyl)amino)-5-nitropyridin-3-yl)sulfonyl)benzamide | MS-ESI (m/z): 958 [M + 1]$^+$ |

TABLE 1-continued

| EXAMPLE | STRUCTURE | NAME | DATA |
| --- | --- | --- | --- |
| 53 | 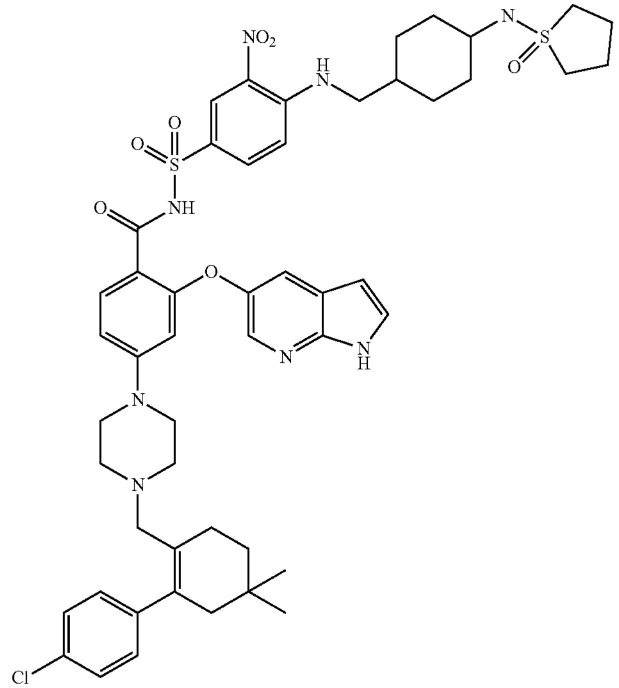 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-nitro-4-(((4-((1-oxidotetrahydro-1$\lambda^6$-thiophen-1-ylidene)amino)cyclohexyl)methyl)amino)phenyl)sulfonyl)benzamide | MS-ESI (m/z): 983 [M + 1]$^+$ |
| 54 | 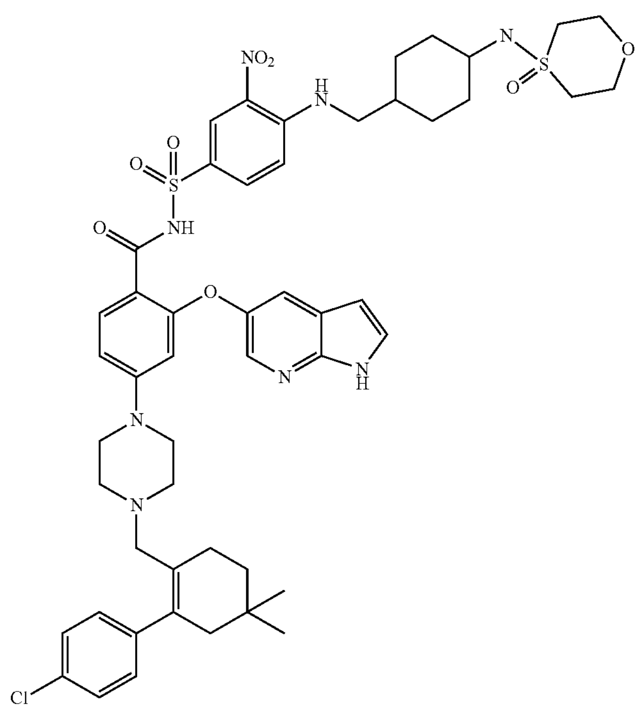 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-nitro-4-(((4-((4-oxido-1,4$\lambda^6$-oxathian-4-ylidene)amino)cyclohexyl)methyl)amino)phenyl)sulfonyl)benzamide | MS-ESI (m/z): 999 [M + 1]$^+$ |

TABLE 1-continued

| EXAMPLE | STRUCTURE | NAME | DATA |
|---|---|---|---|
| 55 | 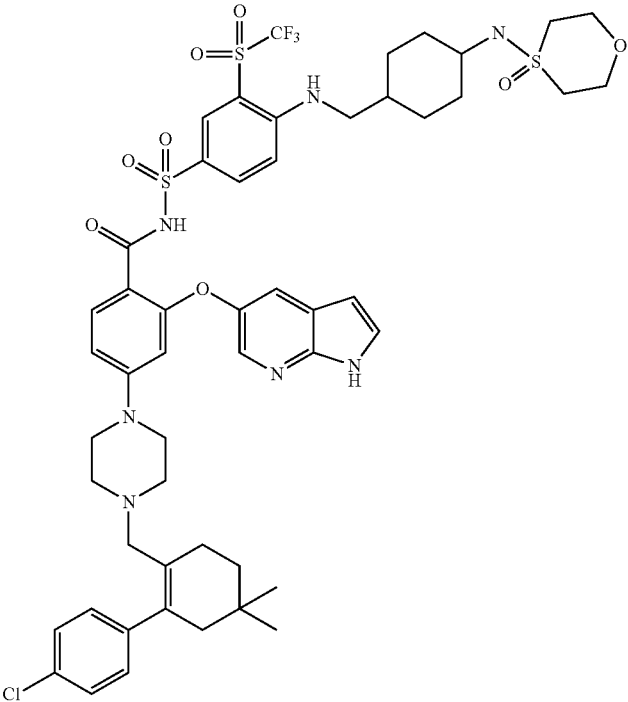 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((4-(4-oxido-1,4λ⁶-oxathian-4-ylidene)amino)cyclohexyl)methyl)amino)-3-((trifluoromethyl)sulfonyl)phenyl)sulfonyl)benzamide | MS-ESI (m/z): 1086 [M + 1]⁺ |
| 56 | 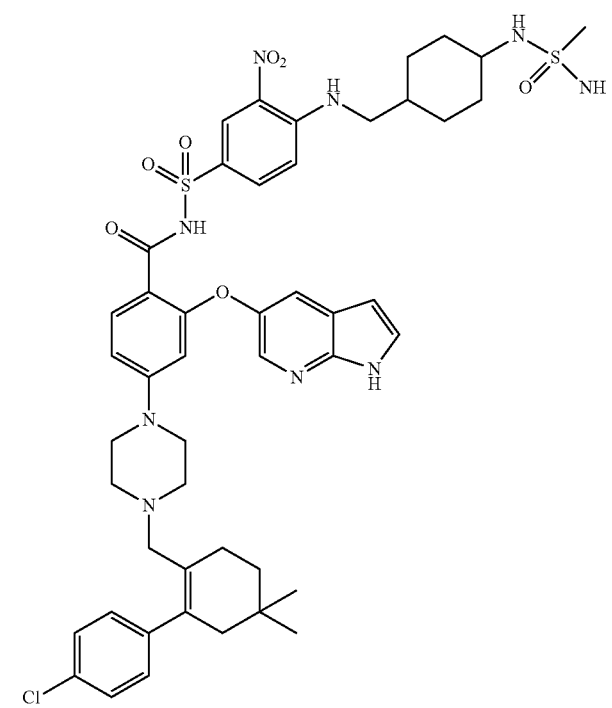 | 4-(4-{[2-(4-chlorophenyl)-4,4-dimethylcyclohex-1-en-1-yl]methyl}piperazin-1-yl)-N-(4-{[(4-methanesulfonoimidamidocyclohexyl)methyl]amino}-3-nitrobenzenesulfonyl)-2-{1H-pyrrolo[2,3-b]pyridine-5-yloxy}benzamide | MS-ESI (m/z): 958 [M + 1]⁺ |

TABLE 1-continued

| EXAMPLE | STRUCTURE | NAME | DATA |
|---|---|---|---|
| 57 | 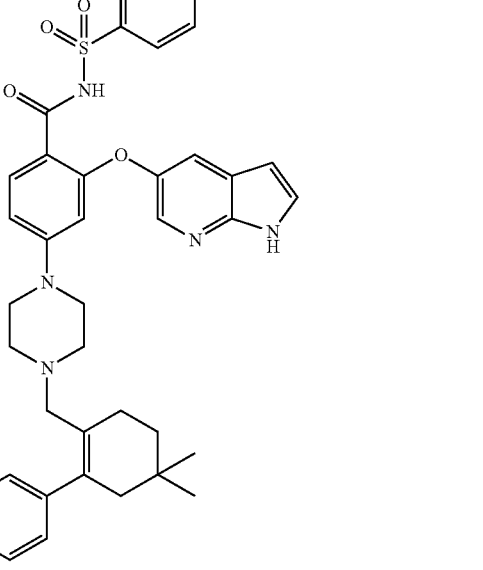 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((5-((dimethyl(oxo)-$\lambda^6$-sulfanylidene)amino)tetrahydro-2H-pyran-2-yl)methyl)amino)-3-nitrophenyl)sulfonyl)benzamide | MS-ESI (m/z): 959 [M + 1]$^+$ |
| 58 | 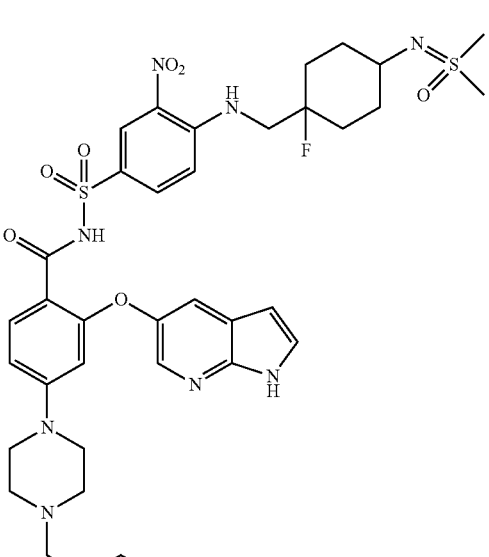 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((4-((dimethyl(oxo)-$\lambda^6$-sulfanylidene)amino)-1-fluorocyclohexyl)methyl)amino)-3-nitrophenyl)sulfonyl)benzamide | MS-ESI (m/z): 975 [M + 1]$^+$ |

TABLE 1-continued

| EXAMPLE | STRUCTURE | NAME | DATA |
|---|---|---|---|
| 59 | 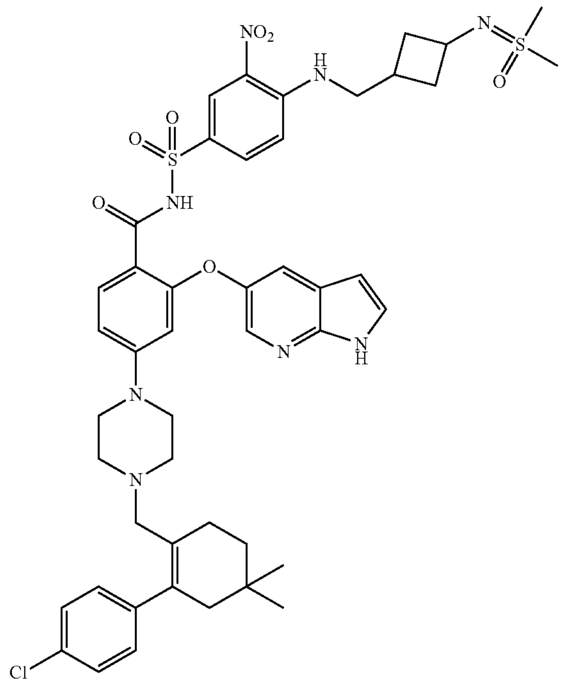 [SMILES: CC1(C)CCC(CN2CCN(c3ccc(C(=O)NS(=O)(=O)c4ccc(NCC5CC(N=S(C)(C)=O)C5)c([N+](=O)[O-])c4)c(Oc4cnc5[nH]ccc5c4)c3)CC2)=C(c2ccc(Cl)cc2)C1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((3-((dimethyl(oxo)-$\lambda^6$-sulfanylidene)amino)cyclobutyl)methyl)amino)-3-nitrophenyl)sulfonyl)benzamide | MS-ESI (m/z): 929 [M + 1]$^+$ |
| 60 | 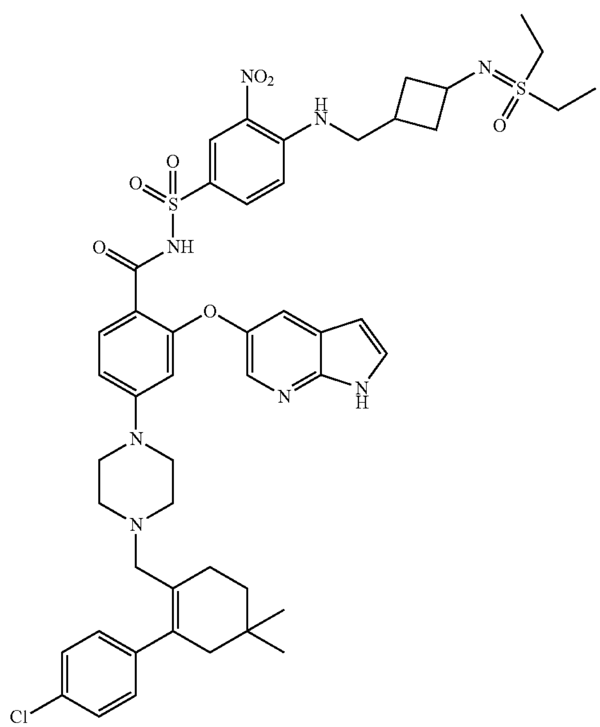 [SMILES: CCS(=O)(CC)=NC1CC(CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])C1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((3-((diethyl(oxo)-$\lambda^6$-sulfanylidene)amino)cyclobutyl)methyl)amino)-3-nitrophenyl)sulfonyl)benzamide | MS-ESI (m/z): 957 [M + 1]$^+$ |

TABLE 1-continued

| EXAMPLE | STRUCTURE | NAME | DATA |
|---|---|---|---|
| 61 | 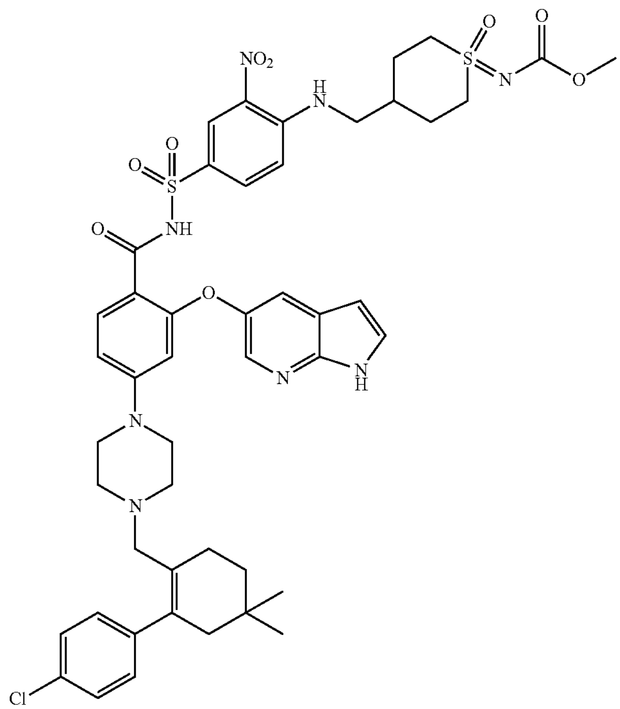 [SMILES: COC(=O)N=S1(=O)CCC(CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | methyl(4-(((4-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-2-nitrophenyl)amino)methyl)-1-oxidotetrahydro-2H-1$\lambda^6$-thiopyran-1-ylidene)carbamate | MS-ESI (m/z): 973 [M + 1]$^+$ |
| 62 | 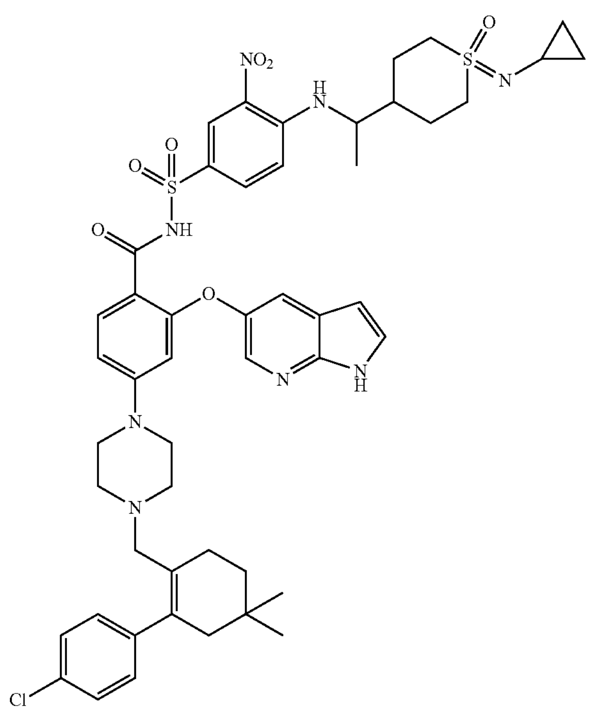 [SMILES: CC(Nc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1[N+](=O)[O-])C1CCS(=O)(=NC2CC2)CC1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(1-(cyclopropylimino)-1-oxidohexahydro-1$\lambda^6$-thiopyran-4-yl)ethyl)amino)-3-nitrophenyl)sulfonyl)benzamide | MS-ESI (m/z): 969 [M + 1]$^+$ |

TABLE 1-continued

| EXAMPLE | STRUCTURE | NAME | DATA |
|---|---|---|---|
| 63 | 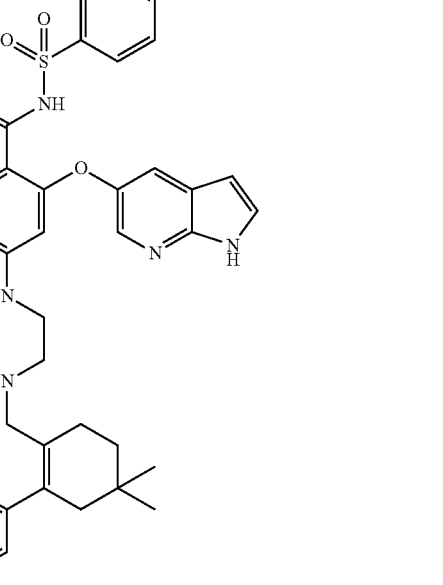 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((4-((dimethyl(oxo)-$\lambda^6$-sulfanylidene)amino)cyclohexyl)methyl)amino)-3-((trifluoromethyl)sulfonyl)phenyl)sulfonyl)benzamide | MS-ESI (m/z): 1044 [M + 1]$^+$ |
| 64 | 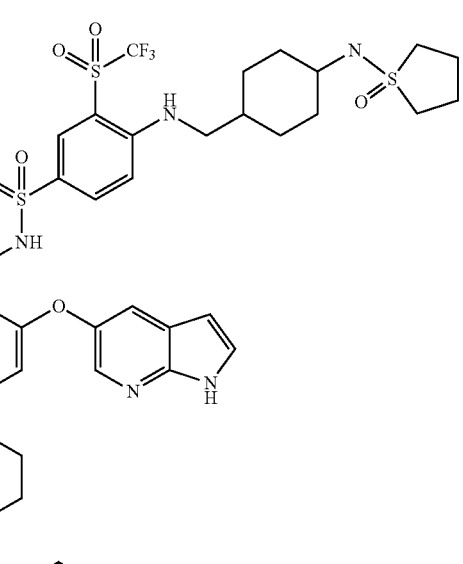 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((4-((1-oxidotetrahydro-1$\lambda^6$-thiophen-1-ylidene)amino)cyclohexyl)methyl)amino)-3-((trifluoromethyl)sulfonyl)phenyl)sulfonyl)benzamide | MS-ESI (m/z): 1070 [M + 1]$^+$ |

TABLE 1-continued

| EXAMPLE | STRUCTURE | NAME | DATA |
|---|---|---|---|
| 65 | 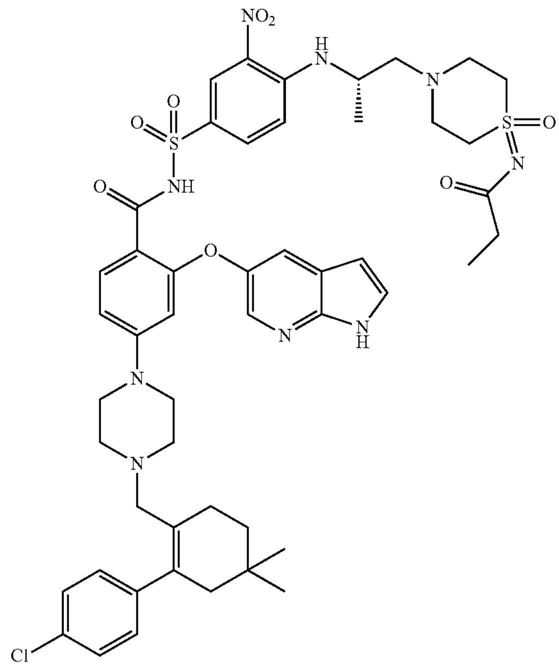 [SMILES: CCC(=O)N=S1(=O)CCN(C[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-nitro-4-((l-(1-oxido-1-(propionylimino)-1λ⁶-thiomorpholino)propan-2-yl)amino)phenyl)sulfonyl)benzamide | MS-ESI (m/z): 1000 [M + 1]⁺ |
| 66 | 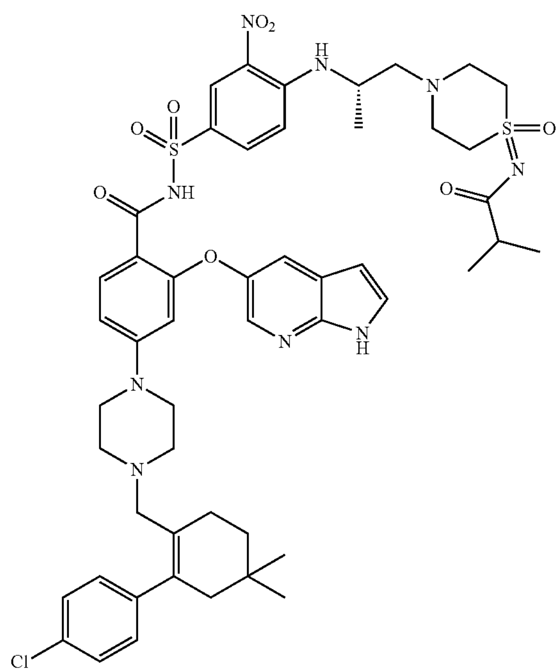 [SMILES: CC(C)C(=O)N=S1(=O)CCN(C[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-(((1-(1-(isobutyrylimino)-1-oxido-1λ⁶-thiomorpholino)propan-2-yl)amino)-3-nitrophenyl)sulfonyl)benzamide | MS-ESI (m/z): 1014 [M + 1]⁺ |

TABLE 1-continued

| EXAMPLE | STRUCTURE | NAME | DATA |
|---|---|---|---|
| 67 | 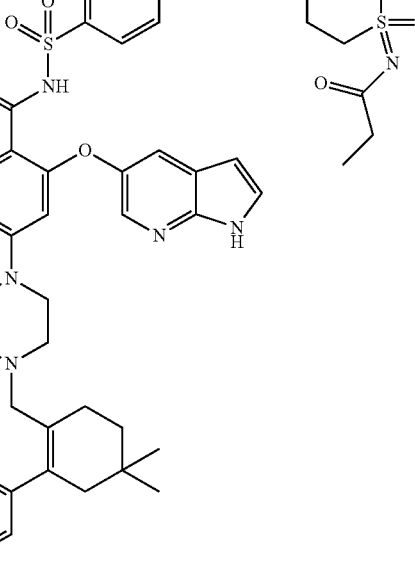 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-nitro-4-((2-(1-oxido-1-(propionyl imino)-1$\lambda^6$-thiomorpholino)ethyl)amino)phenyl)sulfonyl)benzamide | MS-ESI (m/z): 986 [M + 1]$^+$ |
| 68 | 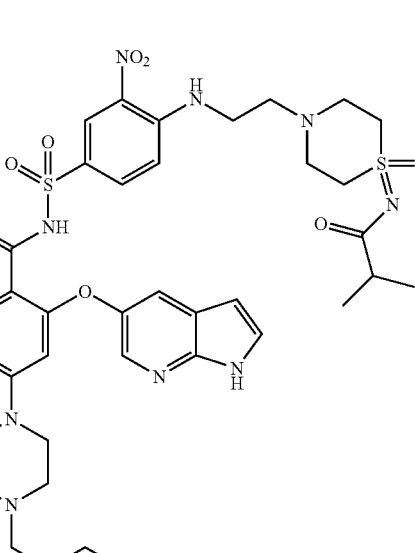 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((2-(1-(isobutyrylimino)-1-oxido-1$\lambda^6$-thiomorpholino)ethyl)amino)-3-nitrophenyl)sulfonyl)benzamide | MS-ESI (m/z): 1000 [M + 1]$^+$ |

TABLE 1-continued

| EXAMPLE | STRUCTURE | NAME | DATA |
|---|---|---|---|
| 69 | 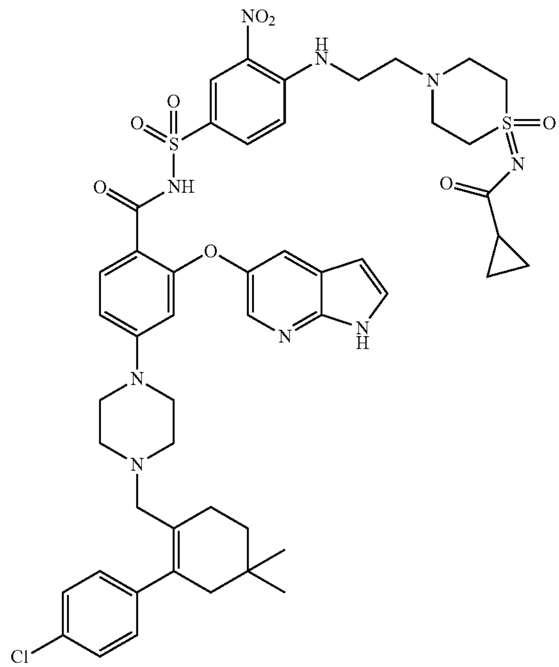 [SMILES: CC1(C)CCC(CN2CCN(c3ccc(C(=O)NS(=O)(=O)c4ccc(NCCN5CCS(=O)(=NC(=O)C6CC6)CC5)c([N+](=O)[O-])c4)c(Oc4cnc5[nH]ccc5c4)c3)CC2)=C(c2ccc(Cl)cc2)C1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((2-(1-((cyclopropanecarbonyl)imino)-1-oxido-1$\lambda^6$-thiomorpholino)ethyl)amino)-3-nitrophenyl)sulfonyl)benzamide | MS-ESI (m/z): 998 [M + 1]$^+$ |
| 70 | 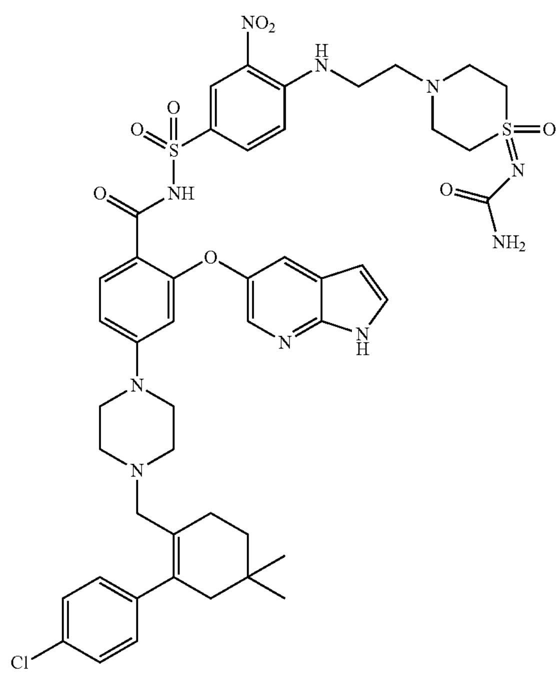 [SMILES: CC1(C)CCC(CN2CCN(c3ccc(C(=O)NS(=O)(=O)c4ccc(NCCN5CCS(=O)(=NC(N)=O)CC5)c([N+](=O)[O-])c4)c(Oc4cnc5[nH]ccc5c4)c3)CC2)=C(c2ccc(Cl)cc2)C1] | 2-((1H-pyrrolo[2,3-b]pyridin-5-yl)oxy)-N-((4-((2-(1-(carbamoylimino)-1-oxido-1$\lambda^6$-thiomorpholino)ethyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 973 [M + 1]$^+$ |

TABLE 1-continued

| EXAMPLE | STRUCTURE | NAME | DATA |
|---|---|---|---|
| 71 | 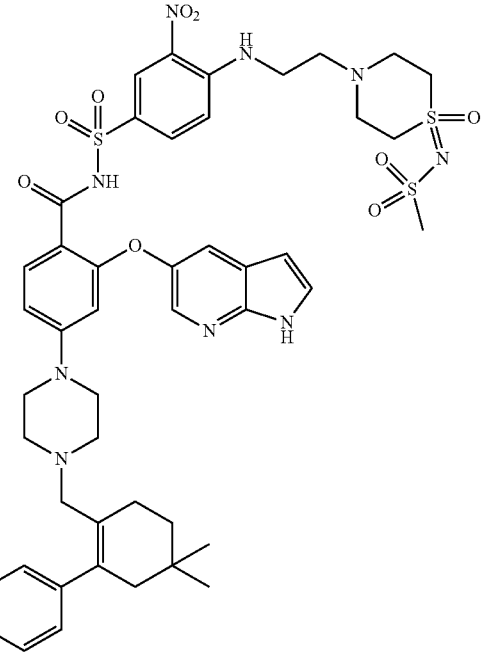 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((2-(1-((methylsulfonyl)imino)-1-oxido-1$\lambda^6$-thiomorpholino)ethyl)amino)-3-nitrophenyl)sulfonyl)benzamide | MS-ESI (m/z): 1008 [M + 1]$^+$ |
| 72 | 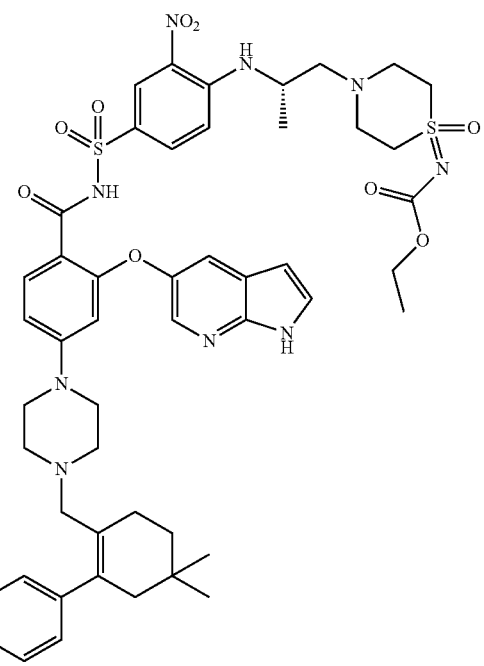 | ethyl (S)-(4-(2-((4-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-2-nitrophenyl)amino)propyl)-1-oxido-1$\lambda^6$-thiomorpholin-1-ylidene)carbamate | MS-ESI (m/z): 1016 [M + 1]$^+$ |

TABLE 1-continued

| EXAMPLE | STRUCTURE | NAME | DATA |
|---|---|---|---|
| 73 | 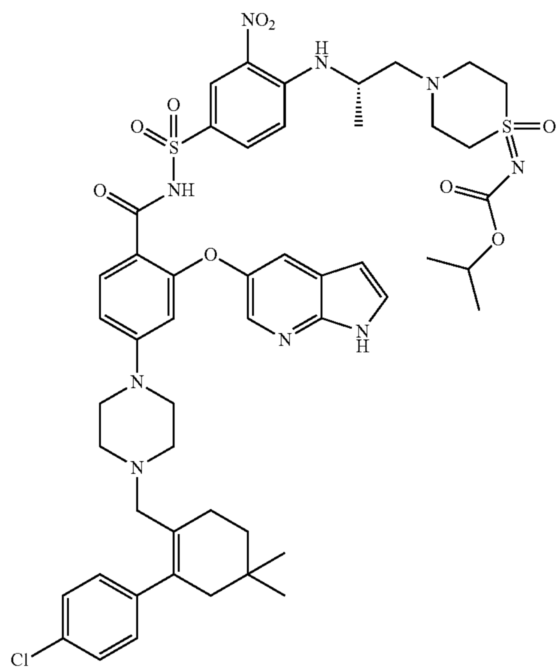 [SMILES: CC(C)OC(=O)N=S1(=O)CCN(C[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | isopropyl (S)-(4-(2-((4-(N-(2-(((1H-pyrrolo[2,3-b]pyridin-5-yl)oxy)-4-(((4'-chloro-5,5-dimethyl-3,4,5,6-tetrahydro-[1,1'-biphenyl]-2-yl)methyl)piperazin-1-yl)benzoyl)sulfamoyl)-2-nitrophenyl)amino)propyl)-1-oxido-1λ⁶-thiomorpholin-1-ylidene)carbamate | MS-ESI (m/z): 1030 [M + 1]⁺ |
| 74 | 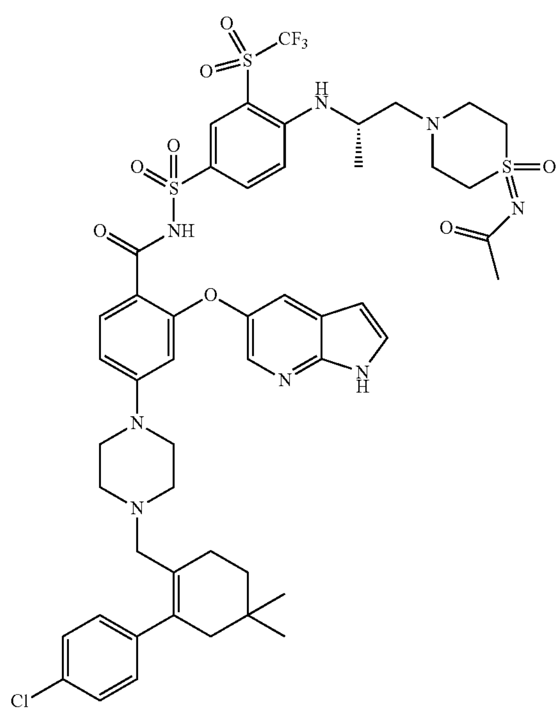 [SMILES: CC(=O)N=S1(=O)CCN(C[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2S(=O)(=O)C(F)(F)F)CC1] | (S)-2-((1H-pyrrolo[2,3-b]pyridin-5-yl)oxy)-N-((4-((1-(1-(acetylimino)-1-oxido-1λ⁶-thiomorpholino)propan-2-yl)amino)-3-((trifluoromethyl)sulfonyl)phenyl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 1073 [M + 1]⁺ |

TABLE 1-continued

| EXAMPLE | STRUCTURE | NAME | DATA |
|---|---|---|---|
| 75 | 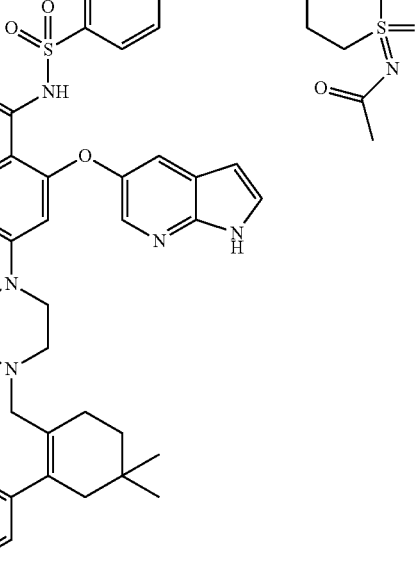 | 2-((1H-pyrrolo[2,3-b]pyridin-5-yl)oxy)-N-((4-((2-(1-(acetylimino)-1-oxido-1λ⁶-thiomorpholino)ethyl)amino)-3-((trifluoromethyl)sulfonyl)phenyl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 1059 [M + 1]⁺ |
| 76 | 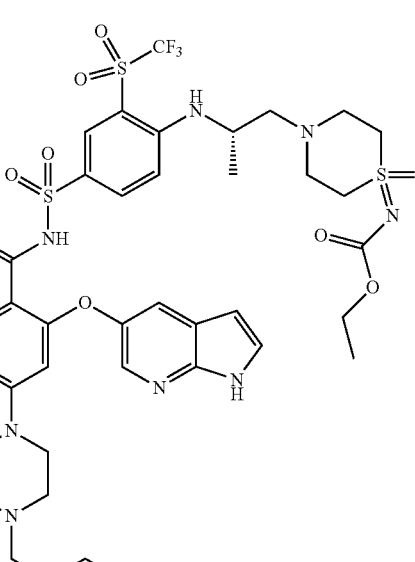 | ethyl (S)-(4-(2-((4-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)propyl)-1-oxido-1λ⁶-thiomorpholin-1-ylidene)carbamate | MS-ESI (m/z): 1103 [M + 1]⁺ |

TABLE 1-continued

| EXAMPLE | STRUCTURE | NAME | DATA |
|---------|-----------|------|------|
| 77 | 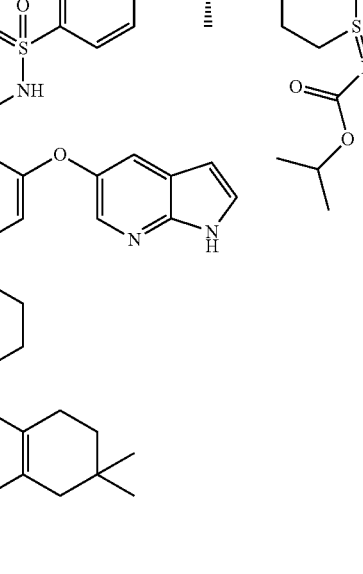 | isopropyl (S)-(4-(2-((4-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)propyl)-1-oxido-1$\lambda^6$-thiomorpholin-1-ylidene)carbamate | MS-ESI (m/z): 1117 [M + 1]$^+$ |
| 78 | 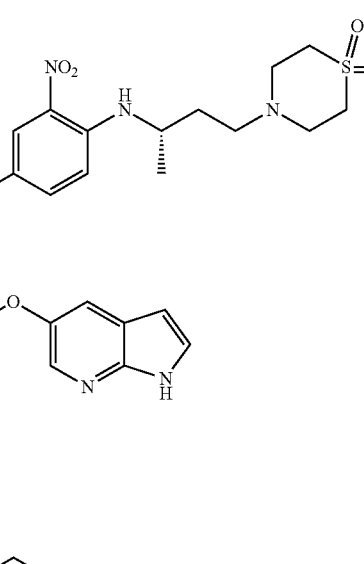 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((4-(1-(ethylimino)-1-oxido-1$\lambda^6$-thiomorpholino)butan-2-yl)amino)-3-nitrophenyl)sulfonyl)benzamide | MS-ESI (m/z): 986 [M + 1]$^+$ |

TABLE 1-continued

| EXAMPLE | STRUCTURE | NAME | DATA |
|---|---|---|---|
| 79 | 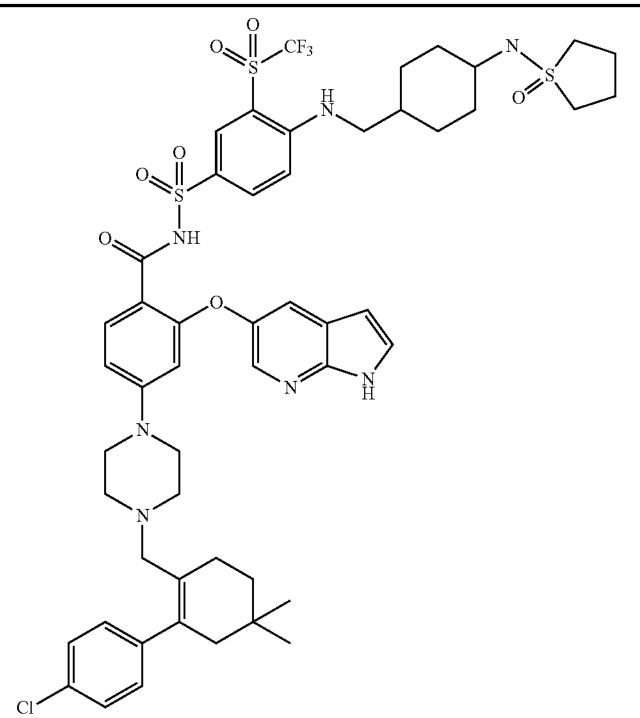 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((4-(1-(cyclopropylimino)-1-oxido-1λ6-thiomorpholino)butan-2-yl)amino)-3-nitrophenyl)sulfonyl)benzamide | MS-ESI (m/z): 998 [M + 1]+ |
| 80 | 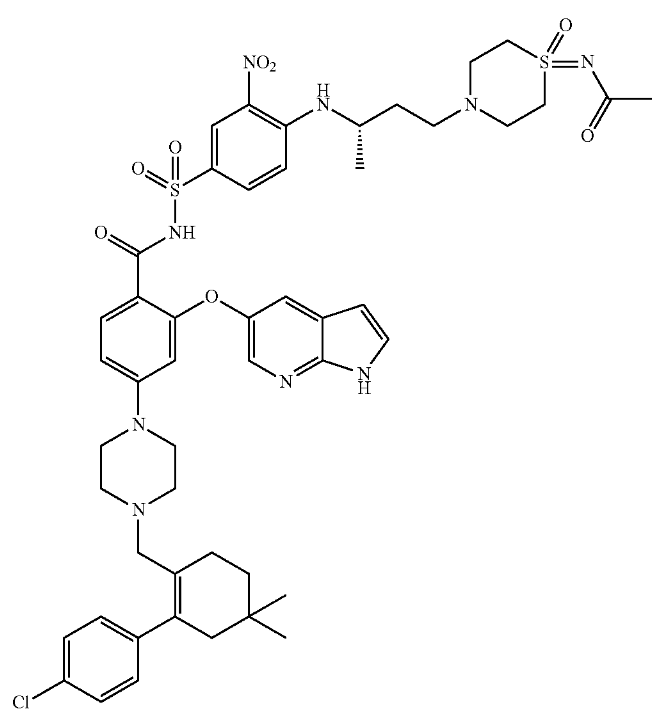 [SMILES: CC(=O)N=S1(=O)CCN(CC[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | (S)-2-((1H-pyrrolo[2,3-b]pyridin-5-yl)oxy)-N-(4-((4-(1-(acetylimino)-1-oxido-1λ6-thiomorpholino)butan-2-yl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 1000 [M + 1]+ |

TABLE 1-continued

| EXAMPLE | STRUCTURE | NAME | DATA |
|---|---|---|---|
| 81 | 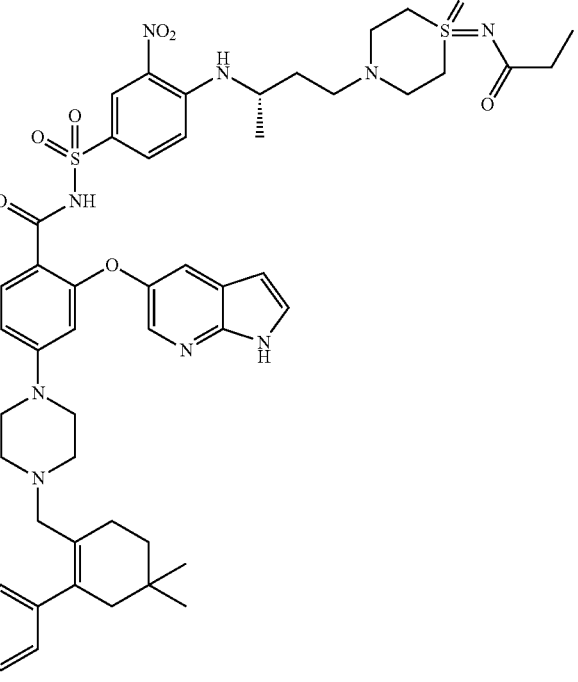 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-nitro-4-(((4-(1-oxido-1-(propionylimino)-1$\lambda^6$-thiomorpholino)butan-2-yl)amino)phenyl)sulfonyl)benzamide | MS-ESI (m/z): 1014 [M + 1]$^+$ |
| 82 | 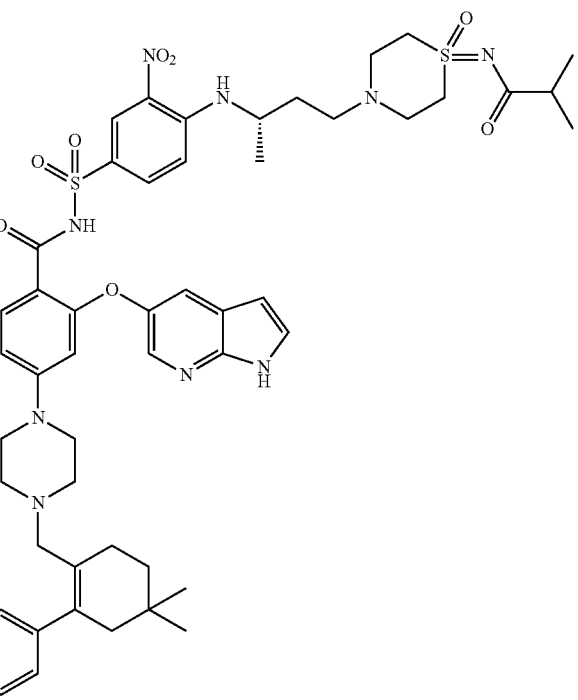 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((4-(1-(isobutyrylimino)-1-oxido-1$\lambda^6$-thiomorpholino)butan-2-yl)amino)-3-nitrophenyl)sulfonyl)benzamide | MS-ESI (m/z): 1028 [M + 1]$^+$ |

TABLE 1-continued

| EXAMPLE | STRUCTURE | NAME | DATA |
|---|---|---|---|
| 83 | 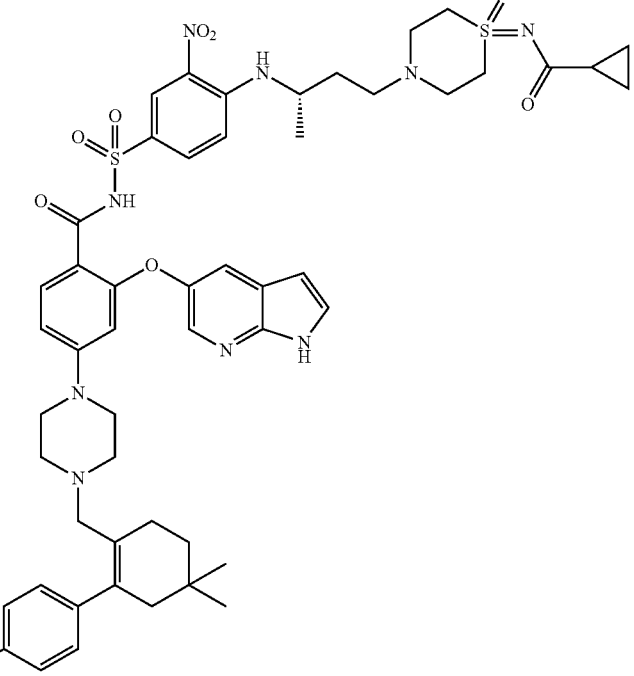 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((4-(1-((cyclopropanecarbonyl)imino)-1-oxido-1$\lambda^6$-thiomorpholino)butan-2-yl)amino)-3-nitrophenyl)sulfonyl)benzamide | MS-ESI (m/z): 1026 [M + 1]$^+$ |
| 84 | 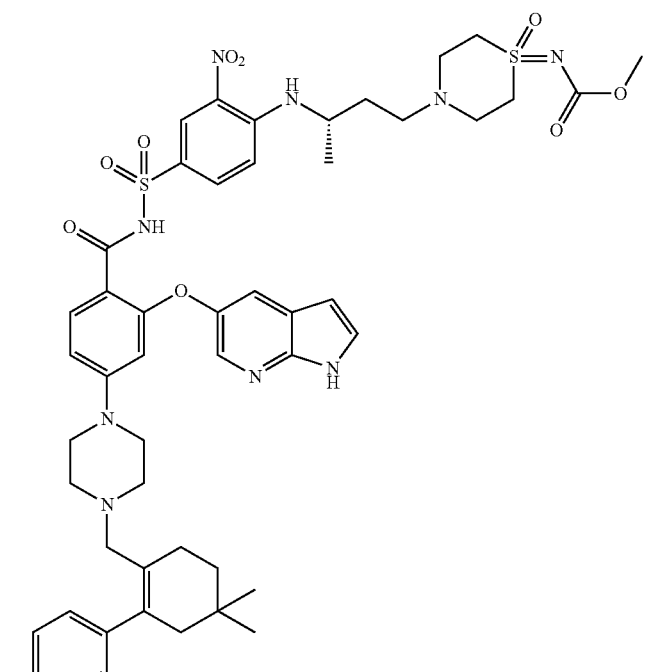 | methyl (S)-(4-(3-((4-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-2-nitrophenyl)amino)butyl)-1-oxido-1$\lambda^6$-thiomorpholin-1-ylidene)carbamate | MS-ESI (m/z): 1016 [M + 1]$^+$ |

TABLE 1-continued

| EXAMPLE | STRUCTURE | NAME | DATA |
|---|---|---|---|
| 85 | 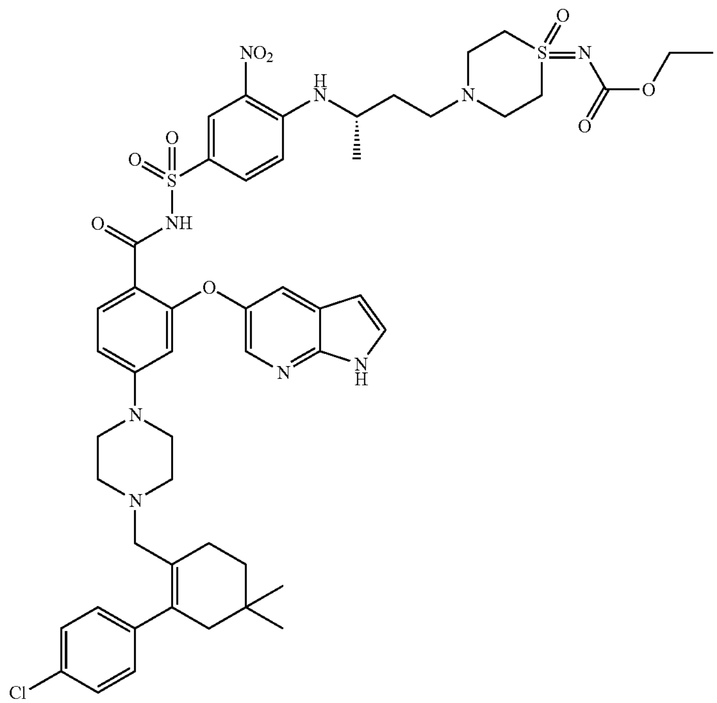 [SMILES: CCOC(=O)N=S1(=O)CCN(CC[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | ethyl (S)-(4-(3-((4-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-2-nitrophenyl)amino)butyl)-1-oxido-1λ$^6$-thiomorpholin-1-ylidene)carbamate | MS-ESI (m/z): 1030 [M + 1]$^+$ |
| 86 | 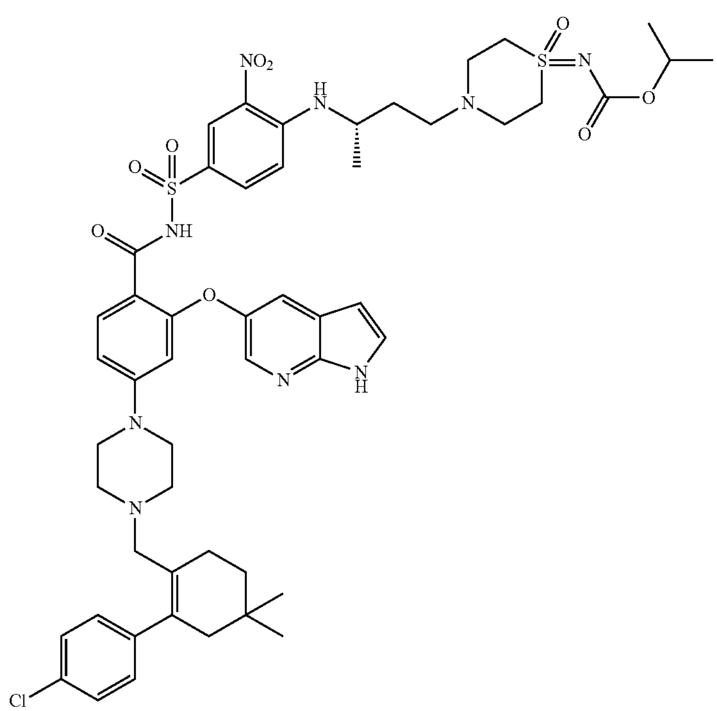 [SMILES: CC(C)OC(=O)N=S1(=O)CCN(CC[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | isopropyl (S)-(4-(3-((4-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-2-nitrophenyl)amino)butyl)-1-oxido-1λ$^6$-thiomorpholin-1-ylidene)carbamate | MS-ESI (m/z): 1044 [M + 1]$^+$ |

TABLE 1-continued

| EXAMPLE | STRUCTURE | NAME | DATA |
|---|---|---|---|
| 87 | 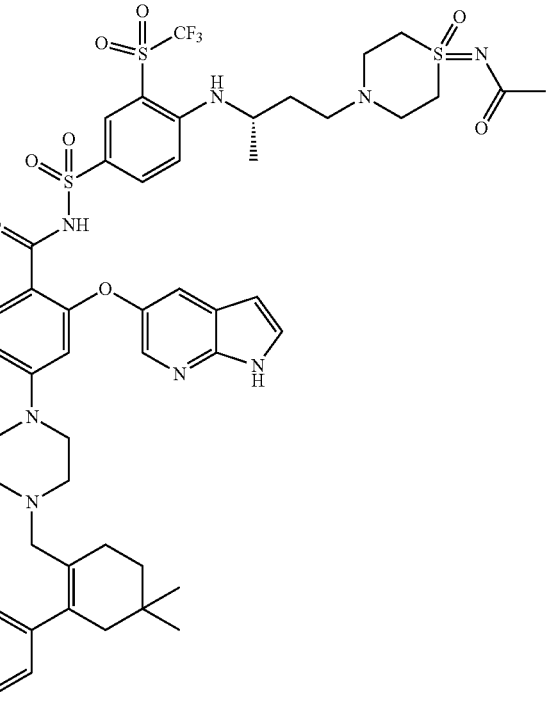 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((4-(1-(ethylimino)-1-oxido-1$\lambda^6$-thiomorpholino)butan-2-yl)amino)-3-((trifluoromethyl)sulfonyl)phenyl)sulfonyl)benzamide | MS-ESI (m/z): 1073 [M + 1]$^+$ |
| 88 | 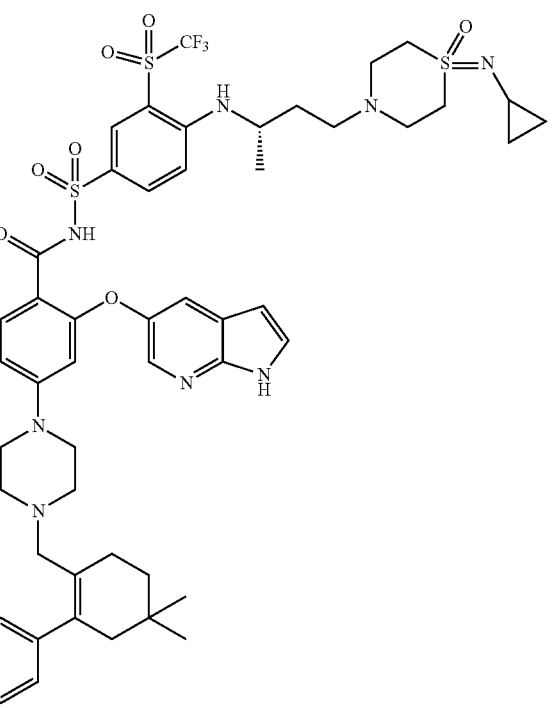 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((4-(1-(cyclopropylimino)-1-oxido-1$\lambda^6$-thiomorpholino)butan-2-yl)amino)-3-((trifluoromethyl)sulfonyl)phenyl)sulfonyl)benzamide | MS-ESI (m/z): 1085 [M + 1]$^+$ |

TABLE 1-continued

| EXAMPLE | STRUCTURE | NAME | DATA |
|---|---|---|---|
| 89 | 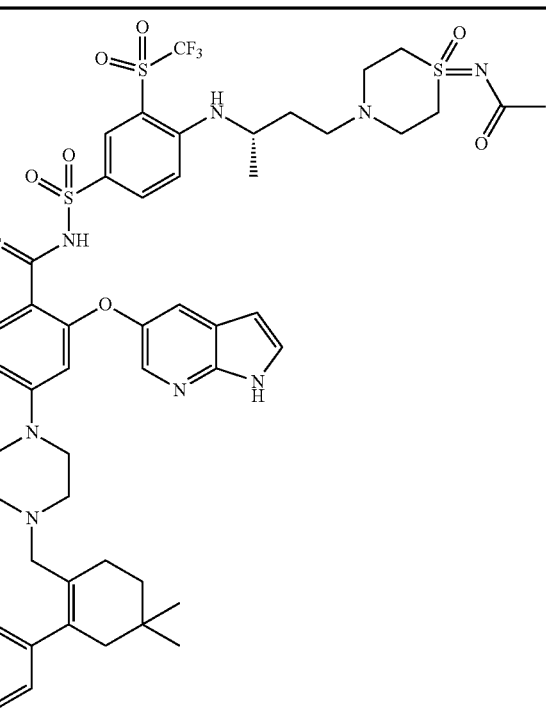 | (S)-2-((1H-pyrrolo[2,3-b] pyridin-5-yl)oxy)-N-((4-((4-(1-(acetylimino)-1-oxido-1$\lambda^6$-thiomorpholino) butan-2-yl)amino)-3-((trifluoromethyl)sulfonyl) phenyl)sulfonyl)-4-(4-((4'-chloro-5,5-dimethyl-3,4,5,6-tetrahydro-[1,1'-biphenyl]-2-yl)methyl) piperazin-1-yl)benzamide | MS-ESI (m/z): 1087 [M + 1]$^+$ |
| 90 | 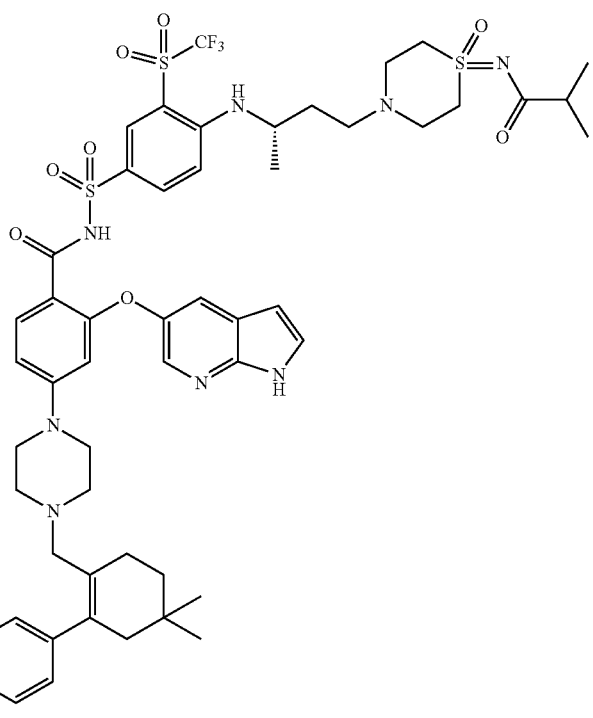 | (S)-2-((1H-pyrrolo[2,3-b] pyridin-5-yl)oxy)-4-(4-((4'-chloro-5,5-dimethyl-3,4,5,6-tetrahydro-[1,1'-biphenyl]-2-yl)methyl) piperazin-1-yl)-N-((4-((4-(1-(isobutyrylimino)-1-oxido-1$\lambda^6$-thiomorpholino) butan-2-yl)amino)-3-((trifluoromethyl) sulfonyl)phenyl)sulfonyl) benzamide | MS-ESI (m/z): 1115 [M + 1]$^+$ |

TABLE 1-continued

| EXAMPLE | STRUCTURE | NAME | DATA |
|---|---|---|---|
| 91 | 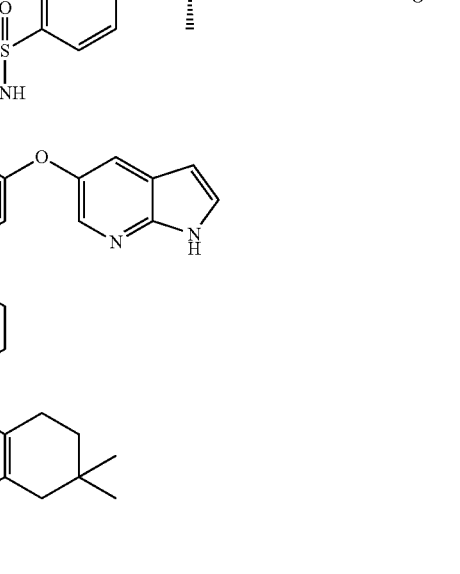 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((4-(1-((cyclopropanecarbonyl)imino)-1-oxido-1λ⁶-thiomorpholino)butan-2-yl)amino)-3-((trifluoromethyl)sulfonyl)phenyl)sulfonyl)benzamide | MS-ESI (m/z): 1113 [M + 1]⁺ |
| 92 | 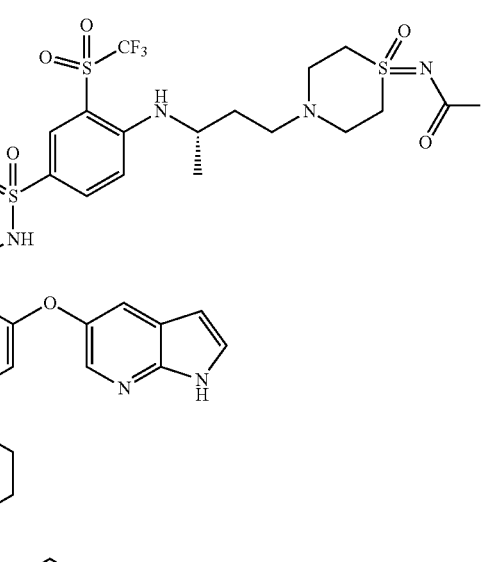 | methyl (S)-(4-(3-((4-(N-(2-((1H-pyrrolo[2,3-b]pyridin-5-yl)oxy)-4-((4'-chloro-5,5-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)butyl)-1-oxido-1λ⁶-thiomorpholin-1-ylidene)carbamate | MS-ESI (m/z): 1103 [M + 1]⁺ |

TABLE 1-continued

| EXAMPLE | STRUCTURE | NAME | DATA |
|---|---|---|---|
| 93 | 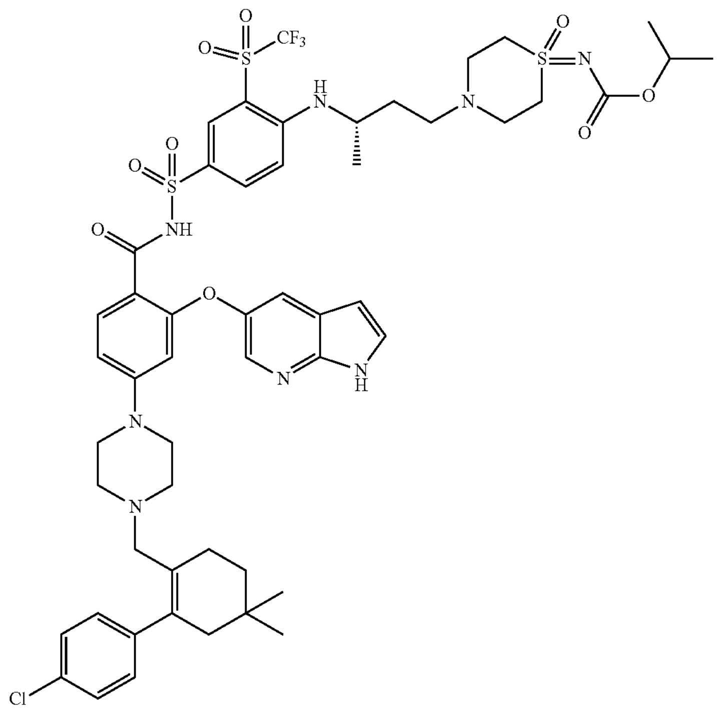 [SMILES: CC(C)OC(=O)N=S1(=O)CCN(CC[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2S(=O)(=O)C(F)(F)F)CC1] | isopropyl (S)-(4-(3-((4-(N-(2-((1H-pyrrolo[2,3-b]pyridin-5-yl)oxy)-4-((4'-chloro-5,5-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)butyl)-1-oxido-1λ⁶-thiomorpholin-1-ylidene)carbamate | MS-ESI (m/z): 1131 [M + 1]⁺ |
| 94 | 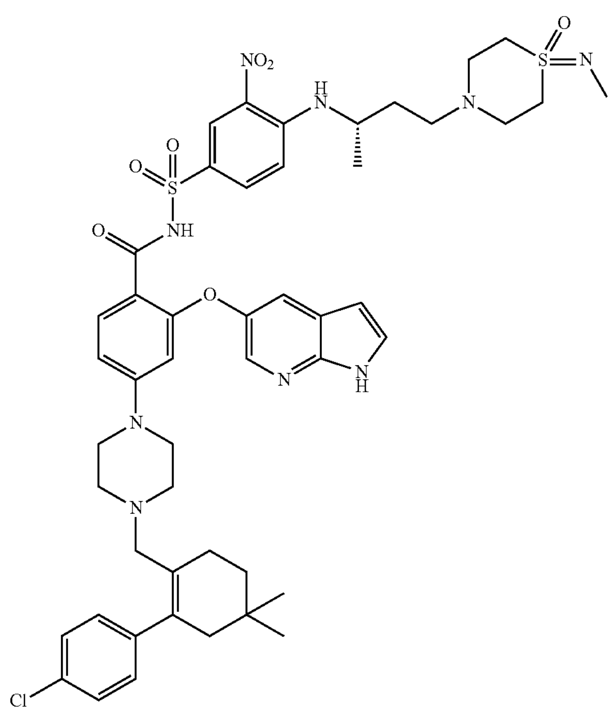 [SMILES: CN=S1(=O)CCN(CC[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((4-(1-(methylimino)-1-oxido-1λ⁶-thiomorpholino)butan-2-yl)amino)-3-nitrophenyl)sulfonyl)benzamide | MS-ESI (m/z): 972 [M + 1]⁺ |

TABLE 1-continued

| EXAMPLE | STRUCTURE | NAME | DATA |
|---|---|---|---|
| 95 | 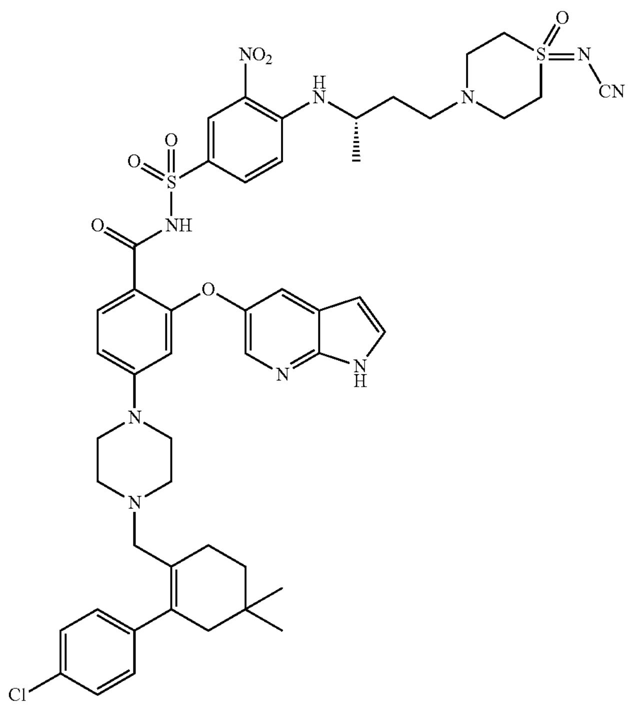 [SMILES: C[C@@H](CCN1CCS(=O)(=NC#N)CC1)Nc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1[N+](=O)[O-]] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((4-(1-(cyanoimino)-1-oxido-1λ⁶-thiomorpholino)butan-2-yl)amino)-3-nitrophenyl)sulfonyl)benzamide | MS-ESI (m/z): 983 [M + 1]⁺ |
| 96 | 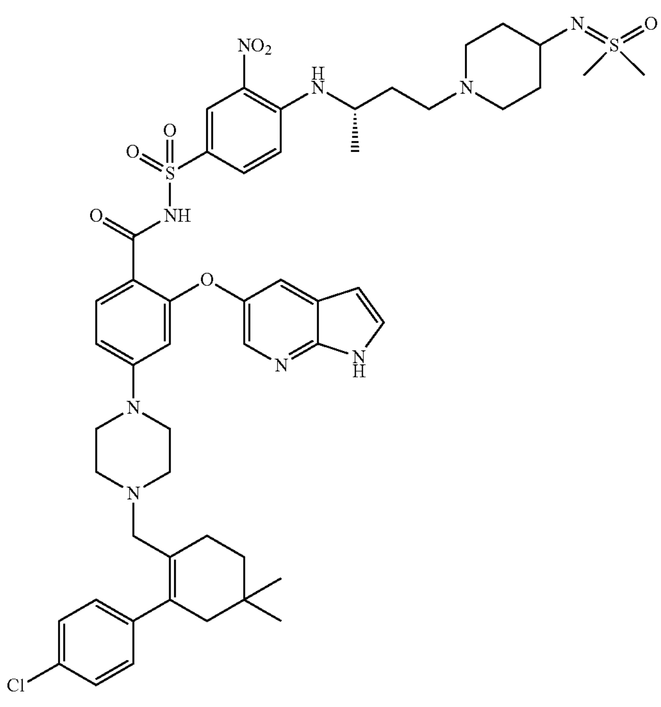 | (S)-2-((1H-pyrrolo[2,3-b]pyridin-5-yl)oxy)-4-((4'-chloro-5,5-dimethyl-3,4,5,6-tetrahydro-[1,1'-biphenyl]-2-yl)methyl)piperazin-1-yl)-N-((4-((4-(4-((dimethyl(oxo)-λ⁶-sulfanylidene)amino)piperidin-1-yl)butan-2-yl)amino)-3-nitrophenyl)sulfonyl)benzamide | MS-ESI (m/z): 943 [M + 1]⁺ |

TABLE 1-continued

| EXAMPLE | STRUCTURE | NAME | DATA |
| --- | --- | --- | --- |
| 97 | 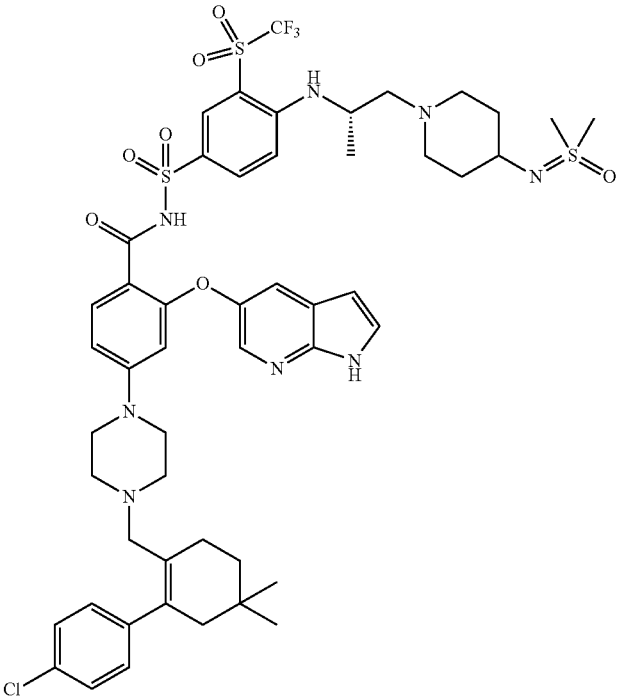 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((1-(4-((dimethyl(oxo)-$\lambda^6$-sulfanylidene)amino)piperidin-1-yl)propan-2-yl)amino)-3-nitrophenyl)sulfonyl)benzamide | MS-ESI (m/z): 943 [M + 1]$^+$ |
| 98 | 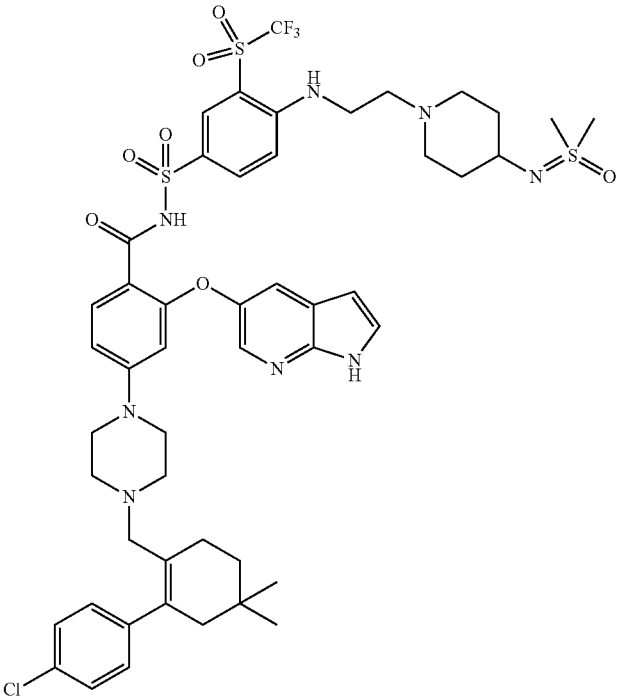 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-((2-(4-((dimethyl(oxo)-$\lambda^6$-sulfanylidene)amino)piperidin-1-yl)ethyl)amino)-3-nitrophenyl)sulfonyl)benzamide | MS-ESI (m/z): 943 [M + 1]$^+$ |

Reference Compound 1

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide (Reference Compound 1)

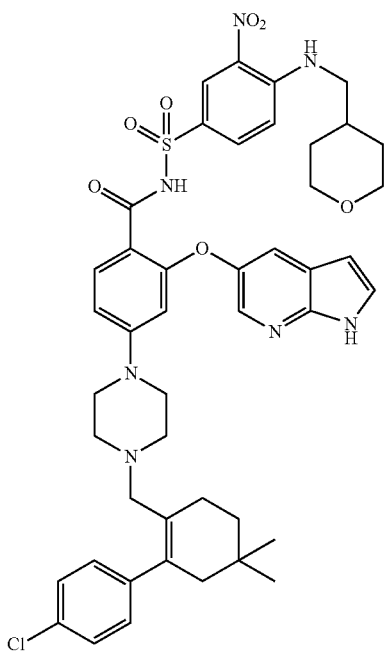 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

Reference compound 1 was disclosed and prepared following essentially the same procedures outlined in US 2014/0275540.

Cell Proliferation Assays

MTS testing kit was purchased from Promega. The RPMI-1640, Fetal bovine serum and Penicillin-Streptomycin were purchased from Gibco. Dimethyl sulfoxide (DMSO) was purchased from Sigma.

To investigate whether a compound is able to inhibit the activity of Bcl-2 in cells, a mechanism-based assay using DOHH2 (DSMZ No.® ACC 47) and RS4; 11 (ATCC® CRL-1873™) cell was developed. In this assay, inhibition of Bcl-2 was detected by the inhibition of DOHH2 and RS4; 11 cells proliferation. DOHH2 and RS4; 11 cells were cultured in culture flasks to 40-80% confluence in RPMI-1640 plus 10% fetal bovine serum. Cells were collected and plated onto 96-well plates at desired cell density (DOHH2: 5000 cells/well; RS4; 11: 30000 cells/well). Plates were incubated overnight at 37° C., with 5% $CO_2$ to adhere. Compounds were added to the plates, and the final compound concentrations were 10000, 3333, 1111, 270, 124, 41, 14, 4.6 and 1.5 nM. Plates plated with DOHH2 or RS4; 11 cells were placed at 37° C., with 5% $CO_2$ for 120 h (DOHH2) or 72 h (RS4; 11) respectively. 20 μl MTS/100 μl medium mixture solution were added to each well and incubate the plates for exactly 2 hours. The reaction was stopped by adding 25 μl 10% SDS per well. Measure absorbance at 490 nm and 650 nm (reference wavelength). ICso was calculated using GraphPad Prism 5.0.

Select compounds prepared as described above were assayed according to the biological procedures described herein. The results are given in the table 2.

TABLE 2

| Example | RS4; 11 $IC_{50}$ (nM) | DOHH2 $IC_{50}$ (nM) |
| --- | --- | --- |
| 2 | 163 | 427 |
| 5 | 43 | 92 |
| 6 | 36 | 150 |
| 7 | 55 | 111 |
| 8 | 33 | 99 |
| 9A | 4 | 67 |
| 9B | 5 | 11 |
| 10 | 133 | / |
| 13 | 397 | 615 |
| 14 | 520 | / |
| 17 | 111 | 132 |
| 20 | 333 | 388 |
| 28 | 122 | / |
| 29 | 323 | / |
| 30 | 43 | 132 |
| 31 | 135 | / |
| 32 | 438 | / |
| 33 | 101 | / |
| 34 | 106 | 38 |
| 35 | 60 | 181 |
| 36 | 232 | / |
| 37 | 12 | 228 |
| 38 | 28 | 108 |
| 39 | 40 | 163 |
| 40 | 29 | 84 |
| / | / | / |
| 43 | 102 | 271 |
| 44 | 21 | 20 |
| 45 | 119 | 121 |
| 46 | 155 | / |
| 48 | 173 | / |
| 49 | 54 | 107 |
| 50A | 3 | 3.5 |
| 50B | 4 | 13.4 |
| 52 | 2 | 29 |
| 53 | 7 | 11 |
| 54 | 4 | 9 |
| 55 | 231 | 346 |
| 56 | 12 | 50 |
| 57 | 20 | 30 |
| 58 | 6 | 16 |
| 59 | 35 | 82 |
| 60 | 21 | 49 |
| 61 | 56 | 161 |
| 62 | 160 | / |
| 64 | 216 | 320 |
| 65 | 11 | 31 |
| 66 | 11 | 23 |
| 67 | 32 | 138 |
| 68 | 24 | 217 |
| 69 | 165 | / |
| / | / | / |
| 71 | 258 | / |
| 72 | 68 | 119 |
| 73 | 94 | 263 |
| 76 | 208 | 247 |
| 78 | 16 | 11 |
| 79 | 14 | 11 |
| 80 | 47 | 95 |
| 81 | 7 | 30 |
| 82 | 10 | 18 |
| 83 | 18 | 47 |
| 84 | 11 | 15 |
| 85 | 36 | 30 |
| 86 | 23 | 35 |
| 87 | 145 | 266 |
| 88 | 187 | 464 |
| 89 | 53 | 112 |
| 90 | 116 | 225 |
| 91 | 119 | 255 |
| 92 | 109 | 53 |
| 93 | 184 | 537 |
| 94 | 27 | 15 |
| 95 | 22 | 71 |
| 96 | 20 | 26 |
| 97 | 1 | 325 |
| 98 | 2 | 176 |

TABLE 2-continued

| Example | RS4; 11 IC$_{50}$ (nM) | DOHH2 IC$_{50}$ (nM) |
|---|---|---|
| Reference compound 1 | 18 | 57 |

What is claimed is:
1. A compound of formula (I)

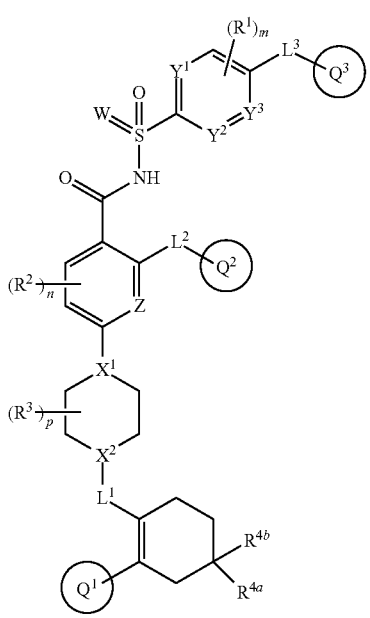

or a pharmaceutically acceptable salt thereof, wherein
L$^1$ is —CH$_2$-;
L$^2$ is selected from O and S;
L$^3$ is —N(R$^{A7}$)(CR$^{C7}$R$^{D7}$)$_t$—;
W is O;
X$^1$ and X$^2$ are N;
Y$^1$, Y$^2$ and Y$^3$ are C;
Z is C;
Q$^1$ is

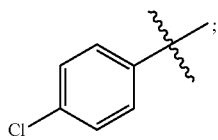

Q$^2$ is

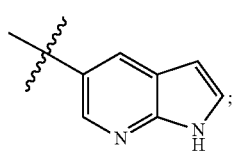 [SMILES: *c1cnc2[nH]ccc2c1]

Q$^3$ is heterocyclyl containing the moiety —(O=)S (=NR$^{E8}$)— or —P(O)(R$^{A8}$)— as a ring member,
wherein heterocyclyl is unsubstituted or substituted with at least one substituent independently selected from R$^X$,
or Q$^3$ is selected from C$_{4-6}$ cycloalkyl and heterocyclyl, which is substituted with —(CR$^{C8}$R$^{D8}$)$_t$N=S(=O) R$^{A8}$R$^{B8}$ or —N(R$^{A8}$)(R$^{E8}$N=)S(=O)R$^{B8}$;
each R$^1$ is selected from NO$_2$ and S(=O)$_2$CF$_3$;
each R$^2$ is selected from hydrogen and halogen;
each R$^3$ is hydrogen;
R$^{4a}$ and R$^{4b}$ are methyl;
each R$^{A7}$ and R$^{B8}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent independently selected from R$^X$;
and each R$^{A8}$ is selected from C$_{1-10}$ alkyl;
or each "R$^{A8}$ and R$^{B8}$" together with the atom(s) to which they are attached form a 4- to 12-membered heterocyclic ring containing 0, 1 or 2 additional heteroatoms independently selected from oxygen, sulfur, nitrogen and phosphorus, and optionally substituted with 1, 2 or 3 R$^X$ groups;
each R$^{C7}$, R$^{C8}$, R$^{D7}$ and R$^{D8}$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl and heteroaryl-C$_{1-4}$ alkyl, wherein alkyl, alkenyl, alkynyl, cycloalkyl, heterocyclyl, aryl and heteroaryl are each unsubstituted or substituted with at least one substituent independently selected from R$^X$;
or each "R$^{C7}$ and R$^{D7}$" and "R$^{C8}$ and R$^{D8}$" together with the carbon atom(s) to which they are attached form a 3- to 12-membered ring containing 0, 1 or 2 heteroatoms independently selected from oxygen, sulfur and nitrogen, and optionally substituted with 1, 2 or 3 R$^X$ groups;
each R$^{E8}$ is selected from hydrogen, C$_{3-10}$ cycloalkyl, —CN, —S(O)$_r$R$^{a1}$, —C(O)R$^{a1}$, —C(O)OR$^{a1}$, —C(O) NR$^{a1}$R$^{b1}$;
each R$^X$ is independently selected from C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, halogen, —CN, —NO$_2$, —(CR$^{c1}$R$^{d1}$)$_t$NR$^{a1}$R$^{b1}$, —(CR$^{c1}$R$^{d1}$)$_t$OR$^{b1}$, —(CR$^{c1}$R$^{d1}$)$_t$S(O)$_r$R$^{b1}$, —(CR$^{c1}$R$^{d1}$)$_t$S(O)$_2$OR$^{b1}$, —(CR$^{c1}$R$^{d1}$)$_t$OS(O)$_2$R$^{b1}$, —(CR$^{c1}$R$^{d1}$)$_t$P(O)R$^{a1}$R$^{b1}$, —(CR$^{c1}$R$^{d1}$)$_t$P(O)(OR$^{a1}$)(OR$^{b1}$), —(CR$^{c1}$R$^{d1}$)$_t$C(O)R$^{a1}$, —(CR$^{c1}$R$^{d1}$)$_t$C(O)OR$^{b1}$, —(CR$^{c1}$R$^{d1}$)$_t$OC(O)R$^{b1}$, —(CR$^{c1}$R$^{d1}$)$_t$C(O) NR$^{a1}$R$^{b1}$, —(CR$^{c1}$R$^{d1}$)$_t$NR$^{a1}$C(O)R$^{b1}$, —(CR$^{c1}$R$^{d1}$)$_t$OC(O)NR$^{a1}$R$^{b1}$, —(CR$^{c1}$R$^{d1}$)$_t$NR$^{a1}$C(O)OR$^{b1}$, —(CR$^{c1}$R$^{d1}$)$_t$NR$^{a1}$C(O)NR$^{a1}$R$^{b1}$, —(CR$^{c1}$R$^{d1}$)$_t$NR$^{a1}$C(S)NR$^{a1}$R$^{b1}$, —(CR$^{c1}$R$^{d1}$)$_t$S(O)$_r$NR$^{a1}$R$^{b1}$, —(CR$^{c1}$R$^{d1}$)$_t$NR$^{a1}$S(O)$_r$R$^{b1}$, —(CR$^{c1}$R$^{d1}$)$_t$NR$^{a1}$S(O)$_2$NR$^{a1}$R$^{b1}$, —(CR$^{c1}$R$^{d1}$)$_t$S(O)(=NR$^{e1}$)R$^{b1}$, —(CR$^{c1}$R$^{d1}$)$_t$N=S(O)R$^{a1}$R$^{b1}$, —(CR$^{c1}$R$^{d1}$)$_t$NR$^{a1}$S(O)(=NR$^{e1}$)R$^{b1}$, —(CR$^{c1}$R$^{d1}$)$_t$S(O)(=NR$^{e1}$)NR$^{a1}$R$^{b1}$, —(CR$^{c1}$R$^{d1}$)$_t$NR$^{a1}$S(O)(=NR$^{e1}$)NR$^{a1}$R$^{b1}$, —(CR$^{c1}$R$^{d1}$)$_t$C(=NR$^{e1}$)R$^{a1}$, —(CR$^{c1}$R$^{d1}$)$_t$C(=N—OR$^{b1}$)R$^{a1}$, —(CR$^{c1}$R$^{d1}$)$_t$C(=NR$^{e1}$)NR$^{a1}$R$^{b1}$, —(CR$^{c1}$R$^{d1}$)$_t$NR$^{a1}$C(=NR$^{e1}$)R$^{b1}$ and —(CR$^{c1}$R$^{d1}$)$_t$NR$^{a1}$C(=NR$^{e1}$)NR$^{a1}$R$^{b1}$, wherein alkyl, alkenyl, alkynyl, cycloalkyl, heterocyclyl, aryl and heteroaryl are each unsubstituted or substituted with at least one substituent independently selected from $R^Y$;

each $R^{a1}$ and each $R^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent independently selected from $R^Y$;

or $R^{c1}$ and $R^{d1}$ together with the atom(s) to which they are attached form a 4- to 12-membered heterocyclic ring containing 0, 1 or 2 additional heteroatoms independently selected from oxygen, sulfur, nitrogen and phosphorus, and optionally substituted with 1, 2 or 3 $R^Y$ groups;

each $R^{c1}$ and each $R^{d1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent independently selected from $R^Y$;

or $R^{c1}$ and $R^{d1}$ together with the carbon atom(s) to which they are attached form a 3- to 12-membered ring containing 0, 1 or 2 heteroatoms independently selected from oxygen, sulfur and nitrogen, and optionally substituted with 1, 2 or 3 $R^Y$ groups;

each $R^{e1}$ is independently selected from hydrogen, $C_{1-10}$ alkyl, $C_{3-10}$ cycloalkyl, $C_{3-10}$ cycloalkyl-$C_{1-4}$ alkyl, —CN, —NO$_2$, —OR$^{a2}$, —SR$^{a2}$, —S(O)$_r$R$^{a2}$, —S(O)$_r$NR$^{a2}$R$^{b2}$, —C(O)R$^{a2}$, —C(O)OR$^{a2}$ and —C(O)NR$^{a2}$R$^{b2}$;

$R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, —CN, —NO$_2$, —(CR$^{c2}$R$^{d2}$)$_t$NR$^{a2}$R$^{b2}$, —(CR$^{c2}$R$^{d2}$)$_t$OR$^{b2}$, —(CR$^{c2}$R$^{d2}$)$_t$S(O)$_r$R$^{b2}$, —(CR$^{c2}$R$^{d2}$)$_t$S(O)$_2$OR$^{b2}$, —(CR$^{c2}$R$^{d2}$)$_t$OS(O)$_2$R$^{b2}$, —(CR$^{c2}$R$^{d2}$)$_t$P(O)R$^{a2}$R$^{b2}$, —(CR$^{c2}$R$^{d2}$)$_t$P(O)(OR$^{a2}$)(OR$^{b2}$), —(CR$^{c2}$R$^{d2}$)$_t$C(O)R$^{a2}$, —(CR$^{c2}$R$^{d2}$)$_t$C(O)OR$^{b2}$, —(CR$^{c2}$R$^{d2}$)$_t$OC(O)R$^{b2}$, —(CR$^{c2}$R$^{d2}$)$_t$C(O)NR$^{a2}$R$^{b2}$, —(CR$^{c2}$R$^{d2}$)$_t$NR$^{a2}$C(O)R$^{b2}$, —(CR$^{c2}$R$^{d2}$)$_t$OC(O)NR$^{a2}$R$^{b2}$, —(CR$^{c2}$R$^{d2}$)$_t$NR$^{a2}$C(O)OR$^{b2}$, —(CR$^{c2}$R$^{d2}$)$_t$NR$^{a2}$C(O)NR$^{a2}$R$^{b2}$, —(CR$^{c2}$R$^{d2}$)$_t$NR$^{a2}$C(S)NR$^{a2}$R$^{b2}$, —(CR$^{c2}$R$^{d2}$)$_t$S(O)$_r$NR$^{a2}$R$^{b2}$, —(CR$^{c2}$R$^{d2}$)$_t$NR$^{a2}$S(O)$_r$R$^{b2}$, —(CR$^{c2}$R$^{d2}$)$_t$NR$^{a2}$S(O)$_2$NR$^{a2}$R$^{b2}$, —(CR$^{c2}$R$^{d2}$)$_t$S(O)(=NR$^{e2}$)R$^{b2}$, —(CR$^{c2}$R$^{d2}$)$_t$N=S(O)R$^{a2}$R$^{b2}$, —(CR$^{c2}$R$^{d2}$)$_t$NR$^{a2}$S(O)(=NR$^{e2}$)R$^{b2}$, —(CR$^{c2}$R$^{d2}$)$_t$S(O)(=NR$^{e2}$)NR$^{a2}$R$^{b2}$, —(CR$^{c2}$R$^{d2}$)$_t$NR$^{a2}$S(O)(=NR$^{e2}$)NR$^{a2}$R$^{b2}$, —(CR$^{c2}$R$^{d2}$)$_t$C(=NR$^{e2}$)R$^{a2}$, —(CR$^{c2}$R$^{d2}$)$_t$C(=N—OR$^{b2}$)R$^{a2}$, —(CR$^{c2}$R$^{d2}$)$_t$C(=NR$^{e2}$)NR$^{a2}$R$^{b2}$, —(CR$^{c2}$R$^{d2}$)$_t$NR$^{a2}$C(=NR$^{e2}$)R$^{b2}$ and —(CR$^{c2}$R$^{d2}$)$_t$NR$^{a2}$C(=NR$^{e2}$)NR$^{a2}$R$^{b2}$, wherein alkyl, alkenyl, alkynyl, cycloalkyl, heterocyclyl, aryl and heteroaryl are each unsubstituted or substituted with at least one substituent independently selected from OH, —CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent independently selected from halogen, —CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a2}$ and $R^{b2}$ together with the atom(s) to which they are attached form a 4- to 12-membered heterocyclic ring containing 0, 1 or 2 additional heteroatoms independently selected from oxygen, sulfur, nitrogen and phosphorus, and optionally substituted with 1 or 2 substituents, independently selected from halogen, —CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a 3- to 12-membered ring containing 0, 1 or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, —CN, —NO$_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, —C(O)$C_{1-4}$ alkyl, —C(O)$C_{3-10}$ cycloalkyl, —C(O)OC$_{1-4}$ alkyl, —C(O)OC$_{3-10}$ cycloalkyl, —C(O)NH$_2$, —C(O)NH($C_{1-4}$ alkyl), —C(O)N($C_{1-4}$ alkyl)$_2$, —C(O)NH($C_{3-10}$ cycloalkyl), —C(O)N($C_{3-10}$ cycloalkyl)$_2$, —S(O)$_2$$C_{1-4}$ alkyl, —S(O)$_2$$C_{3-10}$ cycloalkyl, —S(O)$_2$NH$_2$, —S(O)$_2$NH($C_{1-4}$ alkyl), —S(O)$_2$N($C_{1-4}$ alkyl)$_2$, —S(O)$_2$NH($C_{3-10}$ cycloalkyl) and —S(O)$_2$N($C_{3-10}$ cycloalkyl)$_2$;

m is selected from 0, 1, 2, 3 and 4;
n is selected from 0, 1, 2 and 3;
p is selected from 0, 1, 2, 3 and 4;
each r is independently selected from 0, 1 and 2;
each t is independently selected from 0, 1, 2, 3 and 4.

2. The compound of claim 1 or a pharmaceutically acceptable salt thereof, wherein Q is selected from

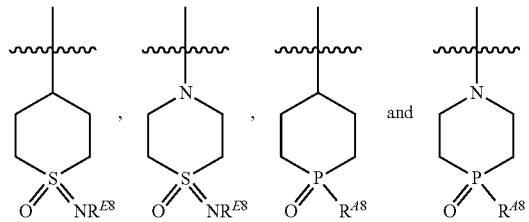

which is unsubstituted or substituted with at least one substituent independently selected from $R^X$, wherein the ⌇ symbol indicates the point of attachment to the rest of the molecule.

3. The compound of claim 1 or a pharmaceutically acceptable salt thereof, wherein $Q^3$ is selected from cyclobutyl, cyclohexyl, piperidinyl, tetrahydro-2H-pyranyl, which is substituted with $-N=S(=O)R^{A8}R^{B8}$ or $-N(R^{A8})(R^{E8}N=)S(=O)R^{B8}$, wherein $R^{A8}$ and $R^{B8}$ are independently selected from $C_{1-10}$ alkyl, or $R^{A8}$ and $R^{B8}$ together with the sulfur atom to which they are attached form a 4- to 6-membered heterocyclic ring containing 0, 1 or 2 additional heteroatoms independently selected from oxygen, sulfur, nitrogen and phosphorus, and optionally substituted with 1, 2 or 3 $R^X$ groups.

4. The compound of claim 1 or a pharmaceutically acceptable salt thereof, wherein m is 1.

5. A compound selected from the group consisting of

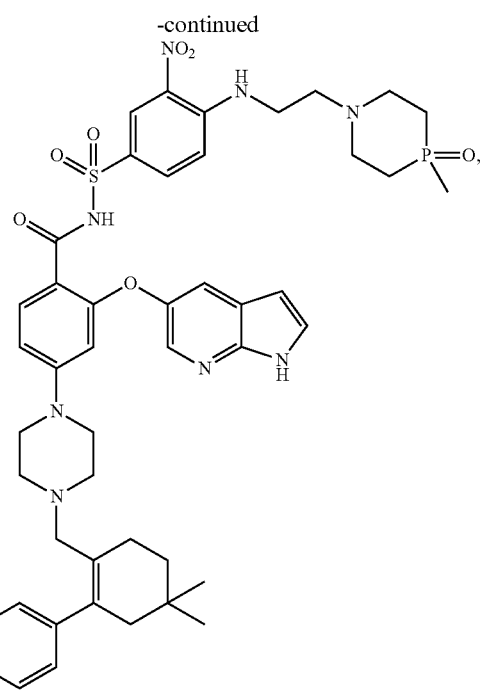

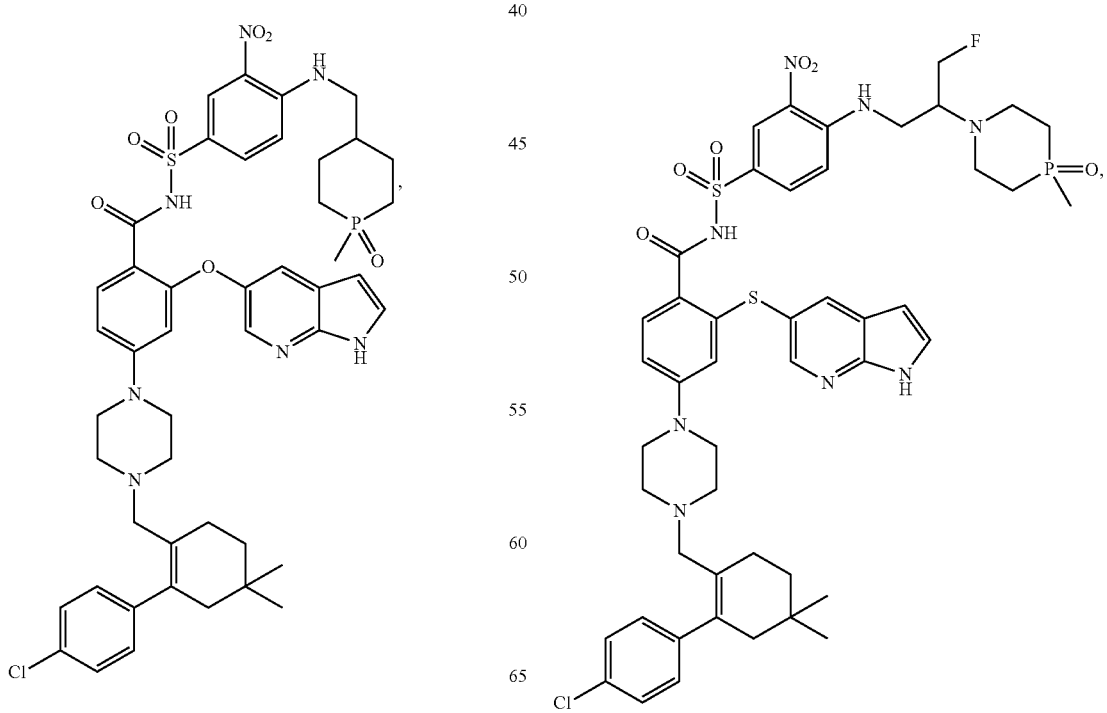

259
-continued
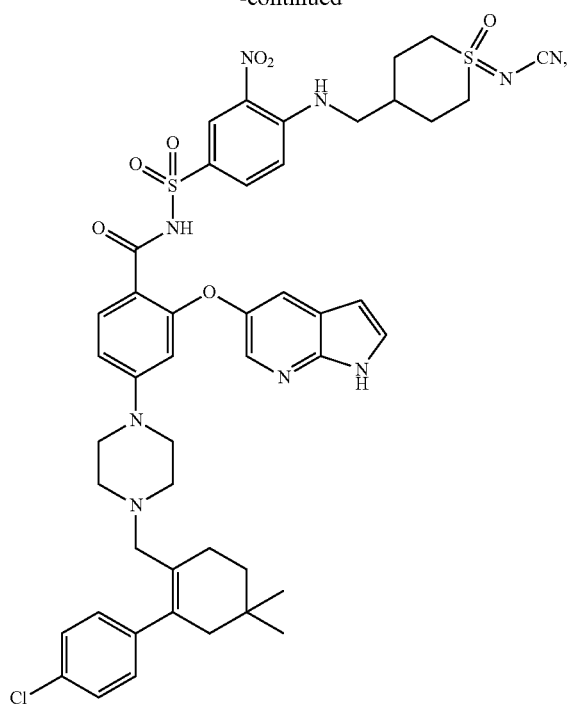
260
-continued
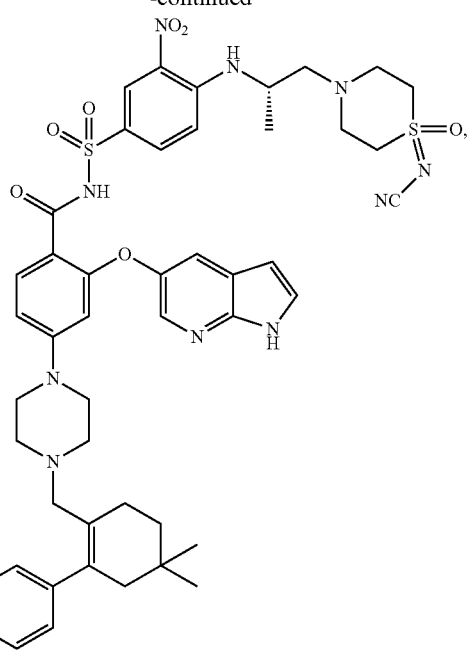
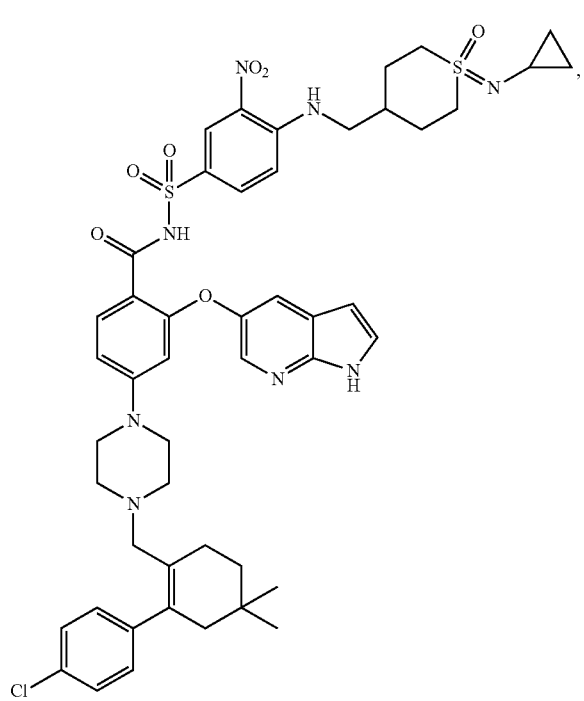

261
-continued
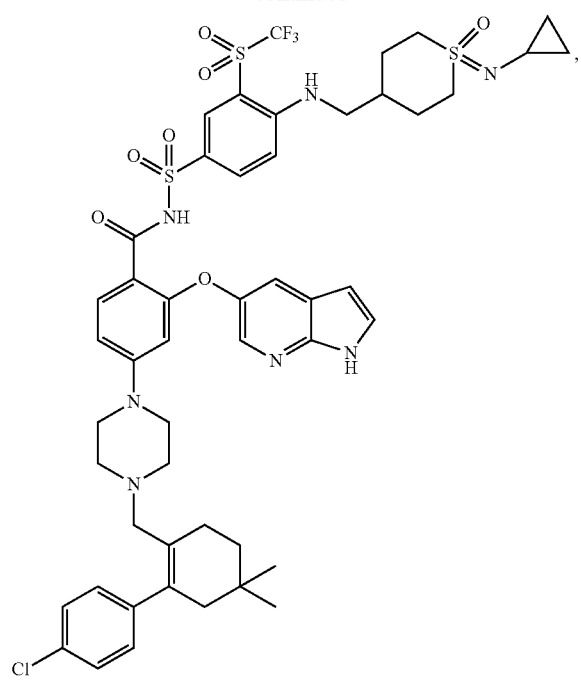
262
-continued
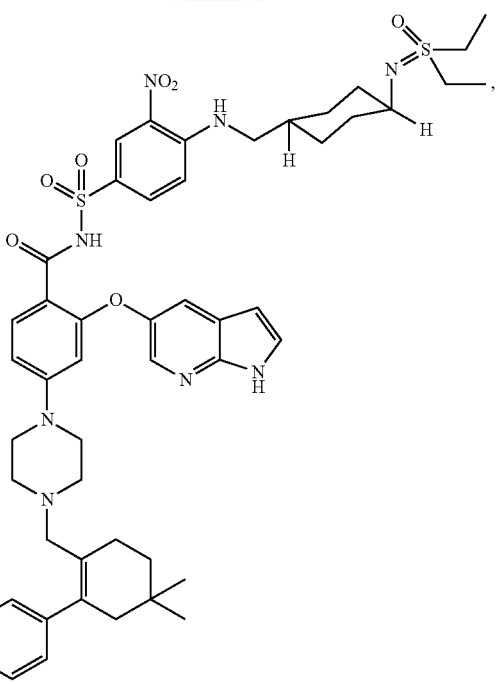
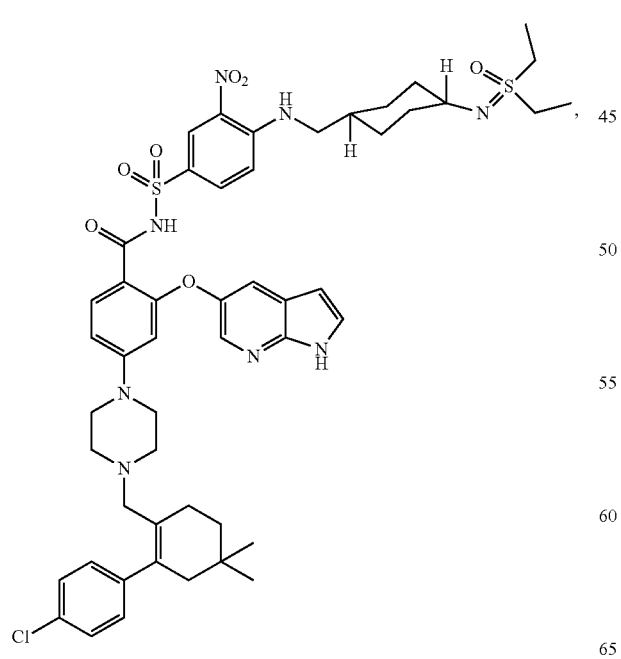

263
-continued
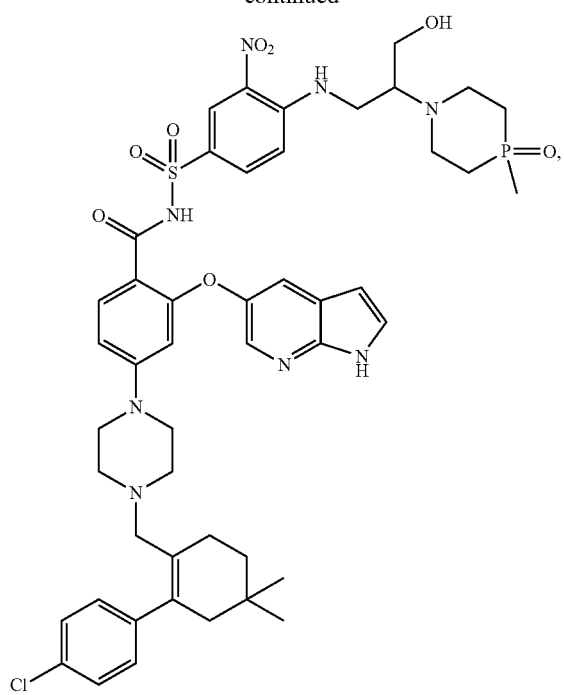
264
-continued
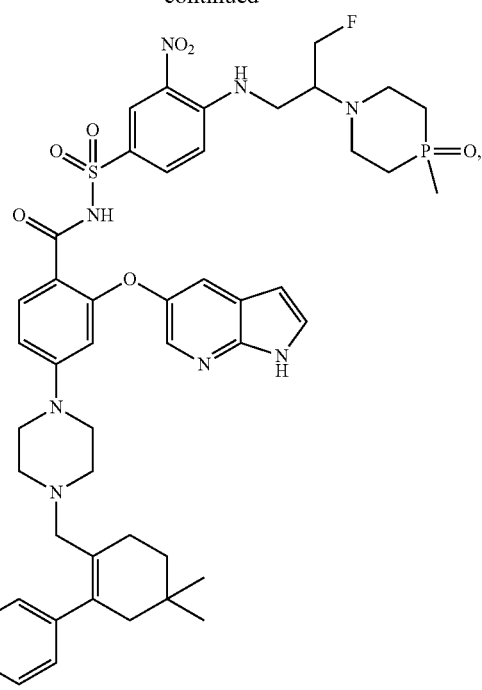
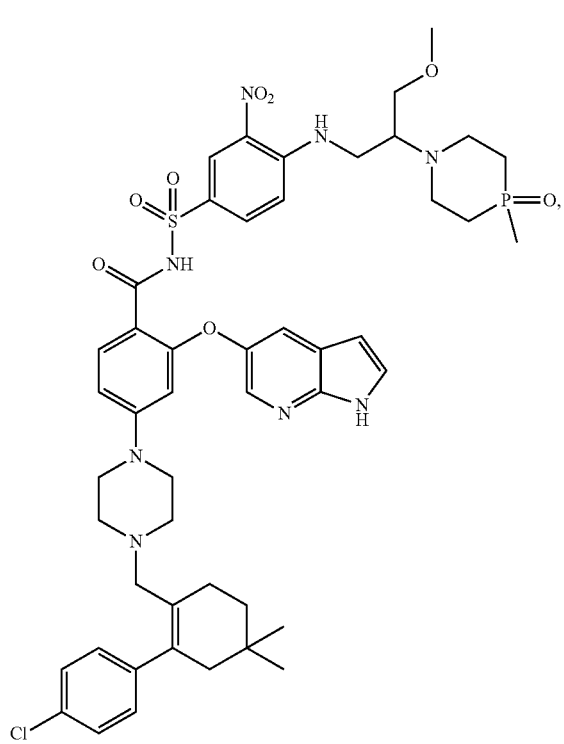
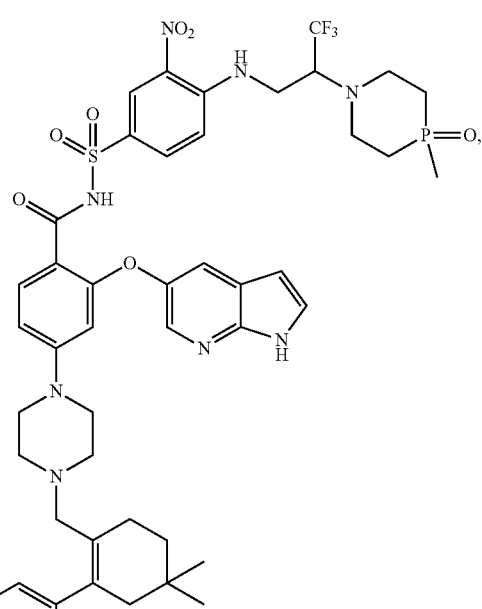

265
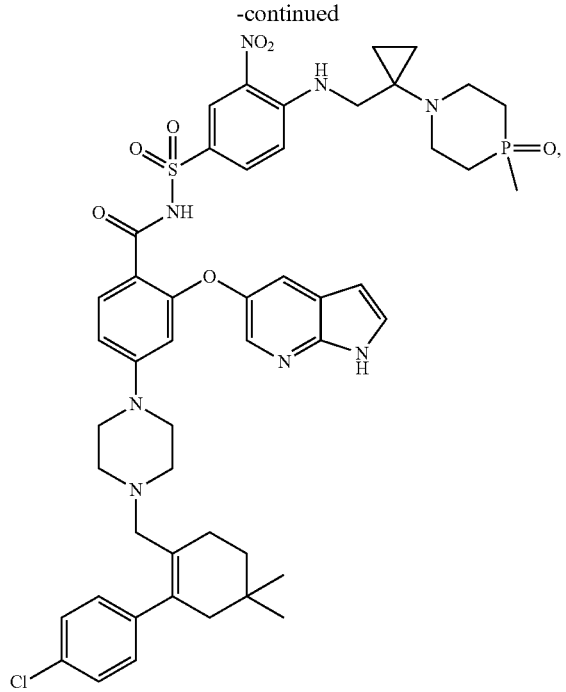
266
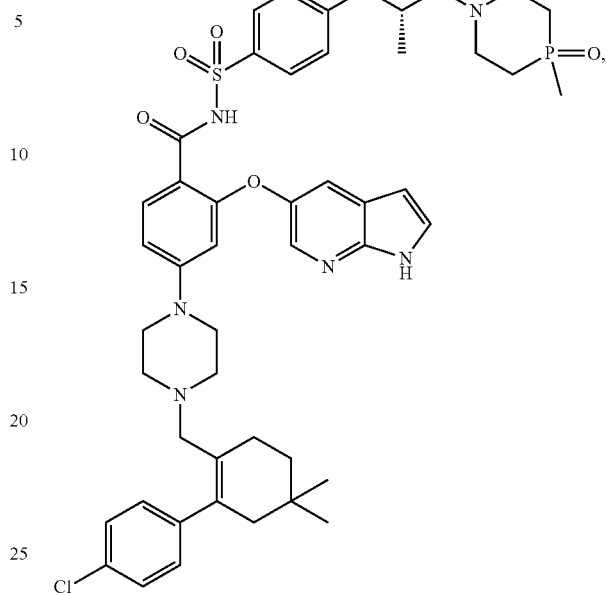

267
-continued
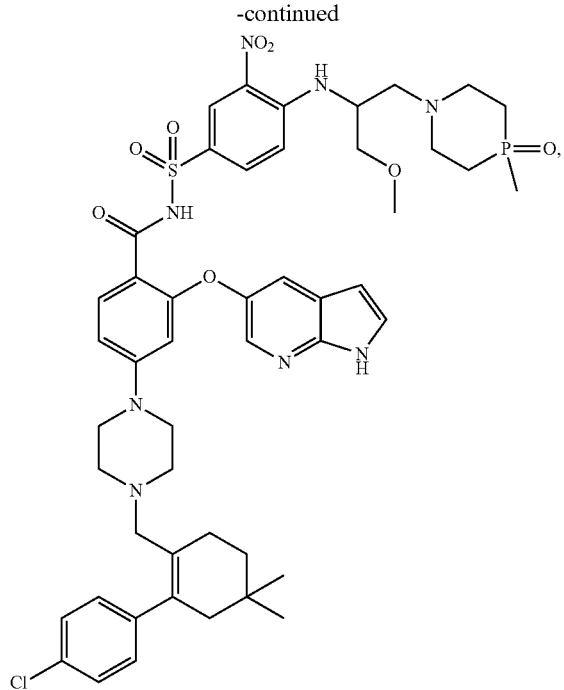
268
-continued
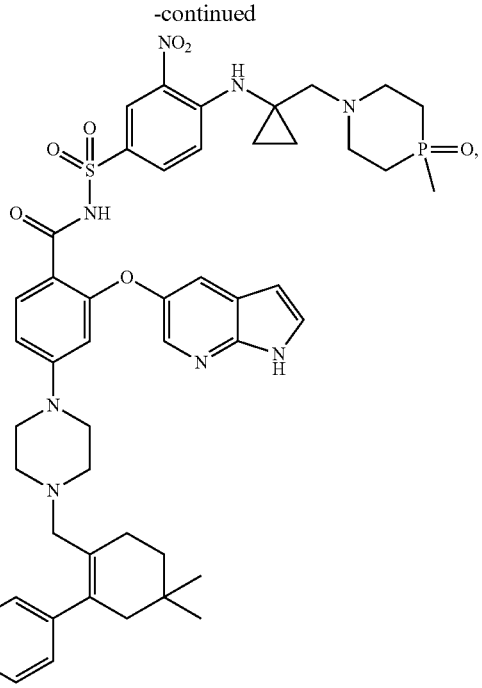

269
-continued
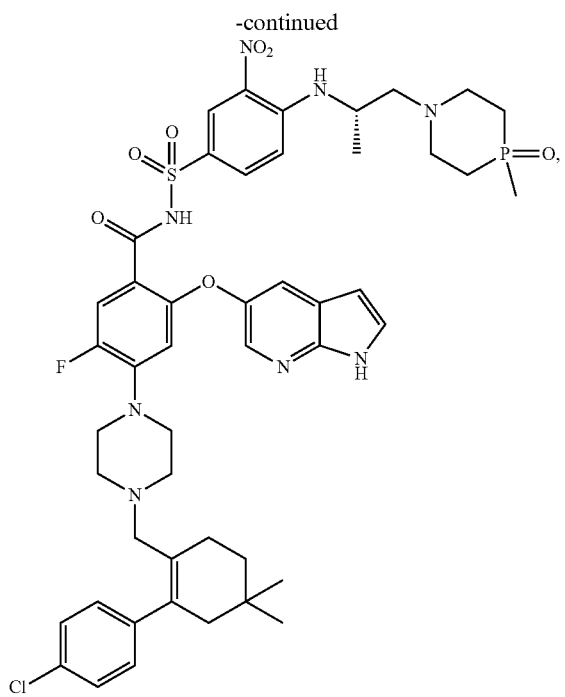
270
-continued
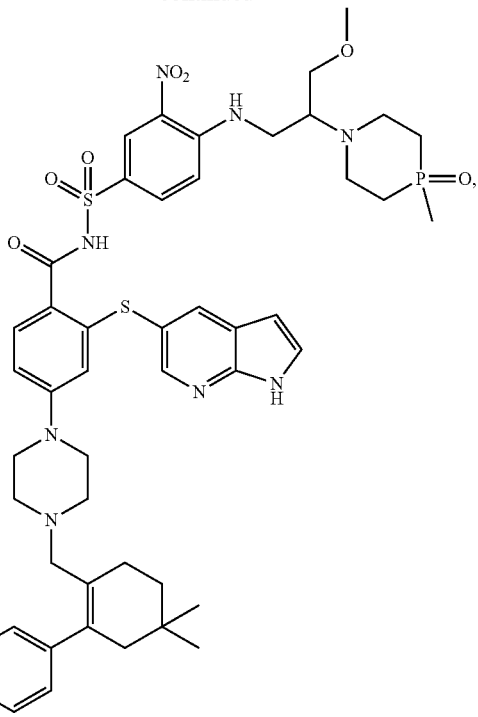
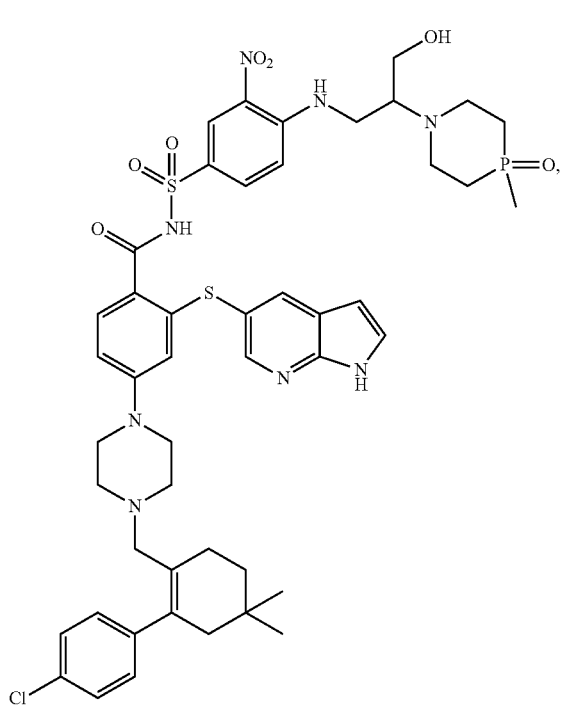
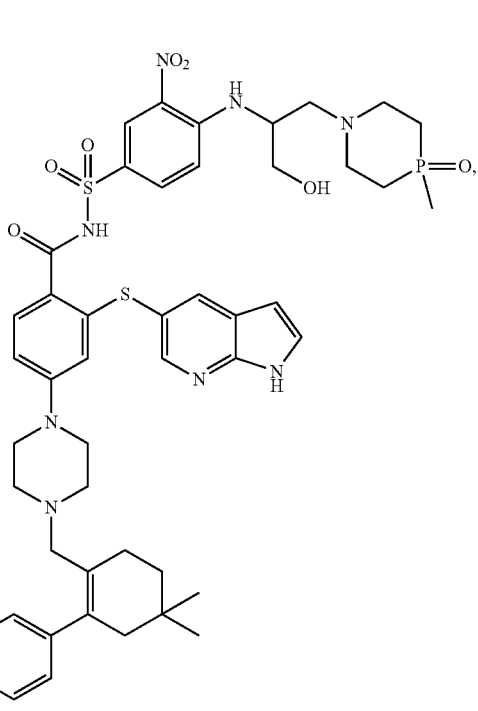

271
-continued
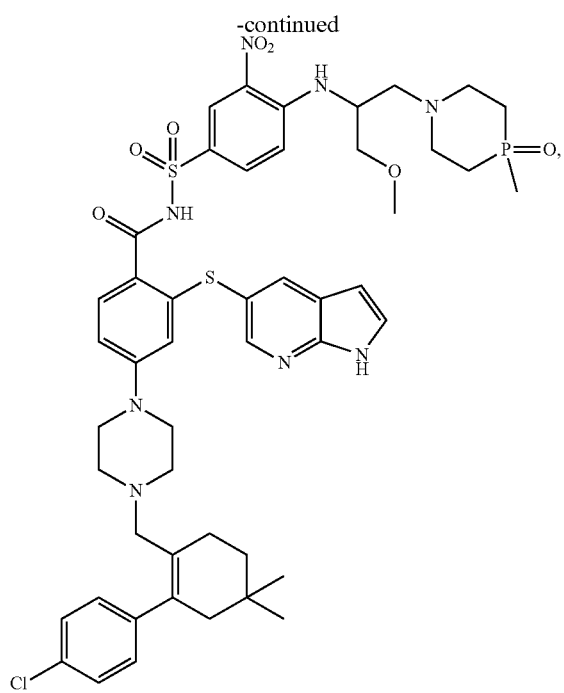
272
-continued
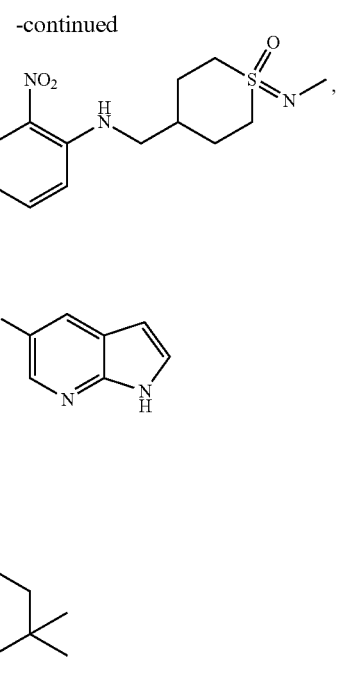
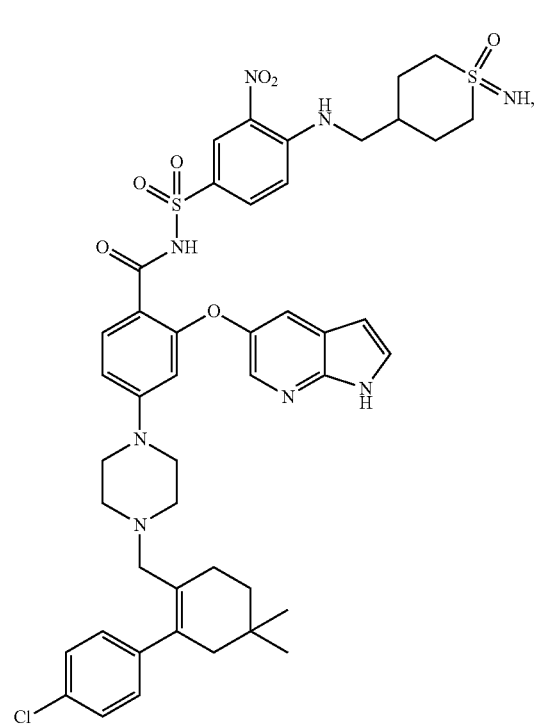
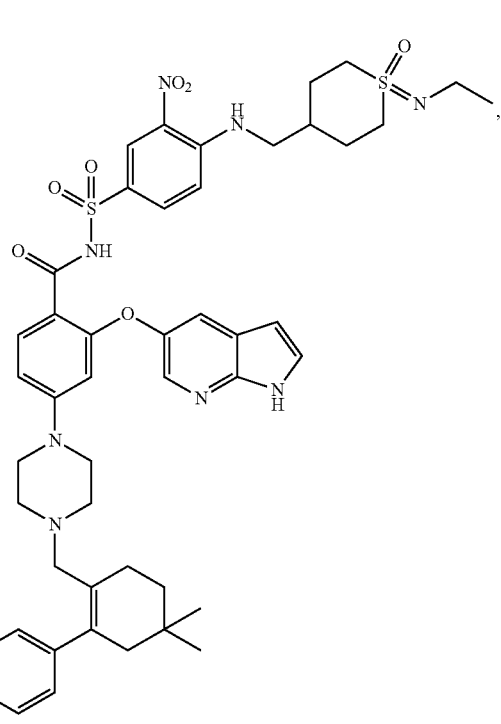

273
-continued
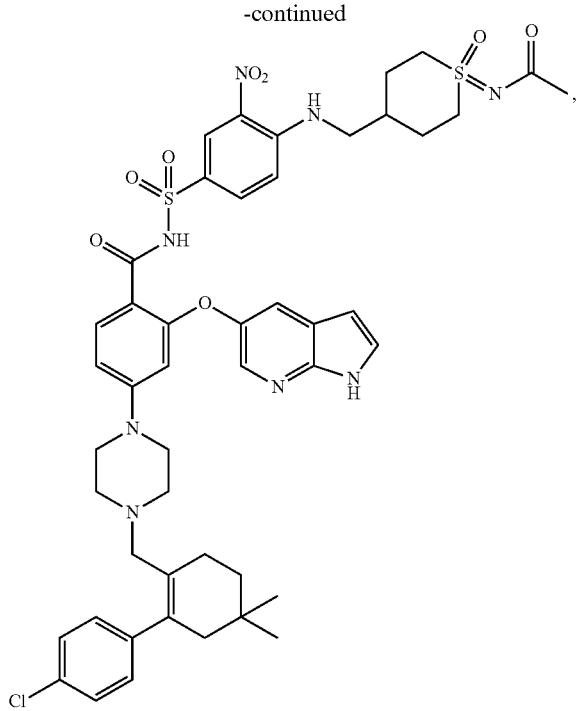
274
-continued
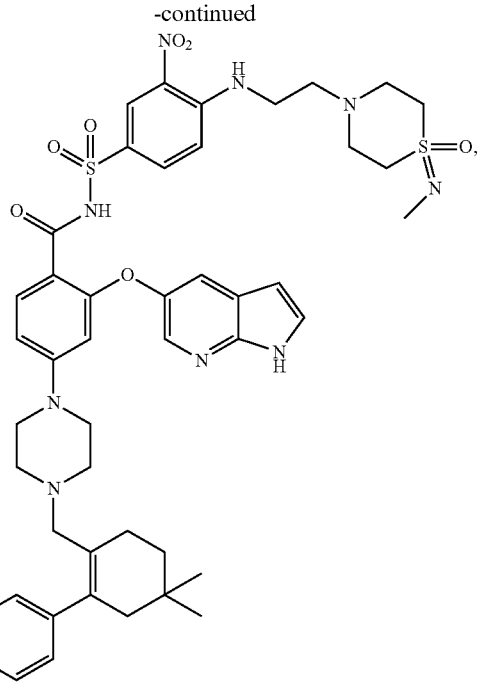
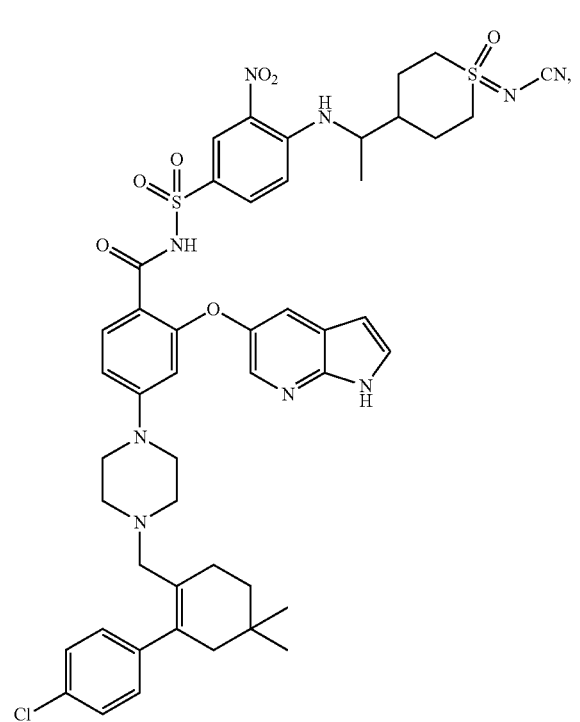

275
-continued
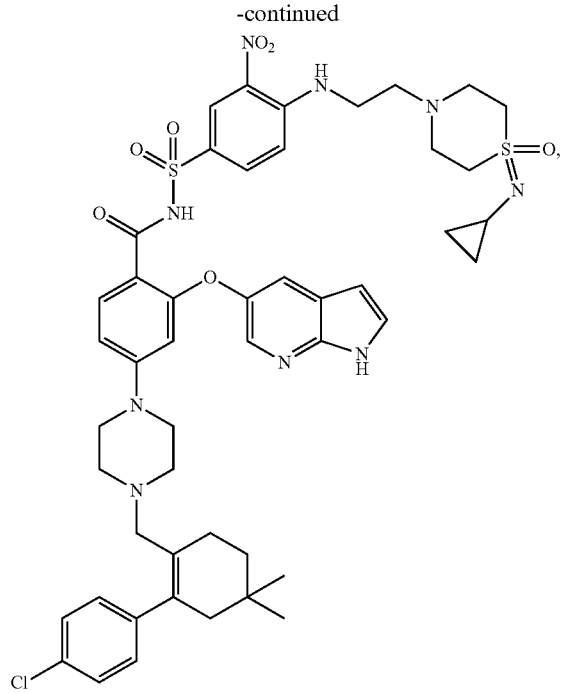
276
-continued
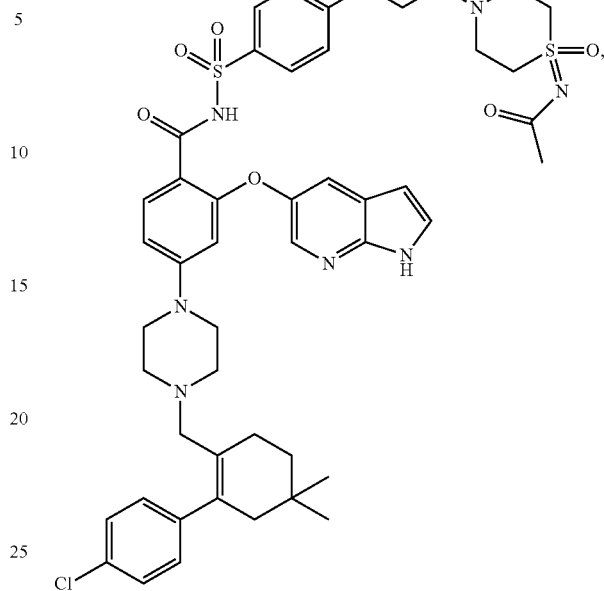
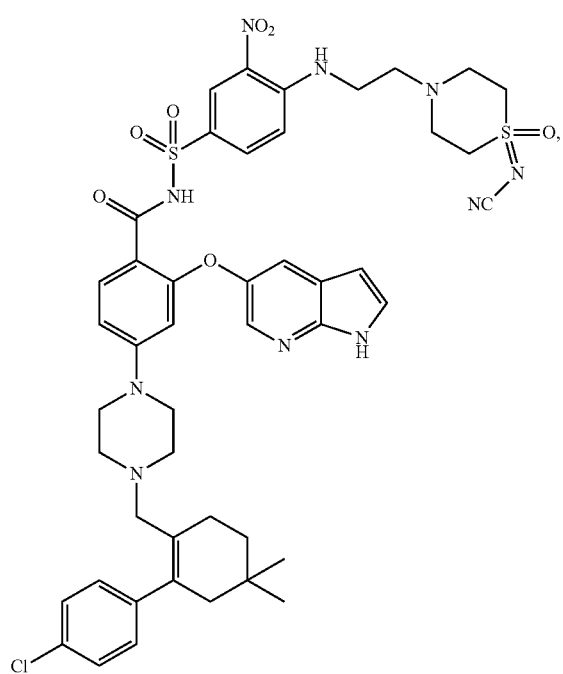

277
-continued
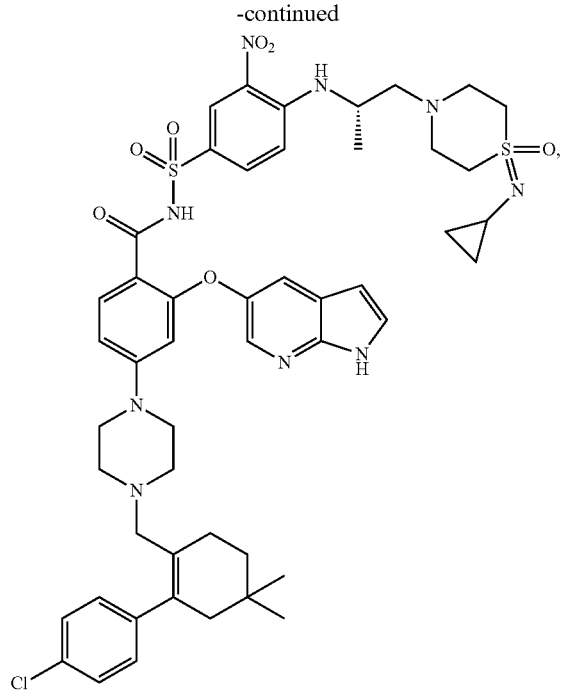
278
-continued
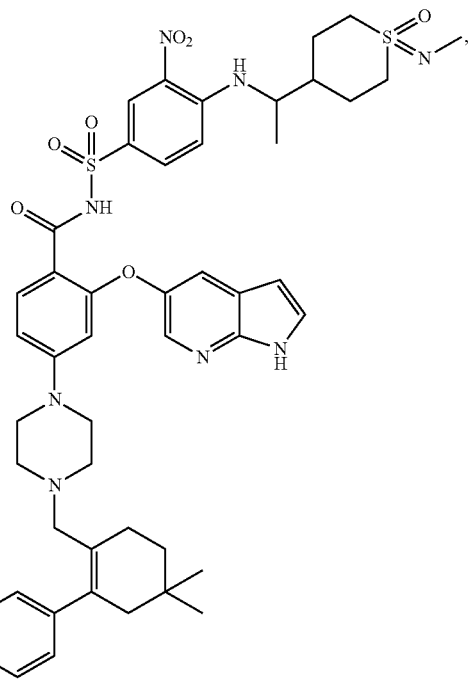
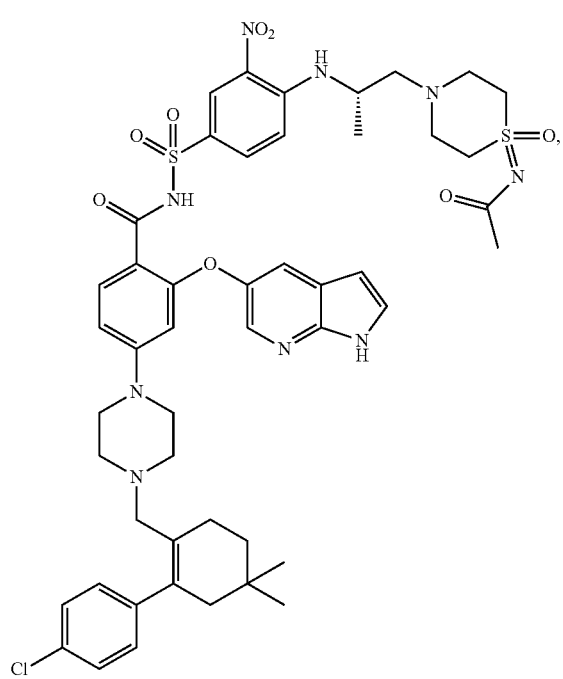 [SMILES: CC(=O)N=S1(=O)CCN(C[C@H](C)Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1]
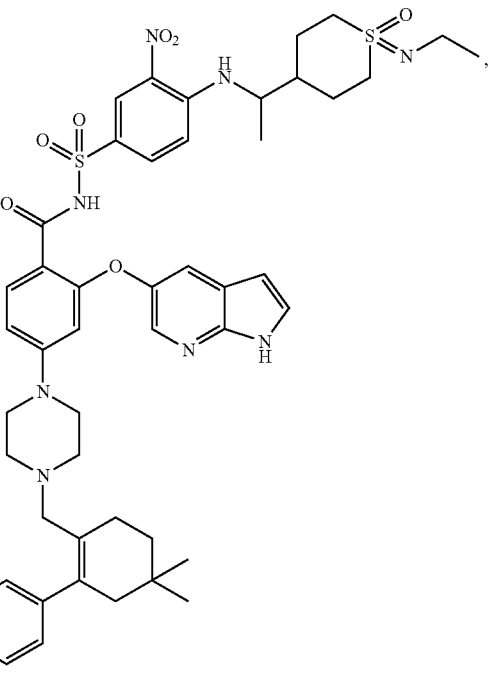

279
-continued
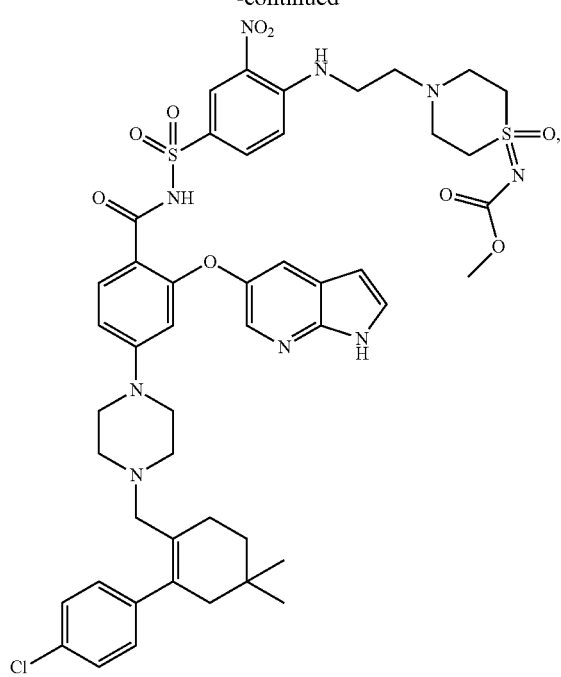
280
-continued
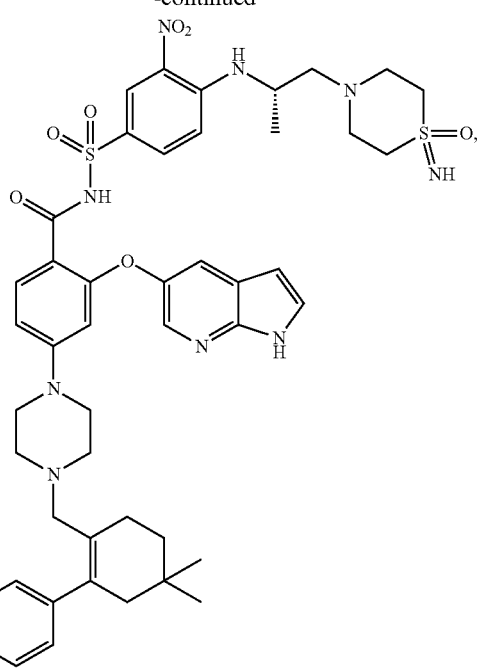
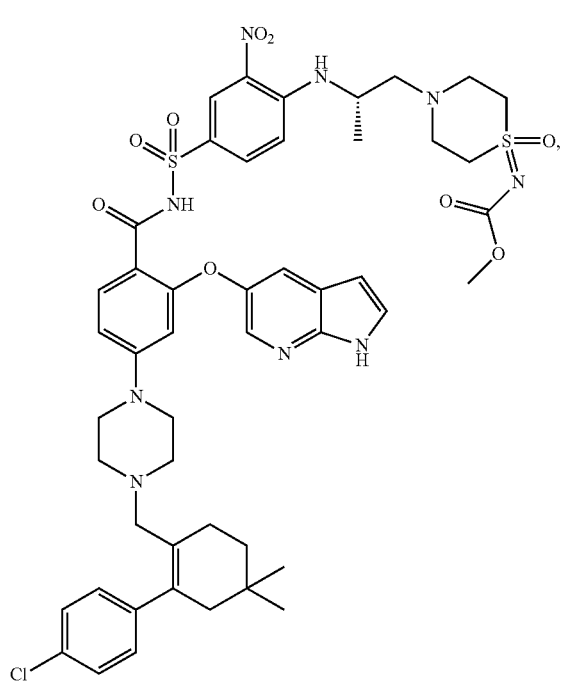
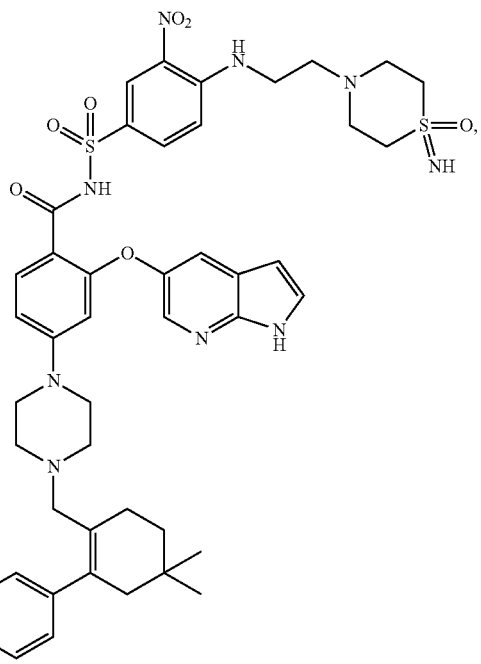

281
-continued
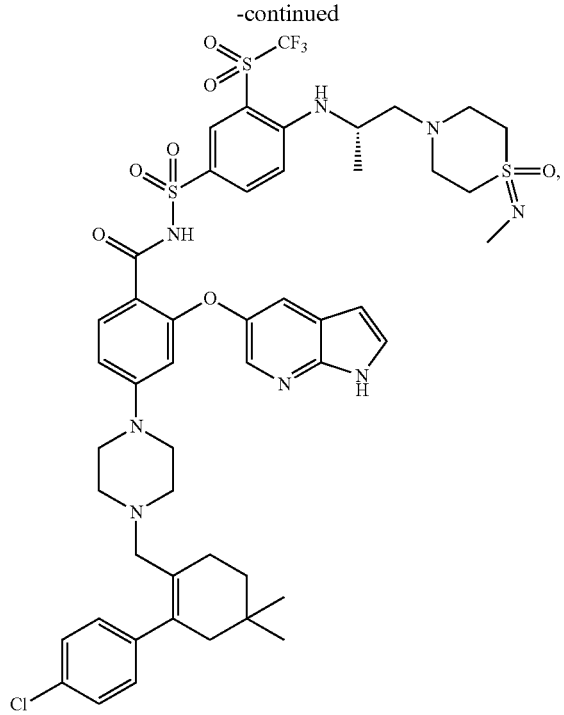
282
-continued
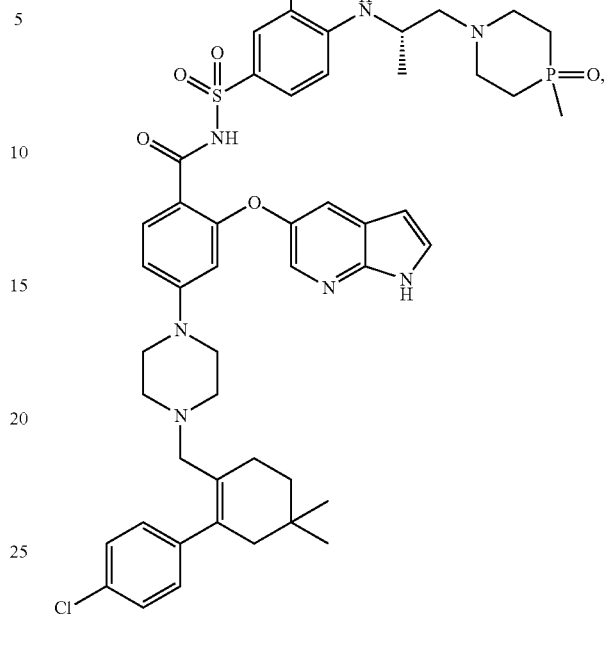
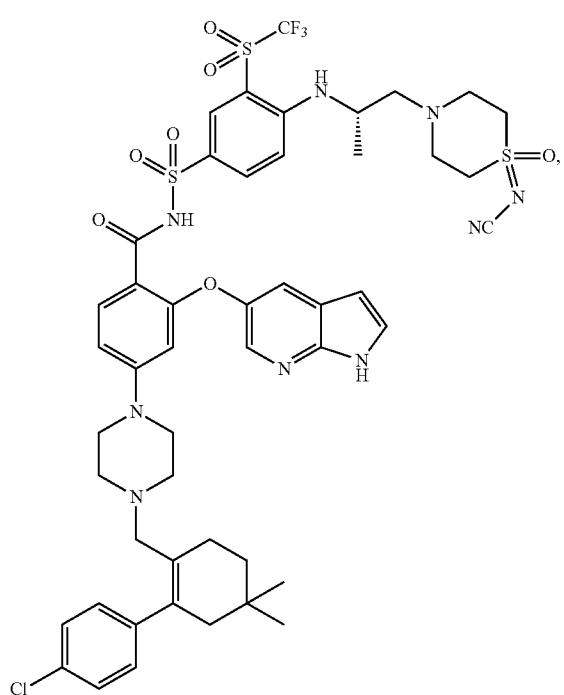
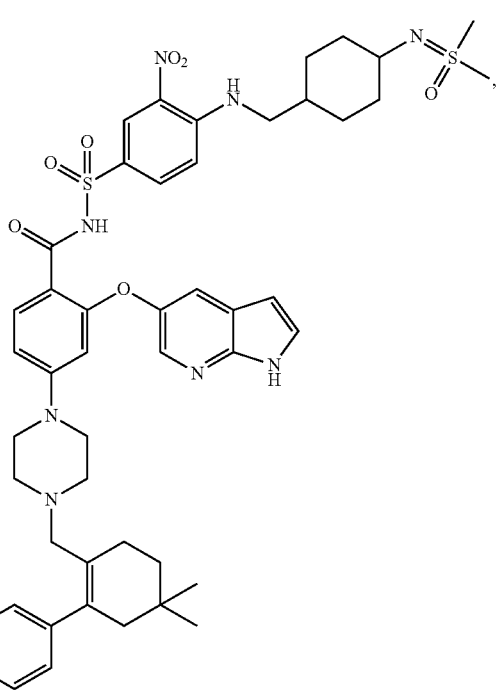

283
-continued
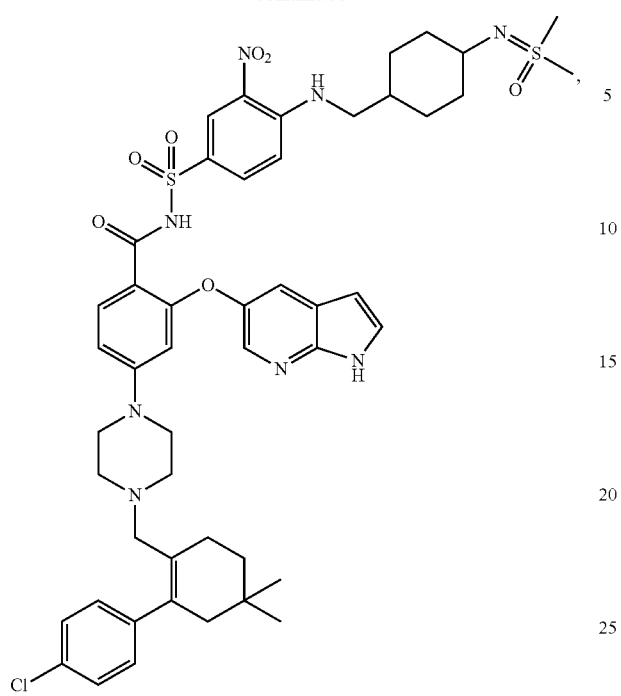
284
-continued
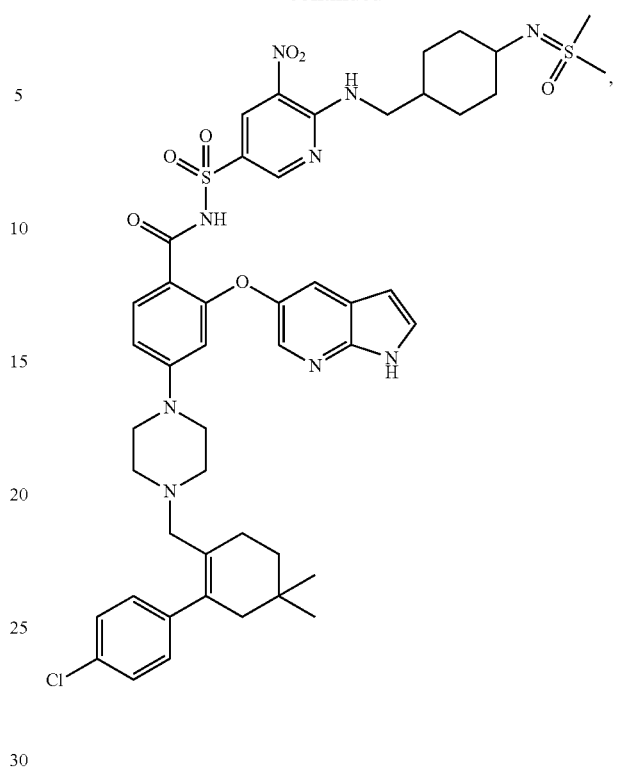
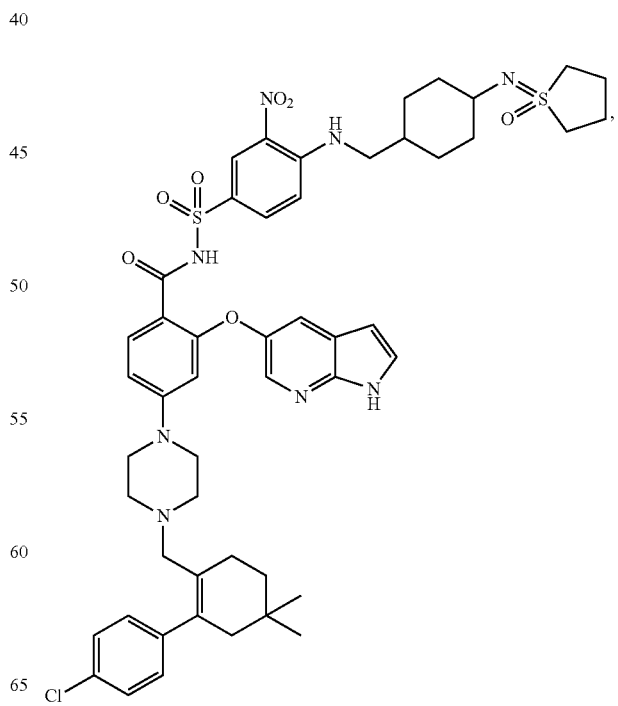

285
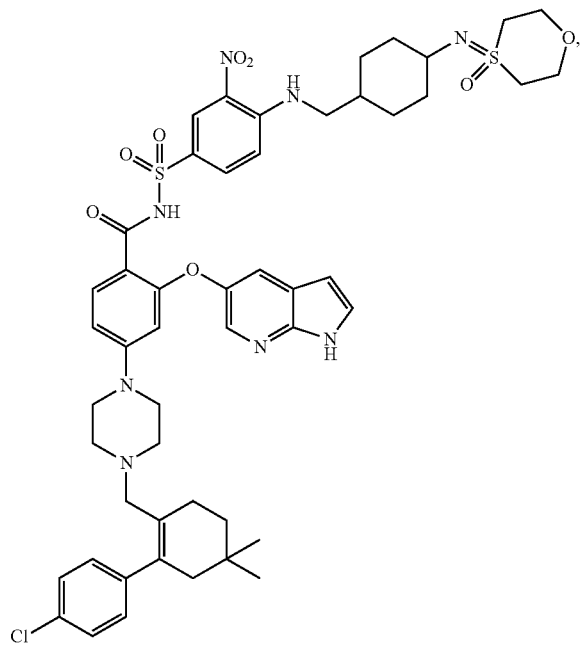
286
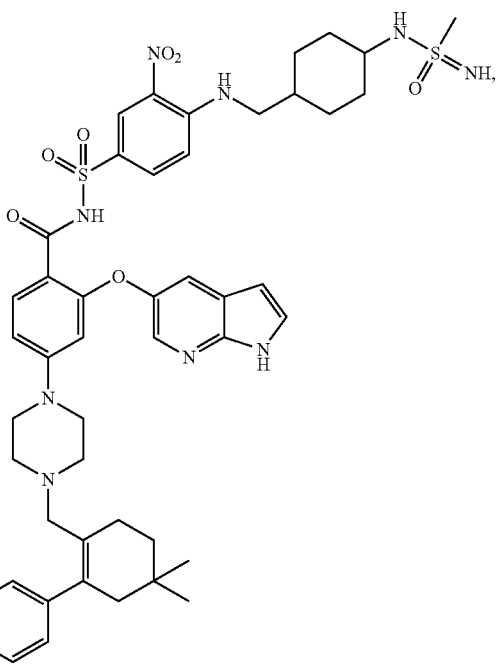
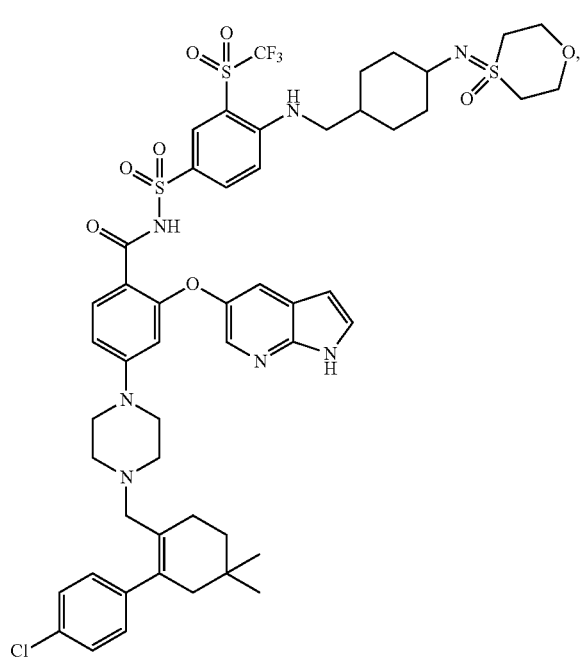

287
-continued
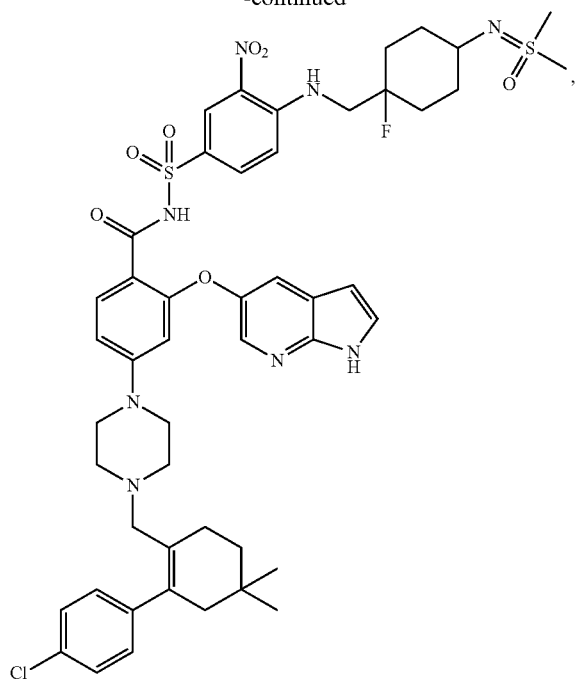
288
-continued
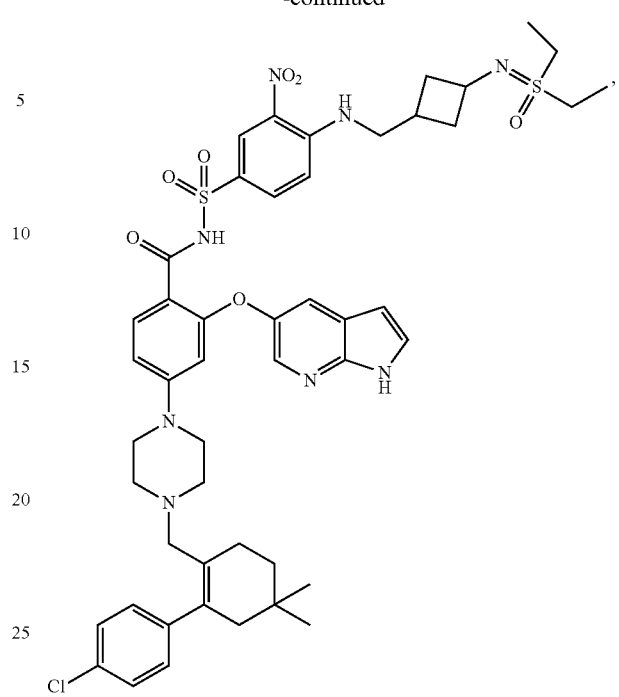
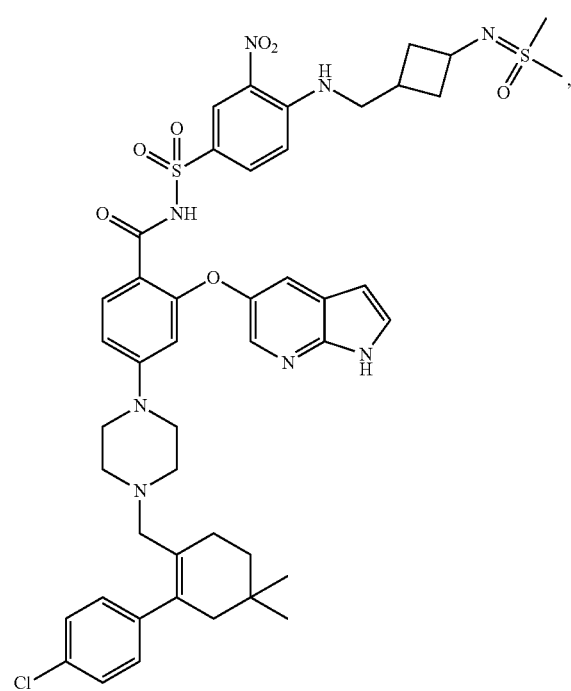
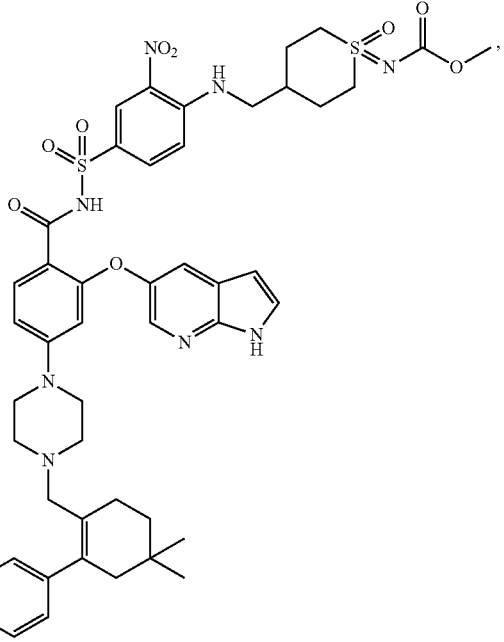

289
-continued
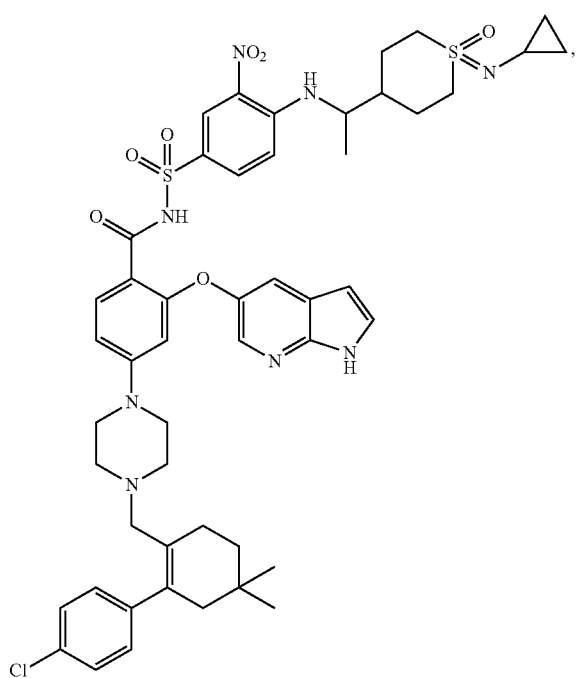
290
-continued
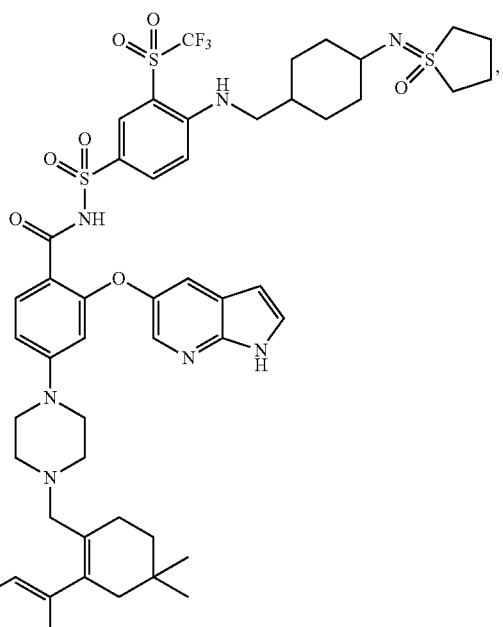
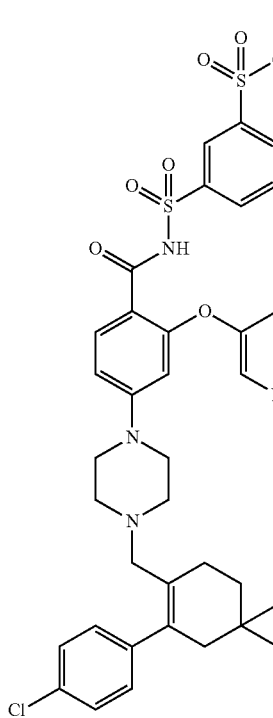
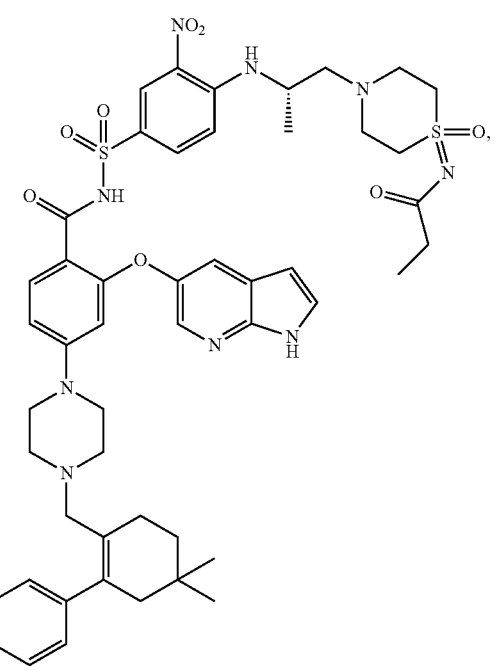

291
-continued
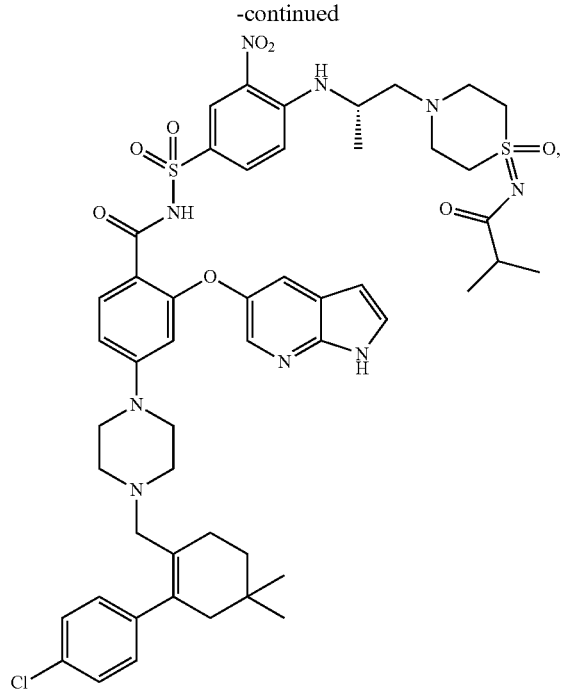
292
-continued
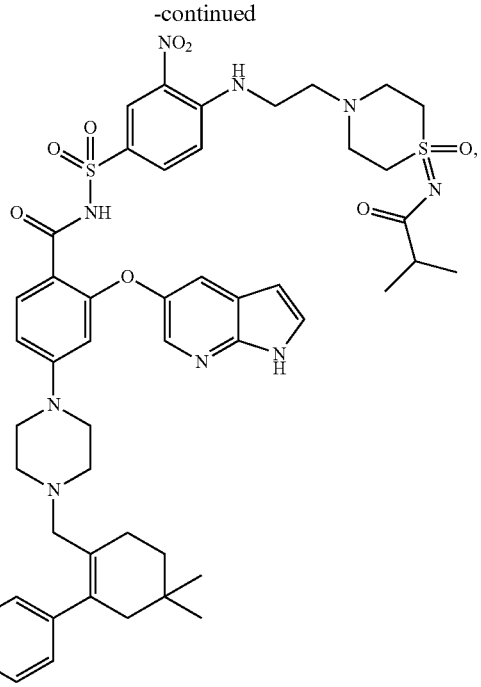
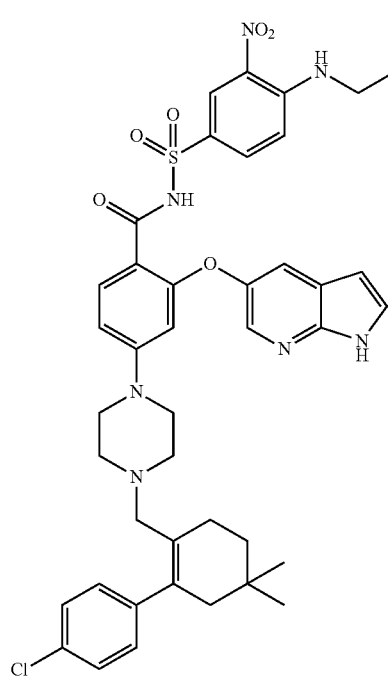
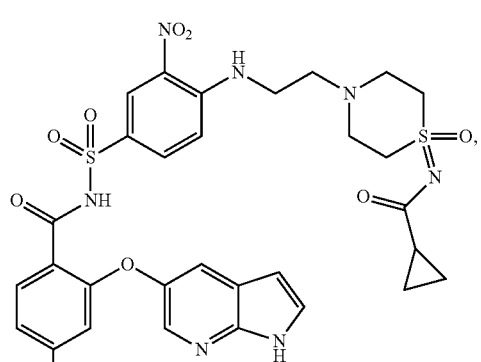

293
-continued
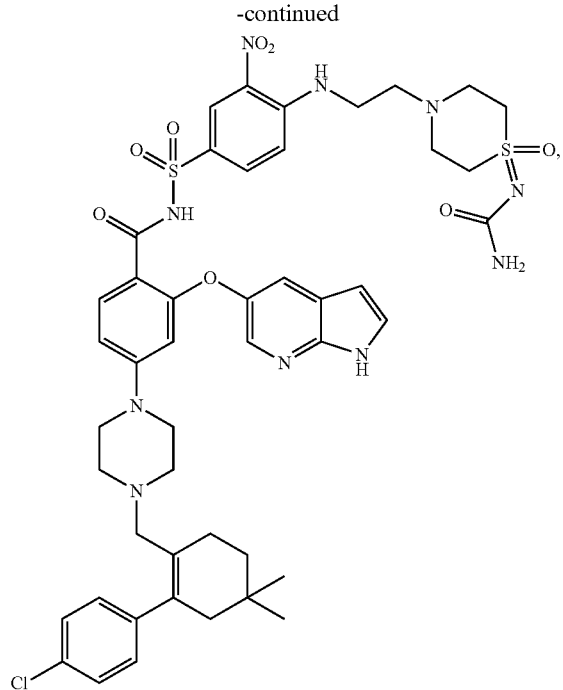
294
-continued
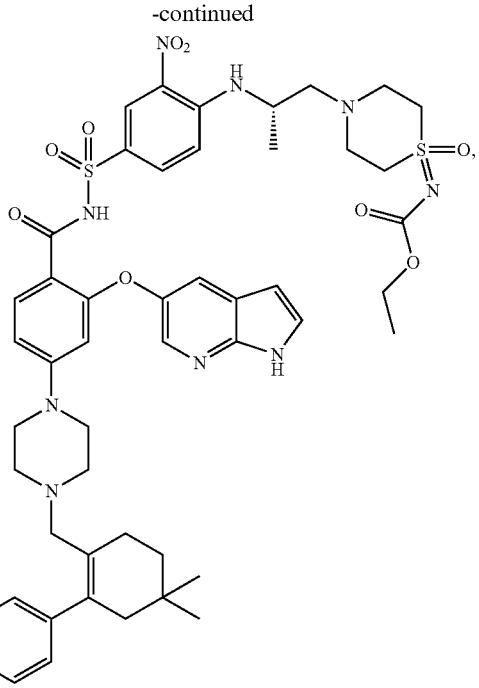
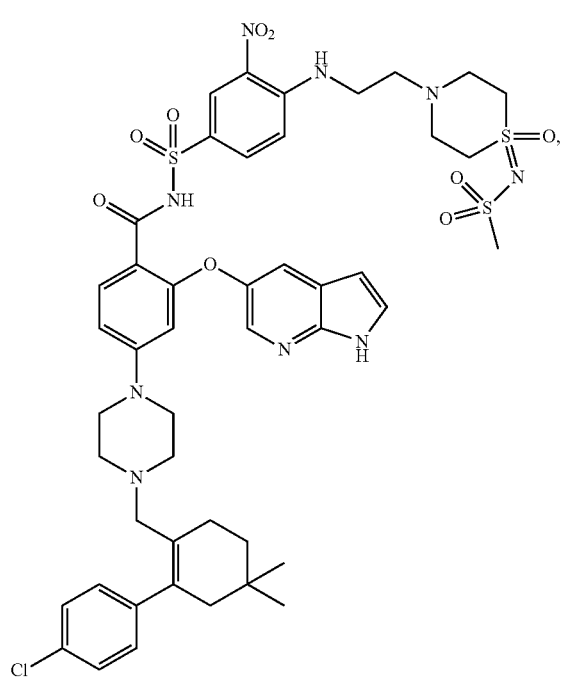

295
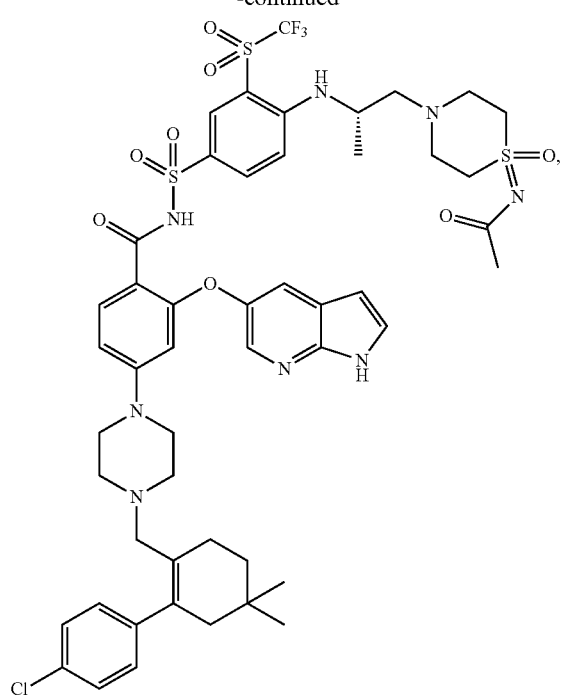
296
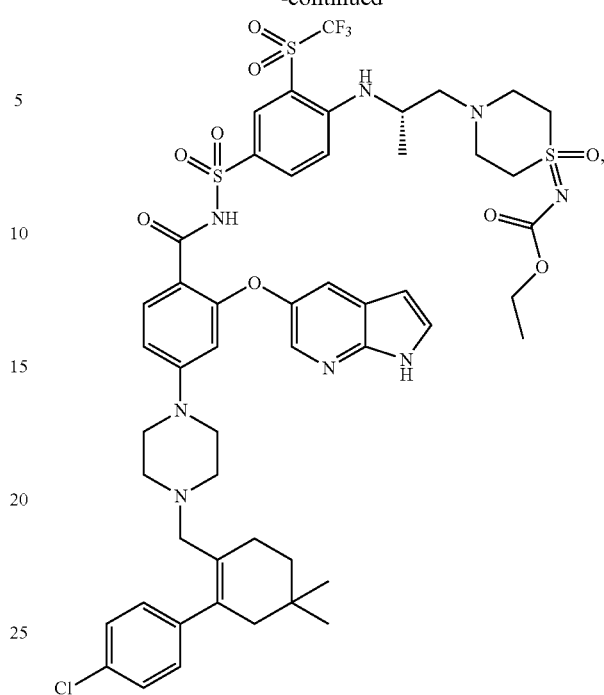
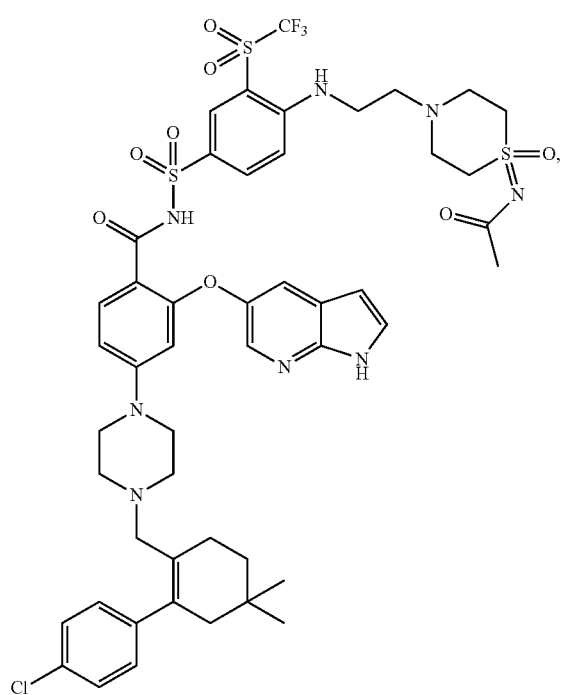
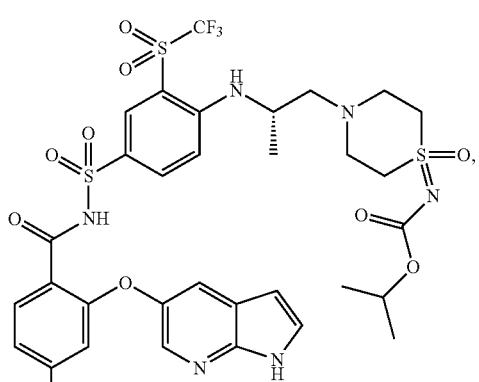

297
-continued
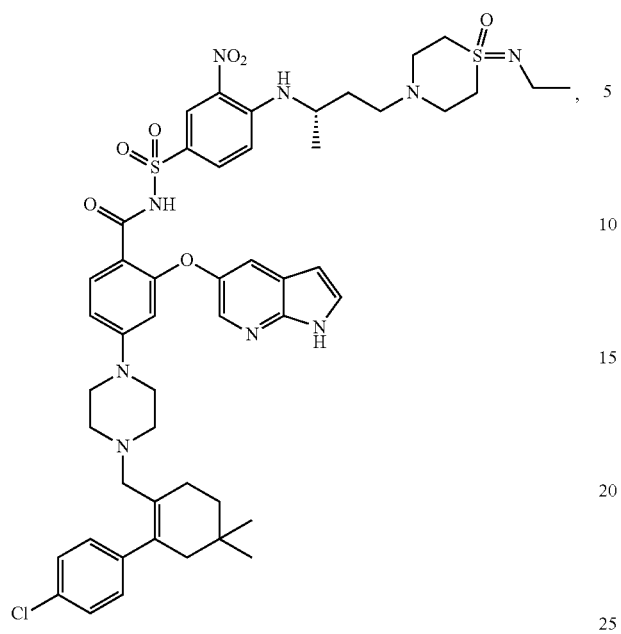
298
-continued
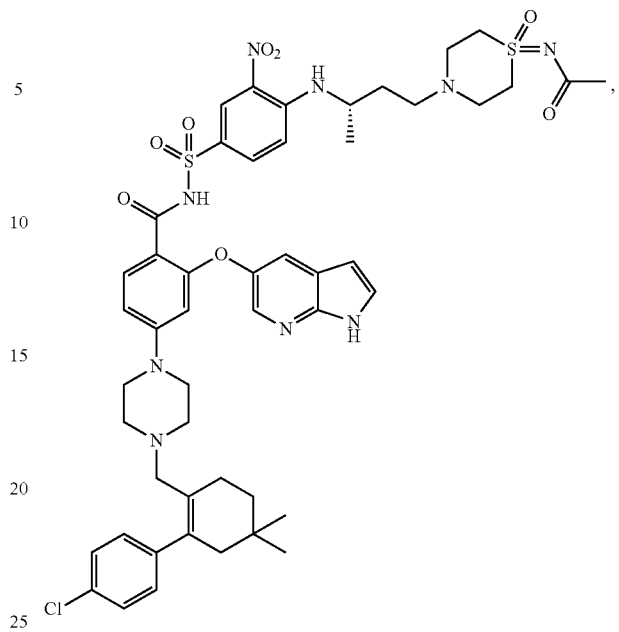
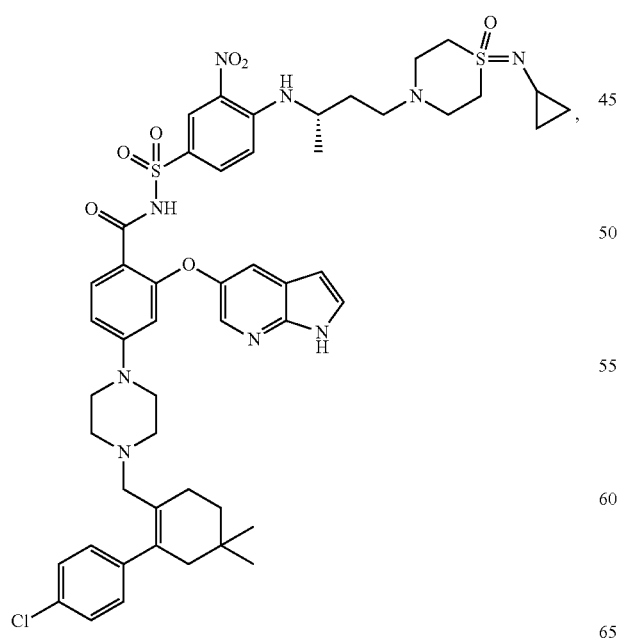
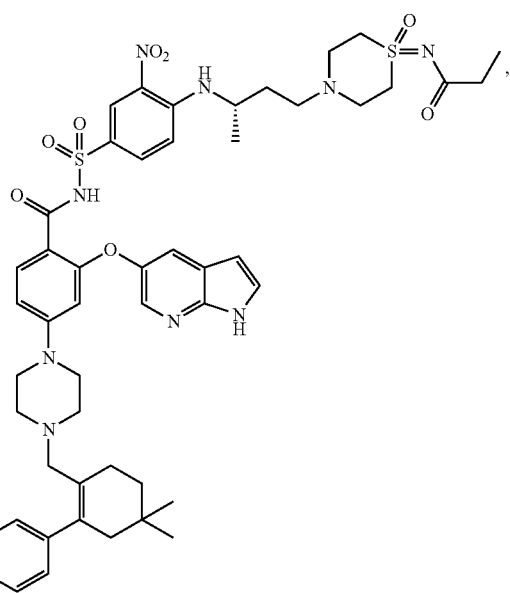

299
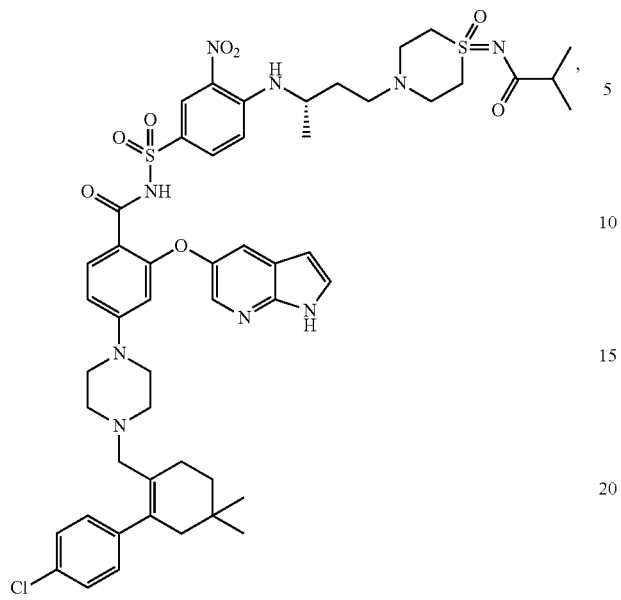
300
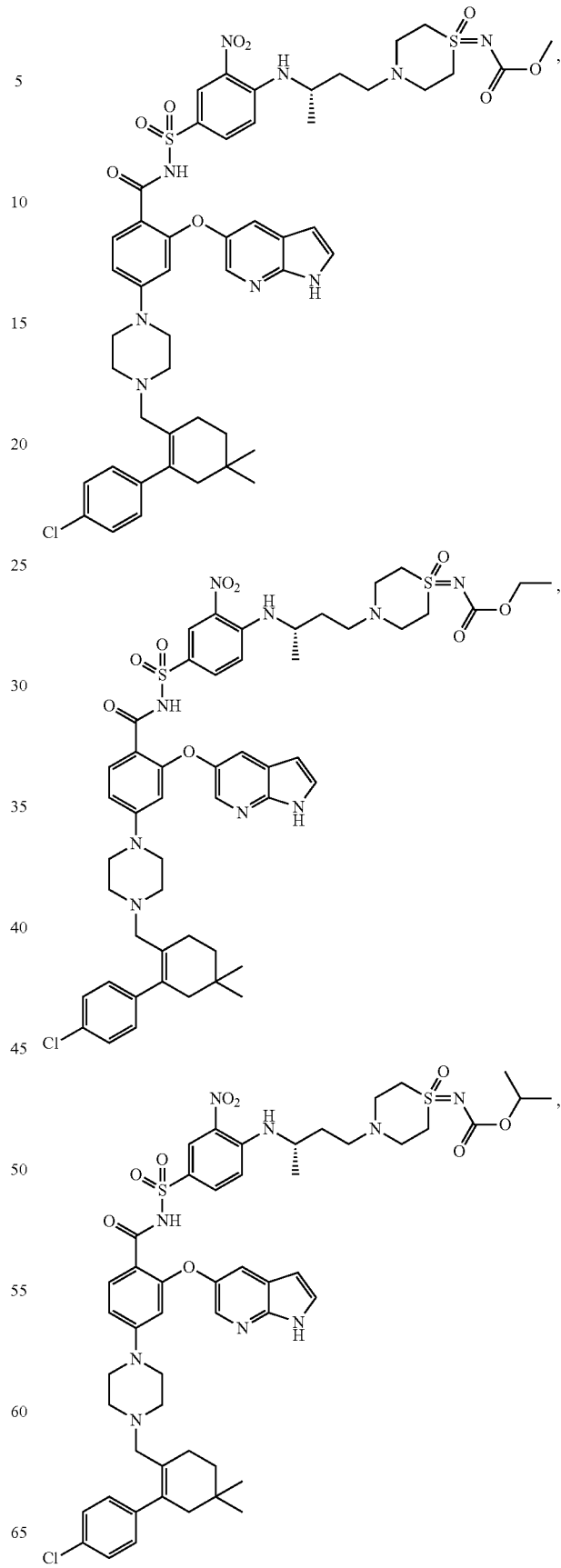

301
-continued
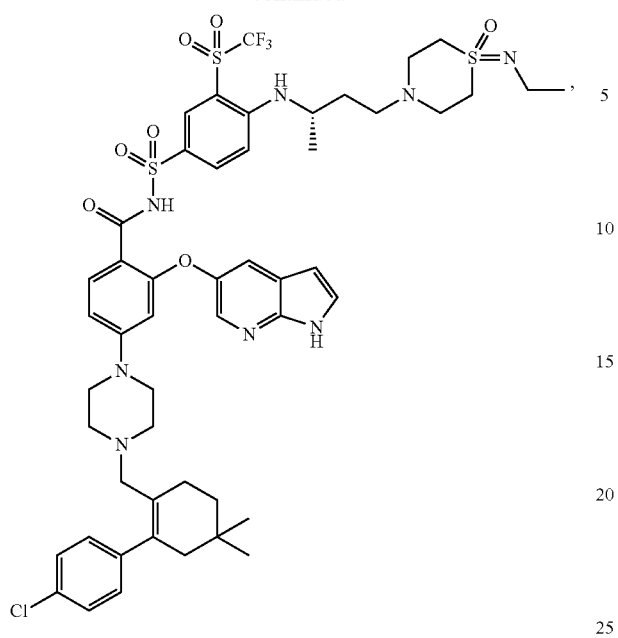
302
-continued
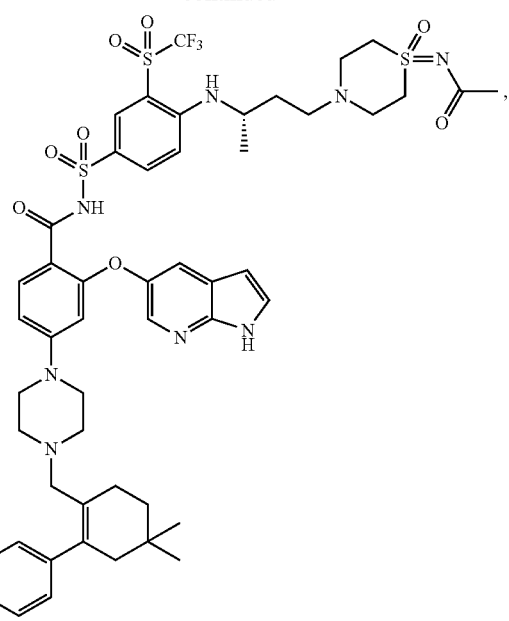
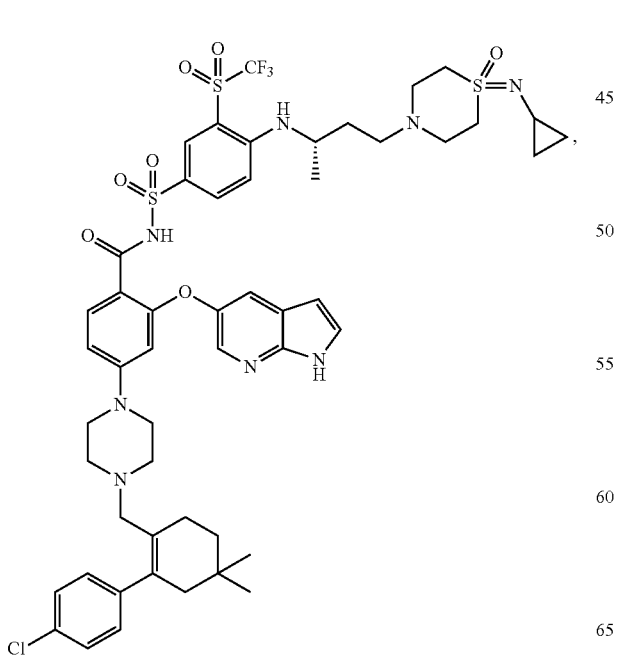
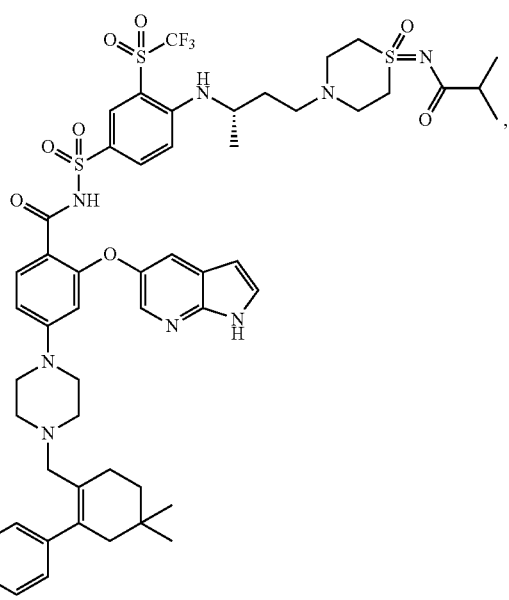

303
-continued
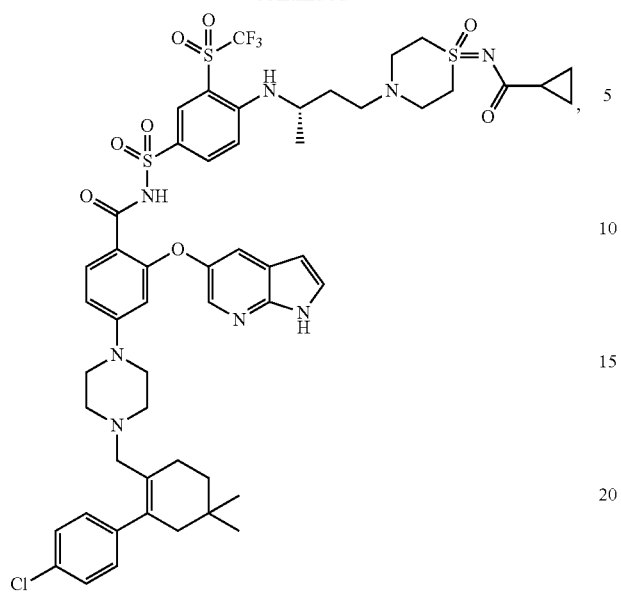
304
-continued
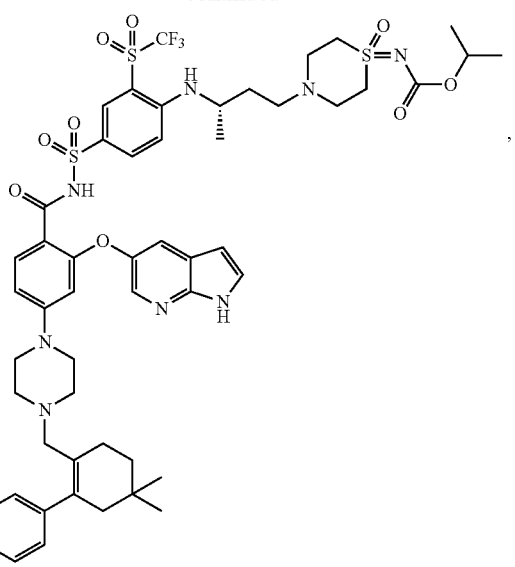
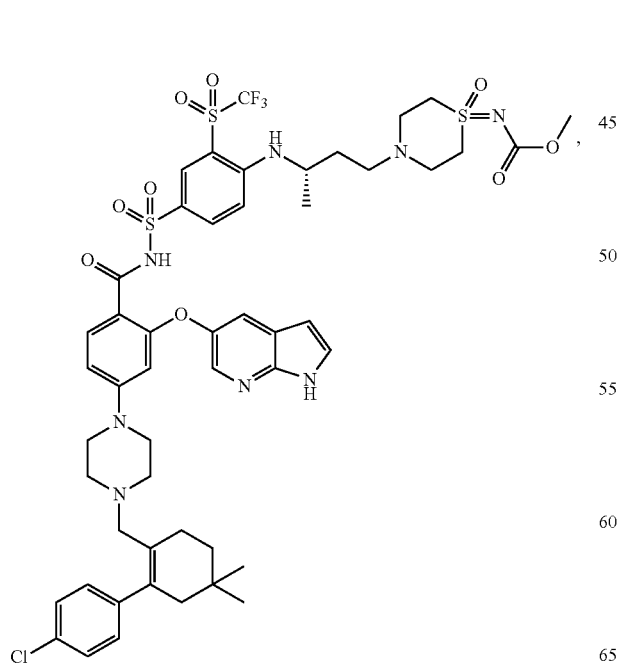
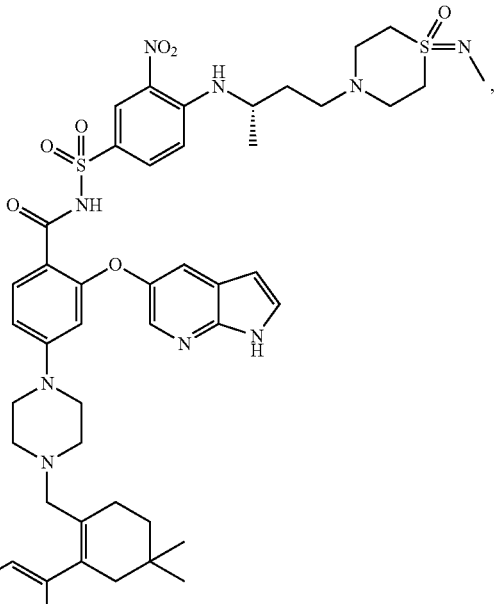

305
-continued

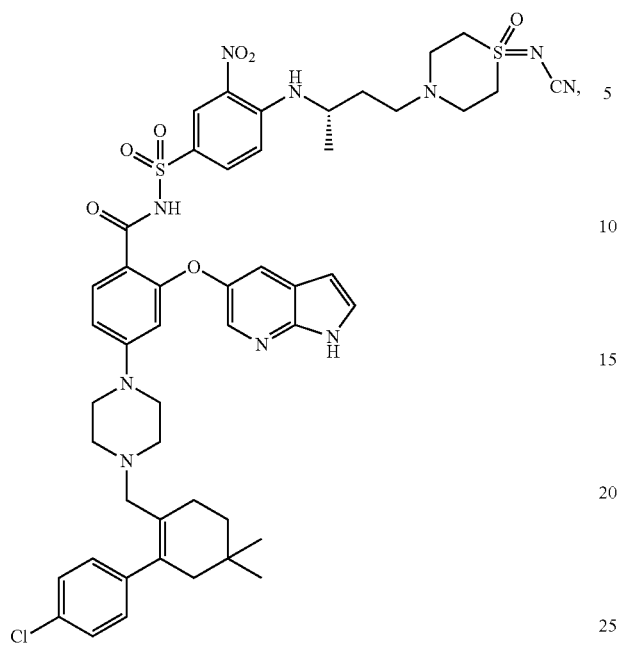

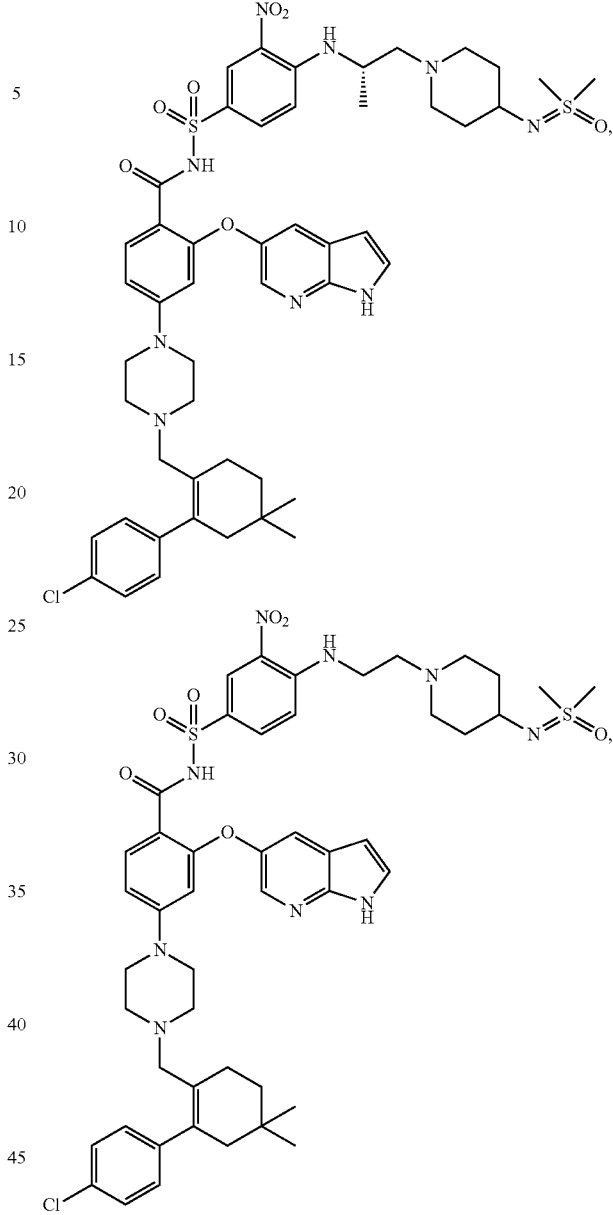

306
-continued and pharmaceutically acceptable salts thereof.

6. A pharmaceutical composition, comprising a compound of claim 1, or a pharmaceutically acceptable salt thereof, and at least one pharmaceutically acceptable carrier.

7. A method of treating a cell-proliferative disorder, comprising administering to a subject in need of such treatment an effective amount of a compound of claim 1 or a pharmaceutically acceptable salt thereof.

8. A pharmaceutical composition, comprising a compound of claim 5, or a pharmaceutically acceptable salt thereof, and at least one pharmaceutically acceptable carrier.

9. A method of treating a cell-proliferative disorder, comprising administering to a subject in need of such treatment an effective amount of a compound of claim 5 or a pharmaceutically acceptable salt thereof.

10. The method of claim 7, wherein the compound, or a pharmaceutically acceptable alt thereof, is administered in combination with a second therapeutic agent.

11. The method of claim 9, wherein the compound, or a pharmaceutically acceptable salt thereof, is administered in combination with a second therapeutic agent.

12. The method of claim 7, wherein the cell-proliferative disorder is lymphoma, osteosarcoma, melanoma or a breast, renal, prostate, colorectal, thyroid, ovarian, pancreatic, neuronal, lung, uterine, or gastrointestinal tumor.

13. The method of claim 9, wherein the cell-proliferative disorder is lymphoma, osteosarcoma, melanoma or a breast, renal, prostate, colorectal, thyroid, ovarian, pancreatic, neuronal, lung, uterine, or gastrointestinal tumor.

* * * * *

UNITED STATES PATENT AND TRADEMARK OFFICE
CERTIFICATE OF CORRECTION

Page 1 of 1

PATENT NO. : 11,053,239 B2
APPLICATION NO. : 16/475826
DATED : July 6, 2021
INVENTOR(S) : Xingdong Zhao et al.

It is certified that error appears in the above-identified patent and that said Letters Patent is hereby corrected as shown below:

On the Title Page
Column 1, Line 1, (TITLE): "BLC-2-SELECTIVE" should read -- BCL-2-SELECTIVE --

In the Specification
Column 1, Line 1, (TITLE): "BLC-2-SELECTIVE" should read -- BCL-2-SELECTIVE --

In the Claims
Claim 1, Column 254, Line 59: ")(=NR$^{c1}$)R$^{b1}$," should read -- )(=NR$^{e1}$)R$^{b1}$, --
Claim 1, Column 254, Line 61: "(=NR$^{c1}$)R$^{b1}$," should read -- (=NR$^{e1}$)R$^{b1}$, --
Claim 1, Column 255, Line 11: "R$^{C1}$" should read -- R$^{a1}$ --
Claim 1, Column 255, Line 33: "S(O)$_t$R$^{a2}$," should read -- S(O)$_r$R$^{a2}$, --
Claim 1, Column 255, Line 35: "R$^{b2}$;" should read -- R$^{b2}$, --
Claim 1, Column 256, Line 43: "R$^{e2}$" should read -- R$^{c2}$ --
Claim 2, Column 257, Line 2: "Q" should read -- Q$^3$ --

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*